US008309519B2

(12) United States Patent
Li et al.

(10) Patent No.: US 8,309,519 B2
(45) Date of Patent: Nov. 13, 2012

(54) COMPOSITIONS AND METHODS FOR INHIBITING VASCULAR PERMEABILITY

(75) Inventors: Dean Li, Salt Lake City, UT (US); Christopher Jones, Salt Lake City, UT (US); Nyall London, Bountiful, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 13/111,776

(22) Filed: May 19, 2011

(65) Prior Publication Data

US 2011/0263483 A1 Oct. 27, 2011

Related U.S. Application Data

(63) Continuation of application No. 12/518,730, filed as application No. PCT/US2007/025354 on Dec. 11, 2007, now Pat. No. 7,994,130.

(60) Provisional application No. 60/869,526, filed on Dec. 11, 2006.

(51) Int. Cl.
*A61K 38/16* (2006.01)
*A61K 38/17* (2006.01)
*C07K 14/435* (2006.01)

(52) U.S. Cl. ........ 514/13.3; 514/21.2; 514/1.1; 530/350

(58) Field of Classification Search .................. None
See application file for complete search history.

(56) References Cited

U.S. PATENT DOCUMENTS

| | | | |
|---|---|---|---|
| 3,610,795 A | 10/1971 | Antoine |
| 3,687,808 A | 8/1972 | Merigan |
| 4,469,863 A | 9/1984 | Ts'o |
| 4,476,301 A | 10/1984 | Imbach |
| 4,587,044 A | 5/1986 | Miller |
| 4,605,735 A | 8/1986 | Miyoshi |
| 4,667,025 A | 5/1987 | Miyoshi |
| 4,762,779 A | 8/1988 | Snitman |
| 4,789,737 A | 12/1988 | Miyoshi |
| 4,824,941 A | 4/1989 | Gordon |
| 4,828,979 A | 5/1989 | Klevan |
| 4,835,263 A | 5/1989 | Nguyen |
| 4,845,205 A | 7/1989 | Dinh |
| 4,868,116 A | 9/1989 | Morgan |
| 4,876,335 A | 10/1989 | Yamane |
| 4,897,355 A | 1/1990 | Eppstein |
| 4,904,582 A | 2/1990 | Tullis |
| 4,948,882 A | 8/1990 | Ruth |
| 4,958,013 A | 9/1990 | Letsinger |
| 4,980,286 A | 12/1990 | Morgan |
| 4,981,957 A | 1/1991 | Lebleu |
| 5,023,243 A | 6/1991 | Tullis |
| 5,034,506 A | 7/1991 | Summerton |
| 5,082,830 A | 1/1992 | Brakel |
| 5,109,124 A | 4/1992 | Ramachandran |
| 5,112,963 A | 5/1992 | Pieles |
| 5,118,800 A | 6/1992 | Smith |
| 5,118,802 A | 6/1992 | Smith |
| 5,130,302 A | 7/1992 | Spielvogel |
| 5,134,066 A | 7/1992 | Rogers |
| 5,135,917 A | 8/1992 | Burch |
| 5,138,045 A | 8/1992 | Cook |
| 5,166,315 A | 11/1992 | Summerton |
| 5,168,053 A | 12/1992 | Altman |
| 5,175,273 A | 12/1992 | Bischofberger |
| 5,176,996 A | 1/1993 | Hogan |
| 5,177,196 A | 1/1993 | Meyer |
| 5,185,444 A | 2/1993 | Summerton |
| 5,188,897 A | 2/1993 | Suhadolnik |
| 5,214,134 A | 5/1993 | Weis |
| 5,214,136 A | 5/1993 | Lin |
| 5,216,141 A | 6/1993 | Benner |
| 5,218,105 A | 6/1993 | Cook |
| 5,235,033 A | 8/1993 | Summerton |
| 5,245,022 A | 9/1993 | Weis |
| 5,254,469 A | 10/1993 | Warren, III |
| 5,258,506 A | 11/1993 | Urdea |
| 5,262,536 A | 11/1993 | Hobbs, Jr. |
| 5,264,423 A | 11/1993 | Cohen |
| 5,264,562 A | 11/1993 | Matteucci |
| 5,264,564 A | 11/1993 | Matteucci |

(Continued)

FOREIGN PATENT DOCUMENTS

WO    WO 89/07136    8/1989

(Continued)

OTHER PUBLICATIONS

Notification of Transmittal of the International Search Report and the Written Opinion of the International Searching Authority issued Oct. 5, 2004 in International Application No. PCT/US2003/020508.
Supplemental European Search Report issued May 8, 2009 in European National Application No. EP03762219.
Preliminary Amendment filed Dec. 21, 2004 in corresponding National Phase U.S. Appl. No. 10/519,342.
Office Action issued Apr. 29, 2008 in corresponding National Phase U.S. Appl. No. 10/519,342.
Response to Office Action filed Oct. 29, 2008 in corresponding National Phase U.S. Appl. No. 10/519,342.
Final Office Action issued Feb. 19, 2009 in corresponding National Phase U.S. Appl. No. 10/519,342.

(Continued)

*Primary Examiner* — Christine J Saoud
*Assistant Examiner* — Jon M Lockard
(74) *Attorney, Agent, or Firm* — Stoel Rives LLP; Samuel E. Webb; Yury M. Colton

(57) ABSTRACT

Compounds, compositions and methods for inhibiting vascular permeability and pathologic angiogenesis are described herein. Methods for producing and screening compounds and compositions capable of inhibiting vascular permeability and pathologic angiogenesis are also described herein. Pharmaceutical compositions are included in the compositions described herein. The compositions described herein are useful in, for example, methods of inhibiting vascular permeability and pathologic angiogenesis, including methods of inhibiting vascular permeability and pathologic angiogenesis induced by specific angiogenic, permeability and inflammatory factors, such as, for example VEGF, bFGF and thrombin. Methods for treating specific diseases and conditions are also provided herein.

2 Claims, 31 Drawing Sheets

U.S. PATENT DOCUMENTS

| | | |
|---|---|---|
| 5,272,250 A | 12/1993 | Spielvogel |
| 5,276,019 A | 1/1994 | Cohen |
| 5,278,302 A | 1/1994 | Caruthers |
| 5,286,717 A | 2/1994 | Cohen |
| 5,292,873 A | 3/1994 | Rokita |
| 5,294,533 A | 3/1994 | Lupski |
| 5,317,098 A | 5/1994 | Shizuya |
| 5,319,080 A | 6/1994 | Leumann |
| 5,321,131 A | 6/1994 | Agrawal |
| 5,334,711 A | 8/1994 | Sproat |
| 5,359,044 A | 10/1994 | Cook |
| 5,367,066 A | 11/1994 | Urdea |
| 5,371,241 A | 12/1994 | Brush |
| 5,391,723 A | 2/1995 | Priest |
| 5,393,878 A | 2/1995 | Leumann |
| 5,399,676 A | 3/1995 | Froehler |
| 5,405,938 A | 4/1995 | Summerton |
| 5,405,939 A | 4/1995 | Suhadolnik |
| 5,414,077 A | 5/1995 | Lin |
| 5,416,203 A | 5/1995 | Letsinger |
| 5,432,272 A | 7/1995 | Benner |
| 5,434,257 A | 7/1995 | Matteucci |
| 5,436,330 A | 7/1995 | Taira |
| 5,446,137 A | 8/1995 | Maag |
| 5,451,463 A | 9/1995 | Nelson |
| 5,453,496 A | 9/1995 | Caruthers |
| 5,455,233 A | 10/1995 | Spielvogel |
| 5,457,187 A | 10/1995 | Gmeiner |
| 5,459,255 A | 10/1995 | Cook |
| 5,466,677 A | 11/1995 | Baxter |
| 5,466,786 A | 11/1995 | Buhr |
| 5,470,967 A | 11/1995 | Huie |
| 5,476,766 A | 12/1995 | Gold |
| 5,476,925 A | 12/1995 | Letsinger |
| 5,480,975 A | 1/1996 | Goldberg |
| 5,484,908 A | 1/1996 | Froehler |
| 5,486,603 A | 1/1996 | Buhr |
| 5,489,677 A | 2/1996 | Sanghvi |
| 5,502,177 A | 3/1996 | Matteucci |
| 5,503,978 A | 4/1996 | Schneider |
| 5,510,475 A | 4/1996 | Agrawal |
| 5,512,439 A | 4/1996 | Hornes |
| 5,512,667 A | 4/1996 | Reed |
| 5,514,785 A | 5/1996 | Van Ness |
| 5,519,126 A | 5/1996 | Hecht |
| 5,519,134 A | 5/1996 | Acevedo |
| 5,525,465 A | 6/1996 | Haralambidis |
| 5,525,711 A | 6/1996 | Hawkins |
| 5,536,821 A | 7/1996 | Agrawal |
| 5,539,082 A | 7/1996 | Nielsen |
| 5,541,306 A | 7/1996 | Agrawal |
| 5,541,307 A | 7/1996 | Cook |
| 5,541,313 A | 7/1996 | Ruth |
| 5,543,293 A | 8/1996 | Gold |
| 5,545,730 A | 8/1996 | Urdea |
| 5,550,111 A | 8/1996 | Suhadolnik |
| 5,552,538 A | 9/1996 | Urdea |
| 5,552,540 A | 9/1996 | Haralambidis |
| 5,561,225 A | 10/1996 | Maddry |
| 5,563,253 A | 10/1996 | Agrawal |
| 5,565,552 A | 10/1996 | Magda |
| 5,567,810 A | 10/1996 | Weis |
| 5,567,811 A | 10/1996 | Misiura |
| 5,571,799 A | 11/1996 | Tkachuk |
| 5,574,142 A | 11/1996 | Meyer, Jr. |
| 5,576,427 A | 11/1996 | Cook |
| 5,578,717 A | 11/1996 | Urdea |
| 5,578,718 A | 11/1996 | Cook |
| 5,580,731 A | 12/1996 | Chang |
| 5,580,737 A | 12/1996 | Polisky |
| 5,580,967 A | 12/1996 | Joyce |
| 5,585,481 A | 12/1996 | Arnold, Jr. |
| 5,587,361 A | 12/1996 | Cook |
| 5,587,371 A | 12/1996 | Sessler |
| 5,587,469 A | 12/1996 | Cook |
| 5,591,584 A | 1/1997 | Chang |
| 5,591,722 A | 1/1997 | Montgomery |
| 5,594,121 A | 1/1997 | Froehler |
| 5,595,726 A | 1/1997 | Magda |
| 5,595,873 A | 1/1997 | Joyce |
| 5,596,086 A | 1/1997 | Matteucci |
| 5,596,091 A | 1/1997 | Switzer |
| 5,597,696 A | 1/1997 | Linn |
| 5,597,909 A | 1/1997 | Urdea |
| 5,599,923 A | 2/1997 | Sessler |
| 5,599,928 A | 2/1997 | Hemmi |
| 5,602,240 A | 2/1997 | Mesmaeker |
| 5,608,046 A | 3/1997 | Cook |
| 5,610,289 A | 3/1997 | Cook |
| 5,610,300 A | 3/1997 | Altmann |
| 5,614,617 A | 3/1997 | Cook |
| 5,616,466 A | 4/1997 | Cantor |
| 5,618,704 A | 4/1997 | Sanghvi |
| 5,623,070 A | 4/1997 | Cook |
| 5,624,824 A | 4/1997 | Yuan |
| 5,625,050 A | 4/1997 | Beaton |
| 5,627,053 A | 5/1997 | Usman |
| 5,627,158 A | 5/1997 | Cho-Chung |
| 5,631,115 A | 5/1997 | Ohtsuka |
| 5,631,146 A | 5/1997 | Szostak |
| 5,633,133 A | 5/1997 | Long |
| 5,633,360 A | 5/1997 | Bischofberger |
| 5,639,873 A | 6/1997 | Barascut |
| 5,641,754 A | 6/1997 | Iversen |
| 5,645,985 A | 7/1997 | Froehler |
| 5,646,020 A | 7/1997 | McSwiggen |
| 5,646,031 A | 7/1997 | DeYoung |
| 5,646,042 A | 7/1997 | Stinchcomb |
| 5,646,265 A | 7/1997 | McGee |
| 5,650,316 A | 7/1997 | Aggarwal |
| 5,652,094 A | 7/1997 | Usman |
| 5,652,107 A | 7/1997 | Lizardi |
| 5,658,873 A | 8/1997 | Bertsch-Frank |
| 5,663,312 A | 9/1997 | Chaturvedula |
| 5,670,633 A | 9/1997 | Cook |
| 5,677,437 A | 10/1997 | Teng |
| 5,677,439 A | 10/1997 | Weis |
| 5,681,941 A | 10/1997 | Cook |
| 5,683,873 A | 11/1997 | George |
| 5,683,874 A | 11/1997 | Kool |
| 5,683,902 A | 11/1997 | Hampel |
| 5,688,670 A | 11/1997 | Szostak |
| 5,688,941 A | 11/1997 | Cook |
| 5,691,317 A | 11/1997 | Cho-Chung |
| 5,693,535 A | 12/1997 | Draper |
| 5,693,773 A | 12/1997 | Kandimalla |
| 5,700,920 A | 12/1997 | Altmann |
| 5,712,384 A | 1/1998 | Symonds |
| 5,714,331 A | 2/1998 | Buchardt |
| 5,719,262 A | 2/1998 | Buchardt |
| 5,728,521 A | 3/1998 | Yuan |
| 5,731,295 A | 3/1998 | Draper |
| 5,731,424 A | 3/1998 | Toothman |
| 5,770,715 A | 6/1998 | Sugiyama |
| 5,780,228 A | 7/1998 | Parma |
| 5,780,607 A | 7/1998 | Goodnow, Jr. |
| 5,786,138 A | 7/1998 | Swenson |
| 5,786,462 A | 7/1998 | Schneider |
| 5,792,613 A | 8/1998 | Schmidt |
| 5,795,721 A | 8/1998 | Rabin |
| 5,807,718 A | 9/1998 | Joyce |
| 5,811,300 A | 9/1998 | Sullivan |
| 5,834,185 A | 11/1998 | Ts'O |
| 5,837,855 A | 11/1998 | Chowrira |
| 5,846,713 A | 12/1998 | Pagratis |
| 5,849,903 A | 12/1998 | Pietrzkowski |
| 5,856,103 A | 1/1999 | Gray |
| 5,856,188 A | 1/1999 | Hampel |
| 5,856,463 A | 1/1999 | Prydz |
| 5,858,660 A | 1/1999 | Eaton |
| 5,861,254 A | 1/1999 | Schneider |
| 5,861,288 A | 1/1999 | Usman |
| 5,864,026 A | 1/1999 | Jensen |
| 5,866,701 A | 2/1999 | Hampel |
| 5,869,246 A | 2/1999 | Matsuo |
| 5,869,248 A | 2/1999 | Yuan |
| 5,869,253 A | 2/1999 | Draper |

| | | | |
|---|---|---|---|
| 5,869,339 | A | 2/1999 | Hampel |
| 5,869,641 | A | 2/1999 | Jayasena |
| 5,874,566 | A | 2/1999 | Veerapanane |
| 5,877,021 | A | 3/1999 | Stinchcomb |
| 5,877,022 | A | 3/1999 | Stinchcomb |
| 5,877,162 | A | 3/1999 | Werner |
| 5,891,683 | A | 4/1999 | Usman |
| 5,891,684 | A | 4/1999 | Usman |
| 5,910,408 | A | 6/1999 | Szostak |
| 5,919,772 | A | 7/1999 | Szyf |
| 5,955,590 | A | 9/1999 | Levina |
| 5,958,691 | A | 9/1999 | Pieken |
| 5,962,426 | A | 10/1999 | Glazer |
| 5,972,699 | A | 10/1999 | Draper |
| 5,972,704 | A | 10/1999 | Draper |
| 5,985,621 | A | 11/1999 | Usman |
| 5,989,906 | A | 11/1999 | Thompson |
| 5,989,908 | A | 11/1999 | Scanlon |
| 5,990,088 | A | 11/1999 | Ensoli |
| 5,994,320 | A | 11/1999 | Low |
| 5,998,193 | A | 12/1999 | Keese |
| 5,998,203 | A | 12/1999 | Matulic-Adamic |
| 5,998,602 | A | 12/1999 | Torrence |
| 6,001,988 | A | 12/1999 | Parma |
| 6,005,095 | A | 12/1999 | Capaccioli |
| 6,007,995 | A | 12/1999 | Baker |
| 6,011,020 | A | 1/2000 | Gold |
| 6,013,443 | A | 1/2000 | Heilig |
| 6,013,522 | A | 1/2000 | Monia |
| 6,017,756 | A | 1/2000 | Draper |
| 6,017,898 | A | 1/2000 | Pietrzkowski |
| 6,018,042 | A | 1/2000 | Mett |
| 6,020,130 | A | 2/2000 | Gold |
| 6,022,962 | A | 2/2000 | Chowrira |
| 6,025,198 | A | 2/2000 | Bennett |
| 6,028,186 | A | 2/2000 | Tasset |
| 6,030,776 | A | 2/2000 | Eaton |
| 6,033,910 | A | 3/2000 | Monia |
| 6,040,296 | A | 3/2000 | Nyce |
| 6,046,004 | A | 4/2000 | Wu |
| 6,046,319 | A | 4/2000 | Power |
| 6,051,698 | A | 4/2000 | Janjic |
| 6,057,437 | A | 5/2000 | Kamiya |
| 6,372,958 | B1 | 4/2002 | Li |
| 2003/0170621 | A1 | 9/2003 | McCarthy |
| 2003/0175733 | A1 | 9/2003 | Kirst |
| 2003/0236210 | A1 | 12/2003 | Geng |
| 2004/0071711 | A1 | 4/2004 | Bicknell |
| 2005/0142138 | A1 | 6/2005 | St. Croix |
| 2006/0105995 | A1 | 5/2006 | Fujimoto |
| 2006/0160729 | A1 | 7/2006 | Li |
| 2007/0099251 | A1 | 5/2007 | Zhang |
| 2010/0222401 | A1 | 9/2010 | Li |

FOREIGN PATENT DOCUMENTS

| | | |
|---|---|---|
| WO | WO 90/02806 | 3/1990 |
| WO | WO 92/03566 | 3/1992 |
| WO | WO 93/22434 | 11/1993 |
| WO | WO 95/24489 | 9/1995 |
| WO | WO 97/18312 | 5/1997 |
| WO | WO 98/58057 | 12/1998 |
| WO | WO 98/58058 | 12/1998 |
| WO | WO 99/07409 | 2/1999 |
| WO | WO 99/32619 | 7/1999 |
| WO | WO 00/01846 | 1/2000 |
| WO | WO 00/44895 | 8/2000 |
| WO | WO 00/44941 | 8/2000 |
| WO | WO 01/29058 | 4/2001 |
| WO | WO 01/36646 | 5/2001 |
| WO | WO 02/22660 | 3/2002 |
| WO | WO 02/36771 | 5/2002 |
| WO | WO 02/44321 | 6/2002 |
| WO | WO 2004/003163 | 8/2004 |
| WO | WO 2006/053903 | 5/2006 |
| WO | WO 2008/073441 | 6/2008 |
| WO | WO 2009/129408 | 10/2009 |
| WO | WO 2010/068917 | 6/2010 |

OTHER PUBLICATIONS

Response to Final Office Action issued May 19, 2009 in corresponding National Phase U.S. Appl. No. 10/519,342.
Office Action issued Jun. 24, 2009 in corresponding National Phase U.S. Appl. No. 10/519,342.
Response to Office Action filed Sep. 24, 2009 in corresponding National Phase U.S. Appl. No. 10/519,342.
Office Action issued Dec. 9, 2009 in corresponding National Phase U.S. Appl. No. 10/519,342.
Response to Office Action filed Jun. 9, 2010 in corresponding National Phase U.S. Appl. No. 10/519,342.
Final Office Action issued Jul. 21, 2010 in corresponding National Phase U.S. Appl. No. 10/519,342.
Notification of Transmittal of the International Search Report and the Written Opinion of the International Searching Authority issued Sep. 2, 2008 in International Application No. PCT/US2007/025354.
Notification of Transmittal of the International Search Report and the Written Opinion of the International Searching Authority issued Nov. 5, 2009 in International Application No. PCT/US2009/040848.
Notification Concerning Transmittal of the International Preliminary Report on Patentability issued Jun. 16, 2009 in International Application No. PCT/US2007/025354, now WO 2008/073441.
Notification Concerning Transmittal of the International Preliminary Report on Patentability issued Oct. 28, 2010 in International Application No. PCT/US2009/040848, now WO 2009/129408.
Preliminary Amendment filed Dec. 29, 2009 in co-pending U.S. Appl. No. 12/667,168.
Notification of Transmittal of the Supplemental European Search Report and the European Search Opinion issued Feb. 22, 2010 in European Application No. 07867716.8.
Notification of Transmittal of the International Search Report and the Written Opinion of the International Searching Authority issued Jun. 17, 2010 in International Application No. PCT/US2009/067746.
U.S. Appl. No. 60/362,485, filed Mar. 8, 2002.
Abdel-Ghafar, A.N., et al., 2008. Update on avian influenza A (H5N1) virus infection in humans. N Engl J Med 358:261-273.
Abrahmsen, Lars, et al., "Engineering Subtilisin and Its Substrates for Efficient Ligation of Peptide Bonds in Aqueous Solution," J. Biol. Chem. 256, 10803-10808, 1991.
Afzal A, Shaw LC, Ljubimov AV, Boulton ME, Segal MS, Grant MB. Retinal and choroidal microangiopathies: Therapeutic opportunities. Microvasc Res 2007.
Allen, James M. et al., "Improved Adeno-Associated Virus Vector Production with Transfection of a Single Helper Adenovirus Gene, E4orf6," Molecular Therapy, vol. 1, No. 1., Jan. 2000, 88-95.
Almquist, Ronald G., et al., "Derivatives of the Potent Angiotension Converting Enzyme Inhibitor 5(S)-Benzamido-4-oxo-6-phenylhexanoyl-L-proline: Effect of Changes at Positions 2 and 5 of the Hexanoic Acid Portion," J. Med. Chem. 1982, 25, 1292-1299.
Armour KL, Clark MR, Hadley AG, Williamson LM. Recombinant human IgG molecules lacking Fcgamma receptor I binding and monocyte triggering activities. Eur J Immunol 1999; 29(8):2613-24.
Balasubramanian, et al., "Arf6 and microtubules in adhesion-dependent trafficking of lipid rafts," Nature cell biology 9, 1381-1391 (2007).
Baggiolini, Marco, et al., "Interleukin-8, a chemotactic and inflammatory cytokine," FEBS 11242, vol. 307, No. 1, 97-101, 1992.
Bagshawe, K.D., "A cycotoxic agent can be generated selectively at cancer sites," Br. J. Cancer (1988).
Bagshawe, K.D., "The First Bagshawe Lecture: Towards Generating Cytotoxic Agents at Cancer Sites," Br. J. Cancer (1989), 60, 275-281.
Banerji, et al., "A Lymphocyte-Specific Cellular Enhancer Is Located Downstream of the Joining Region in Immunoglobulin Heavy Chain Genes, " Cell, vol. 33, 729-740, Jul. 1983.
Bantel-Schaal, et al., "Endocytosis of Adeno-Associated Virus Type 5 Leads to Accumulation of Virus Particles in the Golgi Compartment," Journal of Virology, Mar. 2002, p. 2340-2349.
Bartlett, Jeffrey S., et al., "Infectious Entry Pathway of Adeno-Associated Virus and Adeno-Associated Virus Vectors," Journal of Virology, Mar. 2000, p. 2777-2785.
Bashaw, G.J., Kidd, T., Murray, D., Pawson, T., and Goodman, C.S. (2000). Repulsive axon guidance: Abelson and Enabled play opposing roles downstream of the roundabout receptor. Cell 101, 703-715.

Battelli, M.G., et al., "T lymphocyte killing by a xanthine-oxidase-containing immunotoxin," Cancer Immunol Immunother (1992) 35: 421-425.

Battye, R., Stevens, A., and Jacobs, J.R. (1999). Axon repulsion from the midline of the *Drosophila* CNS requires slit function. Development 126, 2475-2481.

Battye R, Stevens A, Perry RL, Jacobs JR. Repellent signaling by Slit requires the leucine-rich repeats. J Neurosci 2001; 21(12):4290-8.

Bedell, V.M., Yeo, S.Y., Park, K.W., Chung. J., Seth, P., Shivalingappa, V., Zhao, J., Obara, T., Sukhatme, V.P., Drummond, I.A., Li, D.Y., and Ramchandran, R. (2005). Roundabout4 is essential for angiogenesis in vivo. Proc. Natl. Acad. Sci. U.S.A. 102, 6373-6378.

Ben-Israel, Haggit, et al., "Adenovirus and Cell Cycle Control," Frontiers in Bioscience, 7, d1369-1395, May 1, 2002.

Benner, Steven A. "Expanding the genetic lexicon: incorporating non-standard amino acids into proteins by ribosome-based synthesis," TIBTECH May 1994, vol. 12, pp. 158-163.

Berg, et al., "The Activin-Like Kinase Gene: Genomic Structure and Mutations in Hereditary Hemorrhagic Telangiectasia Type 2," 1997, Am. J. Hum. Genet. 61(1) 60-7.

Berkner, Kathleen L., et al., "Abundant Expression of Polyomavirus Middle T Antigen and Dihydrofolate Reductase in an Adenovirus Recombinant," Journal of Virology, Apr. 1987, p. 1213-1220.

Bernstein, Emily, et al., "Role for a bidentate ribonuclease in the initiation step of RNA interference," Nature, vol. 409, Jan. 18, 2001, p. 363-366.

Bossis, Ioannis, et al., "Cloning of an Avian Adeno-Associated Virus (AAAV) and Generation of Recombinant AAAV Particles," Journal of Virology, Jun. 2003, p. 6799-6810.

Bout, Abraham, et al., "Lung Gene Therapy: In Vivo Adenovirus-Mediated Gene Transfer to Rhesus Monkey Airway Epithelium," Human Gene Therapy 5:3-10 (1994), p. 3-10.

Brigham, Kenneth L., "Expression of a Prokaryotic Gene in Cultured Lung Endothelial Cells after Lipofection with a Plasmid Vector," Am. J. Respir. Cell Col. Biol., vol. 1, pp. 95-100, 1989.

Brooks, P.C., Clark, R.A., and Cheresh, D.A. (1994). Requirement of vascular integrin alpha v beta 3 for angiogenesis. Science 264, 569-571.

Brooks, P.C., Montgomery, A.M., Rosenfeld, M., Reisfeld, R.A., Hu, T., Klier, G., and Cheresh, D.A. (1994). Integrin alpha v beta 3 antagonists promote tumor regression by inducing apoptosis of angiogenic blood vessels. Cell 30, 1157-1164.

Brose, et al., "Slit Proteins: Key Regulations of Axon Guidance, Axonal Branching, and Cell Migration," 2000, Curr. Opin. Neurobiol. 10(1) 95-102.

Brose, K., Bland, K.S., Wang, K.H., Arnott, D., Henzel, W., Goodman, C.S., Tessier-Lavigne, M., and Kidd, T. (1999). Slit proteins bind Robo receptors and have an evolutionarily conserved role in repulsive axon guidance. Cell 19, 795-806.

Brown DM, Kaiser PK, Michels M, Soubrane G, Heier JS, Kim RY, Sy JP, Schneider S; ANCHOR Study Group. Ranibizumab versus verteporfin for neovascular age-related macular degeneration. N Engl J Med. 2006 355(14):1432-44.

Brown, M.C., and Turner, C.E. (2004). Paxillin: adapting to change. Physiol. Rev. 84, 1315-1339.

Brown, Dennis T., et al., "Penetration of Host Cell Membranes by Adenovirus 2," Journal of Vibology, Aug. 1973, p. 386-396.

Brown, Valerie I,, et al., "Review Article: Molecular and Cellular Mechanisms of Receptor-Mediated Endocytosis," DNA and Cell Biology, vol. 10, No. 6, 1991, pp. 399-409.

Byzova, T.V., Goldman, C.K., Pampori, N., Thomas, K.A., Bett, A., Shattil, S.J., and Plow, E.F. (2000). A mechanism for modulation of cellular responses to VEGF: activation of the integrins. Mol. Cell 6, 851-860.

Cahill, Spencer J. Anthony, et al, "Site-specific mutagenesis with unnatural amino acids," TIBS 14—Oct. 1989, pp. 400-403.

Caillaud, Catherine, et al., "Adenoviral Vector as a Gene Delivery System into Cultured Rat Neuronal and Glial Cells," European Journal of Neuroscience, vol. 5, pp. 1287-1291, 1993.

Carmeliet P, Tessier-Lavigne M. Common mechanisms of nerve and blood vessel wiring. Nature 2005; 436(7048):193-200.

Carrara, Gioia, et al., "Two helices plus a linker: A small model substrate for eukaryotic Rnase P," Proc. Natl. Acad. Sci. USA, vol. 92, pp. 2627-2631, Mar. 1995 Biochemistry.

Chang, Long-Sheng, et al., "The Adenovirus DNA-Binding Protein Stimulates the Rate of Transcription Directed by Adenovirus and Adeno-Associated Virus Promoters," Journal of Virology, May 1990, p. 2103-2109.

Chardonnet, Yvette, et al., "Early Events in the Interaction of Adenoviruses with HeLa Cells," VIBOLOGY 40, 462-477 (1970).

Chedotal, A. 2007. "Slits and Their Receptors," Adv Exp Med Biol 621:65-80.

Cheng HJ, Nakamoto M, Bergemann AD, Flanagan JG. Complementary gradients in expression and binding of ELF-1 and Mek4 in development of the topographic retinotectal projection map. Cell 1995; 82(3):371-81.

Chiorini, John A., et al., "Sequence Requirements for Stable Binding and Function of Rep68 on the Adeno-Associated Virus Type 2 Inverted Terminal Repeats," Journal of Virology, Nov. 1994, p. 7448-7457.

Chun DW, Heier JS, Topping TM, Duker JS, Bankert JM. A pilot study of multiple intravitreal injections of ranibizumab in patients with center-involving clinically significant diabetic macular edema. Ophthalmology 2006; 113(10):1706-12.

Clark-Lewis, Ian, et al., "Chemical Synthesis, Purification, and Characterization of Two Inflammatory Proteins, Neutrophil Activating Peptide 1 (Interleukin-8) and Neutrophil Activating Peptide 2" Biochemistry 1991, 30, 3128-3135.

Clark-Lewis, Ian, et al., "Structural Requirements for Interleukin-8 Function Identified by Design of Analogs and CXC Chemokine Hybrids," vol. 269, No. 23, Issue of Jun. 10, pp. 16075-16081, 1994.

Collins, S.J., et al., 1978. Terminal differentiation of human promyelocytic leukemia cells induced by dimethyl sulfoxide and other polar compounds. Proc Natl Acad Sci U S A 75:2458-2462.

Cotter, Murray A., et al., "Molecular genetic analysis of herpesviruses and their potential use as vectors for gene thereapy applications," Current Opinion in Molecular Therapeutics (1999) 1(5); 633-644.

Creighton, Thomas E., "Proteins: Structures and Molecular Principles," Protein Biosynthesis, pp. 79-86, 1984.

Crooke, Stanley T., et al., "Pharmacokinetic Properties of Several Novel Oligonucleotide Analogs in mice," The Journal of Pharmacology and Experimental Therapeutics, vol. 277, No. 2, pp. 923-937, 1996.

Cross MJ, Dixelius J, Matsumoto T, Claesson-Welsh L. VEGF-receptor signal transduction. Trends in biochemical sciences 2003; 28(9):488-94.

Culotti JG, Merz DC. DCC and netrins. Curr Opin Cell Biol 1998; 10(5):609-13.

Database GenPept Accession No. AA31867 Nov. 15, 2001.

Database EMBL Accession No. AF361473 Nov. 16, 2001.

Davidson, Dominque, et al., "Overproduction of Polyomavirus Middle T Antigen in Mammalian Cells through the Use of an Adenovirus Vector," Journal of Virology, Apr. 1987, p. 1226-1239.

Dawson, Philip E., et al., "Synthesis of Proteins by Native Chemical Litigation," Science, vol. 266, 4 Nov. 1994, pp. 776-779.

Dejana, et al., "The Role of Adherens Junction and VE-Cadherin in the Control of Vascular Permeability," J. Cell Sci. Jul. 1, 2008, vol. 121(Pt 13), p. 2115-2122.

de Jong, M.D., et al., 2006. Fatal outcome of human influenza A (H5N1) is associated with high viral load and hypercytokinemia. Nat Med 12:1203-1207.

De Lisle Milton, R.C., et al., "Synthesis of Proteins by Chemical Ligation of Unprotected Peptide Segments: Mirro-Image Enzyme Molecules, D- & L-HIV Protease Analogs," Techniques in Protein Chemistry IV, pp. 257-267, 1993.

DeWan, Andrew, et al., "HTRA1 Promoter Polymorphism in Wet Age-Related Macular Degeneration," Science, vol. 314, Nov. 10, 2006, pp. 989-992.

Diabetic Retinopathy Clinical Research Network, Scott IU, Edwards AR, Beck RW, Bressler NM, Chan CK, Elman MJ, Friedman SM, Greven CM, Maturi RK, Pieramici DJ, Shami M, Singerman LJ, Stockdale CR. A phase II randomized clinical trial of intravitreal bevacizumab for diabetic macular edema. Ophthalmology. 2007 114(10):1860-7.

Dinarello, C.A. 1997. Proinflammatory and Antiinflammatory Cytokines as Mediators in the Pathogenesis of Septic Shock. Chest, 112:321S-329S.

Dickson BJ. Molecular mechanisms of axon guidance. Science 2002; 298(5600):1959-64.

Dong QG, Bernasconi S, Lostaglio S, et al. A general strategy for isolation of endothelial cells from murine tissues. Characterization of two endothelial cell lines from the murine lung and subcutaneous sponge implants. Arterioscler Thromb Vasc Biol 1997; 17(8):1599-604.

Dorrell M, Uusitalo-Jarvinen H, Aguilar E, Friedlander M. Ocular neovascularization: basic mechanisms and therapeutic advances. Sury Ophthalmol. 2007 52 Suppl 1:S3-19.

Drescher U, Kremoser C, Handwerker C, Loschinger J, Noda M, Bonhoeffer F. In vitro guidance of retinal ganglion cell axons by RAGS, a 25 kD tectal protein related to ligands for Eph receptor tyrosine kinases. Cell 1995; 82(3):359-70.

D'Souza-Schorey, C., and Chavrier, P. (2006). ARF proteins: roles in membrane traffic and beyond. Nat. Rev. Mol. Cell. Biol. 7, 347-358.

Eichmann, et al., "Neural Guidance Molecules Regulate Vascular Remodeling and Vessel Navigation," Genes Dev. May 1, 2005; 19(9):1013-21.

Elbashir, Sayda M., et al., "RNA interference is mediated by 21- and 22-nucleotide RNAs," Genes & Development 15:188-200, 2001.

Elbashir, Sayda M., et al., "Duplexes of 21-nucleotide RNAs mediate RNA interference in cultured mammalian cells," Nature, vol. 411, May 24, 2001, pp. 494-498.

Eliceiri BP, Cheresh DA. (2000). Role of alpha v integrins during angiogenesis. Cancer J. 6, S245-249.

Eliceiri BP, Paul R, Schwartzberg PL, Hood JD, Leng J, Cheresh DA. Selective requirement for Src kinases during VEGF-induced angiogenesis and vascular permeability. Molecular cell 1999; 4(6):915-24.

Eliceiri BP, Puente XS, Hood JD, et al. Src-mediated coupling of focal adhesion kinase to integrin alpha(v)beta5 in vascular endothelial growth factor signaling. The Journal of cell biology 2002; 157(1):149-60.

Englisch, Uwe, et al., "Chemically Modified Oligonucleotides as Probes and Inhibitors," Angewandte Chemie, vol. 30, No. 6, Jun. 1991, pp. 613-729.

Felgner, Philip L., et al., "Lipofection: A highly efficient, lipid-mediated DNA-transfection procedure," Proc. Natl. Acad. Sci. USA, vol. 84, pp. 7413-7417, Nov. 1987, pp. 7413-7417.

Fiers, W., et al., "Complete nucleotide sequence of SV40 DNA," Nature, vol. 273, May 11, 1978, pp. 113-120.

Fire, Andrew, et al., "Potent and specific genetic interference by double-stranded RNA in Caenorhabditis elegans," Nature, vol. 391, Feb. 19, 1998, pp. 806-811.

Forster, Anthony C., "External Guide Sequences for an RNA Enzyme," Science, vol. 249, Aug. 17, 1990, pp. 783-786.

Francis, S.E., Goh, K.L., Hodivala-Dilke, K., Bader, B.L., Stark, M., Davidson, D., and Hynes, R.O. (2002). Central roles of alpha5beta1 integrin and fibronectin in vascular development in mouse embryos and embryoid bodies. Arterioscler. Thromb. Vasc. Biol. 22, 927-933.

Fujiwara, et al., "Potential Role of the Slit/Robo Signal Pathway in Angiogenesis," Vasc Med. 2006 Nat;11(2):115-21.

Gait, Michael J., "Oligoribonucleotides," Antisense Research and Applications, 1993 by CRC Press, Inc., Chapter 16, pp. 289-301.

Gao, Guang-Ping, et al., "Novel adeno-associated viruses from rhesus monkeys as vectors for human gene therapy," PNAS, vol. 99, No. 18, Sep. 3, 2002, 11854-11859.

Garrett TA, Van Buul JD, Burridge K. VEGF-induced Rac1 activation in endothelial cells is regulated by the guanine nucleotide exchange factor Vav2. Experimental cell research 2007; 313(15):3285-97.

Gasse, P., et al. IL-1 R1/MyD88 signaling and the inflammasome are essential in pulmonary inflammation and fibrosis in mice. J Clin Invest 117, 3786-3799 (2007).

Gavard J, Gutkind JS. VEGF controls endothelial-cell permeability by promoting the beta-arrestin-dependent endocytosis of VE-cadherin. Nature cell biology 2006; 8(11):1223-34.

Geng, et al., "Slit, a Neuronal Guidance Molecule, Mediates Angiogenesis," FASEB Journal, (Mar. 7, 2001) vol. 15, No. 4, pp. A8.

Gerhardt H, Golding M, Fruttiger M, et al. VEGF guides angiogenic sprouting utilizing endothelial tip cell filopodia. The Journal of cell biology 2003; 161(6):1163-77.

Goldfinger, L.E., Han, J., Kiosses, W.B., Howe, A.K., and Ginsberg, M.H. (2003). Spatial restriction of alpha4 integrin phosphorylation regulates lamellipodial stability and alpha4beta1-dependent cell migration. J. Cell Biol. 162, 731-741.

Gomes, R.N., et al., 2006. Increased susceptibility to septic and endotoxic shock in monocyte chemoattractant protein 1/cc chemokine ligand 2-deficient mice correlates with reduced interleukin 10 and enhanced macrophage migration inhibitory factor production. Shock 26:457-463.

Gomez-Foix, Anna M., et al., "Adenovirus-mediated Transfer of the Muscle Glycogen Phosphorylase Gene into Hepatocytes Confers Altered Regulation of Glycogen Metabolism," The Journal of Biological Chemistry, vol. 267, No. 36, Issue of Dec. 15, pp. 25129-25134, 1992.

Greenaway, P.J., et al., "Human cytomegalovirus DNA: BamHl, EcoRl and Pstl restriction endonuclease cleavage maps," Gene, 18 (1982) 355-360.

Gupta, N., et al., 2007. Intrapulmonary delivery of bone marrow-derived mesenchymal stem cells improves survival and attenuates endotoxin-induced acute lung injury in mice. J Immunol 179:1855-1863.

Guthrie, S., "Axon Guidance: Robos Make the Rules," 2001 Curr. Biol 17:11(8) R300-3.

Guzman, Raul J., et al., "Efficient Gene Transfer Into Myocardium by Direct Injection of Adenovirus Vectors," Circulation Research, vol. 73, No. 6, Dec. 1993, pp. 1202-1206.

Hafner, et al., "Inhibition of Cytohesins by SecinH3 leads to hepatic insulin resistance," Nature. 2006, vol. 444(7121), p. 941-944.

Hafner, et al., "Displacement of Protein-Bound Aptamers with Small Molecules Screened by Fluorescence Polarization," Nat Protoc (2008), 3, 579-587.

Hagel, M., George, E.L., Kim, A., Tamimi, R., Opitz, S.L., Turner, C.E., Imamoto, A., and Thomas, S.M. (2002). The adaptor protein paxillin is essential for normal development in the mouse and is a critical transducer of fibronectin signaling. Mol. Cell. Biol. 22, 901-915.

Haj-Ahmad, Yousef, et al., "Development of a Helper-Independent Human Adenovirus Vector and Its Use in the Transfer of the Herpes Simplex Virus Thymidine Kinase Gene," Journal of Virology, Jan. 1986, p. 267-274.

Hammond, Scott M., et al., "An RNA-directed nuclease mediates post-transcriptional gene silencing in Drosophila cells," Nature, vol. 404, Mar. 16, 2000, pp. 293-296.

Han, J., Liu, S., Rose, D.M., Schlaepfer, D.D., McDonald, H., and Ginsberg, M.H. (2001). Phosphorylation of the integrin alpha 4 cytoplasmic domain regulates paxillin binding. J. Biol. Chem. 276, 40903-40909.

Handbook of Monoclonal Antibodies, pp. 303-435, 1985.

Hann, Michael M., et al., "On the Double Bond Isostere of the Peptide Bond: Preparation of an Enkephalin Analogue," J.C.S. Perkin I, 1982, pp. 307-314.

Hannon, Gregory J., et al., "RNA interference," Nature, vol. 418, Jul. 11, 2002, pp. 244-251.

Hohenester, E., Hussain, S., and Howitt, J.A. (2006). Interaction of the guidance molecule Slit with cellular receptors. Biochem. Soc. Trans. 34, 418-421.

Holladay, Mark W., et al., "Synthesis of Hydroxyethylene and Ketomethylene Dipeptide Isosteres," Tetrahedron Letters. vol. 24, No. 41, pp. 4401-4404, 1983.

Hong K, Hinck L, Nishiyama M, Poo MM, Tessier-Lavigne M, Stein E. A ligand-gated association between cytoplasmic domains of UNC5 and DCC family receptors converts netrin-induced growth cone attraction to repulsion. Cell 1999; 97(7):927-41.

Howitt JA, Clout NJ, Hohenester E. Binding site for Robo receptors revealed by dissection of the leucine-rich repeat region of Slit. Embo J 2004; 23(22):4406-12.

Hruby, Victor J., "Conformational Restrictions of Biologically Active Peptides Via Amino Acid Side Chain Groups," Life Sciences, vol. 31, pp. 189-199, 1982.

Hu, H., Li, M., Labrador, J.P., McEwen, J., Lai, E.C., Goodman, C.S., and Bashaw, G.J. (2005). Cross GTPase-activating protein (CrossGAP)/Vilse links the Roundabout receptor to Rac to regulate midline repulsion. Proc. Natl. Acad. Sci. U.S.A. 102, 4613-4618.

Hubbard, W.J., M. Choudhry, M.G. Schwacha, J.D. Kerby, L.W. Rue, 3rd, K.I. Bland, and I.H. Chaudry. 2005. Cecal ligation and puncture. Shock 24 Suppl 1:52-57.

Hudson, Derek, et al., "Methionine Enkephalin and Isosteric Analogues," J. Peptide Protein Res. 14, 1979, 177-185.

Hughes, Brenda J., et al., "Monoclonal Antibody Targeting of Liposomes to Mouse Lung in Vivo," Cancer Research 49, 6214-6220, Nov. 15, 1989.

Huminiecki, L., and Bicknell, R. (2000). In silico cloning of novel endothelialspecific genes. Genome Res. 10, 1796-1806.

Huminiecki, L., Gorn, M., Suchting, S., Poulsom, R., and Bicknell, R. (2002). Magic roundabout is a new member of the roundabout receptor family that is endothelial specific and expressed at sites of active angiogenesis. Genomics 79, 547-552.

Ibba, Michael, "Strategies for in vitro and in vivo translation with non-natural amino acids," Biotechnology and Genetic Engineering Reviews, vol. 13, Dec. 1995, pp. 197-216.

Ibba, Michael, et al., "Towards Engineering Proteins by Site-Directed Incorporation In Vivo of Non-Natural Amino Acids," Bio/Technology, vol. 12,, Jul. 1994, pp. 676-682.

Ikeda, S., et al., "Novel role of ARF6 in vascular endothelial growth factor-induced signaling and angiogenesis." Circulation research 96, 467-475 (2005).

Itakura, Keiichi, et al., "Synthesis and Use of Synthetic Oligonucleotides," Ann. Rev. Biochem. 1984, 53:323-56.

Jaeger, John A., et al., "Predicting Optimal and Suboptimal Secondary Structure for RNA," Methods of Enzymology, vol. 183, pp. 281-306, 1990.

Jaeger, John A., et al., "Improved predictions of secondary structures for RNA," Proc. Natl. Acad. Sci. USA, vol. 86, pp. 7706-7710, Oct. 1989.

Jain RK. Molecular regulation of vessel maturation. Nat Med 2003; 9(6):685-93.

Janik, J.E., et al., "Efficient Synthesis of Adeno-Associated Virus Structural Proteins Requires Both Adenovirus DNA Binding Protein and VA I RNA," Virology 168, 320-329 (1988).

Jennings-White, Clive, et al., "Synthesis of Ketomethylene Analogs of Dipeptides," Tetrahedron Letters, vol. 23, No. 25, pp. 2533-2534, 1982.

Jin, S.W., Beis, D., Mitchell, T., Chen, J.N., and Stainier, D.Y. (2005). Cellular and molecular analyses of vascular tube and lumen formation in zebrafish. Development 132, 5199-5209.

Johnson, et al., "Mutations in the Activin Receptor-Like Kinase 1 Gene Hereditary Hemorrhagic Telangiectasia Type 2," 1996, Nat. Genet. 13(2) 189-95.

Jones CA, Li DY. Common cues regulate neural and vascular patterning. Curr Opin Genet Dev. Aug. 2007; 17(4):332-6.

Jones, Christopher A., "Robo4 stabilizes the vascular network by inhibiting pathologic angiogenesis and endothelial hyperpermeability," Nature Medicine, vol. 14, No. 4, Apr. 2008, pp. 448-453.

Jones, et al. (2009), Slit2-Robo4 Signaling Promotes Vascular Stability by Blocking Arf6 Activity, Nature Cell Biology, 11, 1325-1331 (2009).

Kabanov, Alenxander V., et al., "A new class of antivirals: antisense oligonucleotides combined with a hydrophobic substituent effectively inhibit influenza virus reproduction and synthesis of virus-specific proteins in MDCK cells," FEBS Letters, vol. 259, No. 2, 327-330, 1990.

Kanellis, J., Garcia, G.E., Li, P., Parra, G., Wilson, C.B., Rao, Y., Han, S., Smith, C.W., Johnson, R.J., Wu, J.Y., and Feng, L. (2004). Modulation of inflammation by slit protein in vivo in experimental crescentic glomerulonephritis. Am. J. Pathol. 165, 341-352.

Katoh Y, Katoh M. Comparative genomics on SLIT1, SLIT2, and SLIT3 orthologs. Oncol Rep 2005; 14(5):1351-5.

Kaur, S., Castellone, M.D., Bedell, V.M., Konar, M., Gutkind, J.S., and Ramchandran, R. (2006). Robo4 signaling in endothelial cells implies attraction guidance mechanisms. J. Biol. Chem. 281, 11347-11356.

Kidd, T., Bland, K.S., and Goodman, C.S. (1999). Slit is the midline repellent for the robo receptor in *Drosophila*. Cell 96, 785-794.

Kidd, T., Brose, K., Mitchell, K.J., Fetter, R.D., Tessier-Lavigne, M., Goodman, C.S., and Tear, G. (1998). Roundabout controls axon crossing of the CNS midline and defines a novel subfamily of evolutionarily conserved guidance receptors. Cell 92, 205-215.

Kimmel, C.B., Ballard, W.W., Kimmel, S.R., Ullmann, B., and Schilling, T.F. (1995). Stages of embryonic development of the zebrafish. Dev. Dyn. 203, 253-310.

Kirshenbaum, Lorrie A., et al., "Highly Efficient Gene Transfer into Adult Ventricular Myocytes by Recombinant Adenovirus," J. Clin. Invest., vol. 92, Jul. 1993, 381-387.

Klein, Robert J., et al., "Complement Factor H Polymorphism in Age-Related Macular Degneration," Science, vol. 308, Apr. 15, 2005, pp. 385-389.

Kobasa, D., et al., 2007; Aberrant innate immune response in lethal infection of macaques with the 1918 influenza virus. Nature 445:319-323.

Krishnakumar, et al., "H NMR Studies of Interleukin 8 Analogs: Characterization of the Domains Essential for Function," Biochemistry 1994, 33, 6623-6630.

Kunkel, Thomas A., et al., "Rapid and Efficient Site-Specific Mutagenesis without Phenotypic Selection," Methods in Enzymology, vol. 154, 367-382, 1987.

Laimins, L.A., et al., "Osmotic control of *kdp* operon expression in *Escherichia coli*," Proc. Natl. Acad. Sci. USA, vol. 78, No. 1, pp. 464-468, 1981.

Lantry LE. Ranibizumab, a mAb against VEGF-A for the potential treatment of age-related macular degeneration and other ocular complications. Curr Opin Mol Ther. 2007 9(6):592-602.

Lauffenburger, D.A., and Horwitz, A.F. (1996). Cell migration: a physically integrated molecular process. Cell 84, 359-369.

Lawson, N.D., and Weinstein, B.M. (2002). In vivo imaging of embryonic vascular development using transgenic zebrafish. Dev. Biol. 248, 307-318.

Le Gal La Salle, G., et al., "An Adenovirus Vector for Gene Transfer into Neurons and Glia in the Brain," Science, vol. 259, Feb. 12, 1993, 988-990.

Letsinger, Robert L., "Cholesteryl-conjugated oligonucleotides: Synthesis, properties, and activity as inhibitors of replication of human immunodeficiency virus in cell culture," Proc. Natl. Acad. Sci. USA, vol. 86, pp. 6553-6556. Sep. 1989.

Lewis, et al., "Efficient Delivery of SiRNA for Inhibition of Gene Expression in Postnatal Mice," Nature Genetics, 32:107 108 (2002).

Li, H.S., Chen, J.H., Wu, W., Fagaly, T., Zhou, L., Yuan, W., Dupuis, S., Jiang, Z.H., Nash, W., Gick, C., Ornitz, D.M., Wu, J.Y., and Rao, Y. (1999). Vertebrate slit, a secreted ligand for the transmembrane protein roundabout, is a repellent for olfactory bulb axons. Cell 19, 807-818.

Li Q, Olsen BR. Increased angiogenic response in aortic explants of collagen XVIII/endostatin-null mice. Am J Pathol 2004; 165(2):415-24.

Lim YC, Garcia-Cardena G, Allport JR, et al. Heterogeneity of endothelial cells from different organ sites in T-cell subset recruitment. Am J Pathol 2003; 162(5):1591-601.

Lima e Silva R, Saishin Y, Saishin Y, et al. Suppression and regression of choroidal neovascularization by polyamine analogues. Investigative ophthalmology & visual science 2005; 46(9):3323-30.

Little M, Rumballe B, Georgas K, Yamada T, Teasdale RD. Conserved modularity and potential for alternate splicing in mouse and human Slit genes. Int J Dev Biol 2002; 46(4):385-91.

Litzinger, David C., et al., "Biodistribution and immunotargetability of ganglioside-stabilized dioleoylphosphatidylethanolamine liposomes," Biochimica et Biophysica Acta, 1104 (1992) 179-187.

Liu, S., and Ginsberg, M.H. (2000). Paxillin binding to a conserved sequence motif in the alpha 4 integrin cytoplasmic domain. J. Biol. Chem. 275, 22736-22742.

Liu, S., Kiosses, W.B., Rose, D.M., Slepak, M., Salgia, R., Griffin, J.D., Turner, C.E., Schwartz, M.A., and Ginsberg, M.H. (2002). A fragment of paxillin binds the alpha 4 integrin cytoplasmic domain (tail) and selectively inhibits alpha 4-mediated cell migration. J. Biol. Chem. 277, 20887-20894.

Liu, S., Thomas, S.M., Woodside, D.G., Rose, D.M., Kiosses, W.B., Pfaff, M., and Ginsberg, M.H. (1999). Binding of paxillin to alpha4 integrins modifies integrin-dependent biological responses. Nature 402, 676-681.

Long, H., et al. Conserved roles for Slit and Robo proteins in midline commissural axon guidance. Neuron 42, 213-223 (2004).

Lundstrom, A., Gallio, M., Englund, C., Steneberg, P., Hemphala, J., Aspenstrom, P., Keleman, K., Falileeva, L., Dickson, B.J., and Samakovlis, C. (2004). Vilse, a conserved Rac/Cdc42 GAP mediating Robo repulsion in tracheal cells and axons. Genes Dev. 18, 2161-2171.

Lusky, Monka, et al., "Bovine Papilloma Virus Contains an Activator of Gene Expression at the Distal End of the Early Transcription Unit," Molecular and Cellular Biology, Jun. 1983, p. 1108-1122.

Ma, et al., "Dual Branch-Promoting and Branch-Repelling Actions of Slit/Robo Signaling on Peripheral and Central Branches of Developing Sensory Axons." J. Neurosci. 2007, vol. 27(25), p. 6843-6851.

Mahabeleshwar, et al., "Mechanisms of integrin-vascular endothelial growth factor receptor cross-activation in angiogenesis." Circulation research 101, 570-580 (2007).

Maniatis, T., et al., Molecular Cloning, A Laboratory Manual, Chapter 5, 1989.

Manoharan, Muthiah, et al., "Introduction of a Lipophilic Thioether Tether in the Minor Groove of Nucleic Acids for Antisense Applications," Bioorganic & Medicinal Chemistry Letters, vol. 3, No. 12, pp. 2765-2770, 1993.

Manoharan, Muthiah, et al., "Cholic Acid-Oligonucleotide Conjugates for Antisense Applications," Bioorganic & Medicinal Chemistry Letters, vol. 4, No. 8, pp. 1053-1060, 1994.

Manoharan, M., et al., "Chemical Modifications to Improve Uptake and Bioavailability of Antisense Oligonucleotides," Annals New York Academy of Sciences, pp. 306-309, 1992.

Manoharan, Muthiah, et al., "Oligonucleotide Conjugates: Alteration of the Pharmacokinetic Properties of Antisense Agents," Nucleosides & Necleotides, 14(3-5), 969-973 (1995).

Manoharan, Muthiah, et al., "Lipidic Nucleic Acids," Tetrahedron Letters, vol. 36, No. 21, pp. 3651-3654, 1995.

Marillat, V., Cases, O., Nguyen-Ba-Charvet, K.T., Tessier-Lavigne, M., Sotelo, C., and Chedotal, A. (2002). Spatiotemporal expression patterns of slit and robo genes in the rat brain. J. Comp. Neurol. 442, 130-155.

Martinez, Javier, et al., "Single-Stranded Antisense siRNAs Guide Target RNA Cleavage in RNAi," Cell, vol. 110, 563-574, Sep. 6, 2002.

Massie, Bernard, et al., "Construction of a Helper-Free Recombinant Adenovirus That Expresses Polyomavirus Large T Antigen," Molecular and Cellular Biology, Aug. 1986, p. 2872-2883.

Matute-Bello, G., C.W. Frevert, and T.R. Martin, 2008. "Animal Models of Acute Lung Injury," Am J Physiol Lung Cell Mol Physiol 295: L379-399.

Matthay MA, Zimmerman GA. (2005). Acute lung injury and the acute respiratory distress syndrome: four decades of inquiry into pathogenesis and rational management. Am J Respir Cell Mol Biol.; 33(4):319-27.

McCaffery, et al., Nature, 418:38-39 (2002).

Metzger, R.J., et al., 2008. The branching programme of mouse lung development. Nature 453:745-750.

Mishra, Rakesh Kumar, et al., "Improved leishmanicidal effect of phosphorotioate antisense oligonucleotides by LDI-mediated delivery," Biochimica et Biophysica Acta 1264 (1995) 229-237.

Moitra, J., S. Sammani, and J.G. Garcia. 2007. Re-evaluation of Evans Blue dye as a marker of albumin clearance in murine models of acute lung injury. Transl Res 150:253-265.

Morley, John, "K+ channel openers and suppression of airway hyper-reactivity," TIPS—Dec. 1994, vol. 15, pp. 463-468.

Morsey, Manai A., et al., "Efficient Adenoviral-mediated Ornithine Transcarbamylase Expression in Deficient Mouse and Human Hepatocytes," J. Clin. Invest., vol. 92, Sep. 1993, 1580-1586.

Moullier, Philippe, et al., "Correction of lysosomal storage in the liver and spleen of MPS VII mice by implantation of genetically modified skin fibroblasts," Nature Genetics, vol. 4, Jun. 1993, pp. 154-159.

Mouw, Matthew B., et al., "Adeno-Associated Virus RNAs Appear in a Temporal Order and Their Splicing is Stimulated during Coinfection with Adenovirus," Journal of Virology, Nov. 2000, p. 9878-9888.

Mulligan, Richard C., "The Basic Science of Gene Therapy," Science, vol. 260, May 14, 1993, 926-932.

Mulligan, R.C., et al., "Expression of a Bacterial Gene in Mammalian Cells," Science, vol. 209, Sep. 19, 1980, 1422-1427.

Nakamura, K., Yano, H., Uchida, H., Hashimoto, S., Schaefer, E., and Sabe, H. (2000). Tyrosine phosphorylation of paxillin alpha is involved in temporospatial regulation of paxillin-containing focal adhesion formation and F-actin organization in motile cells. J. Biol. Chem. 275, 27155-27164.

Napoli, Caroly, et al., "Introduction of a Chimeric Chalcone Cynthase Gene into Petunia Results in Reversible Co-Suppression of Homologous Genes in trans," The Plant Cell, vol. 2, 279-289, Apr. 1990.

Narang, S.A., et al., "Chemical Synthesis of Deoxyoligonucleotides by the Modified Triester Method," Methods in Enzymology, vol. 65, pp. 610-620, 1980.

Navankasattusas, S., K.J. Whitehead, A. Suli, L.K. Sorensen, A.H. Lim, J. Zhao, K.R. Thomas, C.B. Chien, and D.Y. Li. The netrin receptor, Unc5b, promotes angiogenesis in specific vascular beds. *Development* (in press), 2008.

Needleman, Saul B., et al., "A General Method Applicable to the Search for Similarities in the Amino Acid Sequence of Two Proteins," J. Mol. Biol. (1970) 48, 443-453.

Ngo, et al. (1994). "Computational Complexity, Protein Structure Prediction, and the Levinthal Paradox," In Merz and Le Grand (Eds.) The Protein Folding Problem and Tertiary Structure prediction. Berkhauser: Boston, pp. 491-495.

Nguyen, et al., "Diversity and Specificity of Actions of Slit2 Proteolytic Fragments in Axon Guidance," J Neurosci. Jun. 15, 2001;21(12):4281-9.

Nielsen, Peter E., et al., "Peptide Nucleic Acid (PNA), A DNA Mimic with a Peptide Backbone," Bioconjugate Chem. 1994, 5, 307.

Nielsen, Peter E., et al., "Sequence-Selective Recognition of DNA by Strand Displacement with a Thymine-Substituted Polyamide," Science, New Series, vol. 254, No. 5037 (Dec. 6, 1991), pp. 1497-1500.

Nishiya, N., Kiosses, W.B., Han, J., and Ginsberg, M.H. (2005). An alpha4 integrin-paxillin-Arf-GAP complex restricts Rac activation to the leading edge of migrating cells. Nat. Cell Biol. 7, 343-352.

Nobes, C.D., and Hall, A. (1995). Rho, rac, and cdc42 GTPases regulate the assembly of multimolecular focal complexes associated with actin stress fibers, lamellipodia, and filopodia. Cell 81, 53-62.

Nobes, C.D. & Hall, A. Rho GTPases control polarity, protrusion, and adhesion during cell movement. The Journal of cell biology 144, 1235-1244 (1999).

Nykanen, Antti, et al., "ATP Requirements and Small Interfering RNA Structure in the RNA Interference Pathway," Cell, vol. 107, 309-321, Nov. 2, 2001.

Oberhauser, Berndt, et al., "Effective incorporation of 2'-O-methyl-oligoribonucleotides into liposomes and enhanced cell association through modification with thiocholesterol," Nucleic Acids Research, vol. 20, No. 3, 1992, 533-538.

Ojima T, Takagi H, Suzuma K, Oh H, Suzuma I, Ohashi H, Watanabe D, Suganami E, Murakami T, Kurimoto M, Honda Y, Yoshimura N. EphrinA1 inhibits vascular endothelial growth factor-induced intracellular signaling and suppresses retinal neovascularization and blood-retinal barrier breakdown. Am J Pathol. Jan. 2006; 168(1):331-9.

Okada, et al., "A Three-Kilobase Fragmetn of the Human Robo4 Promoter Directs Cell Type-Specificexpression in Endothelium," Circ. Res. Jun. 22, 2007; 100(12):1712-22.

Osborne, Timothy F., et al., "Transcription Control Region Within the Protein-Coding Portion of Adenovirus E1A Genes," Molecular and Cellular Biology, Jul. 1984, p. 1293-1305.

Ozaki H, Seo MS, Ozaki K, et al. Blockade of vascular endothelial cell growth factor receptor signaling is sufficient to completely prevent retinal neovascularization. Am J Pathol 2000; 156(2):697-707.

Park KW, Crouse D, Lee M, et al. The axonal attractant Netrin-1 is an angiogenic factor. Proc Natl Acad Sci U S A 2004; 101(46):16210-5.

Park, K.W., Morrison, C.M., Sorensen, L.K., Jones, C.A., Rao, Y., Chien, C.B., Wu, J.Y., Urness, L.D., and Li, D.Y. (2003). Robo4 is a vascular-specific receptor that inhibits endothelial migration. Dev. Biol. 261, 251-267.

Patel, et al., "Slit Proteins Are Not Dominant Chemorepellents for Olfactory Tract and Spinal Motor Axons," Development Company of Biologists, Dec. 1, 2001 vol. 128(24) pp. 2031-5037.

Pearson, William R., et al., "Improved tools for biological sequence comparison," Proc. Natl. Acad. Sci. USA, vol. 85, pp. 2444-2448, Apr. 1988.

Pietersz, Geoffrey A., et al., "Antibody Conjugates for the Treatment of Cancer," Immunological Reviews 1997, No. 129, pp. 57-80.

Plummer, Nicholas W., et al., "Loss of p53 Sensitizes Mice with a Mutation in Ccm1 (KRIT1) to Development of Cerebral Vascular Malformations," American Journal of Pathology, vol. 165, No. 5 Nov. 2004, pp. 1509-1518.

Potter, M.D., S. Barbero, and D.A. Cheresh. 2005. "Tyrosine Phosphorylation of VE-Cadherin Prevents Binding of p120-and Beta-Catenin and Maintains the Cellular Mesenchymal State." J Biol Chem 280:31906-31912.

Ragot, T., et al., "Replication-defective recombinant adenovirus expressing the Epstein-Barr virus (EBV) envelope glycoprotein gp340/220 induces protective immunity against EBV-induced lymphomas in the cottontop tamarin," Journal of General Virology (1997), 74, 501-507.

Rajarathnam K, et al., Biochemistry 33:6623-30 (1994).

Ram, Zvi, et al., "In Situ Retroviral-mediated Gene Transfer for the Treatment of Brain Tumors in Rats," Cancer Research 53, 83-88, Jan. 1, 1993.

Raper JA. Semaphorins and their receptors in vertebrates and invertebrates. Curr Opin Neurobiol 2000; 10(1):88-94.

Reutershan J, Morris MA, Burcin TL, Smith DF, Chang D, Saprito MS, Ley K. Critical role of endothelial CXCR2 in LPS-induced neutrophil migration into the lung. J Clin Invest. 2006 116(3):695-702.

Rhee, et al., Cables Links Robo-Bound Abl Kinase to N-Cadherin-Bound B-Catenin to Mediate Slit-Induced Modulation of Adhesion and Transcription. Nat Cell Biol. 2007, vol. 9(8), p. 883-892.

Rich, Devra P., et al., "Development and Analysis of Recombinant Adenoviruses for Gene Therapy of Cystic Fibrosis," Human Gene Therapy 4:461-476 (1993).

Ridley, A.J., Schwartz, M.A., Burridge, K., Firtel, R.A., Ginsberg, M.H., Borisy, G., Parsons, J.T., and Horwitz, A.R. (2003). Cell migration: integrating signals from front to back. Science. 302, 1704-1709.

Rizo, Josep, et al., "Constrained Peptides: Models of Bioactive Peptides and Protein Substructures," Annu. Rev. Biochem. 1992, 61:387-418.

Roessler, Blake J., et al, "Adenoviral-mediated Gene Transfer to Rabbit Synovium in Vivo," Rapid Publication, vol. 92, Aug. 1993, 1085-1092.

Roffler, S.R., et al., "Anti-neoplastic glucuronide prodrug treatment of human tumor cells targeted with a monoclonal antibody-enzyme conjugate," Biochemical Pharmacology, vol. 42, No. 10, Oct. 24, 1991, pp. 2062-2065.

Rosenfeld PJ, Brown DM, Heier JS, et al. Ranibizumab for neovascular age-related macular degeneration. N Engl J Med 2006; 355(14):1419-31.

Ruhrberg C, Gerhardt H, Golding M, et al. Spatially restricted patterning cues provided by heparin-binding VEGF-A control blood vessel branching morphogenesis. Genes & development 2002; 16(20):2684-98.

Russo, R., et al. Role of the chemokine receptor CXCR2 in bleomycin-induced pulmonary inflammation and fibrosis. Am J Respir Cell Mol Biol (2008).

Saison-Behmoaras, T., et al., "Short modified antisense oligonucleotides directed against Ha-ras point mutation induce selective cleavage of the mRNA and inhibit T24 cells proliferation," The EMBO Journal, vol. 10, No. 5, pp. 1111-1118, 1991.

Salgia, R., Li, J.L., Ewaniuk, D.S., Wang, Y.B., Sattler, M., Chen, W.C., Richards, W., Pisick, E., Shapiro, G.I., Rollins, B.J., Chen, L.B., Griffin, J.D., and Sugarbaker, D.J. (1999). Expression of the focal adhesion protein paxillin in lung cancer and its relation to cell motility. Oncogene. 18, 67-77.

Sambrook, J., et al., "Molecular Cloning—A Laboratory Manual," 1989.

Sanlioglu, Salih, et al., "Endocytosis and Nuclear Trafficking of Adeno-Associated Virus Type 2 Are Controlled by Rac1 and Phosphatidylinositol-3 Kinase Activation," Journal of Virology, Oct. 2000, p. 9184-9196.

Santy, L.C., et al., "Activation of ARF6 by Arno Stimulates Epithelial Cell Migration Through Downstream Activation of Both Rac1 and Phospholipase D," J. Cell. Biol., 2001, vol. 154, pp. 599-610.

Scaringe, et al., "Chemical Synthesis of Biologically Active Oligoribonucleotides Using B-Cyanoethyl Protected Ribonucleoside Phosphoramidites," Nucleic Acids Res., 18:5433 5441 (1990).

Schnolzer, Martina, et al., "Contructing Proteins by Dovetailing Unprotected Synthetic Peptides: Backbone-Engineered HIV Protease," Science, vol. 256, Apr. 10, 1992, pp. 221-225.

Seeger, M., Tear, G., Ferres-Marco, D., and Goodman, C.S. (1993). Mutations affecting growth cone guidance in Drosophila: genes necessary for guidance toward or away from the midline. Neuron 10, 409-426.

Senger, et al., (1997). "Angiogenesis promoted by vascular endothelial growth factor: regulation through alpha1beta1 and alpha2beta1 integrins," Proc. Natl. Acad. Sci. U.S.A. 94, 13612-13617.

Senter, Peter D., et al, "Generation of 5-Fluorouracil from 5-Fluorcytosine by Monoclonal Antibody-Cytosine Deaminase Conjugates," Bioconjugate Chem. 1991, 2, 447-451.

Seth, Pankaj, et al., "Magic Roundabout, a Tumor Endothelial Marker: Expression and Signaling," Biochemical and Biophysical Research Communications, vol. 332, No. 2m Jul. 1, 2005, pp. 533-541.

Seth, Prem, et al., "Role of a Low-pH Environment in Adenovirus Enhancement of the Toxicity of a Pseudomonas Exotoxin-Epidermal Growth Factor Conjugate," Journal of Virology, Sep. 1984, pp. 650-655.

Seth, Prem, et al., "Evidence that the Penton Base of Adenovirus Is Involved in Potentiation of Toxicity of Pseudomonas Exotoxin Conjugated to Epidermal Growth Factor," Molecular and Cellular Biology, Aug. 1984, p. 1528-1533.

Senger, D.R., Claffey, K.P., Benes, J.E., Perruzzi, C.A., Sergiou, A.P., and Detmar, M. (1997). Angiogenesis promoted by vascular endothelial growth factor: regulation through alpha1beta1 and alpha2beta1 integrins. Proc. Natl. Acad. Sci. U.S.A. 94, 13612-13617.

Senter, Peter D., et al, "Generation of Cytotoxic Agents by Targeted Enzymes," Bioconjugate Chem., 1993, 4, 3-9.

Seth, P., Lin, Y., Hanai, J., Shivalingappa, V., Duyao, M.P., and Sukhatme, V.P. Magic roundabout, a tumor endothelial marker: expression and signaling. Biochem. Biophys. Res. Commun. 332, 533-541, 2005.

Sharp, Phillip A., et al., "RNA interference—2001," Genes & Development 15:485-490.

Shea, Regan G., et al., "Synthesis, hybridization properties and antiviral activity of lipid-oligodeoxynucleotide conjugates," Nucleic Acids Research, vol. 18, No. 13, 3777-3783, 1990.

Sheldon, et al. (2008) "Active Involvement of Robo1 and Robo4 in Filopodia Formation and Endothelial Cell Motility Mediated Via WASP and Other Activ Nucleation-Promoting Factors," The FASEB Journal, vol. 2, pp. 513-522.

Shields RL, Namenuk AK, Hong K, et al. High resolution mapping of the binding site on human IgG1 for Fc gamma RI, Fc gamma RII, Fc gamma RIII, and FcRn and design of IgG1 variants with improved binding to the Fc gamma R. J Biol Chem 2001; 276(9):6591-604.

Shima, et al., "Vascular Developmental Biology: Getting Nervous," Curr Opin Genet Dev. Oct. 2000;10(5):536-42.

Sidwell, R.W., et al., 2005. In vitro and in vivo influenza virus-inhibitory effects of viramidine. Antiviral Res 68:10-17.

Smith LE, Wesolowski E, McLellan A, et al. Oxygen-induced retinopathy in the mouse. Investigative ophthalmology & visual science 1994; 35(1):101-11.

Smith, Thomas W., et al, "Cardiac Glycoside-Specific Antibodies in the Treatment of Digitalis Intoxication," Antibodies in Human Diagnosis and Therapy, Raven Press, New York 1977, pp. 365-389.

Smith, Temple F., et al., "Comparison of Biosequences," Advances in Applied Mathematics 2, 482-489 (1981).

Soga, N., Connolly, J.O., Chellaiah, M., Kawamura, J., and Hruska, K.A. (2001). Rac regulates vascular endothelial growth factor stimulated motility. Cell Commun. Adhes. 8, 1-13.

Soga, N., Namba, N., McAllister, S., Cornelius, L., Teitelbaum, S.L., Dowdy, S.F., Kawamura, J., and Hruska, K.A. (2001). Rho family GTPases regulate VEGFstimulated endothelial cell motility. Exp. Cell Res. 269, 73-87.

Soldi, R., Mitola, S., Strasly, M., Defilippi, P., Tarone, G., and Bussolino, F. (1999). Role of alphavbeta3 integrin in the activation of vascular endothelial growth factor receptor-2. EMBO J. 18, 882-892.

Song, et al., "RNA Interference Targeting Fas Protects Mice from Fulminant Hepatitis," Nature Medicine, 9:347 351 (2003).

Song, et al., "The Cell Biology of Neuronal Navigation," 2001 Nat Cell Biol (3) E81-8.

Southern, P.J., et al., "Transformation of Mammalian Cells to Antibiotic Resistance with a Bacterial Gene Under Control of the SV40 Early Region Promoter," Journal of Molecular and Applied Genetics 1: 327-341, 1982.

Spatola, A.F., "Chemistry and biochemistry of amino acids, peptides and proteins," vol. 7, 1983, pp. 267-357.

Spatola, Arno F., et al., "Structure-Activity Relationships of Enkephalins Containing Serially Replaced Thiomethylene Amide Bond Surrogates," Life Sciences, vol. 38, Apr. 1986, pp. 1243-1249.

Stein E, Tessier-Lavigne M. Hierarchical organization of guidance receptors: silencing of netrin attraction by slit through a Robo/DCC receptor complex. Science 2001; 291(5510):1928-38.

Suchting, S., Heal, P., Tahtis, K., Stewart, L.M., and Bicknell, R. (2005). Soluble Robo4 receptor inhibits in vivo angiogenesis and endothelial cell migration. FASEB J. 19, 121-138.

Sugden, Bill, et al., "A Vector That Replicates as a Plasmid and Can Be Efficiency Selected in B-Lymphoblasts Transformed by Epstein-Barr Virus," Molecular and Cellular Biology, Feb. 1985, p. 410-413.

Sullivan, et al., "New Molecular Pathways in Angiogenesis," Br. J. Cancer, Jul. 21, 2003, vol. 89, No. 2, pp. 228-231.

Sun, Tian-Qiang, et al., "Human Artificial Episomal Chromosomes for Cloning Large DNA Fragments in Human Cells," Nature Genetics, vol. 8, 1994, 33-41.

Svensson, Ulla, "Role of Vesicles During Adenovirus 2 Internatlization into HeLa Cells," Journal of Virology, Aug. 1985, p. 442-449.

Svinarchuk, FP, et al., "Inhibition of HIV Proliferation in MT-4 Cells by Antisense Oligonucleotide Conjugated to Lipophilic Groups," Biochimie (1993) 75, 49-54.

Tager, A., et al. The lysophosphatidic acid receptor LPA1 links pulmonary fibrosis to lung injury by mediating fibroblast recruitment and vascular leak. Nat Med 14, 45-54 (2008).

Thorson, Jon S., et al., "A Biosynthetic Approach for the Incorporation of Unnatural Amino Acids into Proteins," Methods in Molecular Biology, vol. 77, pp. 43-73, 1998.

Turner, C.E. (2000). Paxillin interactions. J. Cell Sci. 113, 139-140.

Turner, C.E., "Paxillin and focal adhesion signalling," Nature cell biology 2, E231-236 (2000).

Uemura A, Kusuhara S, Katsuta H, Nishikawa S. Angiogenesis in the mouse retina: a model system for experimental manipulation. Experimental cell research 2006; 312(5):676-83.

Ui-Tei, Kumiko, et al., "Sensitive Assay of RNA Interference in *Drosophila* and Chinese Hamster Cultured Cells Using Firefly Luciferase Gene as Target," FEBS Letters 479 (2000) 79-82.

Usman, et al., "The Automated Chemical Synthesis of Long Oligoribuncleotides Using 2'-O-Silylated Ribonucleosude 3'-O-Phosphoramidites on a Controlled-Pore Glass Support, Synthesis of a 43-Nucleotide Sequence Similar to the 3'-Half Molecule of an *Escherichia coli* Formylmethionine tRNA" J. Am. Chem. Soc., 109:7845 7854 (1987).

Urness LD, Li DY. Wiring the vascular circuitry: from growth factors to guidance cues. Curr Top Dev Biol 2004; 62:87-126.

Urness, et al., Arteriousvenous Malformations in Mice Lacking Activin Receptor-Like Kinase-1, 2000, Nature Genetics 26:328-331.

Varga, Mikael J., et al., "Infectious Entry Pathway of Adenovirus Type 2," Journal of Virology, Nov. 1991, p. 6061-6070.

Verma, Inder M., "Retroviral Vectors for Gene Transfer," Microbiology-1985, pp. 229-232.

Vestweber, D. 2008. "VE-cadherin: The Major Endothelial Adhesion Molecule Controlling Cellular Junctions and Blood Vessel Formation." Arterioscler Thromb Vasc Biol 28:223-232.

Walters, Robert W., et al., "Binding of Adeno-Associated Virus Type 5 to 2,3-Linked Sialic Acid is Required for Gene Transfer," The Journal of Biological Chemistry, vol. 276, No. 23, Jun. 8, pp. 20610-20616, 2001.

Wang, B., Xiao, Y., Ding, B.B., Zhang, N., Yuan, X., Gui, L., Qian, K.X., Duan, S., Chen, Z., Rao, Y., and Geng, J.G. (2003). Induction of tumor angiogenesis by Slit-Robo signaling and inhibition of cancer growth by blocking Robo activity. Cancer Cell 4, 19-29.

Wang, K.H. et al. Biochemical purification of a mammalian slit protein as a positive regulator of sensory axon elongation and branching. Cell 96, 771-784 (1999).

Wang, et al., "Targeting Slit-Roundabout Signaling Inhibits Tumor Angiogenesis in Chemical-Induced Squamous Cell Carcinogenesis," Cancer Sci. Mar. 2008; 99(3):510-7.

Ware, L.B. and M.A. Matthay. 2000. "The Acute Respiratory Distress Syndrome," N Engl J Med 342:1334-1349.

Watanabe D, Suzuma K, Matsui S, Kurimoto M, Kiryu J, Kita M, Suzuma I, Ohashi H, Ojima T, Murakami T, Kobayashi T, Masuda S, Nagao M, Yoshimura N, Takagi H. Erythropoietin as a retinal angiogenic factor in proliferative diabetic retinopathy. N Engl J Med. 2005 353(8):782-92.

Waterhouse, Peter M., et al., "Virus Resistance and Gene Silencing in Plants can be Induced by Simultaneous Expression of Sense and Antisense RNA," Proc. Natl. Acad. Sci. USA, vol. 95, pp. 13959-13964, Nov. 1998.

Weinstein, B.M. (2002). Plumbing the mysteries of vascular development using the zebrafish. Semin. Cell Dev. Biol. 13, 515-522.

Wells, J.A. (1990). "Additivity of Mutational Effects in Proteins." Biochemistry. 29(37):8509-8517.

Werdich XQ, McCollum GW, Rajaratnam VS, Penn JS. Variable oxygen and retinal VEGF levels: correlation with incidence and severity of pathology in a rat model of oxygen-induced retinopathy. Exp Eye Res 2004; 79(5):623-30.

West, K.A., Zhang, H., Brown, M.C., Nikolopoulos, S.N., Riedy, M.C., Horwitz, A.F., and Turner, C.E. (2001). The LD4 motif of paxillin regulates cell spreading and motility through an interaction with paxillin kinase linker (PKL). J. Cell Biol. 154, 161-176.

White, R., et al., "Sets of Linked Genetic Markers for Human Chromosomes," Annu. Rev. Genet. 1988 22:259-279.

Wickham, Thomas J., et al., "Integrins $avg_3$ and $avg_5$ Promote Adenovirus Internalization but Not Virus Attachment," Cell, vol. 73, 309-319, Apr. 22, 1993.

Wilkinson DG, Bhatt S, Herrmann BG. Expression pattern of the mouse T gene and its role in mesoderm formation. Nature 1990; 343(6259):657-9.

Wilson BD, Ii M, Park KW, et al. Netrins promote developmental and therapeutic angiogenesis. Science 2006; 313(5787):640-4.

Wojciak-Stothard, B., Potempa, S., Eichholtz, T., and Ridley, A.J. (2001). Rho and Rac but not Cdc42 regulate endothelial cell permeability. J. Cell Sci. 114, 1343-1355.

Wong, K., Ren, X.R., Huang, Y.Z., Xie, Y., Liu, G., Saito, H., Tang, H., Wen, L., Brady-Kalnay, S.M., Mei, L., Wu, J.Y., Xiong, W.C., and Rao, Y. (2001). Signal transduction in neuronal migration: roles of GTPase activating proteins and the small GTPase Cdc42 in the Slit-Robo pathway. Cell 107, 209-221.

Wu, J.Y., Feng, L., Park, H.T., Havlioglu, N., Wen, L., Tang, H., Bacon, K.B., Jiang, Z., Zhang, X., and Rao, Y. (2001). The neuronal repellent Slit inhibits leukocyte chemotaxis induced by chemotactic factors. Nature 410, 948-952.

Wu, W., Wong, K., Chen, J., Jiang, Z., Dupuis, S., Wu, J.Y., and Rao, Y. (1999). Directional guidance of neuronal migration in the olfactory system by the protein Slit. Nature 400, 331-336.

Xia, et al., "SiRNA-Mediated Gene Silencing in Vitro and in Vivo," Nature Biotech., 20:1006 1010 (2002).

Xiao, K., J. Garner, K.M. Buckley, P.A. Vincent, C.M. Chiasson, E. Dejana, V. Faundez, and A.P. Kowalczyk. 2005. "p120-Catenin Regulates Clathrin-Dependent Endocytosis of VE-cadherin." Mol Biol Cell 16:5141-5151.

Xu Q, Qaum T, Adamis AP. Sensitive blood-retinal barrier breakdown Quantitation using evans blue. Invest Ophthalmol Vis Sci. 2001; 42(3):789-94.

Yano, H., Mazaki, Y., Kurokawa, K., Hanks, S.K., Matsuda, M., and Sabe, H. (2004). Roles played by a subset of integrin signaling molecules in cadherinbased cell-cell adhesion. J. Cell Biol. 166, 283-295.

Yano, H., Uchida, H., Iwasaki, T., Mukai, M., Akedo, H., Nakamura, K., Hashimoto, S., and Sabe, H. (2000). Paxillin alpha and Crk-associated substrate exert opposing effects on cell migration and contact inhibition of growth through tyrosine phosphorylation. Proc. Natl. Acad. Sci. U.S.A. 97, 9076-9081.

Yu, T.W., Hao, J.C., Lim, W., Tessier-Lavigne, M., and Bargmann, C.I. (2002). Shared receptors in axon guidance: SAX-3/Robo signals via UNC-34/Enabled and a Netrin-independent UNC-40/DCC function. Nat. Neurosci. 5, 1147-1154.

Yuan, Yan, et al., "Targeted Cleavage of mRNA by Human RNase P," Proc. Natl. Acad. Sci., vol. 89, pp. 8006-8010, Sep. 1992.

Yuan, Yan, et al., "Substrate Recognition by Human RNase P: Identification of Small, Model Substrates for the Enzyme," The EMBO Journal, vol. 14, No. 1, pp. 159-168, 1995.

Yuan, W., Zhou, L., Chen, J.H., Wu, J.Y., Rao, Y., and Ornitz, D.M. (1999). The mouse SLIT family: secreted ligands for ROBO expressed in patterns that suggest a role in morphogenesis and axon guidance. Dev. Biol. 212, 290-306.

Yuminamochi, T., Yatomi, Y., Osada, M., Ohmori, T., Ishii, Y., Nakazawa, K., Hosogaya, S., and Ozaki, Y. (2003). Expression of the LIM proteins paxillin and Hic-5 in human tissues. J. Histochem. Cytochem. 51, 513-521.

Zabner, Joseph, et al., "Adenovirus-Mediated Gene Transfer Transiently Corrects the Chloride Transport Defect in Nasal Epithelia of Patients with Cystic Fibrosis," Cell, vol. 75, 207-216, Oct. 22, 1993.

Zabner, Joseph, et al., "Safety and Efficacy of Repetitive Adenovirus-Mediated Transfer of CFTR cDNA to Airway Epithelia of Primates and Cotton Rats," Nature Genetics, vol. 6, Jan. 1994, pp. 75-83.

Zallen, J.A., Yi, B.A., and Bargmann, C.I. (1998). The conserved immunoglobulin superfamily member SAX-3/Robo directs multiple aspects of axon guidance in *C. elegans*. Cell 92, 217-227.

Zamore & Aronin, "SiRNAs Knock Down Hepatitus," Nature Medicine, 9:266 267 (2003).

Zhang, Q. et al. Small-molecule synergist of the Wnt/beta-catenin signaling pathway. Proceedings of the National Academy of Sciences of the United States of America 104, 7444-7448 (2007).

Zhang, et al. (2009). Repulsive Axon Guidance Molecule Slit3 is a Novel Angiogenic Factor. Blood. 114(19):4300-4309.

Zhu, Y., Li, H., Zhou, L., Wu, J.Y., and Rao, Y. (1999). Cellular and molecular guidance of GABAergic neuronal migration from an extracortical origin to the neocortex. Neuron 23, 473-485.

Zimmerman, G.A., et al., 1985. Thrombin stimulates the adherence of neutrophils to human endothelial cells in vitro. J Clin Invest 76:2235-2246.

Zoller, Mark J., "New Recombinant DNA Methodology for Protein Engineering," Current Opinion in Biotechnology, vol. 3, 1992, pp. 348-354.

Zuker, Michael, "On Finding All Suboptimal Foldings of an RNA Molecule," Science, New Series, vol. 244, No. 4900 (Apr. 7, 1989), pp. 48-52.

A *wild-type*

B *robo4* MO

C *robo4* MO & *wild-type robo4* RNA

D *robo4* MO & *robo4Δtail* RNA

E *wild-type*　　　　　　　　　*robo4* MO

— DLAV —
— PAV —
— DA —
— PCV —

Paxillin-LD-V5:   −   −   +   +
Paxillin-Lim-V5:   +   +   −   −
Robo4-HA:   +   −   +   −
pCDNA3:   −   +   −   +

IP: HA (Robo4)
Blot: Paxillin

IP: HA (Robo4)
Blot: HA (Robo4)

Cell Lysates
Blot: V5 (Paxillin)

PaxillinΔLim4-V5:   +   −   −
Paxillin-V5:   −   +   +
Robo4-HA:   +   +   −
pCDNA3:   −   −   +

IP: HA (Robo4)
Blot: V5 (Paxillin)

IP: HA (Robo4)
Blot: HA (Robo4)

Cell Lysates
Blot: V5 (Paxillin)

a  bFGF-induced Tube Formation b  Thrombin-induced *in vitro* Permeability

Avian (H5N1) Flu Survival Curve

— Slit + Virus
--L-- Mock + Virus

FIG. 24

SEQUENCE LISTING

<160> NUMBER OF SEQ ID NOS: 47

<210> SEQ ID NO 1
<211> LENGTH: 1007
<212> TYPE: PRT
<213> ORGANISM: Homo sapiens

<400> SEQUENCE: 1

```
Met Gly Ser Gly Gly Asp Ser Leu Leu Gly Gly Arg Gly Ser Leu Pro
1               5                   10                  15

Leu Leu Leu Leu Leu Ile Met Gly Gly Met Ala Gln Asp Ser Pro Pro
            20                  25                  30

Gln Ile Leu Val His Pro Gln Asp Gln Leu Phe Gln Gly Pro Gly Pro
        35                  40                  45

Ala Arg Met Ser Cys Gln Ala Ser Gly Gln Pro Pro Thr Ile Arg
50                  55                  60

Trp Leu Leu Asn Gly Gln Pro Leu Ser Met Val Pro Asp Pro His
65              70                  75                  80

His Leu Leu Pro Asp Gly Thr Leu Leu Leu Gln Pro Pro Ala Arg
                85                  90                  95

Gly His Ala His Asp Gly Gln Ala Leu Ser Thr Asp Leu Gly Val Tyr
                100                 105                 110

Thr Cys Glu Ala Ser Asn Arg Leu Gly Thr Ala Val Ser Arg Gly Ala
            115                 120                 125

Arg Leu Ser Val Ala Val Leu Arg Glu Asp Phe Gln Ile Gln Pro Arg
130                 135                 140

Asp Met Val Ala Val Val Gly Glu Gln Phe Thr Leu Glu Cys Gly Pro
145                 150                 155                 160

Pro Trp Gly His Pro Glu Pro Thr Val Ser Trp Trp Lys Asp Gly Lys
                165                 170                 175

Pro Leu Ala Leu Gln Pro Gly Arg His Thr Val Ser Gly Gly Ser Leu
            180                 185                 190

Leu Met Ala Arg Ala Glu Lys Ser Asp Glu Gly Thr Tyr Met Cys Val
        195                 200                 205

Ala Thr Asn Ser Ala Gly His Arg Glu Ser Arg Ala Ala Arg Val Ser
210                 215                 220

Ile Gln Glu Pro Gln Asp Tyr Thr Glu Pro Val Glu Leu Leu Ala Val
225                 230                 235                 240

Arg Ile Gln Leu Glu Asn Val Thr Leu Leu Asn Pro Asp Pro Ala Glu
                245                 250                 255

Gly Pro Lys Pro Arg Pro Ala Val Trp Leu Ser Trp Lys Val Ser Gly
            260                 265                 270

Pro Ala Ala Pro Ala Gln Ser Tyr Thr Ala Leu Phe Arg Thr Gln Thr
        275                 280                 285

Ala Pro Gly Gly Gln Gly Ala Pro Trp Ala Glu Glu Leu Leu Ala Gly
290                 295                 300

Trp Gln Ser Ala Glu Leu Gly Gly Leu His Trp Gly Gln Asp Tyr Glu
305                 310                 315                 320

Phe Lys Val Arg Pro Ser Ser Gly Arg Ala Arg Gly Pro Asp Ser Asn
                325                 330                 335

Val Leu Leu Leu Arg Leu Pro Glu Lys Val Pro Ser Ala Pro Pro Gln
            340                 345                 350

Glu Val Thr Leu Lys Pro Gly Asn Gly Thr Val Phe Val Ser Trp Val
        355                 360                 365

Pro Pro Pro Ala Glu Asn His Asn Gly Ile Ile Arg Gly Tyr Gln Val
370                 375                 380

Trp Ser Leu Gly Asn Thr Ser Leu Pro Pro Ala Asn Trp Thr Val Val
385                 390                 395                 400

Gly Glu Gln Thr Gln Leu Glu Ile Ala Thr His Met Pro Gly Ser Tyr
                405                 410                 415
```

```
Cys Val Gln Val Ala Val Thr Gly Ala Gly Ala Gly Glu Pro Ser
            420                 425                 430

Arg Pro Val Cys Leu Leu Leu Glu Gln Ala Met Glu Arg Ala Thr Gln
            435                 440                 445

Glu Pro Ser Glu His Gly Pro Trp Thr Leu Gln Leu Arg Ala Thr
450                 455                 460

Leu Lys Arg Pro Glu Val Ile Ala Thr Cys Gly Val Ala Leu Trp Leu
465                 470                 475                 480

Leu Leu Leu Gly Thr Ala Val Cys Ile His Arg Arg Arg Ala Arg
                485                 490                 495

Val His Leu Gly Pro Gly Leu Tyr Arg Tyr Thr Ser Glu Asp Ala Ile
                500                 505                 510

Leu Lys His Arg Met Asp His Ser Asp Ser Gln Trp Leu Ala Asp Thr
                515                 520                 525

Trp Arg Ser Thr Ser Gly Ser Arg Asp Leu Ser Ser Ser Ser Ser Leu
530                 535                 540

Ser Ser Arg Leu Gly Ala Asp Ala Arg Asp Pro Leu Asp Cys Arg Arg
545                 550                 555                 560

Ser Leu Leu Ser Trp Asp Ser Arg Ser Pro Gly Val Pro Leu Leu Pro
                565                 570                 575

Asp Thr Ser Thr Phe Tyr Gly Ser Leu Ile Ala Glu Leu Pro Ser Ser
                580                 585                 590

Thr Pro Ala Arg Pro Ser Pro Gln Val Pro Ala Val Arg Arg Leu Pro
                595                 600                 605

Pro Gln Leu Ala Gln Leu Ser Ser Pro Cys Ser Ser Asp Ser Leu
                610                 615                 620

Cys Ser Arg Arg Gly Leu Ser Ser Pro Arg Leu Ser Leu Ala Pro Ala
625                 630                 635                 640

Glu Ala Trp Lys Ala Lys Lys Gln Glu Leu Gln His Ala Asn Ser
                645                 650                 655

Ser Pro Leu Leu Arg Gly Ser His Ser Leu Glu Leu Arg Ala Cys Glu
                660                 665                 670

Leu Gly Asn Arg Gly Ser Lys Asn Leu Ser Gln Ser Pro Gly Ala Val
                675                 680                 685

Pro Gln Ala Leu Val Ala Trp Arg Ala Leu Gly Pro Lys Leu Leu Ser
690                 695                 700

Ser Ser Asn Glu Leu Val Thr Arg His Leu Pro Pro Ala Pro Leu Phe
705                 710                 715                 720

Pro His Glu Thr Pro Thr Gln Ser Gln Gln Thr Gln Pro Pro Val
                725                 730                 735

Ala Pro Gln Ala Pro Ser Ser Ile Leu Leu Pro Ala Ala Pro Ile Pro
                740                 745                 750

Ile Leu Ser Pro Cys Ser Pro Ser Pro Gln Ala Ser Ser Leu Ser
                755                 760                 765

Gly Pro Ser Pro Ala Ser Ser Arg Leu Ser Ser Ser Ser Leu Ser Ser
                770                 775                 780

Leu Gly Glu Asp Gln Asp Ser Val Leu Thr Pro Glu Glu Val Ala Leu
785                 790                 795                 800

Cys Leu Glu Leu Ser Glu Gly Glu Glu Thr Pro Arg Asn Ser Val Ser
                805                 810                 815

Pro Met Pro Arg Ala Pro Ser Pro Pro Thr Thr Tyr Gly Tyr Ile Ser
                820                 825                 830

Val Pro Thr Ala Ser Glu Phe Thr Asp Met Gly Arg Thr Gly Gly Gly
                835                 840                 845
```

```
Val Gly Pro Lys Gly Gly Val Leu Leu Cys Pro Pro Arg Pro Cys Leu
    850                 855                 860

Thr Pro Thr Pro Ser Glu Gly Ser Leu Ala Asn Gly Trp Gly Ser Ala
865                 870                 875                 880

Ser Glu Asp Asn Ala Ala Ser Ala Arg Ala Ser Leu Val Ser Ser Ser
                885                 890                 895

Asp Gly Ser Phe Leu Ala Asp Ala His Phe Ala Arg Ala Leu Ala Val
                900                 905                 910

Ala Val Asp Ser Phe Gly Phe Gly Leu Glu Pro Arg Glu Ala Asp Cys
                915                 920                 925

Val Phe Ile Asp Ala Ser Ser Pro Ser Pro Arg Asp Glu Ile Phe
    930                 935                 940

Leu Thr Pro Asn Leu Ser Leu Pro Leu Trp Glu Trp Arg Pro Asp Trp
945                 950                 955                 960

Leu Glu Asp Met Glu Val Ser His Thr Gln Arg Leu Gly Arg Gly Met
                965                 970                 975

Pro Pro Trp Pro Pro Asp Ser Gln Ile Ser Ser Gln Arg Ser Gln Leu
                980                 985                 990

His Cys Arg Met Pro Lys Ala Gly Ala Ser Pro Val Asp Tyr Ser
    995                 1000                1005
```

<210> SEQ ID NO 2
<211> LENGTH: 3872
<212> TYPE: DNA
<213> ORGANISM: Homo sapiens

<400> SEQUENCE: 2

```
gcggccgcga attcggcacg agcagcagga caaagtgctc gggacaagga catagggctg      60
agagtagcca tgggctctgg aggagacagc ctcctggggg caggggttc cctgcctctg      120
ctgctcctgc tcatcatggg aggcatggct caggactccc cgccccagat cctagtccac      180
cccccaggacc agctgttcca gggccctggc cctgccagga tgagctgcca gcctcaggc      240
cagccacctc ccaccatccg ctggttgctg aatgggcagc ccctgagcat ggtgccccca      300
gacccacacc acctcctgcc tgatgggacc cttctgctgc tacagccccc tgcccgggga      360
catgcccacg atggccaggc cctgtccaca gacctgggtg tctacacatg tgaggccagc      420
aaccggcttg gcacggcagt cagcagaggc gctcggctgt ctgtggctgt cctccgggag      480
gatttccaga tccagcctcg ggacatggtg gctgtggtgg gtgagcagtt tactctggaa      540
tgtgggccgc cctgggccca cccagagccc acagtctcat ggtggaaaga tgggaaaccc      600
ctggcccctcc agcccggaag gcacacagtg tccggggggt ccctgctgat ggcaagagca      660
gagaagagtg acgaagggac ctacatgtgt gtggccacca acagcgcagg acatagggag      720
agccgcgcag cccgggtttc catccaggag ccccaggact acacggagcc tgtgagctt      780
ctggctgtgc gaattcagct ggaaaatgtg acactgctga cccggatcc tgcagagggc      840
cccaagccta accggcggt gtggctcagc tggaaggtca gtggccctgc tgcgcctgcc      900
caatcttaca cggccttgtt caggacccag actgccccgg gaggcagggg agctccgtgg      960
gcagaggagc tgctggccgg ctggcagagc gcagagcttg gaggcctcca ctggggccaa      1020
gactacagt caaagtgag accatcctct ggccgggctc gaggccctga cagcaacgtg      1080
ctgctcctga ggctgccgga aaaagtgccc agtgccccac ctcaggaagt gactctaaag      1140
cctggcaatg gcactgtctt tgtgagctgg gtcccaccac ctgctgaaaa ccacaatggc      1200
atcatccgtg gctaccaggt ctggagcctg ggcaacacat cactgccacc agccaactgg      1260
```

```
actgtagttg gtgagcagac ccagctggaa atcgccaccc atatgccagg ctcctactgc   1320
gtgcaagtgg ctgcagtcac tggtgctgga gctggggagc ccagtagacc tgtctgcctc   1380
cttttagagc aggccatgga gcgagccacc caagaaccca gtgagcatgg tccctggacc   1440
ctggagcagc tgagggctac cttgaagcgg cctgaggtca ttgccacctg cggtgttgca   1500
ctctggctgc tgcttctggg caccgccgtg tgtatccacc gccggcgccg agctagggtg   1560
cacctgggcc caggtctgta cagatatacc agtgaggatg ccatcctaaa acacaggatg   1620
gatcacagtg actcccagtg gttggcagac acttggcgtt ccacctctgg ctctcgggac   1680
ctgagcagca gcagcagcct cagcagtcgg ctggggcgg atgcccggga cccactagac   1740
tgtcgtcgct ccttgctctc ctgggactcc cgaagcccg gcgtgcccct gcttccagac   1800
accagcactt tttatggctc cctcatcgct gagctgccct ccagtacccc agccaggcca   1860
agtccccagg tcccagctgt caggcgcctc ccaccccagc tggcccagct tccagcccc    1920 tgttccagct cagacagcct ctgcagccgc aggggactct cttctccccg cttgtctctg   1980
gcccctgcag aggcttggaa ggccaaaaag aagcaggagc tgcagcatgc caacagttcc   2040
ccactgctcc ggggcagcca ctccttggag ctccgggcct gtgagttagg aaatagaggt   2100
tccaagaacc tttcccaaag cccaggagct gtgccccaag ctctggttgc ctggcgggcc   2160
ctgggaccga aactcctcag ctcctcaaat gagctggtta ctcgtcatct ccctccagca   2220 cccctcttc ctcatgaaac tcccccaact cagagtcaac agacccagcc tccggtggca   2280
ccacaggctc cctcctccat cctgctgcca gcagccccca tccccatcct tagcccctgc   2340
agtcccccta gccccaggc ctcttccctc tctggcccca gcccagcttc cagtcgcctg   2400
tccagctcct cactgtcatc cctggggag gatcaagaca gcgtgctgac ccctgaggag   2460
gtagccctgt gcttggaact cagtgagggt gaggagactc ccaggaacag cgtctctccc   2520
atgccaaggg ctccttcacc ccccaccacc tatgggtaca tcagcgtccc aacagcctca   2580
gagttcacgg acatgggcag gactggagga ggggtggggc ccaaggggg agtcttgctg   2640 tgcccacctc ggccctgcct caccccccacc cccagcgagg gctccttagc caatggttgg   2700
ggctcagcct ctgaggacaa tgccgccagc gccagagcca gccttgtcag ctcctccgat   2760
ggctccttcc tcgctgatgc tcactttgcc cgggccctgg cagtggctgt ggatagcttt   2820
ggtttcggtc tagagcccag ggaggcagac tgcgtcttca tagatgcctc atcacctccc   2880
tccccacggg atgagatctt cctgaccccc aacctctccc tgccctgtg ggagtggagg   2940 ccagactggt tggaagacat ggaggtcagc cacacccagc ggctgggaag ggggatgcct   3000
ccctggcccc ctgactctca gatctcttcc cagagaagtc agctccactg tcgtatgccc   3060
aaggctggtg cttctcctgt agattactcc tgaaccgtgt ccctgagact tcccagacgg   3120
gaatcagaac cacttctcct gtccacccac aagacctggg ctgtggtgtg tgggtcttgg   3180
cctgtgtttc tctgcagctg gggtccacct tcccaagcct ccagagagtt ctccctccac   3240
gattgtgaaa acaaatgaaa acaaaattag agcaaagctg acctggagcc ctcagggagc   3300
aaaacatcat ctccacctga ctcctagcca ctgctttctc ctctgtgcca tccactccca   3360
ccaccaggtt gttttggcct gaggagcagc cctgcctgct gctcttcccc caccatttgg   3420
atcacaggaa gtggaggagc cagaggtgcc tttgtgagg acagcagtgg ctgctgggag   3480
agggctgtgg aggaaggagc ttctcggagc cccctctcag ccttacctgg gcccctcctc   3540
tagagaagag ctcaactctc tcccaacctc accatggaaa gaaataatt atgaatgcca   3600 ctgaggcact gaggccctac ctcatgccaa acaaagggtt caaggctggg tctagcgagg   3660
```

```
atgctgaagg aagggaggta tgagaccgta ggtcaaaagc accatcctcg tactgttgtc    3720
actatgagct taagaaattt gataccataa aatggtaaag acttgaaaaa aaaaaaaaaa    3780
aaaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aa                                  3872
```

<210> SEQ ID NO 3
<211> LENGTH: 1534
<212> TYPE: PRT
<213> ORGANISM: Homo sapiens

<400> SEQUENCE: 3

```
Met Ala Leu Thr Pro Gly Trp Gly Ser Ser Ala Gly Pro Val Arg Pro
1               5                   10                  15

Glu Leu Trp Leu Leu Trp Ala Ala Ala Trp Arg Leu Gly Ala Ser
            20                  25                  30

Ala Cys Pro Ala Leu Cys Thr Cys Thr Gly Thr Val Asp Cys His
        35                  40                  45

Gly Thr Gly Leu Gln Ala Ile Pro Lys Asn Ile Pro Arg Asn Thr Glu
    50                  55                  60

Arg Leu Glu Leu Asn Gly Asn Asn Ile Thr Arg Ile His Lys Asn Asp
65                  70                  75                  80

Phe Ala Gly Leu Lys Gln Leu Arg Val Leu Gln Leu Met Glu Asn Gln
                85                  90                  95

Ile Gly Ala Val Glu Arg Gly Ala Phe Asp Asp Met Lys Glu Leu Glu
            100                 105                 110

Arg Leu Arg Leu Asn Arg Asn Gln Leu His Met Leu Pro Glu Leu Leu
        115                 120                 125

Phe Gln Asn Asn Gln Ala Leu Ser Arg Leu Asp Leu Ser Glu Asn Ala
    130                 135                 140

Ile Gln Ala Ile Pro Arg Lys Ala Phe Arg Gly Ala Thr Asp Leu Lys
145                 150                 155                 160

Asn Leu Gln Leu Asp Lys Asn Gln Ile Ser Cys Ile Glu Glu Gly Ala
                165                 170                 175

Phe Arg Ala Leu Arg Gly Leu Glu Val Leu Thr Leu Asn Asn Asn Asn
            180                 185                 190

Ile Thr Thr Ile Pro Val Ser Ser Phe Asn His Met Pro Lys Leu Arg
        195                 200                 205

Thr Phe Arg Leu His Ser Asn His Leu Phe Cys Asp Cys His Leu Ala
    210                 215                 220

Trp Leu Ser Gln Trp Leu Arg Gln Arg Pro Thr Ile Gly Leu Phe Thr
225                 230                 235                 240

Gln Cys Ser Gly Pro Ala Ser Leu Arg Gly Leu Asn Val Ala Glu Val
                245                 250                 255

Gln Lys Ser Glu Phe Ser Cys Ser Gly Gln Gly Glu Ala Gly Arg Val
            260                 265                 270

Pro Thr Cys Thr Leu Ser Ser Gly Ser Cys Pro Ala Met Cys Thr Cys
        275                 280                 285

Ser Asn Gly Ile Val Asp Cys Arg Gly Lys Gly Leu Thr Ala Ile Pro
    290                 295                 300

Ala Asn Leu Pro Glu Thr Met Thr Glu Ile Arg Leu Glu Leu Asn Gly
305                 310                 315                 320

Ile Lys Ser Ile Pro Pro Gly Ala Phe Ser Pro Tyr Arg Lys Leu Arg
                325                 330                 335
```

-continued

Arg Ile Asp Leu Ser Asn Asn Gln Ile Ala Glu Ile Ala Pro Asp Ala
            340                 345                 350

Phe Gln Gly Leu Arg Ser Leu Asn Ser Leu Val Leu Tyr Gly Asn Lys
            355                 360                 365

Ile Thr Asp Leu Pro Arg Gly Val Phe Gly Gly Leu Tyr Thr Leu Gln
    370                 375                 380

Leu Leu Leu Leu Asn Ala Asn Lys Ile Asn Cys Ile Arg Pro Asp Ala
385                 390                 395                 400

Phe Gln Asp Leu Gln Asn Leu Ser Leu Leu Ser Leu Tyr Asp Asn Lys
                405                 410                 415

Ile Gln Ser Leu Ala Lys Gly Thr Phe Thr Ser Leu Arg Ala Ile Gln
            420                 425                 430

Thr Leu His Leu Ala Gln Asn Pro Phe Ile Cys Asp Cys Asn Leu Lys
        435                 440                 445

Trp Leu Ala Asp Phe Leu Arg Thr Asn Pro Ile Glu Thr Ser Gly Ala
    450                 455                 460

Arg Cys Ala Ser Pro Arg Arg Leu Ala Asn Lys Arg Ile Gly Gln Ile
465                 470                 475                 480

Lys Ser Lys Lys Phe Arg Cys Ser Ala Lys Glu Gln Tyr Phe Ile Pro
                485                 490                 495

Gly Thr Glu Asp Tyr Gln Leu Asn Ser Glu Cys Asn Ser Asp Val Val
            500                 505                 510

Cys Pro His Lys Cys Arg Cys Glu Ala Asn Val Val Glu Cys Ser Ser
        515                 520                 525

Leu Lys Leu Thr Lys Ile Pro Glu Arg Ile Pro Gln Ser Thr Ala Glu
    530                 535                 540

Leu Arg Leu Asn Asn Asn Glu Ile Ser Ile Leu Glu Ala Thr Gly Met
545                 550                 555                 560

Phe Lys Lys Leu Thr His Leu Lys Lys Ile Asn Leu Ser Asn Asn Lys
                565                 570                 575

Val Ser Glu Ile Glu Asp Gly Ala Phe Glu Gly Ala Ala Ser Val Ser
            580                 585                 590

Glu Leu His Leu Thr Ala Asn Gln Leu Glu Ser Ile Arg Ser Gly Met
        595                 600                 605

Phe Arg Gly Leu Asp Gly Leu Arg Thr Leu Met Leu Arg Asn Asn Arg
    610                 615                 620

Ile Ser Cys Ile His Asn Asp Ser Phe Thr Gly Leu Arg Asn Val Arg
625                 630                 635                 640

Leu Leu Ser Leu Tyr Asp Asn Gln Ile Thr Thr Val Ser Pro Gly Ala
                645                 650                 655

Phe Asp Thr Leu Gln Ser Leu Ser Thr Leu Asn Leu Leu Ala Asn Pro
            660                 665                 670

Phe Asn Cys Asn Cys Gln Leu Ala Trp Leu Gly Gly Trp Leu Arg Lys
        675                 680                 685

Arg Lys Ile Val Thr Gly Asn Pro Arg Cys Gln Asn Pro Asp Phe Leu
    690                 695                 700

Arg Gln Ile Pro Leu Gln Asp Val Ala Phe Pro Asp Phe Arg Cys Glu
705                 710                 715                 720

Glu Gly Gln Glu Glu Gly Gly Cys Leu Pro Arg Pro Gln Cys Pro Gln
                725                 730                 735

Glu Cys Ala Cys Leu Asp Thr Val Val Arg Cys Ser Asn Lys His Leu
            740                 745                 750

Arg Ala Leu Pro Lys Gly Ile Pro Lys Asn Val Thr Glu Leu Tyr Leu
        755                 760                 765

```
Asp Gly Asn Gln Phe Thr Leu Val Pro Gly Gln Leu Ser Thr Phe Lys
    770                 775                 780

Tyr Leu Gln Leu Val Asp Leu Ser Asn Asn Lys Ile Ser Ser Leu Ser
785                 790                 795                 800

Asn Ser Ser Phe Thr Asn Met Ser Gln Leu Thr Leu Ile Leu Ser
                805                 810                 815

Tyr Asn Ala Leu Gln Cys Ile Pro Pro Leu Ala Phe Gln Gly Leu Arg
            820                 825                 830

Ser Leu Arg Leu Leu Ser Leu His Gly Asn Asp Ile Ser Thr Leu Gln
            835                 840                 845

Glu Gly Ile Phe Ala Asp Val Thr Ser Leu Ser His Leu Ala Ile Gly
    850                 855                 860

Ala Asn Pro Leu Tyr Cys Asp Cys His Leu Arg Trp Leu Ser Ser Trp
865                 870                 875                 880

Val Lys Thr Gly Tyr Lys Glu Pro Gly Ile Ala Arg Cys Ala Gly Pro
                885                 890                 895

Gln Asp Met Glu Gly Lys Leu Leu Thr Thr Pro Ala Lys Lys Phe
            900                 905                 910

Glu Cys Gln Gly Pro Pro Thr Leu Ala Val Gln Ala Lys Cys Asp Leu
            915                 920                 925

Cys Leu Ser Ser Pro Cys Gln Asn Gln Gly Thr Cys His Asn Asp Pro
930                 935                 940

Leu Glu Val Tyr Arg Cys Ala Cys Pro Ser Gly Tyr Lys Gly Arg Asp
945                 950                 955                 960

Cys Glu Val Ser Leu Asn Ser Cys Ser Ser Gly Pro Cys Glu Asn Gly
                965                 970                 975

Gly Thr Cys His Ala Gln Glu Gly Glu Asp Ala Pro Phe Thr Cys Ser
            980                 985                 990

Cys Pro Thr Gly Phe Glu Gly Pro Thr Cys Gly Val Asn Thr Asp Asp
        995                 1000                1005

Cys Val Asp His Ala Cys Ala Asn Gly Gly Val Cys Val Asp Gly
    1010                1015                1020

Val Gly Asn Tyr Thr Cys Gln Cys Pro Leu Gln Tyr Glu Gly Lys
    1025                1030                1035

Ala Cys Glu Gln Leu Val Asp Leu Cys Ser Pro Asp Leu Asn Pro
    1040                1045                1050

Cys Gln His Glu Ala Gln Cys Val Gly Thr Pro Asp Gly Pro Arg
    1055                1060                1065

Cys Glu Cys Met Pro Gly Tyr Ala Gly Asp Asn Cys Ser Glu Asn
    1070                1075                1080

Gln Asp Asp Cys Arg Asp His Arg Cys Gln Asn Gly Ala Gln Cys
    1085                1090                1095

Met Asp Glu Val Asn Ser Tyr Ser Cys Leu Cys Ala Glu Gly Tyr
    1100                1105                1110

Ser Gly Gln Leu Cys Glu Ile Pro Pro His Leu Pro Ala Pro Lys
    1115                1120                1125

Ser Pro Cys Glu Gly Thr Glu Cys Gln Asn Gly Ala Asn Cys Val
    1130                1135                1140

Asp Gln Gly Asn Arg Pro Val Cys Gln Cys Leu Pro Gly Phe Gly
    1145                1150                1155

Gly Pro Glu Cys Glu Lys Leu Leu Ser Val Asn Phe Val Asp Arg
    1160                1165                1170

Asp Thr Tyr Leu Gln Phe Thr Asp Leu Gln Asn Trp Pro Arg Ala
```

-continued

|  |  | 1175 |  |  | 1180 |  |  |  | 1185 |  |  |
|---|---|---|---|---|---|---|---|---|---|---|---|

Asn Ile Thr Leu Gln Val Ser Thr Ala Glu Asp Asn Gly Ile Leu
1190                1195                1200

Leu Tyr Asn Gly Asp Asn Asp His Ile Ala Val Glu Leu Tyr Gln
1205                1210                1215

Gly His Val Arg Val Ser Tyr Asp Pro Gly Ser Tyr Pro Ser Ser
1220                1225                1230

Ala Ile Tyr Ser Ala Glu Thr Ile Asn Asp Gly Gln Phe His Thr
1235                1240                1245

Val Glu Leu Val Ala Phe Asp Gln Met Val Asn Leu Ser Ile Asp
1250                1255                1260

Gly Gly Ser Pro Met Thr Met Asp Asn Phe Gly Lys His Tyr Thr
1265                1270                1275

Leu Asn Ser Glu Ala Pro Leu Tyr Val Gly Gly Met Pro Val Asp
1280                1285                1290

Val Asn Ser Ala Ala Phe Arg Leu Trp Gln Ile Leu Asn Gly Thr
1295                1300                1305

Gly Phe His Gly Cys Ile Arg Asn Leu Tyr Ile Asn Asn Glu Leu
1310                1315                1320

Gln Asp Phe Thr Lys Thr Gln Met Lys Pro Gly Val Val Pro Gly
1325                1330                1335

Cys Glu Pro Cys Arg Lys Leu Tyr Cys Leu His Gly Ile Cys Gln
1340                1345                1350

Pro Asn Ala Thr Pro Gly Pro Met Cys His Cys Glu Ala Gly Trp
1355                1360                1365

Val Gly Leu His Cys Asp Gln Pro Ala Asp Gly Pro Cys His Gly
1370                1375                1380

His Lys Cys Val His Gly Gln Cys Val Pro Leu Asp Ala Leu Ser
1385                1390                1395

Tyr Ser Cys Gln Cys Gln Asp Gly Tyr Ser Gly Ala Leu Cys Asn
1400                1405                1410

Gln Ala Gly Ala Leu Ala Glu Pro Cys Arg Gly Leu Gln Cys Leu
1415                1420                1425

His Gly His Cys Gln Ala Ser Gly Thr Lys Gly Ala His Cys Val
1430                1435                1440

Cys Asp Pro Gly Phe Ser Gly Glu Leu Cys Glu Gln Glu Ser Glu
1445                1450                1455

Cys Arg Gly Asp Pro Val Arg Asp Phe His Gln Val Gln Arg Gly
1460                1465                1470

Tyr Ala Ile Cys Gln Thr Thr Arg Pro Leu Ser Trp Val Glu Cys
1475                1480                1485

Arg Gly Ser Cys Pro Gly Gln Gly Cys Cys Gln Gly Leu Arg Leu
1490                1495                1500

Lys Arg Arg Lys Phe Thr Phe Glu Cys Ser Asp Gly Thr Ser Phe
1505                1510                1515

Ala Glu Glu Val Glu Lys Pro Thr Lys Cys Gly Cys Ala Leu Cys
1520                1525                1530

Ala

<210> SEQ ID NO 4
<211> LENGTH: 5094
<212> TYPE: DNA
<213> ORGANISM: Homo sapiens

<400> SEQUENCE: 4

```
gcgaaacggc agaggagccg agcccctcc gcccaaggcg ccctccctcc gtccgcgcac    60
aggcgccgtc gcttggagga gcaaggtgcc tcccagcccg caggggcgcc gcgcgcaagc   120
ccgcgggctc ttcggtggct ctgccccggg actgcacctg gaggcggccc cggacgggga   180
tggtcagcgg ctgctgccgt ctggctcgcg agcgggacgc tgtgagggca ccatggcgct   240
gactcccggg tggggtcct cggcggggcc ggtccggccg gagctctggc tgctgctgtg   300
ggcagccgcg tggcgcctgg gtgcctcggc gtgccccgcc ctctgcacct gcaccggaac   360
cacggtggac tgccacggca cggggctgca ggccattccc aagaatatac ctcggaacac   420
cgagcgcctg gaactcaatg caacaacat cactcggatc cataagaatg actttgcggg   480
gctcaagcag ctgcgggtgc tgcagctgat ggagaaccag attggagcag tggaacgtgg   540
tgcttttgat gacatgaagg agctggagcg gctgcgactg aaccgaaacc agctgcacat   600
gttaccggaa ctgctgttcc agaacaacca ggctttgtca agactggact tgagtgagaa   660
cgccatccag gccatcccca ggaaagcttt tcggggagct acggacctta aaatttacg   720 gctggacaag aaccagatca gctgcattga ggaaggggcc ttccgtgctc tgcggggct   780 ggaggtgctg accctgaaca caacaatat caccaccatc cccgtgtcca gcttcaacca   840
tatgcccaag ctacggacct tccgcctgca ctccaaccac ctgttttgcg actgccacct   900
ggcctggctc tcgcagtggc tgaggcagcg ccaaccatc gggctcttca cccagtgctc   960
gggcccagcc agcctgcgtg cctcaatgt ggcagaggtc agaagagtg agttcagctg  1020 ctcaggccag ggagaagcgg ggcgcgtgcc cacctgcacc ctgtcctccg gctcctgccc  1080
ggccatgtgc acctgcagca atggcatcgt ggactgtcgt ggaaaaggcc tcactgccat  1140 cccgccaac ctgcccgaga ccatgacgga gatacgcctg gagctgaacg catcaagtc  1200 catccctcct ggagccttct caccctacag aaagctacgg aggatagacc tgagcaacaa  1260
tcagatcgct gagattgcac ccgacgcctt ccagggcctc cgctccctga actcgctggt  1320
cctctatgga aacaagatca cagacctccc ccgtggtgtg tttggaggcc tatacaccct  1380
acagctcctg ctcctgaatg ccaacaagat caactgcatc cggcccgatg ccttccagga  1440
cctgcagaac ctctcactgc tctccctgta tgacaacaag atccagagcc tcgccaaggg  1500 cacttttcacc tccctgcggg ccatccgac tctgcacctg gccagaacc ctttcatttg  1560 cgactgtaac ctcaagtggc tggcagactt cctgcgcacc aatcccatcg agacgagtgg  1620
tgcccgctgt gccagtcccc ggcgcctcgc caacaagcgc atcgggcaga tcaagagcaa  1680
gaagttccgg tgctcagcca agagcagta cttcattcca ggcacggagg attaccagct  1740
gaacagcgag tgcaacagcg acgtggtctg tccccacaag tgccgctgtg aggcaacgt  1800 ggtggagtgc tccagcctga agctcaccaa gatccctgag cgcatccccc agtccacggc  1860
agaactgcga ttgaataaca atgagatttc catcctggag gccactggga tgtttaaaaa  1920
acttacacat ctgaagaaaa tcaatctgag caacaacaag gtgtcagaaa ttgaagatgg  1980
ggccttcgag ggcgcagcct ctgtgagcga gctgcaccta actgccaacc agctggagtc  2040
catccggagc ggcatgttcc ggggtctgga tggcttgagg accctaatgc tgcggaacaa  2100
ccgcatcagc tgcatccaca cgacagctt cacgggcctg cgcaacgtcc ggctcctctc  2160
gctctacgac aaccagatca ccaccgtatc cccaggagcc ttcgacaccc tccagtcccct  2220 ctccacactg aatctcctgg ccaaccctt caactgcaac tgccagctgg cctggctagg  2280
aggctggcta cggaagcgca agatcgtgac gggaaccccg cgatgccaga ccctgacttt  2340
tttgcggcag attcccctgc aggacgtggc cttccctgac ttcaggtgtg aggaaggcca  2400
```

-continued

```
ggaggagggg ggctgcctgc cccgcccaca gtgcccacag gagtgcgcct gcctggacac    2460
cgtggtccga tgcagcaaca agcacctgcg ggccctgccc aagggcattc ccaagaatgt    2520
cacagaactc tatttggacg ggaaccagtt cacgctggtt ccgggacagc tgtctacctt    2580
caagtacctg cagctcgtgg acctgagcaa caacaagatc agttccttaa gcaattcctc    2640
cttcaccaac atgagccagc tgaccactct gatcctcagc tacaatgccc tgcagtgcat    2700
cccgcctttg gccttccagg gactccgctc cctgcgcctg ctgtctctcc acggcaatga    2760
catctccacc ctccaagagg gcatctttgc agacgtgacc tccctgtctc acctggccat    2820
tggtgccaac cccctatact gtgactgcca cctccgctgg ctgtccagct gggtgaagac    2880
tggctacaag gaaccgggca ttgctcgttg tgctgggccc caggacatgg agggcaagct    2940
gctcctcacc acgcctgcca agaagtttga atgccaaggt cctccaacgc tggctgtcca    3000
ggccaagtgt gatctctgct tgtccagtcg gtgccagaac cagggcacct gccacaacga    3060 ccccccttgag gtgtacaggt gcgcctgccc cagcggctat aagggtcgag actgtgaggt    3120
gtccctgaac agctgttcca gtggcccctg tgaaaatggg ggcacctgcc atgcacagga    3180
gggcgaggat gccccgttca cgtgctcctg tcccaccggc tttgaaggac caacctgtgg    3240
ggtgaacaca gatgactgtg tggatcatgc ctgtgccaat ggggggcgtct gtgtggatgg    3300 tgtgggcaac tacacctgcc agtgccccct gcagtatgag ggaaaggcct gtgagcagct    3360
ggtggacttg tgctctccgg atctgaaccc atgtcaacac gaggcccagt gtgtgggcac    3420
cccgatgggg cccaggtgtg agtgcatgcc aggttatgca ggtgacaact gcagtgagaa    3480
ccaggatgac tgcagggacc accgctgcca gaatggggcc cagtgtatgg atgaagtcaa    3540
cagctactcc tgcctctgtg ctgagggcta cagtggacac tctgtgaga tccctccccca    3600 tctgcctgcc cccaagagcc cctgtgaggg gactgagtgc cagaatgggg ccaactgtgt    3660
ggaccagggc aacaggcctg tgtgccagtg cctcccaggc ttcggtggcc ctgagtgtga    3720
gaagttgctc agtgtcaact tgtggatcg ggacacttac ctgcagttca ctgacctgca    3780
aaactggcca cgggccaaca tcacgttgca ggtctccacg gcagaggaca atgggatcct    3840
tctgtacaac ggggacaacg accacattgc agttgagctg taccagggcc atgtgcgtgt    3900
cagctacgac ccaggcagct accccagctc tgccatctac agtgctgaga cgatcaacga    3960
tgggcaattc cacaccgttg agctggttgc cttttgaccag atggtgaatc tctccattga    4020
tggcgggagc cccatgacca tggacaactt tggcaaacat tacacgctca acagcgaggc    4080
gccactctat gtgggaggga tgcccgtgga tgtcaactca gctgccttcc gcctgtggca    4140
gatcctcaac ggcaccggct ccacggttg catccgaaac ctgtacatca caacgagct    4200 gcaggacttc accaagacgc agatgaagcc aggcgtggtg ccaggctgcg aaccctgccg    4260
caagctctac tgcctgcatg gcatctgcca gcccaatgcc accccagggc ccatgtgcca    4320
ctgcgaggct ggctgggtgg gcctgcactg tgaccagccc gctgacggcc cctgccatgg    4380
ccacaagtgt gtccatgggc aatgcgtgcc cctcgacgct cttttcctaca gctgccagtg    4440 ccaggatggg tactcggggg cactgtgcaa ccaggccggg gccctggcag agccctgcag    4500
aggcctgcag tgcctgcatg gccactgcca ggcctcaggc accaagggga cacactgtgt    4560
gtgtgacccc ggcttttcgg gcgagctgtg tgagcaagag tccgagtgcc ggggggaccc    4620
tgtccgggac tttcaccagg tccagagggg ctatgccatc tgccagacca cgcgcccct    4680 gtcatgggtg gagtgccggg gctcgtgccc aggccagggc tgctgccagg ccttcgcgt    4740 gaagcggagg aagttcacct ttgagtgcag cgatgggacc tcttttgccg aggaggtgga    4800
```

-continued

```
aaagcccacc aagtgtggct gtgccctctg cgcatagcgc tgggcgtgga caggccggtg    4860
agggcgggca aggggcccca gccgctgcag cagcggagac agtcgccagc agctgggctg    4920
gggtgcaggt catcacagga cggctcctgg gcagctgggc cctcctgggt ggggtggtgc    4980
cagagcagcc ttttaaaagc aaattgcgcc atagctgggg gcagcggggg tgggcgaggc    5040
ctgagctgcg ggctgccctc tccggaagtc cttgcacaaa taggcgctta ataa          5094
```

<210> SEQ ID NO 5
<211> LENGTH: 1529
<212> TYPE: PRT
<213> ORGANISM: Homo sapiens

<400> SEQUENCE: 5

```
Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
            20                  25                  30

Ser Cys Ser Gly Ser Thr Val Asp Cys His Gly Leu Ala Leu Arg Ser
        35                  40                  45

Val Pro Arg Asn Ile Pro Arg Asn Thr Glu Arg Leu Asp Leu Asn Gly
    50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220

Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
                245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
        275                 280                 285

Lys Gly Leu Thr Glu Ile Pro Thr Asn Leu Pro Glu Thr Ile Thr Glu
    290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
```

```
                    325                 330                 335
Ser Glu Leu Ala Pro Asp Ala Phe Gln Gly Leu Arg Ser Leu Asn Ser
                340                 345                 350
Leu Val Leu Tyr Gly Asn Lys Ile Thr Glu Leu Pro Lys Ser Leu Phe
                355                 360                 365
Glu Gly Leu Phe Ser Leu Gln Leu Leu Leu Asn Ala Asn Lys Ile
            370                 375                 380
Asn Cys Leu Arg Val Asp Ala Phe Gln Asp Leu His Asn Leu Asn Leu
385                 390                 395                 400
Leu Ser Leu Tyr Asp Asn Lys Leu Gln Thr Ile Ala Lys Gly Thr Phe
                405                 410                 415
Ser Pro Leu Arg Ala Ile Gln Thr Met His Leu Ala Gln Asn Pro Phe
                420                 425                 430
Ile Cys Asp Cys His Leu Lys Trp Leu Ala Asp Tyr Leu His Thr Asn
                435                 440                 445
Pro Ile Glu Thr Ser Gly Ala Arg Cys Thr Ser Pro Arg Arg Leu Ala
            450                 455                 460
Asn Lys Arg Ile Gly Gln Ile Lys Ser Lys Phe Arg Cys Ser Ala
465                 470                 475                 480
Lys Glu Gln Tyr Phe Ile Pro Gly Thr Glu Asp Tyr Arg Ser Lys Leu
                485                 490                 495
Ser Gly Asp Cys Phe Ala Asp Leu Ala Cys Pro Glu Lys Cys Arg Cys
            500                 505                 510
Glu Gly Thr Thr Val Asp Cys Ser Asn Gln Lys Leu Asn Lys Ile Pro
            515                 520                 525
Glu His Ile Pro Gln Tyr Thr Ala Glu Leu Arg Leu Asn Asn Asn Glu
            530                 535                 540
Phe Thr Val Leu Glu Ala Thr Gly Ile Phe Lys Lys Leu Pro Gln Leu
545                 550                 555                 560
Arg Lys Ile Asn Phe Ser Asn Asn Lys Ile Thr Asp Ile Glu Glu Gly
                565                 570                 575
Ala Phe Glu Gly Ala Ser Gly Val Asn Glu Ile Leu Leu Thr Ser Asn
            580                 585                 590
Arg Leu Glu Asn Val Gln His Lys Met Phe Lys Gly Leu Glu Ser Leu
            595                 600                 605
Lys Thr Leu Met Leu Arg Ser Asn Arg Ile Thr Cys Val Gly Asn Asp
            610                 615                 620
Ser Phe Ile Gly Leu Ser Ser Val Arg Leu Leu Ser Leu Tyr Asp Asn
625                 630                 635                 640
Gln Ile Thr Thr Val Ala Pro Gly Ala Phe Asp Thr Leu His Ser Leu
                645                 650                 655
Ser Thr Leu Asn Leu Leu Ala Asn Pro Phe Asn Cys Asn Cys Tyr Leu
                660                 665                 670
Ala Trp Leu Gly Glu Trp Leu Arg Lys Arg Ile Val Thr Gly Asn
            675                 680                 685
Pro Arg Cys Gln Lys Pro Tyr Phe Leu Lys Glu Ile Pro Ile Gln Asp
            690                 695                 700
Val Ala Ile Gln Asp Phe Thr Cys Asp Asp Gly Asn Asp Asn Ser
705                 710                 715                 720
Cys Ser Pro Leu Ser Arg Cys Pro Thr Glu Cys Thr Cys Leu Asp Thr
                725                 730                 735
Val Val Arg Cys Ser Asn Lys Gly Leu Lys Val Leu Pro Lys Gly Ile
                740                 745                 750
```

```
Pro Arg Asp Val Thr Glu Leu Tyr Leu Asp Gly Asn Gln Phe Thr Leu
    755                 760                 765

Val Pro Lys Glu Leu Ser Asn Tyr Lys His Leu Thr Leu Ile Asp Leu
    770                 775                 780

Ser Asn Asn Arg Ile Ser Thr Leu Ser Asn Gln Ser Phe Ser Asn Met
785                 790                 795                 800

Thr Gln Leu Leu Thr Leu Ile Leu Ser Tyr Asn Arg Leu Arg Cys Ile
                805                 810                 815

Pro Pro Arg Thr Phe Asp Gly Leu Lys Ser Leu Arg Leu Leu Ser Leu
            820                 825                 830

His Gly Asn Asp Ile Ser Val Val Pro Glu Gly Ala Phe Asn Asp Leu
                835                 840                 845

Ser Ala Leu Ser His Leu Ala Ile Gly Ala Asn Pro Leu Tyr Cys Asp
850                 855                 860

Cys Asn Met Gln Trp Leu Ser Asp Trp Val Lys Ser Glu Tyr Lys Glu
865                 870                 875                 880

Pro Gly Ile Ala Arg Cys Ala Gly Pro Gly Glu Met Ala Asp Lys Leu
                885                 890                 895

Leu Leu Thr Thr Pro Ser Lys Lys Phe Thr Cys Gln Gly Pro Val Asp
                900                 905                 910

Val Asn Ile Leu Ala Lys Cys Asn Pro Cys Leu Ser Asn Pro Cys Lys
                915                 920                 925

Asn Asp Gly Thr Cys Asn Ser Asp Pro Val Asp Phe Tyr Arg Cys Thr
930                 935                 940

Cys Pro Tyr Gly Phe Lys Gly Gln Asp Cys Asp Val Pro Ile His Ala
945                 950                 955                 960

Cys Ile Ser Asn Pro Cys Lys His Gly Gly Thr Cys His Leu Lys Glu
                965                 970                 975

Gly Glu Glu Asp Gly Phe Trp Cys Ile Cys Ala Asp Gly Phe Glu Gly
                980                 985                 990

Glu Asn Cys Glu Val Asn Val Asp Asp Cys Glu Asp Asn Asp Cys Glu
            995                 1000                1005

Asn Asn Ser Thr Cys Val Asp Gly Ile Asn Asn Tyr Thr Cys Leu
    1010                1015                1020

Cys Pro Pro Glu Tyr Thr Gly Glu Leu Cys Glu Glu Lys Leu Asp
    1025                1030                1035

Phe Cys Ala Gln Asp Leu Asn Pro Cys Gln His Asp Ser Lys Cys
    1040                1045                1050

Ile Leu Thr Pro Lys Gly Phe Lys Cys Asp Cys Thr Pro Gly Tyr
    1055                1060                1065

Val Gly Glu His Cys Asp Ile Asp Phe Asp Asp Cys Gln Asp Asn
    1070                1075                1080

Lys Cys Lys Asn Gly Ala His Cys Thr Asp Ala Val Asn Gly Tyr
    1085                1090                1095

Thr Cys Ile Cys Pro Glu Gly Tyr Ser Gly Leu Phe Cys Glu Phe
    1100                1105                1110

Ser Pro Pro Met Val Leu Pro Arg Thr Ser Pro Cys Asp Asn Phe
    1115                1120                1125

Asp Cys Gln Asn Gly Ala Gln Cys Ile Val Arg Ile Asn Glu Pro
    1130                1135                1140

Ile Cys Gln Cys Leu Pro Gly Tyr Gln Gly Glu Lys Cys Glu Lys
    1145                1150                1155

Leu Val Ser Val Asn Phe Ile Asn Lys Glu Ser Tyr Leu Gln Ile
    1160                1165                1170
```

Pro Ser Ala Lys Val Arg Pro Gln Thr Asn Ile Thr Leu Gln Ile
1175                1180                1185

Ala Thr Asp Glu Asp Ser Gly Ile Leu Leu Tyr Lys Gly Asp Lys
1190                1195                1200

Asp His Ile Ala Val Glu Leu Tyr Arg Gly Arg Val Arg Ala Ser
1205                1210                1215

Tyr Asp Thr Gly Ser His Pro Ala Ser Ala Ile Tyr Ser Val Glu
1220                1225                1230

Thr Ile Asn Asp Gly Asn Phe His Ile Val Glu Leu Leu Ala Leu
1235                1240                1245

Asp Gln Ser Leu Ser Leu Ser Val Asp Gly Gly Asn Pro Lys Ile
1250                1255                1260

Ile Thr Asn Leu Ser Lys Gln Ser Thr Leu Asn Phe Asp Ser Pro
1265                1270                1275

Leu Tyr Val Gly Gly Met Pro Gly Lys Ser Asn Val Ala Ser Leu
1280                1285                1290

Arg Gln Ala Pro Gly Gln Asn Gly Thr Ser Phe His Gly Cys Ile
1295                1300                1305

Arg Asn Leu Tyr Ile Asn Ser Glu Leu Gln Asp Phe Gln Lys Val
1310                1315                1320

Pro Met Gln Thr Gly Ile Leu Pro Gly Cys Glu Pro Cys His Lys
1325                1330                1335

Lys Val Cys Ala His Gly Thr Cys Gln Pro Ser Ser Gln Ala Gly
1340                1345                1350

Phe Thr Cys Glu Cys Gln Glu Gly Trp Met Gly Pro Leu Cys Asp
1355                1360                1365

Gln Arg Thr Asn Asp Pro Cys Leu Gly Asn Lys Cys Val His Gly
1370                1375                1380

Thr Cys Leu Pro Ile Asn Ala Phe Ser Tyr Ser Cys Lys Cys Leu
1385                1390                1395

Glu Gly His Gly Gly Val Leu Cys Asp Glu Glu Asp Leu Phe
1400                1405                1410

Asn Pro Cys Gln Ala Ile Lys Cys Lys His Gly Lys Cys Arg Leu
1415                1420                1425

Ser Gly Leu Gly Gln Pro Tyr Cys Glu Cys Ser Ser Gly Tyr Thr
1430                1435                1440

Gly Asp Ser Cys Asp Arg Glu Ile Ser Cys Arg Gly Glu Arg Ile
1445                1450                1455

Arg Asp Tyr Tyr Gln Lys Gln Gln Gly Tyr Ala Ala Cys Gln Thr
1460                1465                1470

Thr Lys Lys Val Ser Arg Leu Glu Cys Arg Gly Gly Cys Ala Gly
1475                1480                1485

Gly Gln Cys Cys Gly Pro Leu Arg Ser Lys Arg Arg Lys Tyr Ser
1490                1495                1500

Phe Glu Cys Thr Asp Gly Ser Ser Phe Val Asp Glu Val Glu Lys
1505                1510                1515

Val Val Lys Cys Gly Cys Thr Arg Cys Val Ser
1520                1525

<210> SEQ ID NO 6
<211> LENGTH: 3872
<212> TYPE: DNA
<213> ORGANISM: Homo sapiens

<400> SEQUENCE: 6

-continued

```
gcggccgcga attcggcacg agcagcagga caaagtgctc gggacaagga catagggctg      60
agagtagcca tgggctctgg aggagacagc ctcctggggg cagggggttc cctgcctctg     120
ctgctcctgc tcatcatggg aggcatggct caggactccc cgccccagat cctagtccac     180
ccccaggacc agctgttcca gggccctggc cctgccagga tgagctgcca agcctcaggc     240
cagccacctc ccaccatccg ctggttgctg aatgggcagc ccctgagcat ggtgccccca     300
gacccacacc acctcctgcc tgatgggacc cttctgctgc tacagccccc tgcccgggga     360
catgcccacg atggccaggc cctgtccaca gacctgggtg tctacacatg tgaggccagc     420
aaccggcttg gcacggcagt cagcagaggc gctcggctgt ctgtggctgt cctccgggag     480
gatttccaga tccagcctcg ggacatggtg gctgtggtgg gtgagcagtt tactctggaa     540
tgtgggccgc cctgggccca cccagagccc acagtctcat ggtggaaaga tgggaaaccc     600
ctggccctcc agcccggaag gcacacagtg tccggggggt ccctgctgat ggcaagagca     660
gagaagagtg acgaagggac ctacatgtgt gtggccacca acagcgcagg acataggag      720 agccgcgcag cccgggtttc catccaggag ccccaggact acacggagcc tgtggagctt     780
ctggctgtgc gaattcagct ggaaaatgtg acactgctga accggatcc tgcagagggc      840 cccaagccta accggcggt gtggctcagc tggaaggtca gtggccctgc tgcgcctgcc      900
caatcttaca cggccttgtt caggacccag actgccccgg gaggccaggg agctccgtgg     960
gcagaggagc tgctggccgg ctggcagagc gcagagcttg gaggcctcca ctggggccaa    1020
gactacgagt tcaaagtgag accatcctct ggccgggctc gaggccctga cagcaacgtg    1080
ctgctcctga ggctgccgga aaaagtgccc agtgccccac ctcaggaagt gactctaaag    1140
cctggcaatg gcactgtctt tgtgagctgg gtcccaccac ctgctgaaaa ccacaatggc    1200
atcatccgtg gctaccaggt ctggagcctg ggcaacacat cactgccacc agccaactgg    1260
actgtagttg gtgagcagac ccagctgaa atcgccaccc atatgccagg ctcctactgc    1320
gtgcaagtgg ctgcagtcac tggtgctgga gctggggagc ccagtagacc tgtctgcctc    1380
cttttagagc aggccatgga gcgagccacc caagaaccca gtgagcatgg tccctggacc    1440
ctggagcagc tgagggctac cttgaagcgg cctgaggtca ttgccacctg cggtgttgca    1500
ctctggctgt gcttctggg caccgccgtg tgtatccacc gccggcgccg agctagggtg    1560
cacctgggcc caggtctgta cagatatacc agtgaggatg ccatcctaaa acacaggatg    1620
gatcacagtg actcccagtg gttggcagac acttggcgtt ccactctgg ctctcgggac    1680 ctgagcagca gcagcagcct cagcagtcgg ctgggggcgg atgcccggga cccactagac    1740
tgtcgtcgct ccttgctctc ctgggactcc cgaagcccg gcgtgcccct gcttccagac    1800
accagcactt tttatggctc cctcatcgct gagctgccct ccagtacccc agccaggcca    1860 agtcccagg tcccagctgt caggcgcctc ccacccagc tggcccagct ctccagcccc    1920
tgttccagct cagacagcct ctgcagccgc agggactct cttctccccg cttgtctctg    1980
gcccctgcag aggcttggaa ggccaaaaag aagcaggagc tgcagcatgc caacagttcc    2040
ccactgctcc ggggcagcca ctccttggag ctccgggcct gtgagttagg aaatagaggt    2100
tccaagaacc tttcccaaag cccaggagct gtgcccaag ctctggttgc ctggcgggcc    2160
ctgggaccga aactcctcag ctcctcaaat gagctggtta tcgtcatct ccctccagca    2220 cccctctttc tcatgaaaac tcccccaact cagagtcaac agacccagcc tccggtggca    2280
ccacaggctc cctcctccat cctgctgcca gcagcccca tccccatcct tagccctgc    2340 agtccccta gccccaggc ctcttccctc tctggcccca gcccagcttc cagtcgcctg    2400
```

```
tccagctcct cactgtcatc cctgggggag gatcaagaca gcgtgctgac ccctgaggag    2460
gtagccctgt gcttggaact cagtgagggt gaggagactc ccaggaacag cgtctctccc    2520
atgccaaggg ctccttcacc ccccaccacc tatgggtaca tcagcgtccc aacagcctca    2580
gagttcacgg acatgggcag gactggagga ggggtggggc caaggggggg agtcttgctg    2640
tgcccacctc ggccctgcct cacccccacc cccagcgagg gctccttagc caatggttgg    2700
ggctcagcct ctgaggacaa tgccgccagc gccagagcca gccttgtcag ctcctccgat    2760
ggctccttcc tcgctgatgc tcactttgcc cgggccctgg cagtggctgt ggatagcttt    2820
ggtttcggtc tagagcccag ggaggcagac tgcgtcttca tagatgcctc atcacctccc    2880
tccccacggg atgagatctt cctgaccccc aacctctccc tgcccctgtg ggagtggagg    2940
ccagactggt tggaagacat ggaggtcagc cacacccagc ggctgggaag ggggatgcct    3000
ccctggcccc ctgactctca gatctcttcc cagagaagtc agctccactg tcgtatgccc    3060
aaggctggtg cttctcctgt agattactcc tgaaccgtgt ccctgagact tcccagacgg    3120
gaatcagaac cacttctcct gtccaccccac aagacctggg ctgtggtgtg tgggtcttgg    3180
cctgtgtttc tctgcagctg gggtccacct tcccaagcct ccagagagtt ctccctccac    3240
gattgtgaaa acaaatgaaa acaaaattag agcaaagctg acctggagcc ctcagggagc    3300
aaaacatcat ctccacctga ctcctagcca ctgctttctc ctctgtgcca tccactccca    3360
ccaccaggtt gttttggcct gaggagcagc cctgcctgct gctcttcccc caccatttgg    3420
atcacaggaa gtgaggagc cagaggtgcc tttgtggagg acagcagtgg ctgctgggag    3480
agggctgtgg aggaaggagc ttctcggagc cccctctcag ccttacctgg gcccctcctc    3540 tagagaaag ctcaactctc tcccaacctc accatggaaa gaaataatt atgaatgcca    3600 ctgaggcact gaggccctac ctcatgccaa acaagggtt caaggctggg tctagcgagg    3660
atgctgaagg aagggaggta tgagaccgta ggtcaaaagc accatcctcg tactgttgtc    3720
actatgagct taagaaattt gataccataa aatggtaaag acttgaaaaa aaaaaaaaa    3780 aaaaaaaaa aaaaaaaaaa aaaaaaaaaa aaaaaaaaaa aaaaaaaaaa aaaaaaaaaa    3840
aaaaaaaaaa aaaaaaaaaa aaaaaaaaaa aa                                  3872
```

<210> SEQ ID NO 7
<211> LENGTH: 1523
<212> TYPE: PRT
<213> ORGANISM: Homo sapiens

<400> SEQUENCE: 7

```
Met Ala Pro Gly Trp Ala Gly Val Gly Ala Ala Val Arg Ala Arg Leu
1               5                   10                  15

Ala Leu Ala Leu Ala Leu Ala Ser Val Leu Ser Gly Pro Pro Ala Val
                20                  25                  30

Ala Cys Pro Thr Lys Cys Thr Cys Ser Ala Ala Ser Val Asp Cys His
            35                  40                  45

Gly Leu Gly Leu Arg Ala Val Pro Arg Gly Ile Pro Arg Asn Ala Glu
        50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

Val Ser Val Ile Glu Arg Gly Ala Phe Gln Asp Leu Lys Gln Leu Glu
                100                 105                 110
```

-continued

Arg Leu Arg Leu Asn Lys Asn Lys Leu Gln Val Leu Pro Glu Leu Leu
    115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Ile Thr Asp Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Val Gly Gln Phe Thr
225                 230                 235                 240

Leu Cys Met Ala Pro Val His Leu Arg Gly Phe Asn Val Ala Asp Val
                245                 250                 255

Gln Lys Lys Glu Tyr Val Cys Pro Ala Pro His Ser Glu Pro Pro Ser
            260                 265                 270

Cys Asn Ala Asn Ser Ile Ser Cys Pro Ser Pro Cys Thr Cys Ser Asn
        275                 280                 285

Asn Ile Val Asp Cys Arg Gly Lys Gly Leu Met Glu Ile Pro Ala Asn
    290                 295                 300

Leu Pro Glu Gly Ile Val Glu Ile Arg Leu Gln Asn Ser Ile Lys
305                 310                 315                 320

Ala Ile Pro Ala Gly Ala Phe Thr Gln Tyr Lys Lys Leu Lys Arg Ile
                325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
        355                 360                 365

Glu Ile Ala Lys Gly Leu Phe Asp Gly Leu Val Ser Leu Gln Leu Leu
    370                 375                 380

Leu Leu Asn Ala Asn Lys Ile Asn Cys Leu Arg Val Asn Thr Phe Gln
385                 390                 395                 400

Asp Leu Gln Asn Leu Asn Leu Ser Leu Tyr Asp Asn Lys Leu Gln
                405                 410                 415

Thr Ile Ser Lys Gly Leu Phe Ala Pro Leu Gln Ser Ile Gln Thr Leu
            420                 425                 430

His Leu Ala Gln Asn Pro Phe Val Cys Asp Cys His Leu Lys Trp Leu
        435                 440                 445

Ala Asp Tyr Leu Gln Asp Asn Pro Ile Glu Thr Ser Gly Ala Arg Cys
    450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Ser Arg Phe Ser
                485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Val Arg Ile Pro Ser
        515                 520                 525

His Leu Pro Glu Tyr Val Thr Asp Leu Arg Leu Asn Asp Asn Glu Val
    530                 535                 540

```
Ser Val Leu Glu Ala Thr Gly Ile Phe Lys Lys Leu Pro Asn Leu Arg
545                 550                 555                 560

Lys Ile Asn Leu Ser Asn Asn Lys Ile Lys Glu Val Arg Glu Gly Ala
                565                 570                 575

Phe Asp Gly Ala Ala Ser Val Gln Glu Leu Met Leu Thr Gly Asn Gln
            580                 585                 590

Leu Glu Thr Val His Gly Arg Val Phe Arg Gly Leu Ser Gly Leu Lys
        595                 600                 605

Thr Leu Met Leu Arg Ser Asn Leu Ile Gly Cys Val Ser Asn Asp Thr
    610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Leu Ser
                645                 650                 655

Thr Ile Asn Leu Leu Ser Asn Pro Phe Asn Cys Asn Cys His Leu Ala
            660                 665                 670

Trp Leu Gly Lys Trp Leu Arg Lys Arg Arg Ile Val Ser Gly Asn Pro
        675                 680                 685

Arg Cys Gln Lys Pro Phe Phe Leu Lys Glu Ile Pro Ile Gln Asp Val
    690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Met Glu Thr Val Val
                725                 730                 735

Arg Cys Ser Asn Lys Gly Leu Arg Ala Leu Pro Arg Gly Met Pro Lys
            740                 745                 750

Asp Val Thr Glu Leu Tyr Leu Glu Gly Asn His Leu Thr Ala Val Pro
        755                 760                 765

Arg Glu Leu Ser Ala Leu Arg His Leu Thr Leu Ile Asp Leu Ser Asn
    770                 775                 780

Asn Ser Ile Ser Met Leu Thr Asn Tyr Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
            820                 825                 830

Asn Asp Ile Ser Ser Val Pro Glu Gly Ser Phe Asn Asp Leu Thr Ser
        835                 840                 845

Leu Ser His Leu Ala Leu Gly Thr Asn Pro Leu His Cys Asp Cys Ser
    850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Pro Met Ala Asp Arg Leu Leu Leu
                885                 890                 895

Thr Thr Pro Thr His Arg Phe Gln Cys Lys Gly Pro Val Asp Ile Asn
            900                 905                 910

Ile Val Ala Lys Cys Asn Ala Cys Leu Ser Ser Pro Cys Lys Asn Asn
        915                 920                 925

Gly Thr Cys Thr Gln Asp Pro Val Glu Leu Tyr Arg Cys Ala Cys Pro
    930                 935                 940

Tyr Ser Tyr Lys Gly Lys Asp Cys Thr Val Pro Ile Asn Thr Cys Ile
945                 950                 955                 960

Gln Asn Pro Cys Gln His Gly Gly Thr Cys His Leu Ser Asp Ser His
```

```
                        965                 970                 975
Lys Asp Gly Phe Ser Cys Ser Cys Pro Leu Gly Phe Glu Gly Gln Arg
                980                 985                 990
Cys Glu Ile Asn Pro Asp Asp Cys  Glu Asp Asn Asp Cys  Glu Asn Asn
            995                1000                1005
Ala Thr  Cys Val Asp Gly Ile  Asn Asn Tyr Val Cys  Ile Cys Pro
    1010                1015                1020
Pro Asn  Tyr Thr Gly Glu Leu  Cys Asp Glu Val Ile  Asp His Cys
    1025                1030                1035
Val Pro  Glu Leu Asn Leu Cys  Gln His Glu Ala Lys  Cys Ile Pro
    1040                1045                1050
Leu Asp  Lys Gly Phe Ser Cys  Glu Cys Val Pro Gly  Tyr Ser Gly
    1055                1060                1065
Lys Leu  Cys Glu Thr Asp Asn  Asp Asp Cys Val Ala  His Lys Cys
    1070                1075                1080
Arg His  Gly Ala Gln Cys Val  Asp Thr Ile Asn Gly  Tyr Thr Cys
    1085                1090                1095
Thr Cys  Pro Gln Gly Phe Ser  Gly Pro Phe Cys Glu  His Pro Pro
    1100                1105                1110
Pro Met  Val Leu Leu Gln Thr  Ser Pro Cys Asp Gln  Tyr Glu Cys
    1115                1120                1125
Gln Asn  Gly Ala Gln Cys Ile  Val Val Gln Glu Pro  Thr Cys
    1130                1135                1140
Arg Cys  Pro Pro Gly Phe Ala  Gly Pro Arg Cys Glu  Lys Leu Ile
    1145                1150                1155
Thr Val  Asn Phe Val Gly Lys  Asp Ser Tyr Val Glu  Leu Ala Ser
    1160                1165                1170
Ala Lys  Val Arg Pro Gln Ala  Asn Ile Ser Leu Gln  Val Ala Thr
    1175                1180                1185
Asp Lys  Asp Asn Gly Ile Leu  Leu Tyr Lys Gly Asp  Asn Asp Pro
    1190                1195                1200
Leu Ala  Leu Glu Leu Tyr Gln  Gly His Val Arg Leu  Val Tyr Asp
    1205                1210                1215
Ser Leu  Ser Ser Pro Pro Thr  Thr Val Tyr Ser Val  Glu Thr Val
    1220                1225                1230
Asn Asp  Gly Gln Phe His Ser  Val Glu Leu Val Thr  Leu Asn Gln
    1235                1240                1245
Thr Leu  Asn Leu Val Val Asp  Lys Gly Thr Pro Lys  Ser Leu Gly
    1250                1255                1260
Lys Leu  Gln Lys Gln Pro Ala  Val Gly Ile Asn Ser  Pro Leu Tyr
    1265                1270                1275
Leu Gly  Gly Ile Pro Thr Ser  Thr Gly Leu Ser Ala  Leu Arg Gln
    1280                1285                1290
Gly Thr  Asp Arg Pro Leu Gly  Gly Phe His Gly Cys  Ile His Glu
    1295                1300                1305
Val Arg  Ile Asn Asn Glu Leu  Gln Asp Phe Lys Ala  Leu Pro Pro
    1310                1315                1320
Gln Ser  Leu Gly Val Ser Pro  Gly Cys Lys Ser Cys  Thr Val Cys
    1325                1330                1335
Lys His  Gly Leu Cys Arg Ser  Val Glu Lys Asp Ser  Val Val Cys
    1340                1345                1350
Glu Cys  Arg Pro Gly Trp Thr  Gly Pro Leu Cys Asp  Gln Glu Ala
    1355                1360                1365
```

```
Arg Asp Pro Cys Leu Gly His Arg Cys His His Gly Lys Cys Val
    1370            1375                1380

Ala Thr Gly Thr Ser Tyr Met Cys Lys Cys Ala Glu Gly Tyr Gly
    1385            1390                1395

Gly Asp Leu Cys Asp Asn Lys Asn Asp Ser Ala Asn Ala Cys Ser
    1400            1405                1410

Ala Phe Lys Cys His His Gly Gln Cys His Ile Ser Asp Gln Gly
    1415            1420                1425

Glu Pro Tyr Cys Leu Cys Gln Pro Gly Phe Ser Gly Glu His Cys
    1430            1435                1440

Gln Gln Glu Asn Pro Cys Leu Gly Gln Val Val Arg Glu Val Ile
    1445            1450                1455

Arg Arg Gln Lys Gly Tyr Ala Ser Cys Ala Thr Ala Ser Lys Val
    1460            1465                1470

Pro Ile Met Glu Cys Arg Gly Gly Cys Gly Pro Gln Cys Cys Gln
    1475            1480                1485

Pro Thr Arg Ser Lys Arg Arg Lys Tyr Val Phe Gln Cys Thr Asp
    1490            1495                1500

Gly Ser Ser Phe Val Glu Glu Val Glu Arg His Leu Glu Cys Gly
    1505            1510                1515

Cys Leu Ala Cys Ser
    1520

<210> SEQ ID NO 8
<211> LENGTH: 1523
<212> TYPE: PRT
<213> ORGANISM: Homo sapiens

<400> SEQUENCE: 8

Met Ala Pro Gly Trp Ala Gly Val Gly Ala Ala Val Arg Ala Arg Leu
1               5                   10                  15

Ala Leu Ala Leu Ala Leu Ala Ser Val Leu Ser Gly Pro Pro Ala Val
                20                  25                  30

Ala Cys Pro Thr Lys Cys Thr Cys Ser Ala Ala Ser Val Asp Cys His
            35                  40                  45

Gly Leu Gly Leu Arg Ala Val Pro Arg Gly Ile Pro Arg Asn Ala Glu
    50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

Val Ser Val Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Ile Thr Asp Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205
```

-continued

```
Thr Leu Arg Leu His Ser Asn His Leu Tyr Cys Asp Cys His Leu Ala
    210                 215                 220
Trp Leu Ser Asp Trp Leu Arg Gln Arg Arg Thr Val Gly Gln Phe Thr
225                 230                 235                 240
Leu Cys Met Ala Pro Val His Leu Arg Gly Phe Asn Val Ala Asp Val
                    245                 250                 255
Gln Lys Lys Glu Tyr Val Cys Pro Ala Pro His Ser Glu Pro Pro Ser
                260                 265                 270
Cys Asn Ala Asn Ser Ile Ser Cys Pro Ser Pro Cys Thr Cys Ser Asn
            275                 280                 285
Asn Ile Val Asp Cys Arg Gly Lys Gly Leu Met Glu Ile Pro Ala Asn
    290                 295                 300
Leu Pro Glu Gly Ile Val Glu Ile Arg Leu Glu Gln Asn Ser Ile Lys
305                 310                 315                 320
Ala Ile Pro Ala Gly Ala Phe Thr Gln Tyr Lys Lys Leu Lys Arg Ile
                    325                 330                 335
Asp Ile Ser Lys Asn Gln Ile Ser Asp Ile Ala Pro Asp Ala Phe Gln
                340                 345                 350
Gly Leu Lys Ser Leu Thr Ser Leu Val Leu Tyr Gly Asn Lys Ile Thr
            355                 360                 365
Glu Ile Ala Lys Gly Leu Phe Asp Gly Leu Val Ser Leu Gln Leu Leu
    370                 375                 380
Leu Leu Asn Ala Asn Lys Ile Asn Cys Leu Arg Val Asn Thr Phe Gln
385                 390                 395                 400
Asp Leu Gln Asn Leu Asn Leu Leu Ser Leu Tyr Asp Asn Lys Leu Gln
                    405                 410                 415
Thr Ile Ser Lys Gly Leu Phe Ala Pro Leu Gln Ser Ile Gln Thr Leu
                420                 425                 430
His Leu Ala Gln Asn Pro Phe Val Cys Asp Cys His Leu Lys Trp Leu
            435                 440                 445
Ala Asp Tyr Leu Gln Asp Asn Pro Ile Glu Thr Ser Gly Ala Arg Cys
    450                 455                 460
Ser Ser Pro Arg Arg Leu Ala Asn Lys Arg Ile Ser Gln Ile Lys Ser
465                 470                 475                 480
Lys Lys Phe Arg Cys Ser Gly Ser Glu Asp Tyr Arg Ser Arg Phe Ser
                    485                 490                 495
Ser Glu Cys Phe Met Asp Leu Val Cys Pro Glu Lys Cys Arg Cys Glu
                500                 505                 510
Gly Thr Ile Val Asp Cys Ser Asn Gln Lys Leu Val Arg Ile Pro Ser
            515                 520                 525
His Leu Pro Glu Tyr Val Thr Asp Leu Arg Leu Asn Asp Asn Glu Val
    530                 535                 540
Ser Val Leu Glu Ala Thr Gly Ile Phe Lys Lys Leu Pro Asn Leu Arg
545                 550                 555                 560
Lys Ile Asn Leu Ser Asn Asn Lys Ile Lys Glu Val Arg Glu Gly Ala
                    565                 570                 575
Phe Asp Gly Ala Ala Ser Val Gln Glu Leu Met Leu Thr Gly Asn Gln
                580                 585                 590
Leu Glu Thr Val His Gly Arg Val Phe Arg Gly Leu Ser Gly Leu Lys
            595                 600                 605
Thr Leu Met Leu Arg Ser Asn Leu Ile Gly Cys Val Ser Asn Asp Thr
    610                 615                 620
Phe Ala Gly Leu Ser Ser Val Arg Leu Leu Ser Leu Tyr Asp Asn Arg
625                 630                 635                 640
```

```
Ile Thr Thr Ile Thr Pro Gly Ala Phe Thr Thr Leu Val Ser Leu Ser
            645                 650                 655

Thr Ile Asn Leu Leu Ser Asn Pro Phe Asn Cys Asn Cys His Leu Ala
            660                 665                 670

Trp Leu Gly Lys Trp Leu Arg Lys Arg Ile Val Ser Gly Asn Pro
            675                 680                 685

Arg Cys Gln Lys Pro Phe Phe Leu Lys Glu Ile Pro Ile Gln Asp Val
690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Met Glu Thr Val Val
                725                 730                 735

Arg Cys Ser Asn Lys Gly Leu Arg Ala Leu Pro Arg Gly Met Pro Lys
            740                 745                 750

Asp Val Thr Glu Leu Tyr Leu Glu Gly Asn His Leu Thr Ala Val Pro
            755                 760                 765

Arg Glu Leu Ser Ala Leu Arg His Leu Thr Leu Ile Asp Leu Ser Asn
770                 775                 780

Asn Ser Ile Ser Met Leu Thr Asn Tyr Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
            820                 825                 830

Asn Asp Ile Ser Ser Val Pro Glu Gly Ser Phe Asn Asp Leu Thr Ser
            835                 840                 845

Leu Ser His Leu Ala Leu Gly Thr Asn Pro Leu His Cys Asp Cys Ser
            850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Pro Met Ala Asp Arg Leu Leu Leu
                885                 890                 895

Thr Thr Pro Thr His Arg Phe Gln Cys Lys Gly Pro Val Asp Ile Asn
            900                 905                 910

Ile Val Ala Lys Cys Asn Ala Cys Leu Ser Ser Pro Cys Lys Asn Asn
            915                 920                 925

Gly Thr Cys Thr Gln Asp Pro Val Glu Leu Tyr Arg Cys Ala Cys Pro
930                 935                 940

Tyr Ser Tyr Lys Gly Lys Asp Cys Thr Val Pro Ile Asn Thr Cys Ile
945                 950                 955                 960

Gln Asn Pro Cys Gln His Gly Gly Thr Cys His Leu Ser Asp Ser His
                965                 970                 975

Lys Asp Gly Phe Ser Cys Ser Cys Pro Leu Gly Phe Glu Gly Gln Arg
            980                 985                 990

Cys Glu Ile Asn Pro Asp Asp Cys  Glu Asp Asn Asp Cys Glu Asn Asn
            995                 1000                1005

Ala Thr Cys Val Asp Gly Ile Asn Asn Tyr Val Cys Ile Cys Pro
            1010                1015                 1020

Pro Asn Tyr Thr Gly Glu Leu Cys Asp Glu Val Ile Asp His Cys
            1025                1030                 1035

Val Pro Glu Leu Asn Leu Cys Gln His Glu Ala Lys Cys Ile Pro
            1040                1045                 1050

Leu Asp Lys Gly Phe Ser Cys Glu Cys Val Pro Gly Tyr Ser Gly
```

|      |      |      |      |      |      |      |      |      |      |
|------|------|------|------|------|------|------|------|------|------|
|      |      | 1055 |      |      | 1060 |      |      | 1065 |      |
| Lys  | Leu  | Cys  | Glu  | Thr  | Asp  | Asn  | Asp  | Cys  | Val  | Ala  | His  | Lys  | Cys  |
|      |      | 1070 |      |      | 1075 |      |      | 1080 |      |
| Arg  | His  | Gly  | Ala  | Gln  | Cys  | Val  | Asp  | Thr  | Ile  | Asn  | Gly  | Tyr  | Thr  | Cys  |
|      |      | 1085 |      |      | 1090 |      |      | 1095 |      |
| Thr  | Cys  | Pro  | Gln  | Gly  | Phe  | Ser  | Gly  | Pro  | Phe  | Cys  | Glu  | His  | Pro  | Pro  |
|      |      | 1100 |      |      | 1105 |      |      | 1110 |      |
| Pro  | Met  | Val  | Leu  | Leu  | Gln  | Thr  | Ser  | Pro  | Cys  | Asp  | Gln  | Tyr  | Glu  | Cys  |
|      |      | 1115 |      |      | 1120 |      |      | 1125 |      |
| Gln  | Asn  | Gly  | Ala  | Gln  | Cys  | Ile  | Val  | Val  | Gln  | Gln  | Glu  | Pro  | Thr  | Cys  |
|      |      | 1130 |      |      | 1135 |      |      | 1140 |      |
| Arg  | Cys  | Pro  | Pro  | Gly  | Phe  | Ala  | Gly  | Pro  | Arg  | Cys  | Glu  | Lys  | Leu  | Ile  |
|      |      | 1145 |      |      | 1150 |      |      | 1155 |      |
| Thr  | Val  | Asn  | Phe  | Val  | Gly  | Lys  | Asp  | Ser  | Tyr  | Val  | Glu  | Leu  | Ala  | Ser  |
|      |      | 1160 |      |      | 1165 |      |      | 1170 |      |
| Ala  | Lys  | Val  | Arg  | Pro  | Gln  | Ala  | Asn  | Ile  | Ser  | Leu  | Gln  | Val  | Ala  | Thr  |
|      |      | 1175 |      |      | 1180 |      |      | 1185 |      |
| Asp  | Lys  | Asp  | Asn  | Gly  | Ile  | Leu  | Leu  | Tyr  | Lys  | Gly  | Asp  | Asn  | Asp  | Pro  |
|      |      | 1190 |      |      | 1195 |      |      | 1200 |      |
| Leu  | Ala  | Leu  | Glu  | Leu  | Tyr  | Gln  | Gly  | His  | Val  | Arg  | Leu  | Val  | Tyr  | Asp  |
|      |      | 1205 |      |      | 1210 |      |      | 1215 |      |
| Ser  | Leu  | Ser  | Ser  | Pro  | Pro  | Thr  | Thr  | Val  | Tyr  | Ser  | Val  | Glu  | Thr  | Val  |
|      |      | 1220 |      |      | 1225 |      |      | 1230 |      |
| Asn  | Asp  | Gly  | Gln  | Phe  | His  | Ser  | Val  | Glu  | Leu  | Val  | Thr  | Leu  | Asn  | Gln  |
|      |      | 1235 |      |      | 1240 |      |      | 1245 |      |
| Thr  | Leu  | Asn  | Leu  | Val  | Val  | Asp  | Lys  | Gly  | Thr  | Pro  | Lys  | Ser  | Leu  | Gly  |
|      |      | 1250 |      |      | 1255 |      |      | 1260 |      |
| Lys  | Leu  | Gln  | Lys  | Gln  | Pro  | Ala  | Val  | Gly  | Ile  | Asn  | Ser  | Pro  | Leu  | Tyr  |
|      |      | 1265 |      |      | 1270 |      |      | 1275 |      |
| Leu  | Gly  | Gly  | Ile  | Pro  | Thr  | Ser  | Thr  | Gly  | Leu  | Ser  | Ala  | Leu  | Arg  | Gln  |
|      |      | 1280 |      |      | 1285 |      |      | 1290 |      |
| Gly  | Thr  | Asp  | Arg  | Pro  | Leu  | Gly  | Gly  | Phe  | His  | Gly  | Cys  | Ile  | His  | Glu  |
|      |      | 1295 |      |      | 1300 |      |      | 1305 |      |
| Val  | Arg  | Ile  | Asn  | Asn  | Glu  | Leu  | Gln  | Asp  | Phe  | Lys  | Ala  | Leu  | Pro  | Pro  |
|      |      | 1310 |      |      | 1315 |      |      | 1320 |      |
| Gln  | Ser  | Leu  | Gly  | Val  | Ser  | Pro  | Gly  | Cys  | Lys  | Ser  | Cys  | Thr  | Val  | Cys  |
|      |      | 1325 |      |      | 1330 |      |      | 1335 |      |
| Lys  | His  | Gly  | Leu  | Cys  | Arg  | Ser  | Val  | Glu  | Lys  | Asp  | Ser  | Val  | Val  | Cys  |
|      |      | 1340 |      |      | 1345 |      |      | 1350 |      |
| Glu  | Cys  | Arg  | Pro  | Gly  | Trp  | Thr  | Gly  | Pro  | Leu  | Cys  | Asp  | Gln  | Glu  | Ala  |
|      |      | 1355 |      |      | 1360 |      |      | 1365 |      |
| Arg  | Asp  | Pro  | Cys  | Leu  | Gly  | His  | Arg  | Cys  | His  | His  | Gly  | Lys  | Cys  | Val  |
|      |      | 1370 |      |      | 1375 |      |      | 1380 |      |
| Ala  | Thr  | Gly  | Thr  | Ser  | Tyr  | Met  | Cys  | Lys  | Cys  | Ala  | Glu  | Gly  | Tyr  | Gly  |
|      |      | 1385 |      |      | 1390 |      |      | 1395 |      |
| Gly  | Asp  | Leu  | Cys  | Asp  | Asn  | Lys  | Asn  | Asp  | Ser  | Ala  | Asn  | Ala  | Cys  | Ser  |
|      |      | 1400 |      |      | 1405 |      |      | 1410 |      |
| Ala  | Phe  | Lys  | Cys  | His  | His  | Gly  | Gln  | Cys  | His  | Ile  | Ser  | Asp  | Gln  | Gly  |
|      |      | 1415 |      |      | 1420 |      |      | 1425 |      |
| Glu  | Pro  | Tyr  | Cys  | Leu  | Cys  | Gln  | Pro  | Gly  | Phe  | Ser  | Gly  | Glu  | His  | Cys  |
|      |      | 1430 |      |      | 1435 |      |      | 1440 |      |
| Gln  | Gln  | Glu  | Asn  | Pro  | Cys  | Leu  | Gly  | Gln  | Val  | Val  | Arg  | Glu  | Val  | Ile  |
|      |      | 1445 |      |      | 1450 |      |      | 1455 |      |

-continued

Arg Arg Gln Lys Gly Tyr Ala Ser Cys Ala Thr Ala Ser Lys Val
1460                1465                1470

Pro Ile Met Glu Cys Arg Gly Cys Gly Pro Gln Cys Cys Gln
1475                1480                1485

Pro Thr Arg Ser Lys Arg Arg Lys Tyr Val Phe Gln Cys Thr Asp
1490                1495                1500

Gly Ser Ser Phe Val Glu Glu Val Glu Arg His Leu Glu Cys Gly
1505                1510                1515

Cys Leu Ala Cys Ser
1520

<210> SEQ ID NO 9
<211> LENGTH: 771
<212> TYPE: PRT
<213> ORGANISM: Homo sapiens

<400> SEQUENCE: 9

Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
                20                  25                  30

Lys Leu Ser Tyr Lys Glu Met Leu Glu Ser Asn Asn Val Ile Thr Phe
            35                  40                  45

Asn Gly Leu Ala Asn Ser Ser Ser Tyr His Thr Phe Leu Leu Asp Glu
        50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

-continued

```
Phe Asp Glu Leu Gln Asp Val Phe Leu Met Asn Phe Lys Asp Pro Lys
305                 310                 315                 320
Asn Pro Val Val Tyr Gly Val Phe Thr Thr Ser Ser Asn Ile Phe Lys
            325                 330                 335
Gly Ser Ala Val Cys Met Tyr Ser Met Ser Asp Val Arg Arg Val Phe
        340                 345                 350
Leu Gly Pro Tyr Ala His Arg Asp Gly Pro Asn Tyr Gln Trp Val Pro
    355                 360                 365
Tyr Gln Gly Arg Val Pro Tyr Pro Arg Pro Gly Thr Cys Pro Ser Lys
370                 375                 380
Thr Phe Gly Gly Phe Asp Ser Thr Lys Asp Leu Pro Asp Val Ile
385                 390                 395                 400
Thr Phe Ala Arg Ser His Pro Ala Met Tyr Asn Pro Val Phe Pro Met
            405                 410                 415
Asn Asn Arg Pro Ile Val Ile Lys Thr Asp Val Asn Tyr Gln Phe Thr
        420                 425                 430
Gln Ile Val Val Asp Arg Val Asp Ala Glu Asp Gly Gln Tyr Asp Val
    435                 440                 445
Met Phe Ile Gly Thr Asp Val Gly Thr Val Leu Lys Val Val Ser Ile
450                 455                 460
Pro Lys Glu Thr Trp Tyr Asp Leu Glu Glu Val Leu Leu Glu Glu Met
465                 470                 475                 480
Thr Val Phe Arg Glu Pro Thr Ala Ile Ser Ala Met Glu Leu Ser Thr
            485                 490                 495
Lys Gln Gln Gln Leu Tyr Ile Gly Ser Thr Ala Gly Val Ala Gln Leu
        500                 505                 510
Pro Leu His Arg Cys Asp Ile Tyr Gly Lys Ala Cys Ala Glu Cys Cys
    515                 520                 525
Leu Ala Arg Asp Pro Tyr Cys Ala Trp Asp Gly Ser Ala Cys Ser Arg
530                 535                 540
Tyr Phe Pro Thr Ala Lys Arg Thr Arg Arg Gln Asp Ile Arg Asn
545                 550                 555                 560
Gly Asp Pro Leu Thr His Cys Ser Asp Leu His His Asp Asn His His
            565                 570                 575
Gly His Ser Pro Glu Glu Arg Ile Ile Tyr Gly Val Glu Asn Ser Ser
        580                 585                 590
Thr Phe Leu Glu Cys Ser Pro Lys Ser Gln Arg Ala Leu Val Tyr Trp
    595                 600                 605
Gln Phe Gln Arg Arg Asn Glu Glu Arg Lys Glu Ile Arg Val Asp
610                 615                 620
Asp His Ile Ile Arg Thr Asp Gln Gly Leu Leu Leu Arg Ser Leu Gln
625                 630                 635                 640
Gln Lys Asp Ser Gly Asn Tyr Leu Cys His Ala Val Glu His Gly Phe
            645                 650                 655
Ile Gln Thr Leu Leu Lys Val Thr Leu Glu Val Ile Asp Thr Glu His
        660                 665                 670
Leu Glu Glu Leu Leu His Lys Asp Asp Gly Asp Gly Ser Lys Thr
    675                 680                 685
Lys Glu Met Ser Asn Ser Met Thr Pro Ser Gln Lys Val Trp Tyr Arg
690                 695                 700
Asp Phe Met Gln Leu Ile Asn His Pro Asn Leu Asn Thr Met Asp Glu
705                 710                 715                 720
Phe Cys Glu Gln Val Trp Lys Arg Asp Arg Lys Gln Arg Gln Arg
                725                 730                 735
```

```
Pro Gly His Thr Pro Gly Asn Ser Asn Lys Trp Lys His Leu Gln Glu
            740                 745                 750

Asn Lys Lys Gly Arg Asn Arg Arg Thr His Glu Phe Glu Arg Ala Pro
        755                 760                 765

Arg Ser Val
    770

<210> SEQ ID NO 10
<211> LENGTH: 5672
<212> TYPE: DNA
<213> ORGANISM: Homo sapiens

<400> SEQUENCE: 10
aagcaccact gcagcagacc ttgttaattt ttttttttt tctttccaca caacagttgt      60
gcctcattat ccggtgcctg gctcggaatt tttttttttt tttttctttt tggagggttt    120
gaagtttctg tgcttcagtg actgttacag aagaagaggt gttagtgttg ccatgaggtc    180
ttgattgtct gcatttatga atgaaactga cctaaatcac ctgttacctc cagtttccag    240
attgtttgaa cttctctggc cgcacaatac aggaaggaag actaaagcag caaagggacc    300
tacagcgtct gcagcatggg ctggttaact aggattgtct gtcttttctg gggagtatta    360
cttacagcaa gagcaaacta tcagaatggg aagaacaatg tgccaaggct gaaattatcc    420
tacaaagaaa tgttggaatc caacaatgtg atcactttca atggcttggc caacagctcc    480
agttatcata ccttcctttt ggatgaggaa cggagtaggc tgtatgttgg agcaaaggat    540
cacatatttt cattcgacct ggttaatatc aaggattttc aaaagattgt gtggccagta    600
tcttacacca aagagatga atgcaagtgg gctggaaaag acatcctgaa agaatgtgct    660
aatttcatca aggtacttaa ggcatataat cagactcact tgtacgcctg tggaacgggg    720
gcttttcatc caatttgcac ctacattgaa attggacatc atcctgagga caatattttt    780
aagctggaga actcacattt tgaaaacggc cgtgggaaga gtccatatga ccctaagctg    840
ctgacagcat ccctttttaat agatggagaa ttatactctg gaactgcagc tgattttatg    900
gggcgagact ttgctatctt ccgaactctt gggcaccacc acccaatcag acagagcag     960
catgattcca ggtggctcaa tgatccaaag ttcattagtg cccacctcat ctcagagagt   1020
gacaatcctg aagatgacaa agtatacttt ttcttccgtg aaaatgcaat agatggagaa   1080
cactctggaa aagctactca cgctagaata ggtcagatat gcaagaatga ctttggaggg   1140
cacagaagtc tggtgaataa atggacaaca ttcctcaaag ctcgtctgat ttgctcagtg   1200
ccaggtccaa atggcattga cactcatttt gatgaactgc aggatgtatt cctaatgaac   1260
tttaagagatc ctaaaaatcc agttgtatat ggagtgttta cgacttccag taacattttc   1320
aagggatcag ccgtgtgtat gtatagcatg agtgatgtga aagggtgtt ccttggtcca   1380
tatgcccaca gggatggacc caactatcaa tgggtgcctt atcaaggaag agtccctat   1440
ccacggccag gaacttgtcc cagcaaaaca tttggtggtt ttgactctac aaaggacctt   1500
cctgatgatg ttataaacctt tgcaagaagt catccagcca tgtacaatcc agtgtttcct   1560
atgaacaatc gcccaatagt gatcaaaacg gatgtaaatt atcaatttac acaaattgtc   1620
gtagaccgag tggatgcaga agatggacag tatgatgtta tgtttatcgg aacagatgtt   1680
gggaccgttc ttaaagtagt ttcaattcct aaggagactt ggtatgattt agaagaggtt   1740
ctgctggaag aaatgacagt ttttcgggaa ccgactgcta tttcagcaat ggagctttcc   1800
actaagcagc aacaactata tattggttca acggctgggg ttgcccagct ccctttacac   1860
```

```
cggtgtgata tttacgggaa agcgtgtgct gagtgttgcc tcgcccgaga cccttactgt    1920
gcttgggatg gttctgcatg ttctcgctat tttcccactg caaagagacg cacaagacga    1980
caagatataa gaaatggaga cccactgact cactgttcag acttacacca tgataatcac    2040
catggccaca gccctgaaga gagaatcatc tatggtgtag agaatagtag cacattttg     2100 gaatgcagtc cgaagtcgca gagagcgctg gtctattggc aattccagag gcgaaatgaa    2160
gagcgaaaag aagagatcag agtggatgat catatcatca ggacagatca aggcttctg    2220 ctacgtagtc tacaacagaa ggattcaggc aattacctct gccatgcggt ggaacatggg    2280
ttcatacaaa ctcttcttaa ggtaaccctg gaagtcattg acacagagca tttggaagaa    2340
cttcttcata agatgatga tggagatggc tctaagacca agaaatgtc caatagcatg      2400 acacctagcc agaaggtctg gtacagagac ttcatgcagc tcatcaacca ccccaatctc    2460
aacacaatgg atgagttctg tgaacaagtt tggaaaaggg accgaaaaca acgtcggcaa    2520
aggccaggac atacccccagg gaacagtaac aaatggaagc acttacaaga aaataagaaa   2580
ggtagaaaca ggaggaccca cgaatttgag agggcaccca ggagtgtctg agctgcatta    2640
cctctagaaa cctcaaacaa gtagaaactt gcctagacaa taactggaaa acaaatgca     2700 atatacatga acttttttca tggcattatg tggatgttta caatggtggg aaattcagct    2760
gagttccacc aattataaat taaatccatg agtaactttc ctaataggct ttttttccta    2820
ataccaccac ctaacagaga acacaggtga atgcagatgt tcactttagc agacttaatg    2880
tttcctatga gatttcactg tacaggtttg tctttcttct ttgcctgaga aataaaaatg    2940
tcatttgcca tattgccatc taaaggagaa aaactgcatc agcaaagcca ttgtattgaa    3000
ctaaagtttt aaaatgaact gcatggattt actaagctga tgaatattcc aaaacgtggt    3060
tggattcaag gatatatttt gtctaccggc cctcatgttt gtatgtactt gaggagtaaa    3120
atgagtaaaa tgatactgaa tgaaatgttc tgtggaaata ttaaaaaaa aaaaaaacat     3180 aagccatcca tcatccagaa gaaaaatgga atacactgat ctactactga tgtcttcttt    3240
cagctttgat ctaaagatgt atttttattaa aactataatt taaatgtacc atgaaaaata   3300
tgcagtaaaa attagttgtt ttctaagcta gagtaggatt tgtcttacaa ttattgtgct    3360
atgtagtttt tgttttaaaa attccaatgg tgtgctgctt tctttggaca ttttatttc     3420 aattctataa gagggataga tgacattgtt ctagaaacac atatacatca ttaagagtga    3480
atctctaaaa ccaggatata aattatgctt tatttctctg agaaaatcaa acaaatggaa    3540
gctgttcaca cctcccctt tttaagcatt atctaaatta attttactt gcataatgtt      3600 cttagaaaaa aaacagaac atttaagcag gaaaaaagga agaaacaagt tgattttaa      3660 gtgcatttta ctataatgaa tcaatgaagg gaaaaggaac tgcatatttc atgaaaataa    3720
taagcattgt cttaatatac tgttaataga aatgtgtct taattccgtg cttgaatccc     3780
tgcatgatat ttgagactaa gatctctctt atgattctac caagaattat atctgtgtca    3840
cttaattttt ttaaaagaga gagatcaata actattcaga gcaacatgtt aaaggcaaag    3900
tttccaatca tttacatctg tatcaggtgc ctcttacctt tccttatttta agacaattat   3960 ttgtacaaga aacacatgac tctttcata tcaatgggag ggactttct acaaagtatt      4020 ttccaggatg caacccacat ttaaacaatg taaaattctt tgtttcctgc aacaacttac    4080
aaaataaggt aaaagactaa aattcaagat ttgcttcctt cattgtccta agacgattcg    4140
ttgagaatca ctgactttga gatatttaaa actttcagca ttatactgtg gtttcttttg    4200
cactgcactc acctattcag gactcctccc ccaggttcct catcatgcac aaaaatgcaa    4260
```

-continued

```
agaaaacatc ttattagtaa ttaatgaagc aacattgaaa ttctaactct agctgtcttt    4320
ggattctaat taactcagca tcaatttctc acctcagact acagtgaatt tttatttcct    4380
atcagctgaa atatttcaca gatggaagct catgtttcag ttttaatgac tgccttgaat    4440
aaacaagttg ttgccacttg tttcaaacaa aagcctaaaa ataatctaca ttcaatttta    4500
ggctccattg actaatatgg tgttgctttt ggaagtactg tatatcctca catggaagcc    4560
aaattgttaa attatttgaa ggacacacca ctgtacagaa agtagtgttt caaatataaa    4620
tcgaagaaca aagagtgctc caaaaaatag gtcattcttt tattttcata agtatctaa     4680 actgtactaa cattcagtgt tgtgtttcat tctaaatttg cagctgaaat aaatttattt    4740
gcgatagcag aaatatctta ttattcatcc tcagaaataa aggatttgaa gggatagaga    4800
ttatatgata aatttataga agactttcag aatttgaatg cattttgttt agtgttatga    4860
aatgacaata gaaaaagtc tcgacttcaa ttaaaagtta cacaaacaaa caaatctaca     4920
ggcatgtctt tatataccat caggtctaag ttttcaaaga aaattgtaga tataacttgc    4980
agataactca ttacagtcat aatctctgcc catgtgtatt gagagggggc agtttgcacg    5040
aaaaagaatt attggcccat ttaataattc agctttaaat agactttgtc atatgcatga    5100
atcatcagag atgaaactgt ttgagagact catgtgacct tacgaaaatt acaacagcag    5160
tcttaaagta tgaaaaagat gcatcacagc agagacatta tggcccagtt gatatcaaat    5220
gtaaaatgta aatgcatgta aatgcacact tcattttatg tattatttag taatttgcag    5280
tggtatgtgt ttaatatttt tgctacctac acattaggca aaaaaaagat gtaaataatt    5340
tgggagaaaa agaggaagaa cagtgtaaaa taaaactttc tataagtact ccatttcaat    5400
gtgttcaaca tcatcctaaa aggcaagatt ttcccacgca ggtgacaagg tggtttatgt    5460
actatttaag ggcggaaggt gcgtgcccgt tcaataagca tgttttttgc caggtaggaa    5520
atatgttcca tatctttact tatcattgca tttcagatgg gaactagaaa aactggagag    5580
aaaaatgtaa tgaaactgct gctgtaaatt attccttta gcatgtattc acttgctaaa    5640
tacacatttc ttcaaaataa aaaaaaaaaa aa                                  5672
```

<210> SEQ ID NO 11
<211> LENGTH: 775
<212> TYPE: PRT
<213> ORGANISM: Homo sapiens

<400> SEQUENCE: 11

```
Met Ala Ser Ala Gly His Ile Ile Thr Leu Leu Leu Trp Gly Tyr Leu
1               5                   10                  15

Leu Glu Leu Trp Thr Gly Gly His Thr Ala Asp Thr Thr His Pro Arg
                20                  25                  30

Leu Arg Leu Ser His Lys Glu Leu Leu Asn Leu Asn Arg Thr Ser Ile
            35                  40                  45

Phe His Ser Pro Phe Gly Phe Leu Asp Leu His Thr Met Leu Leu Asp
        50                  55                  60

Glu Tyr Gln Glu Arg Leu Phe Val Gly Gly Arg Asp Leu Val Tyr Ser
65                  70                  75                  80

Leu Ser Leu Glu Arg Ile Ser Asp Gly Tyr Lys Glu Ile His Trp Pro
                85                  90                  95

Ser Thr Ala Leu Lys Met Glu Glu Cys Ile Met Lys Gly Lys Asp Ala
                100                 105                 110

Gly Glu Cys Ala Asn Tyr Val Arg Val Leu His His Tyr Asn Arg Thr
            115                 120                 125
```

-continued

```
His Leu Leu Thr Cys Gly Thr Gly Ala Phe Asp Pro Val Cys Ala Phe
    130                 135                 140
Ile Arg Val Gly Tyr His Leu Glu Asp Pro Leu Phe His Leu Glu Ser
145                 150                 155                 160
Pro Arg Ser Glu Arg Gly Arg Gly Arg Cys Pro Phe Asp Pro Ser Ser
                165                 170                 175
Ser Phe Ile Ser Thr Leu Ile Gly Ser Glu Leu Phe Ala Gly Leu Tyr
            180                 185                 190
Ser Asp Tyr Trp Ser Arg Asp Ala Ala Ile Phe Arg Ser Met Gly Arg
        195                 200                 205
Leu Ala His Ile Arg Thr Glu His Asp Asp Arg Leu Leu Lys Glu
    210                 215                 220
Pro Lys Phe Val Gly Ser Tyr Met Ile Pro Asp Asn Glu Asp Arg Asp
225                 230                 235                 240
Asp Asn Lys Val Tyr Phe Phe Thr Glu Lys Ala Leu Glu Ala Glu
                245                 250                 255
Asn Asn Ala His Ala Ile Tyr Thr Arg Val Gly Arg Leu Cys Val Asn
            260                 265                 270
Asp Val Gly Gly Gln Arg Ile Leu Val Asn Lys Trp Ser Thr Phe Leu
        275                 280                 285
Lys Ala Arg Leu Val Cys Ser Val Pro Gly Met Asn Gly Ile Asp Thr
    290                 295                 300
Tyr Phe Asp Glu Leu Glu Asp Val Phe Leu Leu Pro Thr Arg Asp His
305                 310                 315                 320
Lys Asn Pro Val Ile Phe Gly Leu Phe Asn Thr Thr Ser Asn Ile Phe
                325                 330                 335
Arg Gly His Ala Ile Cys Val Tyr His Met Ser Ser Ile Arg Ala Ala
            340                 345                 350
Phe Asn Gly Pro Tyr Ala His Lys Glu Gly Pro Glu Tyr His Trp Ser
        355                 360                 365
Val Tyr Glu Gly Lys Val Pro Tyr Pro Arg Pro Gly Ser Cys Ala Ser
    370                 375                 380
Lys Val Asn Gly Gly Arg Tyr Gly Thr Thr Lys Asp Tyr Pro Asp Asp
385                 390                 395                 400
Ala Ile Arg Phe Ala Arg Ser His Pro Leu Met Tyr Gln Ala Ile Lys
                405                 410                 415
Pro Ala His Lys Lys Pro Ile Leu Val Lys Thr Asp Gly Lys Tyr Asn
            420                 425                 430
Leu Lys Gln Ile Ala Val Asp Arg Val Glu Ala Glu Asp Gly Gln Tyr
        435                 440                 445
Asp Val Leu Phe Ile Gly Thr Asp Asn Gly Ile Val Leu Lys Val Ile
    450                 455                 460
Thr Ile Tyr Asn Gln Glu Met Glu Ser Met Glu Glu Val Ile Leu Glu
465                 470                 475                 480
Glu Leu Gln Ile Phe Lys Asp Pro Val Pro Ile Ile Ser Met Glu Ile
                485                 490                 495
Ser Ser Lys Arg Gln Gln Leu Tyr Ile Gly Ser Ala Ser Ala Val Ala
            500                 505                 510
Gln Val Arg Phe His His Cys Asp Met Tyr Gly Ser Ala Cys Ala Asp
        515                 520                 525
Cys Cys Leu Ala Arg Asp Pro Tyr Cys Ala Trp Asp Gly Ile Ser Cys
    530                 535                 540
Ser Arg Tyr Tyr Pro Thr Gly Thr His Ala Lys Arg Arg Phe Arg Arg
545                 550                 555                 560
```

```
Gln Asp Val Arg His Gly Asn Ala Ala Gln Gln Cys Phe Gly Gln Gln
            565                 570                 575
Phe Val Gly Asp Ala Leu Asp Lys Thr Glu Glu His Leu Ala Tyr Gly
            580                 585                 590
Ile Glu Asn Asn Ser Thr Leu Leu Glu Cys Thr Pro Arg Ser Leu Gln
            595                 600                 605
Ala Lys Val Ile Trp Phe Val Gln Lys Gly Arg Glu Thr Arg Lys Glu
            610                 615                 620
Glu Val Lys Thr Asp Asp Arg Val Val Lys Met Asp Leu Gly Leu Leu
625                 630                 635                 640
Phe Leu Arg Leu His Lys Ser Asp Ala Gly Thr Tyr Phe Cys Gln Thr
                645                 650                 655
Val Glu His Ser Phe Val His Thr Val Arg Lys Ile Thr Leu Glu Val
            660                 665                 670
Val Glu Glu Glu Lys Val Glu Asp Met Phe Asn Lys Asp Asp Glu Glu
            675                 680                 685
Asp Arg His His Arg Met Pro Cys Pro Ala Gln Ser Ser Ile Ser Gln
            690                 695                 700
Gly Ala Lys Pro Trp Tyr Lys Glu Phe Leu Gln Leu Ile Gly Tyr Ser
705                 710                 715                 720
Asn Phe Gln Arg Val Glu Glu Tyr Cys Glu Lys Val Trp Cys Thr Asp
                725                 730                 735
Arg Lys Arg Lys Lys Leu Lys Met Ser Pro Ser Lys Trp Lys Tyr Ala
            740                 745                 750
Asn Pro Gln Glu Lys Lys Leu Arg Ser Lys Pro Glu His Tyr Arg Leu
            755                 760                 765
Pro Arg His Thr Leu Asp Ser
            770                 775

<210> SEQ ID NO 12
<211> LENGTH: 6474
<212> TYPE: DNA
<213> ORGANISM: Homo sapiens

<400> SEQUENCE: 12
gtttggcaag tcagtgcaag aggctgactt ctgagaggct tccaggagcc cgaagagagg      60
acctccacgg gagaagggag tgcgtgtgct cggttttttt tttttctctc tttttttttt     120
tttttttctga atgaacagct ttgcccaagt gactgaaaaa tacagcttct tcctgaatct     180
accggcgtag ttgctgaaga gcgctctaga caggacatgg ctctgaagac tcactctttg     240
gaatgtcctc ttgctcccgg cttataaaca actgtcccga ggaaagaaag gttttacata     300
gccaaataca gcctgacaaa tggcacttcg gaactgtgct ttctgatgac aacgcgttcg     360
atttctgaca aagcctctcg cacgctgccc ctggagggaa gtcctaagta aaactcagac     420
cctccttaaa gtgaggagcg agggcttgga cggtgaacac ggcagcatgg catccgcggg     480
gcacattatc accttgctcc tgtggggtta cttactggag ctttggacag gaggtcatac     540
agctgatact acccaccccc ggttacgcct gtcacataaa gagctcttga atctgaacag     600
aacatcaata tttcatagcc cttttggatt tcttgatctc catacaatgc tgctggatga     660
atatcaagag aggctcttcg tgggaggcag ggaccttgta tattccctca gcttggagag     720
aatcagtgac ggctataaag agatacactg gccgagtaca gctctaaaaa tggaagaatg     780
cataatgaag ggaaaagatg cgggtgaatg tgcaaattat gttcgggttt tgcatcacta     840
taacaggaca caccttctga cctgtggtac tggagctttt gatccagttt gtgccttcat     900
```

```
cagagttgga tatcatttgg aggatcctct gtttcacctg aatcaccca gatctgagag    960
aggaagggc agatgtcctt ttgacccag ctcctccttc atctccactt taattggtag   1020
tgaattgttt gctggactct acagtgacta ctggagcaga gacgctgcga tcttccgcag   1080
catgggcga ctggcccata ccgcactga gcatgacgat gagcgtctgt tgaaagaacc   1140
aaaatttgta ggttcataca tgattcctga caatgaagac agagatgaca caaagtata   1200
tttctttttt actgagaagg cactggaggc agaaaacaat gctcacgcaa tttacaccag   1260
ggtcgggcga ctctgtgtga atgatgtagg agggcagaga atactggtga ataagtggag   1320
cactttccta aaagcgagac tcgtttgctc agtaccagga atgaatggaa ttgacacata   1380
ttttgatgaa ttagaggacg ttttttgct acctaccaga gatcataaga atccagtgat   1440
atttggactc tttaacacta ccagtaatat ttttcgaggg catgctatat gtgtctatca   1500
catgtctagc attcgggcag ccttcaacgg accatatgca cataaggaag gacctgaata   1560
ccactggtca gtctatgaag gaaaagtccc ttatccaagg cctggttctt gtgccagcaa   1620
agtaaatgga gggagatacg aaccaccaa ggactatcct gatgatgcca tccgatttgc   1680
aagaagtcat ccactaatgt accaggccat aaaacctgcc cataaaaaac caatattggt   1740
aaaaacagat ggaaaatata acctgaaaca aatagcagta gatcgagtgg aagctgagga   1800
tggccaatat gacgtcttgt ttattgggac agataatgga attgtgctga agtaatcac   1860
aatttacaac caagaaatgg aatcaatgga agaagtaatt ctagaagaac ttcagatatt   1920
caaggatcca gttcctatta tttctatgga gatttcttca aaacggcaac agctgtatat   1980
tggatctgct tctgctgtgg ctcaagtcag attccatcac tgtgacatgt atggaagtgc   2040
ttgtgctgac tgctgcctgg ctcgagaccc ttactgtgcc tgggatggca tatcctgctc   2100
ccggtattac ccaacaggca cacatgcaaa aaggcgtttc cggagacaag atgttcgaca   2160
tggaaatgca gctcagcagt gctttggaca acagtttgtt ggggatgctt tggataagac   2220
tgaagaacat ctggcttatg catagagaa caacagtact ttgctggaat gtaccccacg   2280
atctttacaa gcgaaagtta tctggttgt acagaaagga cgtgagacaa gaaaagagga   2340
ggtgaagaca gatgacagag tggttaagat ggaccttggt ttactcttcc taaggttaca   2400
caaatcagat gctgggacct attttgcca gacagtagag catagctttg tccatacggt   2460
ccgtaaaatc accttggagg tagtggaaga ggagaaagtc gaggatatgt ttaacaagga   2520
cgatgaggag acaggcatc acaggatgcc ttgtcctgct cagagtagca tctcgcaggg   2580
agcaaaacca tggtacaagg aattcttgca gctgatcggt tatagcaact tccagagagt   2640
ggaagaatac tgcgagaaag tatggtgcac agatagaaag aggaaaaagc ttaaaatgtc   2700
accctccaag tggaagtatg ccaacccctca ggaaaagaag ctccgttcca aacctgagca   2760
ttaccgcctg cccaggcaca cgctggactc ctgatgggt gagactatct actgtctttt   2820
gaagaattta tatttggaaa gtaaaaaagt aaaaaaataa atcatccaac ttctttgcat   2880
tacttaaaag agatttctgt aatacaggaa tgactatgaa ggtgttataa taaattattc   2940
tacatactca tttgactgga taaactttac ataaaattaa ctaattttt aaataaatgc   3000
attgcttaat ggtttctcat tatgtttatc aaaaaacaac tgtagctgtt attttcagta   3060
cttggctgct tttctgtgaa aattattatt ttacttttgg aagacaagat tattagaata   3120
ttgaagaaaa attggagact tataatcatg gtaaatataa aactaaatat gtttttaatat   3180
ttctgaattt ttcttttcca tcacaatgta agatatgcag aatacaagat actttggcat   3240
tctcatgtga actttctgta ctctttaagg attatttat tagtgttgtt taagccatga   3300
```

```
gtgttaagta gcaggtgtgt tgtgagtgct gtaacccatg aaaggaaaaa tgtcattctg   3360
aggcttgtgc ccttcgtaaa atattcatta aagtacattc acactatttt tgctttataa   3420
cacagtcttt aattttcact cactgtggaa ataaaaacta aggtaacttc tcagaaagat   3480
atcaaatctc agaagaatg tcaaatcaga tgaagttata gttaggattc taactactgt   3540
aaaagatttt tgcttccctc ttgtggtaaa aaaaattata ttctcacaca tttcttttt    3600 ctctacagac ggatatctgt ttaggaaaga tttgaaagca gattatcagt aggtacatgg   3660
atacatcaag ttcatttgca gaaacaaata actgaaataa aaaacatgtt aatccttgta   3720
tcatacttta atatgaaagt attgtttata gataatttat ctcacaagtc aaaaatgaag   3780
attttgcagc actgaaaatc tattaaagct ccaaattta agtttctaaa taatcttcgc    3840
tgaaatctaa aatatactat aacaaccgtg ttttatttgt gaaaaaaata ttaaagtgat   3900
ttgctctcaa atatcaaatt ttcttctctc ttttatatta agagacagaa aattgtttca   3960
tgagttcact taactactga gatattcaga gcattttac ctctctctta aatgttataa    4020 aaacaattg tatttttaag aatgtttatt tatcaaagtc tttccttctt ctattaaata    4080
tttagcaatt acctttctaa aatatgaaat tttgtaagat gttttcacct aaataaaaat   4140
tgaaagcaag tggattacac aggagaacca ttatgaacat ttatttagat attaatctta   4200
aacagtgttt atttcagttt tcaaagttag cttataggtt atacatttaa gttaaagtgc   4260
tcataatcac ttgcaattc attgtaaaat gaacaaatac ataaatattt taagaaaat    4320 ttaagttttat tcagataagt caccatgctt caaaagatct aagaaatgca atatactga   4380 aaattgacat cctctgaaaa ttccacttgc tatttaccca agaatccact ggaggtcatt   4440
actgccatta ataataact gaaaagacta tgtagtgaaa tgtattttta aaaactatat    4500
tcagtaaaag cctgctcaat ttggagaaat agaaccacaa acacagatca caggggcctt   4560
acaaagttta tgtctgaaca aataagtcaa ttaagtacac tttattgaaa attgccttcc   4620
attaacacac aagaaagaaa gcaggatttt ctcctgtatc tgaattttaa aattaaaaag   4680
gcagataaga cataaatagt tatcatttta attgcaataa cacagacaag tagttaatga   4740
tgataacaat ggtgtaactt gtaaactaaa tatttggtaa ctgaagcaat aggcagagga   4800
aaatagcttt tctatgacac aagtcataag aagtccatat actgaagagc gtttgattaa   4860
aataaagtga ctattaacca gaaaagaaac attttacata aaatgctaaa atttattata   4920
ggaaaataaa tcaaacccaa agaaagttta ttcaatgcta atttgaaaga aaattgataa   4980
gaaaactttg agggcccaag tccacaattt ggtgagacca ctaaattta catataatta    5040 tacacacaca tatgtacata tatatgtata taatcttgct tcccgcctgt ttatggcagt   5100
actgaagaga aatgggaaag aagagggagg gagagagaaa gacgaaggga gagagaaagc   5160
agtttccaag gatatgtttc atgtcccacc attttctcag tttctccctc tctctcccaa   5220
cacacacaca cacacacccc tcacatacta taaaataaat cttcactgcc ctatcaaaat   5280
acaaataaat caatctatgc tgttctgtcc ttcttgagaa tctaaaacat accacaaaaa   5340
tacatcccca gtcttttgtt ctgtctgagg ttagaattaa ttcaaattca gaatctgttg   5400
tgagaaatgc ccaggcttta aaattaaaa atggatggat cttctctgaa ctcagggagg   5460
gcacatactt agatacctac aagacttgga ggaattaaga gttcaccctt catctccacca   5520 aattttcccc attttctct ttcttgtaga aggagagaaa ccatgctctc tagcaacatt    5580
gagcaaaaat cataaccact catctaattt ctaagaggca cctccatcga gggccggtct   5640
cctgcttctt tagacctctt ctatctttgt tacaggagag gacctgtgga tagacttagt   5700
```

```
tttgacataa aacaatgccc attcacctcc tccttcagca caacgtcacc cattgggcaa    5760
gagatccaga tttgttaaca aaaaagattt tacttcgtga ttccacgtct ataattctat    5820
attgctaatt ttttcttttg tgtgaattac tgaatatttc agagcaaagc tatcaacttg    5880
gagaaacagg gattaaaaat aaggataaac actaataaga gctctagaaa aagggaaca    5940 gaaagtctgc ctgtttagta agtggcaatt ccatacatat tttagagttt tttctatcta    6000
aaattagtta aatacttaga atgtttgtaa tgagtgttcg atatttgcta taggttttag    6060
ggttttgtaa atcttcatag taattataaa catttgtaaa atttgtaaaa tactataagt    6120
cattttgagt gttggtgtta agcatgaaac aaacagcagc tgttgtcctt aaaaatgaat    6180
tgacctggcc gggcgcggtg gctcacgcct gtaatcccag cactttggga ggccgaggcg    6240
ggtggatcat gaggtcagga gatggagacc atcctggcta acaaggtgaa accccgtctc    6300
tactaaaaat acaaaaaatt agccgggcgc ggtggcgggc gcctgtagtc ccagctactt    6360
gggaggctga ggcaggagaa tggcgtgaac ccgggaagcg gagcttgcag tgagccgaga    6420
ttgcgccact gcagtccgca gtccggcctg ggcgacagag cgagactccg tctc          6474
```

<210> SEQ ID NO 13
<211> LENGTH: 785
<212> TYPE: PRT
<213> ORGANISM: Homo sapiens

<400> SEQUENCE: 13

```
Met Leu Val Ala Gly Leu Leu Leu Trp Ala Ser Leu Leu Thr Gly Ala
 1               5                  10                  15

Trp Pro Ser Phe Pro Thr Gln Asp His Leu Pro Ala Thr Pro Arg Val
            20                  25                  30

Arg Leu Ser Phe Lys Glu Leu Lys Ala Thr Gly Thr Ala His Phe Phe
        35                  40                  45

Asn Phe Leu Leu Asn Thr Thr Asp Tyr Arg Ile Leu Leu Lys Asp Glu
    50                  55                  60

Asp His Asp Arg Met Tyr Val Gly Ser Lys Asp Tyr Val Leu Ser Leu
65                  70                  75                  80

Asp Leu His Asp Ile Asn Arg Glu Pro Leu Ile Ile His Trp Ala Ala
                85                  90                  95

Ser Pro Gln Arg Ile Glu Glu Cys Val Leu Ser Gly Lys Asp Val Asn
            100                 105                 110

Gly Glu Cys Gly Asn Phe Val Arg Leu Ile Gln Pro Trp Asn Arg Thr
        115                 120                 125

His Leu Tyr Val Cys Gly Thr Gly Ala Tyr Asn Pro Met Cys Thr Tyr
    130                 135                 140

Val Asn Arg Gly Arg Arg Ala Gln Ala Thr Pro Trp Thr Gln Thr Gln
145                 150                 155                 160

Ala Val Arg Gly Arg Gly Ser Arg Ala Thr Asp Gly Ala Leu Arg Pro
                165                 170                 175

Met Pro Thr Ala Pro Arg Gln Asp Tyr Ile Phe Tyr Leu Glu Pro Glu
            180                 185                 190

Arg Leu Glu Ser Gly Lys Gly Lys Cys Pro Tyr Asp Pro Lys Leu Asp
        195                 200                 205

Thr Ala Ser Ala Leu Ile Asn Glu Glu Leu Tyr Ala Gly Val Tyr Ile
    210                 215                 220

Asp Phe Met Gly Thr Asp Ala Ala Ile Phe Arg Thr Leu Gly Lys Gln
225                 230                 235                 240
```

```
Thr Ala Met Arg Thr Asp Gln Tyr Asn Ser Arg Trp Leu Asn Asp Pro
                245                 250                 255

Ser Phe Ile His Ala Glu Leu Ile Pro Asp Ser Ala Glu Arg Asn Asp
            260                 265                 270

Asp Lys Leu Tyr Phe Phe Phe Arg Glu Arg Ser Ala Glu Ala Pro Gln
        275                 280                 285

Ser Pro Ala Val Tyr Ala Arg Ile Gly Arg Ile Cys Leu Asn Asp Asp
    290                 295                 300

Gly Gly His Cys Cys Leu Val Asn Lys Trp Ser Thr Phe Leu Lys Ala
305                 310                 315                 320

Arg Leu Val Cys Ser Val Pro Gly Glu Asp Gly Ile Gly Thr His Phe
                325                 330                 335

Asp Glu Leu Gln Asp Val Phe Val Gln Thr Gln Asp Val Arg Asn
            340                 345                 350

Pro Val Ile Tyr Ala Val Phe Thr Ser Ser Gly Ser Val Phe Arg Gly
        355                 360                 365

Ser Ala Val Cys Val Tyr Ser Met Ala Asp Ile Arg Met Val Phe Asn
    370                 375                 380

Gly Pro Phe Ala His Lys Glu Gly Pro Asn Tyr Gln Trp Met Pro Phe
385                 390                 395                 400

Ser Gly Lys Met Pro Tyr Pro Arg Pro Gly Thr Cys Pro Gly Gly Thr
                405                 410                 415

Phe Thr Pro Ser Met Lys Ser Thr Lys Asp Tyr Pro Asp Glu Val Ile
            420                 425                 430

Asn Phe Met Arg Ser His Pro Leu Met Tyr Gln Ala Val Tyr Pro Leu
        435                 440                 445

Gln Arg Arg Pro Leu Val Val Arg Thr Gly Ala Pro Tyr Arg Leu Thr
    450                 455                 460

Thr Ile Ala Val Asp Gln Val Asp Ala Ala Asp Gly Arg Tyr Glu Val
465                 470                 475                 480

Leu Phe Leu Gly Thr Asp Arg Gly Thr Val Gln Lys Val Ile Val Leu
                485                 490                 495

Pro Lys Asp Asp Gln Glu Met Glu Glu Leu Met Leu Glu Glu Val Glu
            500                 505                 510

Val Phe Lys Asp Pro Ala Pro Val Lys Thr Met Thr Ile Ser Ser Lys
        515                 520                 525

Arg Gln Gln Leu Tyr Val Ala Ser Ala Val Gly Val Thr His Leu Ser
    530                 535                 540

Leu His Arg Cys Gln Ala Tyr Gly Ala Ala Cys Ala Asp Cys Cys Leu
545                 550                 555                 560

Ala Arg Asp Pro Tyr Cys Ala Trp Asp Gly Gln Ala Cys Ser Arg Tyr
                565                 570                 575

Thr Ala Ser Ser Lys Arg Arg Ser Arg Arg Gln Asp Val Arg His Gly
            580                 585                 590

Asn Pro Ile Arg Gln Cys Arg Gly Phe Asn Ser Asn Ala Asn Lys Asn
        595                 600                 605

Ala Val Glu Ser Val Gln Tyr Gly Val Ala Gly Ser Ala Ala Phe Leu
    610                 615                 620

Glu Cys Gln Pro Arg Ser Pro Gln Ala Thr Val Lys Trp Leu Phe Gln
625                 630                 635                 640

Arg Asp Pro Gly Asp Arg Arg Glu Ile Arg Ala Glu Asp Arg Phe
                645                 650                 655

Leu Arg Thr Glu Gln Gly Leu Leu Leu Arg Ala Leu Gln Leu Ser Asp
            660                 665                 670
```

```
Arg Gly Leu Tyr Ser Cys Thr Ala Thr Glu Asn Asn Phe Lys His Val
            675                 680                 685
Val Thr Arg Val Gln Leu His Val Leu Gly Arg Asp Ala Val His Ala
    690                 695                 700
Ala Leu Phe Pro Pro Leu Ser Met Ser Ala Pro Pro Pro Gly Ala
705                 710                 715                 720
Gly Pro Pro Thr Pro Pro Tyr Gln Glu Leu Ala Gln Leu Leu Ala Gln
                725                 730                 735
Pro Glu Val Gly Leu Ile His Gln Tyr Cys Gln Gly Tyr Trp Arg His
            740                 745                 750
Val Pro Pro Ser Pro Arg Glu Ala Pro Gly Ala Pro Arg Ser Pro Glu
        755                 760                 765
Pro Gln Asp Gln Lys Lys Pro Arg Asn Arg Arg His His Pro Pro Asp
    770                 775                 780
Thr
785

<210> SEQ ID NO 14
<211> LENGTH: 3540
<212> TYPE: DNA
<213> ORGANISM: Homo sapiens

<400> SEQUENCE: 14
ccgcggcgcc gatcccggct gaggcgcagc ggcgagaggt cgcgggcagg gccatggccc     60
cggggggccg ctagcgcgga ccggcccaac gggagccgct ccgtgccgcc gccgccgccc    120
gggcgcccag gccccgccgc tgcggaagag gtttctagag agtggagcct gcttcctggg    180
ccctaggccc ctcccacaat gcttgtcgcc ggtcttcttc tctgggcttc cctactgacc    240
ggggcctggc catccttccc cacccaggac cacctcccgg ccacgccccg gtccggctc     300
tcattcaaag agctgaaggc cacaggcacc gcccacttct tcaacttcct gctcaacaca    360
accgactacc gaatcttgct caaggacgag gaccacgacc gcatgtacgt gggcagcaag    420
gactacgtgt gtcccctgga cctgcacgac atcaaccgcg agcccctcat tatacactgg    480
gcagcctccc cacagcgcat cgaggaatgc gtgctctcag gcaaggatgt caacggcgag    540
tgtgggaact cgtcaggct catccagccc tggaaccgaa cacacctgta tgtgtgcggg    600
acaggtgcct acaaccccat gtgcacctat gtgaaccgcg gacgccgcgc ccaggccaca    660
ccatggaccc agactcaggc ggtcagaggc cgcggcagca gagccacgga tggtgccctc    720
cgcccgatgc ccacagcccc acgccaggat tacatcttct acctggagcc tgagcgactc    780
gagtcaggga agggcaagtg tccgtacgat cccaagctgg acacagcatc ggccctcatc    840
aatgaggagc tctatgctgg tgtgtacatc gattttatgg gcactgatgc agccatcttc    900
cgcacacttg aaagcagac agccatgcgc acggatcagt acaactcccg gtggctgaac    960
gacccgtcgt tcatccatgc tgagctcatt cctgacagtg cggagcgcaa tgatgataag   1020
ctttacttct tcttccgtga gcggtcggca gaggcgccgc agagcccgc ggtgtacgcc   1080
cgcatcgggc gcatttgcct gaacgatgac ggtggtcact gttgcctggt caacaagtgg   1140
agcacattcc tgaaggcgcg gctcgtctgc tctgtcccgg gcgaggatgg cattgagact   1200
cactttgatg agctccagga cgtgtttgtc cagcagaccc aggacgtgag gaaccctgtc   1260
atttacgctg tctttaccct ctctggctcc gtgttccgag gctctgccgt gtgtgtctac   1320
tccatggctg atattcgcat ggtcttcaac gggccctttg cccacaaaga ggggcccaac   1380
taccagtgga tgcccttctc agggaagatg ccctacccac ggccgggcac gtgccctggt   1440
```

```
ggaaccttca cgccatctat gaagtccacc aaggattatc ctgatgaggt gatcaacttc    1500
atgcgcagcc acccactcat gtaccaggcc gtgtaccctc tgcagcggcg ccccctggta    1560
gtccgcacag gtgctcccta ccgccttacc actattgccg tggaccaggt ggatgcagcc    1620
gacgggcgct atgaggtgct tttcctgggc acagaccgcg ggacagtgca gaaggtcatt    1680
gtgctgccca aggatgacca ggagatggag gagctcatgc tggaggaggt ggaggtcttc    1740
aaggatccag cacccgtcaa gaccatgacc atctcttcta gaggcaaca actctacgtg     1800 gcgtcagccg tgggtgtcac acacctgagc ctgcaccgct gccaggcgta tggggctgcc    1860
tgtgctgact gctgccttgc ccgggaccct tactgtgcct gggatggcca ggcctgctcc    1920
cgctatacag catcctccaa gaggcggagc cgccggcagg acgtccggca cggaaacccc    1980
atcaggcagt gccgtgggtt caactccaat gccaacaaga atgccgtgga gtctgtgcag    2040
tatggcgtgg ccggcagcgc agccttcctt gagtgccagc ccgctcgcc ccaagccact      2100 gttaagtggc tgttccagcg agatcctggt gaccggcgcc gagagattcg tgcagaggac    2160
cgcttcctgc gcacagagca gggcttgttg ctccgtgcac tgcagctcag cgatcgtggc    2220
ctctactcct gcacagccac tgagaacaac tttaagcacg tcgtcacacg agtgcagctg    2280
catgtactgg gccgggacgc cgtccatgct gccctcttcc caccactgtc catgagcgcc    2340
ccgccacccc caggcgcagg ccccccaacg cctccttacc aggagttagc ccagctgctg    2400
gcccagccag aagtgggcct catccaccag tactgccagg ttactggcg ccatgtgccc     2460 cccagcccca gggaggctcc aggggcaccc cggtctcctg agcccaggga ccagaaaaag    2520
ccccggaacc gccggcacca ccctccggac acatgaggcc agctgcctgt gcctgccatg    2580
ggccagccta gccttgtcc cttttaatat aaaagatata tatatatata tatatatata     2640
tataaaatat ctatattcta tacacaccct gcccctgcaa agacagtatt tattggtggg    2700
ttgaatatag cctgcctcag tggcagcatc ctccaaaact tagacccatg ctggtcagag    2760
acggcagaaa acagagcctg cctaaccagg cccagccagt tggtggggcc aggccaggac    2820
cacacagtcc ccagactcag ctggaagtct acctgctgga cagcctccgc caagatctac    2880
aggacaaagg gagggagcaa gccctactcg gatggggcac ggactgtcca cctttctga     2940 tgtgtgttgt cagcctgtgc tgtggcatag acatggatgc gaggaccact ttggagactg    3000
gggtggcctc aagagcacac agagaaggga agaaggggcc atcacaggat gccagcccct    3060
gcctgggttg ggggcactca gccacgacca gccccttcct gggtatttat tctctattta    3120
ttggggatag gagaagaggc atcctgcctg ggtgggacag ccccttcagc cccttctccc    3180
ctccccgcct ggccagggca gggccacccc actctacctc cttagctttc cctgtgccac    3240
tttgactcag aggctgggag catagcagag gggccaggcc caggcagagc tgacgggagg    3300
ccccagctct gaggggaggg ggtccgtggt agaggcctgg ggccggtaga ggctccccag    3360
ggctccctta tgtccaccac ttcagggat gggtgtggat gtaattagct ctgggggca      3420 gttgggtaga tgggtggggg ctcctggtgg ccttctgctg cccaggccac agccgccttt    3480
gggttccatc ttgctaataa acactggctc tgggactaga aaaaaaaaaa aaaaaaaaa     3540
```

<210> SEQ ID NO 15
<211> LENGTH: 231
<212> TYPE: PRT
<213> ORGANISM: Homo sapiens

<400> SEQUENCE: 15

Ser Cys Pro Ala Met Cys Thr Cys Ser Asn Gly Ile Val Asp Cys Arg

```
                1               5                  10                  15
Gly Lys Gly Leu Thr Ala Ile Pro Ala Asn Leu Pro Glu Thr Met Thr
            20                  25                  30

Glu Ile Arg Leu Glu Leu Asn Gly Ile Lys Ser Ile Pro Pro Gly Ala
            35                  40                  45

Phe Ser Pro Tyr Arg Lys Leu Arg Arg Ile Asp Leu Ser Asn Asn Gln
 50                  55                  60

Ile Ala Glu Ile Ala Pro Asp Ala Phe Gln Gly Leu Arg Ser Leu Asn
 65                  70                  75                  80

Ser Leu Val Leu Tyr Gly Asn Lys Ile Thr Asp Leu Pro Arg Gly Val
            85                  90                  95

Phe Gly Gly Leu Tyr Thr Leu Gln Leu Leu Leu Asn Ala Asn Lys
            100                 105                 110

Ile Asn Cys Ile Arg Pro Asp Ala Phe Gln Asp Leu Gln Asn Leu Ser
            115                 120                 125

Leu Leu Ser Leu Tyr Asp Asn Lys Ile Gln Ser Leu Ala Lys Gly Thr
            130                 135                 140

Phe Thr Ser Leu Arg Ala Ile Gln Thr Leu His Leu Ala Gln Asn Pro
145                 150                 155                 160

Phe Ile Cys Asp Cys Asn Leu Lys Trp Leu Ala Asp Phe Leu Arg Thr
                165                 170                 175

Asn Pro Ile Glu Thr Ser Gly Ala Arg Cys Ala Ser Pro Arg Arg Leu
            180                 185                 190

Ala Asn Lys Arg Ile Gly Gln Ile Lys Ser Lys Phe Arg Cys Ser
            195                 200                 205

Ala Lys Glu Gln Tyr Phe Ile Pro Gly Thr Glu Asp Tyr Gln Leu Asn
            210                 215                 220

Ser Glu Cys Asn Ser Asp Val
225                 230

<210> SEQ ID NO 16
<211> LENGTH: 234
<212> TYPE: PRT
<213> ORGANISM: Homo sapiens

<400> SEQUENCE: 16

Leu His Cys Pro Ala Ala Cys Thr Cys Ser Asn Asn Ile Val Asp Cys
 1               5                  10                  15

Arg Gly Lys Gly Leu Thr Glu Ile Pro Thr Asn Leu Pro Glu Thr Ile
            20                  25                  30

Thr Glu Ile Arg Leu Glu Gln Asn Thr Ile Lys Val Ile Pro Pro Gly
            35                  40                  45

Ala Phe Ser Pro Tyr Lys Lys Leu Arg Arg Ile Asp Leu Ser Asn Asn
            50                  55                  60

Gln Ile Ser Glu Leu Ala Pro Asp Ala Phe Gln Gly Leu Arg Ser Leu
 65                  70                  75                  80

Asn Ser Leu Val Leu Tyr Gly Asn Lys Ile Thr Glu Leu Pro Lys Ser
            85                  90                  95

Leu Phe Glu Gly Leu Phe Ser Leu Gln Leu Leu Leu Leu Asn Ala Asn
            100                 105                 110

Lys Ile Asn Cys Leu Arg Val Asp Ala Phe Gln Asp Leu His Asn Leu
            115                 120                 125

Asn Leu Leu Ser Leu Tyr Asp Asn Lys Leu Gln Thr Ile Ala Lys Gly
            130                 135                 140

Thr Phe Ser Pro Leu Arg Ala Ile Gln Thr Met His Leu Ala Gln Asn
```

```
                145                 150                 155                 160
Pro Phe Ile Cys Asp Cys His Leu Lys Trp Leu Ala Asp Tyr Leu His
                165                 170                 175

Thr Asn Pro Ile Glu Thr Ser Gly Ala Arg Cys Thr Ser Pro Arg Arg
                180                 185                 190

Leu Ala Asn Lys Arg Ile Gly Gln Ile Lys Ser Lys Lys Phe Arg Cys
                195                 200                 205

Ser Ala Lys Glu Gln Tyr Phe Ile Pro Gly Thr Glu Asp Tyr Arg Ser
                210                 215                 220

Lys Leu Ser Gly Asp Cys Phe Ala Asp Leu
225                 230

<210> SEQ ID NO 17
<211> LENGTH: 604
<212> TYPE: PRT
<213> ORGANISM: Homo sapiens

<400> SEQUENCE: 17

Met Met Arg Ala Val Trp Glu Ala Leu Ala Leu Ala Ala Val Ala
1               5                   10                  15

Cys Leu Val Gly Ala Val Arg Gly Gly Pro Gly Leu Ser Met Phe Ala
                20                  25                  30

Gly Gln Ala Ala Gln Pro Asp Pro Cys Ser Asp Glu Asn Gly His Pro
                35                  40                  45

Arg Arg Cys Ile Pro Asp Phe Val Asn Ala Ala Phe Gly Lys Asp Val
                50                  55                  60

Arg Val Ser Ser Thr Cys Gly Arg Pro Pro Ala Arg Tyr Cys Val Val
65                  70                  75                  80

Ser Glu Arg Gly Glu Glu Arg Leu Arg Ser Cys His Leu Cys Asn Ala
                85                  90                  95

Ser Asp Pro Lys Lys Ala His Pro Pro Ala Phe Leu Thr Asp Leu Asn
                100                 105                 110

Asn Pro His Asn Leu Thr Cys Trp Gln Ser Glu Asn Tyr Leu Gln Phe
                115                 120                 125

Pro His Asn Val Thr Leu Thr Leu Ser Leu Gly Lys Lys Phe Glu Val
                130                 135                 140

Thr Tyr Val Ser Leu Gln Phe Cys Ser Pro Arg Pro Glu Ser Met Ala
145                 150                 155                 160

Ile Tyr Lys Ser Met Asp Tyr Gly Arg Thr Trp Val Pro Phe Gln Phe
                165                 170                 175

Tyr Ser Thr Gln Cys Arg Lys Met Tyr Asn Arg Pro His Arg Ala Pro
                180                 185                 190

Ile Thr Lys Gln Asn Glu Gln Glu Ala Val Cys Thr Asp Ser His Thr
                195                 200                 205

Asp Met Arg Pro Leu Ser Gly Gly Leu Ile Ala Phe Ser Thr Leu Asp
                210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
                245                 250                 255

Phe Gly Asp Glu Asn Glu Asp Ser Glu Leu Ala Arg Asp Ser Tyr
                260                 265                 270

Phe Tyr Ala Val Ser Asp Leu Gln Val Gly Gly Arg Cys Lys Cys Asn
                275                 280                 285

Gly His Ala Ala Arg Cys Val Arg Asp Arg Thr Asp Ser Leu Val Cys
```

```
              290                 295                 300
Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
                325                 330                 335

Glu Cys Val Ala Cys Asn Cys Asn Leu His Ala Arg Arg Cys Arg Phe
                340                 345                 350

Asn Met Glu Leu Tyr Lys Leu Ser Gly Arg Lys Ser Gly Val Cys
                355                 360                 365

Leu Asn Cys Arg His Asn Thr Ala Gly Arg His Cys His Tyr Cys Lys
370                 375                 380

Glu Gly Tyr Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
                405                 410                 415

Asn Gln Thr Thr Gly Gln Cys Pro Cys Lys Asp Gly Val Thr Gly Ile
                420                 425                 430

Thr Cys Asn Arg Cys Ala Lys Gly Tyr Gln Gln Ser Arg Ser Pro Ile
                435                 440                 445

Ala Pro Cys Ile Lys Ile Pro Val Ala Pro Thr Thr Ala Ala Ser
450                 455                 460

Ser Val Glu Glu Pro Glu Asp Cys Asp Ser Tyr Cys Lys Ala Ser Lys
465                 470                 475                 480

Gly Lys Leu Lys Ile Asn Met Lys Lys Tyr Cys Lys Lys Asp Tyr Ala
                485                 490                 495

Val Gln Ile His Ile Leu Lys Ala Asp Lys Ala Gly Asp Trp Trp Lys
                500                 505                 510

Phe Thr Val Asn Ile Ile Ser Val Tyr Lys Gln Gly Thr Ser Arg Ile
                515                 520                 525

Arg Arg Gly Asp Gln Ser Leu Trp Ile Arg Ser Arg Asp Ile Ala Cys
530                 535                 540

Lys Cys Pro Lys Ile Lys Pro Leu Lys Lys Tyr Leu Leu Leu Gly Asn
545                 550                 555                 560

Ala Glu Asp Ser Pro Asp Gln Ser Gly Ile Val Ala Asp Lys Ser Ser
                565                 570                 575

Leu Val Ile Gln Trp Arg Asp Thr Trp Ala Arg Arg Leu Arg Lys Phe
                580                 585                 590

Gln Gln Arg Glu Lys Lys Gly Lys Cys Lys Lys Ala
                595                 600

<210> SEQ ID NO 18
<211> LENGTH: 1989
<212> TYPE: DNA
<213> ORGANISM: Homo sapiens

<400> SEQUENCE: 18
agcttcgggg gcgagcgctc gtgtgtgtga gtgcgcgccg gccagcgcgc cttctgcggc       60
aggcggacag atcctcggcg cggcagggcc ggggcaagct ggacgcagca tgatgcgcgc      120
agtgtgggag gcgctggcgg cgctggcggc ggtggcgtgc ctggtggcg cggtgcgcgg       180 cgggcccggg ctcagcatgt tcgcgggcca ggcggcgcag cccgatccct gctcggacga      240
gaacggccac ccgcgccgct gcatcccgga ctttgtcaat gcggccttcg gcaaggacgt      300
gcgcgtgtcc agcaccctgc gccggccccc ggcgcgctac tgcgtggtga gcgagcgcgg      360
cgaggagcgg ctgcgctcgt gccacctctg caacgcgtcc gaccccaaga aggcgcaccc      420
```

-continued

```
gcccgccttc ctcaccgacc tcaacaaccc gcacaacctg acgtgctggc agtccgagaa      480
ctacctgcag ttcccgcaca acgtcacgct cacactgtcc ctcggcaaga agttcgaagt      540
gacctacgtg agcctgcagt tctgctcgcc gcggcccgag tccatggcca tctacaagtc      600
catggactac gggcgcacgt gggtgccctt ccagttctac tccacgcagt gccgcaagat      660
gtacaaccgg ccgcaccgcg cgcccatcac caagcagaac gagcaggagg ccgtgtgcac      720
cgactcgcac accgacatgc gcccgctctc gggcggcctc atcgccttca gcacgctgga      780
cgggcggccc tcggcgcacg acttcgacaa ctcgcccgtg ctgcaggact gggtcacggc      840
cacagacatc cgcgtggcct tcagccgcct gcacacgttc ggcgacgaga acgaggacga      900
ctcggagctg gcgcgcgact cgtacttcta cgccggtgtcc gacctgcagg tgggcggccg      960
gtgcaagtgc aacggccacg cggcccgctg cgtgcgcgac cgcaccgaca gcctggtgtg     1020
cgactgcagg cacaacacgg ccggcccgga gtgcgaccgc tgcaagccct tccactacga     1080
ccggccctgg cagcgcgcca cagcccgcga agccaacgag tgcgtggcct gtaactgcaa     1140
cctgcatgcc cggcgctgcc gcttcaacat ggagctctac aagctttcgg ggcgcaagag     1200
cggaggtgtc tgcctcaact gtcgccacaa caccgccggc cgccactgcc attactgcaa     1260
ggagggctac taccgcgaca tgggcaagcc catcacccac cggaaggcct gcaaagcctg     1320
tgattgccac cctgtgggtg ctgctggcaa aacctgcaac caaaccaccg gccagtgtcc     1380
ctgcaaggac ggcgtgacgg gtatcacctg caaccgctgc gccaaaggct accagcagag     1440
ccgctctccc atcgccccct gcataaagat ccctgtagcg ccgccgacga ctgcagccag     1500
cagcgtggag gagcctgaag actgcgattc ctactgcaag gcctccaagg ggaagctgaa     1560
gattaacatg aaaaagtact gcaagaagga ctatgccgtc cagatccaca tcctgaaggc     1620
ggacaaggcg ggggactggt ggaagttcac ggtgaacatc atctccgtgt ataagcaggg     1680
cacgagccgc atccgccgcg gtgaccgaag cctgtggatc cgctcgcggg acatcgcctg     1740
caagtgtccc aaaatcaagc ccctcaagaa gtacctgctg ctgggcaacg cggaggactc     1800
tccggaccag agcggcatcg tggccgataa aagcagcctg gtgatccagt ggcgggacac     1860
gtgggcgcgg cggctgcgca gttccagca gcgtgagaag aagggcaagt gcaagaaggc     1920
ctagcgccga ggcagcgggc gggcgggccg ggcgggcccg agggcggggc gagcgagacg     1980
gcgcttggc                                                            1989
```

<210> SEQ ID NO 19
<211> LENGTH: 580
<212> TYPE: PRT
<213> ORGANISM: Homo sapiens

<400> SEQUENCE: 19

```
Met Pro Gly Trp Pro Trp Gly Leu Leu Leu Thr Ala Gly Thr Leu Phe
1               5                   10                  15

Ala Ala Leu Ser Pro Gly Pro Pro Ala Pro Ala Asp Pro Cys His Asp
                20                  25                  30

Glu Gly Gly Ala Pro Arg Gly Cys Val Pro Gly Leu Val Asn Ala Ala
            35                  40                  45

Leu Gly Arg Glu Val Leu Ala Ser Ser Thr Cys Gly Arg Pro Ala Thr
        50                  55                  60

Arg Ala Cys Asp Ala Ser Asp Pro Arg Ala His Ser Pro Ala Leu
65                  70                  75                  80

Leu Thr Ser Pro Gly Gly Thr Ala Ser Pro Leu Cys Trp Arg Ser Glu
                85                  90                  95
```

```
Ser Leu Pro Arg Ala Pro Leu Asn Val Thr Leu Thr Val Pro Leu Gly
                100                 105                 110
Lys Ala Phe Glu Leu Val Phe Val Ser Leu Arg Phe Cys Ser Ala Pro
            115                 120                 125
Pro Ala Ser Val Ala Leu Leu Lys Ser Gln Asp His Gly Arg Ser Trp
        130                 135                 140
Ala Pro Leu Gly Phe Phe Ser Ser His Cys Asp Leu Asp Tyr Gly Arg
145                 150                 155                 160
Leu Pro Ala Pro Ala Asn Gly Pro Ala Gly Pro Gly Pro Glu Ala Leu
                165                 170                 175
Cys Phe Pro Ala Pro Leu Ala Gln Pro Asp Gly Ser Gly Leu Leu Ala
            180                 185                 190
Phe Ser Met Gln Asp Ser Ser Pro Pro Gly Leu Asp Leu Asp Ser Ser
        195                 200                 205
Pro Val Leu Gln Asp Trp Val Thr Ala Thr Asp Val Arg Val Val Leu
    210                 215                 220
Thr Arg Pro Ser Thr Ala Gly Asp Pro Arg Asp Met Glu Ala Val Val
225                 230                 235                 240
Pro Tyr Ser Tyr Ala Ala Thr Asp Leu Gln Val Gly Gly Arg Cys Lys
                245                 250                 255
Cys Asn Gly His Ala Ser Arg Cys Leu Leu Asp Thr Gln Gly His Leu
            260                 265                 270
Ile Cys Asp Cys Arg His Gly Thr Glu Gly Pro Asp Cys Gly Arg Cys
        275                 280                 285
Lys Pro Phe Tyr Cys Asp Arg Pro Trp Gln Arg Ala Thr Ala Arg Glu
    290                 295                 300
Ser His Ala Cys Leu Ala Cys Ser Cys Asn Gly His Ala Arg Arg Cys
305                 310                 315                 320
Arg Phe Asn Met Glu Leu Tyr Arg Leu Ser Gly Arg Arg Ser Gly Gly
                325                 330                 335
Val Cys Leu Asn Cys Arg His Asn Thr Ala Gly Arg His Cys His Tyr
            340                 345                 350
Cys Arg Glu Gly Phe Tyr Arg Asp Pro Gly Arg Ala Leu Ser Asp Arg
        355                 360                 365
Arg Ala Cys Arg Ala Cys Asp Cys His Pro Val Gly Ala Ala Gly Lys
    370                 375                 380
Thr Cys Asn Gln Thr Thr Gly Gln Cys Pro Cys Lys Asp Gly Val Thr
385                 390                 395                 400
Gly Leu Thr Cys Asn Arg Cys Ala Pro Gly Phe Gln Gln Ser Arg Ser
                405                 410                 415
Pro Val Ala Pro Cys Val Lys Thr Pro Ile Pro Gly Pro Thr Glu Asp
            420                 425                 430
Ser Ser Pro Val Gln Pro Gln Asp Cys Asp Ser His Cys Lys Pro Ala
        435                 440                 445
Arg Gly Ser Tyr Arg Ile Ser Leu Lys Lys Phe Cys Lys Lys Asp Tyr
    450                 455                 460
Ala Val Gln Val Ala Val Gly Ala Arg Gly Glu Ala Arg Gly Ala Trp
465                 470                 475                 480
Thr Arg Phe Pro Val Ala Val Leu Ala Val Phe Arg Ser Gly Glu Glu
                485                 490                 495
Arg Ala Arg Arg Gly Ser Ser Ala Leu Trp Val Pro Ala Gly Asp Ala
            500                 505                 510
Ala Cys Gly Cys Pro Arg Leu Leu Pro Gly Arg Arg Tyr Leu Leu Leu
```

```
                515                 520                 525
Gly Gly Gly Pro Gly Ala Ala Gly Ala Gly Gly Arg Gly Pro
        530                 535                 540
Gly Leu Ile Ala Ala Arg Gly Ser Leu Val Leu Pro Trp Arg Asp Ala
545                 550                 555                 560
Trp Thr Arg Arg Leu Arg Arg Leu Gln Arg Arg Glu Arg Gly Arg
                565                 570                 575
Cys Ser Ala Ala
        580

<210> SEQ ID NO 20
<211> LENGTH: 1986
<212> TYPE: DNA
<213> ORGANISM: Homo sapiens

<400> SEQUENCE: 20
gaggacgcgc caacatcccc gctgctgtgc tgggcccggg gcgtgcccgc cgctgctccc        60
acctctgggc cgggctgggg ccgcccgggg gccctgttcc tcggcattgc gggcctggtg       120
ggcagaaccg cggagagggc ttcttttccc caagggcagc gtcttggggc ccggccactg       180
gctgacccgc agcggctccg gccatgcctg gctggccctg ggggctgctg ctgacggcag       240
gcacgctctt cgccgccctg agtcctgggc gccggcgcc cgccgacccc tgccacgatg        300 agggggggtgc gccccgcggc tgcgtgccag gactggtgaa cgccgccctg ggccgcgagg      360
tgctggcttc cagcacgtgc gggcggccgg ccactcgggc ctgcgacgcc tccgacccgc       420
gacgggcaca ctcccccgcc ctccttactt ccccaggggg cacggccagc cctctgtgct       480
ggcgctcgga gtccctgcct cgggcgcccc tcaacgtgac tctcacggtg ccctgggca       540 aggcttttga gctggtcttc gtgagcctgc gcttctgctc agctccccca gcctccgtgg       600
ccctgctcaa gtctcaggac catgccgca gctgggcccc gctgggcttc ttctcctccc       660
actgtgacct ggactatggc cgtctgcctg ccctgccaa tggcccagct ggcccagggc       720
ctgaggccct gtgcttcccc gcaccccctgg cccagcctga tggcagcggc cttctggcct      780
tcagcatgca ggacagcagc cccccaggcc tggacctgga cagcagccca gtgctccaag       840
actgggtgac cgccaccgac gtccgtgtag tgctcacaag gcctagcacg gcaggtgacc       900
ccagggacat ggaggccgtc gtcccttact cctacgcagc caccgacctc caggtgggcg       960
ggcgctgcaa gtgcaatgga catgcctcac ggtgcctgct ggacacacag gccacctga      1020 tctgcgactg tcggcatggc accgagggcc tgactgcgg ccgctgcaag cccttctact      1080
gcgacaggcc atggcagcgg gccactgccc gggaatccca cgcctgcctc gcttgctcct      1140
gcaacggcca tgcccgccgc tgccgcttca acatggagct gtaccgactg tccgccgcc      1200 gcagcggggg tgtctgtctc aactgccggc acaacaccgc cggccgccac tgccactact      1260
gccgggaggc cttctatcga gaccctggcc gtgccctgag tgaccgtcgg gcttgcaggg      1320
cctgcgactg tcacccggtt ggtgctgctg gcaagacctg caaccagacc acaggccagt      1380
gtccctgcaa ggatggcgtc actggcctca cctgcaaccg ctgcgcgcct ggcttccagc      1440
aaagccgctc cccagtggcg ccctgtgtta agacccctat cctggacccc actgaggaca      1500
gcagccctgt gcagcccag gactgtgact cgcactgcaa acctgcccgt ggcagctacc      1560
gcatcagcct aaagaagttc tgcaagaagg actatgcggt gcaggtggcg gtgggtgcgc      1620
gcggcgaggc gcgcgcgcg tggacacgct cccggtggc ggtgctcgcc gtgttccgga       1680
gcggagagga gcgcgcgcgg cgcgggagta gcgcgctgtg ggtgcccgcc ggggatgcgg      1740
```

```
cctgcggctg cccgcgcctg ctccccggcc gccgctacct cctgctgggg ggcgggcctg    1800
gagccgcggc tggggggcgcg gggggccggg ggcccgggct catcgccgcc cgcggaagcc    1860
tcgtgctacc ctggagggac gcgtggacgc ggcgcctgcg gaggctgcag cgacgcgaac    1920 ggcggggggcg ctgcagcgcc gcctgagccc gccggctggg cagggcggcc gctgctccca    1980
catcta                                                                1986
```

<210> SEQ ID NO 21
<211> LENGTH: 628
<212> TYPE: PRT
<213> ORGANISM: Homo sapiens

<400> SEQUENCE: 21

```
Met Gly Ser Cys Ala Arg Leu Leu Leu Leu Trp Gly Cys Thr Val Val
1               5                   10                  15

Ala Ala Gly Leu Ser Gly Val Ala Gly Val Ser Ser Arg Cys Glu Lys
            20                  25                  30

Ala Cys Asn Pro Arg Met Gly Asn Leu Ala Leu Gly Arg Lys Leu Trp
        35                  40                  45

Ala Asp Thr Thr Cys Gly Gln Asn Ala Thr Glu Leu Tyr Cys Phe Tyr
    50                  55                  60

Ser Glu Asn Thr Asp Leu Thr Cys Arg Gln Pro Lys Cys Asp Lys Cys
65                  70                  75                  80

Asn Ala Ala Tyr Pro His Leu Ala His Leu Pro Ser Ala Met Ala Asp
                85                  90                  95

Ser Ser Phe Arg Phe Pro Arg Thr Trp Trp Gln Ser Ala Glu Asp Val
            100                 105                 110

His Arg Glu Lys Ile Gln Leu Asp Leu Glu Ala Glu Phe Tyr Phe Thr
        115                 120                 125

His Leu Ile Val Met Phe Lys Ser Pro Arg Pro Ala Ala Met Val Leu
    130                 135                 140

Asp Arg Ser Gln Asp Phe Gly Lys Thr Trp Lys Pro Tyr Lys Tyr Phe
145                 150                 155                 160

Ala Thr Asn Cys Ser Ala Thr Phe Gly Leu Glu Asp Asp Val Val Lys
                165                 170                 175

Lys Gly Ala Ile Cys Thr Ser Lys Tyr Ser Ser Pro Phe Pro Cys Thr
            180                 185                 190

Gly Gly Glu Val Ile Phe Lys Ala Leu Ser Pro Pro Tyr Asp Thr Glu
        195                 200                 205

Asn Pro Tyr Ser Ala Lys Val Gln Glu Gln Leu Lys Ile Thr Asn Leu
    210                 215                 220

Arg Val Gln Leu Leu Lys Arg Gln Ser Cys Pro Cys Gln Arg Asn Asp
225                 230                 235                 240

Leu Asn Glu Glu Pro Gln His Phe Thr His Tyr Ala Ile Tyr Asp Phe
                245                 250                 255

Ile Val Lys Gly Ser Cys Phe Cys Asn Gly His Ala Asp Gln Cys Ile
            260                 265                 270

Pro Val His Gly Phe Arg Pro Val Lys Ala Pro Gly Thr Phe His Met
        275                 280                 285

Val His Gly Lys Cys Met Cys Lys His Asn Thr Ala Gly Ser His Cys
    290                 295                 300

Gln His Cys Ala Pro Leu Tyr Asn Asp Arg Pro Trp Glu Ala Ala Asp
305                 310                 315                 320

Gly Lys Thr Gly Ala Pro Asn Glu Cys Arg Thr Cys Lys Cys Asn Gly
                325                 330                 335
```

His Ala Asp Thr Cys His Phe Asp Val Asn Val Trp Glu Ala Ser Gly
                340                 345                 350

Asn Arg Ser Gly Gly Val Cys Asp Asp Cys Gln His Asn Thr Glu Gly
            355                 360                 365

Gln Tyr Cys Gln Arg Cys Lys Pro Gly Phe Tyr Arg Asp Leu Arg Arg
    370                 375                 380

Pro Phe Ser Ala Pro Asp Ala Cys Lys Pro Cys Ser Cys His Pro Val
385                 390                 395                 400

Gly Ser Ala Val Leu Pro Ala Asn Ser Val Thr Phe Cys Asp Pro Ser
                405                 410                 415

Asn Gly Asp Cys Pro Cys Lys Pro Gly Val Ala Gly Arg Arg Cys Asp
            420                 425                 430

Arg Cys Met Val Gly Tyr Trp Gly Phe Gly Asp Tyr Gly Cys Arg Pro
    435                 440                 445

Cys Asp Cys Ala Gly Ser Cys Asp Pro Ile Thr Gly Asp Cys Ile Ser
450                 455                 460

Ser His Thr Asp Ile Asp Trp Tyr His Glu Val Pro Asp Phe Arg Pro
465                 470                 475                 480

Val His Asn Lys Ser Glu Pro Ala Trp Glu Trp Glu Asp Ala Gln Gly
                485                 490                 495

Phe Ser Ala Leu Leu His Ser Gly Lys Cys Glu Cys Lys Glu Gln Thr
            500                 505                 510

Leu Gly Asn Ala Lys Ala Phe Cys Gly Met Lys Tyr Ser Tyr Val Leu
    515                 520                 525

Lys Ile Lys Ile Leu Ser Ala His Asp Lys Gly Thr His Val Glu Val
530                 535                 540

Asn Val Lys Ile Lys Lys Val Leu Lys Ser Thr Lys Leu Lys Ile Phe
545                 550                 555                 560

Arg Gly Lys Arg Thr Leu Tyr Pro Glu Ser Trp Thr Asp Arg Gly Cys
                565                 570                 575

Thr Cys Pro Ile Leu Asn Pro Gly Leu Glu Tyr Leu Val Ala Gly His
            580                 585                 590

Glu Asp Ile Arg Thr Gly Lys Leu Ile Val Asn Met Lys Ser Phe Val
    595                 600                 605

Gln His Trp Lys Pro Ser Leu Gly Arg Lys Val Met Asp Ile Leu Lys
610                 615                 620

Arg Glu Cys Lys
625

<210> SEQ ID NO 22
<211> LENGTH: 3634
<212> TYPE: DNA
<213> ORGANISM: Homo sapiens

<400> SEQUENCE: 22
ggacgggacg gagccggggc agccagaaga ggtgggaaaa gcggaggagg acgcccagga      60
ggaggcggcg gcggcggccg ggaagtgaaa ggtctcgcaa agttcagcgg cggctgcggg     120
cgccgagccc cgggctagcg gcagacgagc ccgcagggcc gctccgcggg gcagcgcagc     180
caggccggct atggtcccgg ggctcccgcc gccccccagg tgcccgggac ccgccaggcc     240
ggtgcgcgag ggtcacccca cctccccgcg cggtcccggc ccctggctcc cagctgccgg     300
cgaccgctga ccgagcccgg cgccccagga ggaggaagaa accagggccc cgttccctcc     360
cgaggacggc ggcgcttcat cccgcagccc agaggtctcg gctcccctcc g caccccgccc     420

-continued

```
ggcccggctg ctcccggctc ctcccggcca tggggagctg cgcgcggctg ctgctgctct    480
ggggctgcac ggtggtggcc gcaggactga gtggagtagc tggagtgagt tcccgctgtg    540
aaaaagcctg caaccctcgg atgggaaatt tggctttggg gcgaaaactc tgggcagaca    600
ccacctgcgg tcagaatgct accgaactgt actgcttcta cagtgagaac acggatctga    660
cttgtcggca gcccaaatgt gacaagtgca atgctgccta tcctcacctg gctcacctgc    720
catctgccat ggcagactca tccttccggt ttcctcgcac atggtggcag tctgcggagg    780
atgtgcacag agaaaagatc cagttagacc tggaagctga attctacttc actcacctaa    840
ttgtgatgtt caagtccccc aggccggctg ccatggtgct ggaccgctcc caggactttg    900
ggaaaacatg gaagccttat aagtactttg cgactaactg ctccgctaca tttggcctgg    960
aagatgatgt tgtcaagaag ggcgctattt gtacttctaa atactccagt ccttttccat   1020
gcactggagg agaggttatt ttcaaagctt tgtcaccacc atacgataca gagaacccct   1080
acagtgccaa agttcaggag cagctgaaga tcaccaacct tcgcgtgcag ctgctgaaac   1140
gacagtcttg tccctgtcag agaaatgacc tgaacgaaga gcctcaacat tttacacact   1200
atgcaatcta tgatttcatt gtcaagggca gctgcttctg caatggccac gctgatcaat   1260
gcatacctgt tcatggcttc agacctgtca aggccccagg aacattccac atggtccatg   1320
ggaagtgtat gtgtaagcac aacacagcag gcagccactg ccagcactgt gccccgttat   1380
acaatgaccg gccatgggag gcagctgatg gcaaaacggg ggctcccaac gagtgcagaa   1440
cctgcaagtg taatgggcat gctgatacct gtcacttcga cgttaatgtg tgggaggcat   1500
cagggaatcg tagtggtggt gtctgtgatg actgtcagca caacacagaa ggacagtatt   1560
gccagaggtg caagccaggc ttctatcgtg acctgcggag acccttctca gctccagatg   1620
cttgcaaacc gtgttcctgc catccagtag gatcagctgt ccttcctgcc aactcagtga   1680
ccttctgcga ccccagcaat ggtgactgcc cttgcaagcc tgggtgtgca gggcgacgtt   1740
gtgacaggtg catggtggga tactggggct tcggagacta tggctgtcga ccatgtgact   1800
gtgcggggag ctgtgaccct atcaccggag actgcatcag cagccacaca gacatagact   1860
ggtatcatga agttcctgac ttccgtcccg tgcacaataa gagcgaacca gcctgggagt   1920
gggaggatgc gcaggggttt tctgcacttc tacactcagg taaatgcgaa tgtaaggaac   1980
agacattagg aaatgccaag gcattctgtg gaatgaaata ttcatatgtg ctaaaaataa   2040
agattttatc agctcatgat aaaggtactc atgttgaggt caatgtgaag attaaaaagg   2100
tcttaaaatc taccaaactg aagatttttcc gaggaaagcg aacattatat ccagaatcat   2160
ggacggacag aggatgcact tgtccaatcc tcaatcctgg tttggaatac cttgtagcag   2220
gacatgagga tataagaaca ggcaaactaa ttgtgaatat gaaaagcttt gtccagcact   2280
ggaaaccttc tcttggaaga aaagtcatgg atattttaaa aagagagtgc aagtagcatt   2340
aagatggata gcacataatg gcacttgtct atgtacaaaa cacaaacttt agagcaagaa   2400
gacctcagac aggaaactgg aatttttttaa agtgccaaaa catatagaaa tgtttgaatg   2460
catgggtctt atctaactta tctcttctgg acccatgttt aaatacagtt ttatttcatg   2520
aagagaaatg aaaaccccta cactgatatc tgttttctat gggactgatt ctgaaattct   2580
taactattaa gaatatttta atagcagcat gacatttagc agtaatccat taagggcagt   2640
acctctaaca aggacgcctt ccagcttcag cgatgttact tacgtttgat gctacttaaa   2700
gtaatgaatg acgttttaag gaatccctaa ccctactatc agaaaggtg tttgttaaag   2760
agccttctct tgtgtgttac gcatgaactt tggtctgtag gtgttaaatg gaacctctcc   2820
```

-continued

```
atgtgtatat agtatttcct tgtataaagc actttactac ctaccacttg tgttgtgaac    2880
gtttggtgac tgctgttgaa agaaggaaaa gggtgtgtga gaaagcctac tgaagcagca    2940
gcactgccac tacatgtgga caaaagtgac catataaaag aagttgtgct atttaactct    3000
gaatacttgg agaaactagg tgaagatgca accagaaagg agaatatgta tgcgtgaagt    3060
ctcagctttg agctggaggc tagattccaa gatgacagcc atgatgaaac ttttttaaaaa   3120 actaaaccag aagagacttt aaaataagag aaagaaatca taaatgtaga catatgcttg    3180
gctaaagggg aaatggactt taaattttaa agagctcatt tgcaatgcac ttgtatacac    3240
ttcaaaaatt attgtagaca cagaatttgt tatattttg tgcttagtat ttaaacctga     3300
acattgaaac agttttcctc cttgtctttc ttaacagtaa tagtcattat atttacctgt    3360
tttttaacac aatgtatgtg atagtcaaaa aatcacagtt tttcattatt attcatcttc    3420
tgtacccacg cataaccact atacatagtt tcttttgtac ttgaatatac aaaacatgaa    3480
cacagtgcca tatgaataat ttacataca gaaccttttt ttctctgaag tcctgtggac     3540
ttgcaaatat atatatatat tgctttgtta atttgttttt atatttcata tatgtaataa    3600
aggaatatga tctgaaaaaa aaaaaaaaaa aaaa                                3634
```

<210> SEQ ID NO 23
<211> LENGTH: 438
<212> TYPE: PRT
<213> ORGANISM: Homo sapiens

<400> SEQUENCE: 23

```
Met Tyr Leu Ser Arg Phe Leu Ser Ile His Ala Leu Trp Val Thr Val
1               5                   10                  15

Ser Ser Val Met Gln Pro Tyr Pro Leu Val Trp Gly His Tyr Asp Leu
            20                  25                  30

Cys Lys Thr Gln Ile Tyr Thr Glu Glu Gly Lys Val Trp Asp Tyr Met
        35                  40                  45

Ala Cys Gln Pro Glu Ser Thr Asp Met Thr Lys Tyr Leu Lys Val Lys
    50                  55                  60

Leu Asp Pro Pro Asp Ile Thr Cys Gly Asp Pro Pro Glu Thr Phe Cys
65                  70                  75                  80

Ala Met Gly Asn Pro Tyr Met Cys Asn Asn Glu Cys Asp Ala Ser Thr
                85                  90                  95

Pro Glu Leu Ala His Pro Pro Glu Leu Met Phe Asp Phe Glu Gly Arg
            100                 105                 110

His Pro Ser Thr Phe Trp Gln Ser Ala Thr Trp Lys Glu Tyr Pro Lys
        115                 120                 125

Pro Leu Gln Val Asn Ile Thr Leu Ser Trp Ser Lys Thr Ile Glu Leu
    130                 135                 140

Thr Asp Asn Ile Val Ile Thr Phe Glu Ser Gly Arg Pro Asp Gln Met
145                 150                 155                 160

Ile Leu Glu Lys Ser Leu Asp Tyr Gly Arg Thr Trp Gln Pro Tyr Gln
                165                 170                 175

Tyr Tyr Ala Thr Asp Cys Leu Asp Ala Phe His Met Asp Pro Lys Ser
            180                 185                 190

Val Lys Asp Leu Ser Gln His Thr Val Leu Glu Ile Ile Cys Thr Glu
        195                 200                 205

Glu Tyr Ser Thr Gly Tyr Thr Thr Asn Ser Lys Ile Ile His Phe Glu
    210                 215                 220

Ile Lys Asp Arg Phe Ala Phe Phe Ala Gly Pro Arg Leu Arg Asn Met
225                 230                 235                 240
```

```
Ala Ser Leu Tyr Gly Gln Leu Asp Thr Thr Lys Lys Leu Arg Asp Phe
            245                 250                 255
Phe Thr Val Thr Asp Leu Arg Ile Arg Leu Leu Arg Pro Ala Val Gly
            260                 265                 270
Glu Ile Phe Val Asp Glu Leu His Leu Ala Arg Tyr Phe Tyr Ala Ile
            275                 280                 285
Ser Asp Ile Lys Val Arg Gly Arg Cys Lys Cys Asn Leu His Ala Thr
        290                 295                 300
Val Cys Val Tyr Asp Asn Ser Lys Leu Thr Cys Glu Cys Glu His Asn
305                 310                 315                 320
Thr Thr Gly Pro Asp Cys Gly Lys Cys Lys Lys Asn Tyr Gln Gly Arg
            325                 330                 335
Pro Trp Ser Pro Gly Ser Tyr Leu Pro Ile Pro Lys Gly Thr Ala Asn
            340                 345                 350
Thr Cys Ile Pro Ser Ile Ser Ser Ile Gly Thr Asn Val Cys Asp Asn
            355                 360                 365
Glu Leu Leu His Cys Gln Asn Gly Gly Thr Cys His Asn Asn Val Arg
        370                 375                 380
Cys Leu Cys Pro Ala Ala Tyr Thr Gly Ile Leu Cys Glu Lys Leu Arg
385                 390                 395                 400
Cys Glu Glu Ala Gly Ser Cys Gly Ser Asp Ser Gly Gln Gly Ala Pro
            405                 410                 415
Pro His Gly Ser Pro Ala Leu Leu Leu Leu Thr Thr Leu Leu Gly Thr
            420                 425                 430
Ala Ser Pro Leu Val Phe
            435

<210> SEQ ID NO 24
<211> LENGTH: 3015
<212> TYPE: DNA
<213> ORGANISM: Homo sapiens

<400> SEQUENCE: 24
tgcagccgga gcagcaccag caacagcaac agcgagcggg acggagttag gaccgctcgg      60
agcgcacagg tctcgagggt gttggtgcca gaagaaaaga atgattgatg ggaaacagac     120
accgggctat agacactcat cctttttgct tcagatactg atatctcagcc tgcttgagca    180
tcccttgtga gctgtgaaca ttgaggatca ctcagggtta tcggatgtac aacgggagag    240
ccatcgcttt gctaaattat tatctgcaat tggacatctt ttacaaaaac caaactagac    300
ctgagtctaa tagatatgtt ctaagacaaa gaaaaagctg caagttgtta acgcctaaca    360
cacaagtatg ttaggcttcc accaaagtcc tcaatatacc tgaatacgca caatatctta    420
actcttcata tttggttttg ggatctgctt tgaggtccca tcttcattta aaaaaaaata    480
cagagaccta cctacccgta cgcatacata catatgtgta tatatatgta aactagacaa    540
agatcgcaga tcataaagca agctctgctt tagtttccaa gaagattaca agaatttag     600
agatgtattt gtcaagattc ctgtcgattc atgccctttg ggttacggtg tcctcagtga    660
tgcagcccta cccttttggtt tggggacatt atgatttgtg taagactcag atttacacgg    720
aagaagggaa agtttgggat tacatggcct gccagccgga atccacggac atgacaaaat    780
atctgaaagt gaaactcgat cctccggata ttacctgtgg agaccctcct gagacgttct    840
gtgcaatggg caatccctac atgtgcaata atgagtgtga tgcgagtacc cctgagctgg    900
cacaccccc tgagctgatg tttgattttg aaggaagaca tccctccaca ttttggcagt    960
```

```
ctgccacttg gaaggagtat cccaagcctc tccaggttaa catcactctg tcttggagca    1020
aaaccattga gctaacagac aacatagtta ttacctttga atctgggcgt ccagaccaaa    1080
tgatcctgga gaagtctctc gattatggac gaacatggca gccctatcag tattatgcca    1140
cagactgctt agatgctttt cacatggatc ctaaatccgt gaaggattta tcacagcata    1200
cggtcttaga aatcatttgc acagaagagt actcaacagg gtatacaaca aatagcaaaa    1260
taatccactt tgaaatcaaa gacaggttcg cgttttttgc tggacctcgc ctacgcaata    1320
tggcttccct ctacggacag ctggatacaa ccaagaaact cagagatttc tttacagtca    1380
cagacctgag gataaggctg ttaagaccag ccgttgggga atatttgta gatgagctac     1440 acttggcacg ctacttttac gcgatctcag acataaaggt gcgaggaagg tgcaagtgta    1500
atctccatgc cactgtatgt gtgtatgaca acagcaaatt gacatgcgaa tgtgagcaca    1560
acactacagg tccagactgt gggaaatgca agaagaatta tcagggccga ccttggagtc    1620
caggctccta tctccccatc cccaaaggca ctgcaaatac ctgtatcccc agtatttcca    1680
gtattggtac gaatgtctgc gacaacgagc tcctgcactg ccagaacgga gggacgtgcc    1740
acaacaacgt gcgctgcctg tgcccggccg catacgggg catcctctgc gagaagctgc    1800
ggtgcgagga ggctggcagc tgcggctccg actctggcca gggcgcgccc ccgcacggct    1860
ccccagcgct gctgctgctg accacgctgc tgggaaccgc cagcccctg gtgttctagg     1920 tgtcacctcc agccacaccg gacgggcctg tgccgtgggg aagcagacac aacccaaaca    1980
tttgctacta acataggaaa cacacacata cagacacccc cactcagaca gtgtacaaac    2040
taagaaggcc taactgaact aagccatatt tatcacccgt ggacagcaca tccgagtcaa    2100
gactgttaat ttctgactcc agaggagttg gcagctgttg atattatcac tgcaaatcac    2160
attgccagct gcagagcata ttgtggattg gaaaggctgc gacagccccc caaacaggaa    2220
agacaaaaaa caaacaaatc aaccgaccta aaaacattgg ctactctagc gtggtgcgcc    2280
ctagtacgac tccgcccagt gtgtggacca accaaatagc attctttgct gtcaggtgca    2340
ttgtgggcat aaggaaatct gttacaagct gccatattgg cctgcttccg tccctgaatc    2400
ccttccaacc tgtgctttag tgaacgttgc tctgtaaccc ttgttggttg aaagatttct    2460
ttgtctgatg ttagtgatgc acatgtgtaa cagccccctc taaaagcgca agccagtcat    2520 accectgtat atcttagcag cactgagtcc agtgcgagca cacacccact atacaagagt    2580
ggctatagga aaaagaaag tgtatctatc cttttgtatt caaatgaagt tattttctt     2640 gaactactgt aatatgtaga tttttgtat tattgccaat ttgtgttacc agacaatctg     2700
ttaatgtatc taattcgaat cagcaaagac tgacatttta ttttgtcctc tttcgttctg    2760
ttttgtttca ctgtgcagag atttctctgt aagggcaacg aacgtgctgg catcaaagaa    2820
tatcagttta catatataac aagtgtaata agattccacc aaaggacatt ctaaatgttt    2880
tcttgttgct taacactgg aagatttaaa gaataaaaac tcctgcataa acaaaaaaaa     2940
aaaaaaaaaa aaaaaaaaa aaaaaaaaaa aaaaaaaaaa aaaaaaaaaa aaaaaaaaaa    3000
aaaaaaaaaa aaaaa                                                    3015

<210> SEQ ID NO 25
<211> LENGTH: 530
<212> TYPE: PRT
<213> ORGANISM: Homo sapiens

<400> SEQUENCE: 25

Met Leu His Leu Leu Ala Leu Phe Leu His Cys Leu Pro Leu Ala Ser
1               5                   10                  15
```

```
Gly Asp Tyr Asp Ile Cys Lys Ser Trp Val Thr Thr Asp Glu Gly Pro
            20                  25                  30
Thr Trp Glu Phe Tyr Ala Cys Gln Pro Lys Val Met Arg Leu Lys Asp
            35                  40                  45
Tyr Val Lys Val Lys Val Glu Pro Ser Gly Ile Thr Cys Gly Asp Pro
 50                  55                  60
Pro Glu Arg Phe Cys Ser His Glu Asn Pro Tyr Leu Cys Ser Asn Glu
 65                  70                  75                  80
Cys Asp Ala Ser Asn Pro Asp Leu Ala His Pro Pro Arg Leu Met Phe
            85                  90                  95
Asp Lys Glu Glu Gly Leu Ala Thr Tyr Trp Gln Ser Ile Thr Trp
            100                 105                 110
Ser Arg Tyr Pro Ser Pro Leu Glu Ala Asn Ile Thr Leu Ser Trp Asn
            115                 120                 125
Lys Thr Val Glu Leu Thr Asp Asp Val Val Met Thr Phe Glu Tyr Gly
            130                 135                 140
Arg Pro Thr Val Met Val Leu Glu Lys Ser Leu Asp Asn Gly Arg Thr
145                 150                 155                 160
Trp Gln Pro Tyr Gln Phe Tyr Ala Glu Asp Cys Met Glu Ala Phe Gly
            165                 170                 175
Met Ser Ala Arg Arg Ala Arg Asp Met Ser Ser Ser Ala His Arg
            180                 185                 190
Val Leu Cys Thr Glu Glu Tyr Ser Arg Trp Ala Gly Ser Lys Lys Glu
            195                 200                 205
Lys His Val Arg Phe Glu Val Arg Asp Arg Phe Ala Ile Phe Ala Gly
            210                 215                 220
Pro Asp Leu Arg Asn Met Asp Asn Leu Tyr Thr Arg Leu Glu Ser Ala
225                 230                 235                 240
Lys Gly Leu Lys Glu Phe Phe Thr Leu Thr Asp Leu Arg Met Arg Leu
            245                 250                 255
Leu Arg Pro Ala Leu Gly Gly Thr Tyr Val Gln Arg Glu Asn Leu Tyr
            260                 265                 270
Lys Tyr Phe Tyr Ala Ile Ser Asn Ile Glu Val Ile Gly Arg Cys Lys
            275                 280                 285
Cys Asn Leu His Ala Asn Leu Cys Ser Met Arg Glu Gly Ser Leu Gln
            290                 295                 300
Cys Glu Cys Glu His Asn Thr Thr Gly Pro Asp Cys Gly Lys Cys Lys
305                 310                 315                 320
Lys Asn Phe Arg Thr Arg Ser Trp Arg Ala Gly Ser Tyr Leu Pro Leu
            325                 330                 335
Pro His Gly Ser Pro Asn Ala Cys Ala Ala Gly Ser Phe Gly Asn
            340                 345                 350
Cys Glu Cys Tyr Gly His Ser Asn Arg Cys Ser Tyr Ile Asp Phe Leu
            355                 360                 365
Asn Val Val Thr Cys Val Ser Cys Lys His Asn Thr Arg Gly Gln His
            370                 375                 380
Cys Gln His Cys Arg Leu Gly Tyr Tyr Arg Asn Gly Ser Ala Glu Leu
385                 390                 395                 400
Asp Asp Glu Asn Val Cys Ile Glu Cys Asn Cys Asn Gln Ile Gly Ser
            405                 410                 415
Val His Asp Arg Cys Asn Glu Thr Gly Phe Cys Glu Cys Arg Glu Gly
            420                 425                 430
Ala Ala Gly Pro Lys Cys Asp Asp Cys Leu Pro Thr His Tyr Trp Arg
```

```
                       435                 440                 445
Gln Gly Cys Tyr Pro Asn Val Cys Asp Asp Gln Leu Leu Cys Gln
        450                 455                 460

Asn Gly Gly Thr Cys Leu Gln Asn Gln Arg Cys Ala Cys Pro Arg Gly
465                 470                 475                 480

Tyr Thr Gly Val Arg Cys Glu Gln Pro Arg Cys Asp Pro Ala Asp Asp
                    485                 490                 495

Asp Gly Gly Leu Asp Cys Asp Arg Ala Pro Gly Ala Ala Pro Arg Pro
                500                 505                 510

Ala Thr Leu Leu Gly Cys Leu Leu Leu Gly Leu Ala Ala Arg Leu
        515                 520                 525

Gly Arg
    530

<210> SEQ ID NO 26
<211> LENGTH: 2428
<212> TYPE: DNA
<213> ORGANISM: Homo sapiens

<400> SEQUENCE: 26
ccatgctgag gccgcgagtc ccgcctgacc ccgtcgctgc ctctccaggg cttctctggg     60
ccgcgcctct gcagactgcg cagccatgct gcatctgctg gcgctcttcc tgcactgcct    120
ccctctggcc tctggggact atgacatctg caaatcctgg gtgaccacag atgagggccc    180
cacctgggag ttctacgcct gccagcccaa ggtgatgcgc ctgaaggact acgtcaaggt    240
gaaggtggag ccctcaggca tcacatgtgg agacccccct gagaggttct gctcccatga    300
gaatccctac ctatgcagca cgagtgtga cgcctccaac ccggacctgg cccacccgcc    360
caggctcatg ttcgacaagg aggaggaggg cctggccacc tactggcaga gcatcacctg    420
gagccgctac cccagcccgc tggaagccaa catcaccctt tcgtggaaca agaccgtgga    480
gctgaccgac gacgtggtga tgaccttcga gtacggccgg cccacggtca tggtcctgga    540
gaagtccctg gacaacgggc gcacctggca gccctaccag ttctacgccg aggactgcat    600
ggaggccttc ggtatgtccg cccgccgggc ccgcgacatg tcatcctcca gcgcgcaccg    660
cgtgctctgc accgaggagt actcgcgctg gcaggctcc aagaaggaga gcacgtgcg    720 cttcgaggtg cgggaccgct cgccatcctt gccggcccc gacctgcgca catggacaa    780 cctctacacg cggctggaga gcgccaaggg cctcaaggag ttcttcaccc tcaccgacct    840
gcgcatgcgc ctgctgcgcc cggcgctggg cggcacctat gtgcagcggg agaacctcta    900
caagtacttc tacgccatct ccaacatcga ggtcatcggc aggtgcaagt gcaacctgca    960
tgccaacctg tgctccatgc gcgagggcag cctgcagtgc gagtgcgagc acaacaccac   1020
cggccccgac tgcggcaagt gcaagaagaa tttccgcacc cggtcctggc gggccggctc   1080
ctacctgccg ctgccccatg gctctcccaa cgcctgtgcc gctgcaggtt cctttggcaa   1140
ctgcgaatgc tacggtcact ccaaccgctg cagctacatt gacttcctga atgtggtgac   1200
ctgcgtcagc tgcaagcaca cacgcgagg tcagcactgc cagcactgcc ggctgggcta   1260
ctaccgcaac ggctcggcag agctggatga tgagaacgtc tgcattgagt gtaactgcaa   1320
ccagatagcc tccgtgcacg accggtgcaa cgagaccggc ttctgcgagt ccgcgagggg   1380
cgcggcgggc cccaagtgcg acgactgcct ccccacgcac tactggcgcc agggctgcta   1440
ccccaacgtg tgcgacgacg accagctgct gtgccgaaac ggaggcacct gcctgcagaa   1500
ccagcgctgc gcctgcccgc gcggctacac cggcgtgcgc tgcgagcagc cccgctgcga   1560
```

```
cccegeegac gatgacggeg gtctggactg cgaccgegeg cccggggccg ccccgcgccc    1620
cgccaccctg ctcggctgcc tgctgctgct ggggctggcc gcccgcctgg gccgctgagc    1680
cccgcccgga ggacgctccc cgcacccgga ggccgggggt cccggggtcc cggggcgggg    1740
ccggcgtccg aggccgggcg gtgagaaggg tgccgcccga ggtgctccca ggtgctactc    1800
agcagggccc cccgcccggc ccgcgctccc gcccgcactg ccctccccccc gcagcagggg    1860 cgccttggga ctccggtccc cgcgcctgcg atttggtttc gttttctttt tgtattatcc    1920
gccgcccagt ccttttttg tctttctctc tctctctttt ttttttttttt ttctggcggt    1980 gagccagagg gtcgggagaa acgctgctcg ccccacaccc cgtcctgcct cccaccacac    2040
ttacacacac gggactgtgg ccgacaccccc ctggcctgtg ccaggctcac gggcggcggc    2100
ggaccccgac ctccagttgc ctacaattcc agtcgctgac ttggtcctgt tttctattct    2160 ttattttcc tgcaacccac cagaccccag gcctcaccgg aggcccggtg accacggaac    2220
tcaccgtctg ggggaggagg agagaaggaa ggggtggggg gcctggaaac ttcgttctgt    2280
agagaactat ttttgtttgt attcactgtc ccctgcaagg gggacggggc gggagcactg    2340
gtcaccgcgg gggccgatgg tggagaatcc gaggagtaaa gagtttgctc actgctgcaa    2400
aaaaaaaaaa aaaaaaaaaa aaaaaaaa                                       2428

<210> SEQ ID NO 27
<211> LENGTH: 36
<212> TYPE: PRT
<213> ORGANISM: Homo sapiens

<400> SEQUENCE: 27

Val Arg Arg Leu Pro Pro Gln Leu Ala Gln Leu Ser Ser Pro Cys Ser
1               5                   10                  15

Ser Ser Asp Ser Leu Cys Ser Arg Arg Gly Leu Ser Ser Pro Arg Leu
            20                  25                  30

Ser Leu Ala Pro
        35

<210> SEQ ID NO 28
<211> LENGTH: 24
<212> TYPE: DNA
<213> ORGANISM: Homo sapiens

<400> SEQUENCE: 28
tttttagcgt acctatgagc agtt                                              24

<210> SEQ ID NO 29
<211> LENGTH: 24
<212> TYPE: DNA
<213> ORGANISM: Homo sapiens

<400> SEQUENCE: 29
caacaccaga cacttacgag tgcc                                              24

<210> SEQ ID NO 30
<211> LENGTH: 24
<212> TYPE: DNA
<213> ORGANISM: Homo sapiens

<400> SEQUENCE: 30
ttcgaaggcc agaattctcc tggc                                              24

<210> SEQ ID NO 31
<211> LENGTH: 20
```

```
<212> TYPE: DNA
<213> ORGANISM: Homo sapiens

<400> SEQUENCE: 31
cccaaggcca acagggaaaa                                                20

<210> SEQ ID NO 32
<211> LENGTH: 20
<212> TYPE: DNA
<213> ORGANISM: Homo sapiens

<400> SEQUENCE: 32
ggtgcccatc tcctgctcaa                                                20

<210> SEQ ID NO 33
<211> LENGTH: 23
<212> TYPE: DNA
<213> ORGANISM: Homo sapiens

<400> SEQUENCE: 33
cccugacgaa agagaagccu auu                                            23

<210> SEQ ID NO 34
<211> LENGTH: 23
<212> TYPE: DNA
<213> ORGANISM: Homo sapiens

<400> SEQUENCE: 34
uaggcuucuc uuucgucagg guu                                            23

<210> SEQ ID NO 35
<211> LENGTH: 21
<212> TYPE: DNA
<213> ORGANISM: Homo sapiens

<400> SEQUENCE: 35
cccctacaaa agaaaaacca a                                              21

<210> SEQ ID NO 36
<211> LENGTH: 1132
<212> TYPE: PRT
<213> ORGANISM: Homo sapiens

<400> SEQUENCE: 36
```

Met Ala Leu Thr Pro Gly Trp Gly Ser Ser Ala Gly Pro Val Arg Pro
1               5                   10                  15

Glu Leu Trp Leu Leu Leu Trp Ala Ala Ala Trp Arg Leu Gly Ala Ser
            20                  25                  30

Ala Cys Pro Ala Leu Cys Thr Cys Thr Gly Thr Thr Val Asp Cys His
        35                  40                  45

Gly Thr Gly Leu Gln Ala Ile Pro Lys Asn Ile Pro Arg Asn Thr Glu
    50                  55                  60

Arg Leu Glu Leu Asn Gly Asn Asn Ile Thr Arg Ile His Lys Asn Asp
65                  70                  75                  80

Phe Ala Gly Leu Lys Gln Leu Arg Val Leu Gln Leu Met Glu Asn Gln
                85                  90                  95

Ile Gly Ala Val Glu Arg Gly Ala Phe Asp Asp Met Lys Glu Leu Glu
            100                 105                 110

Arg Leu Arg Leu Asn Arg Asn Gln Leu His Met Leu Pro Glu Leu Leu
        115                 120                 125

Phe Gln Asn Asn Gln Ala Leu Ser Arg Leu Asp Leu Ser Glu Asn Ala

```
                130              135               140
Ile Gln Ala Ile Pro Arg Lys Ala Phe Arg Gly Ala Thr Asp Leu Lys
145                 150                 155                 160

Asn Leu Arg Leu Asp Lys Asn Gln Ile Ser Cys Ile Glu Glu Gly Ala
                165                 170                 175

Phe Arg Ala Leu Arg Gly Leu Glu Val Leu Thr Leu Asn Asn Asn Asn
                180                 185                 190

Ile Thr Thr Ile Pro Val Ser Ser Phe Asn His Met Pro Lys Leu Arg
            195                 200                 205

Thr Phe Arg Leu His Ser Asn His Leu Phe Cys Asp Cys His Leu Ala
        210                 215                 220

Trp Leu Ser Gln Trp Leu Arg Gln Arg Pro Thr Ile Gly Leu Phe Thr
225                 230                 235                 240

Gln Cys Ser Gly Pro Ala Ser Leu Arg Gly Leu Asn Val Ala Glu Val
                245                 250                 255

Gln Lys Ser Glu Phe Ser Cys Ser Gly Gln Gly Glu Ala Gly Arg Val
                260                 265                 270

Pro Thr Cys Thr Leu Ser Ser Gly Ser Cys Pro Ala Met Cys Thr Cys
            275                 280                 285

Ser Asn Gly Ile Val Asp Cys Arg Gly Lys Gly Leu Thr Ala Ile Pro
290                 295                 300

Ala Asn Leu Pro Glu Thr Met Thr Glu Ile Arg Leu Glu Leu Asn Gly
305                 310                 315                 320

Ile Lys Ser Ile Pro Pro Gly Ala Phe Ser Pro Tyr Arg Lys Leu Arg
                325                 330                 335

Arg Ile Asp Leu Ser Asn Asn Gln Ile Ala Glu Ile Ala Pro Asp Ala
                340                 345                 350

Phe Gln Gly Leu Arg Ser Leu Asn Ser Leu Val Leu Tyr Gly Asn Lys
            355                 360                 365

Ile Thr Asp Leu Pro Arg Gly Val Phe Gly Gly Leu Tyr Thr Leu Gln
        370                 375                 380

Leu Leu Leu Leu Asn Ala Asn Lys Ile Asn Cys Ile Arg Pro Asp Ala
385                 390                 395                 400

Phe Gln Asp Leu Gln Asn Leu Ser Leu Leu Ser Leu Tyr Asp Asn Lys
                405                 410                 415

Ile Gln Ser Leu Ala Lys Gly Thr Phe Thr Ser Leu Arg Ala Ile Gln
                420                 425                 430

Thr Leu His Leu Ala Gln Asn Pro Phe Ile Cys Asp Cys Asn Leu Lys
            435                 440                 445

Trp Leu Ala Asp Phe Leu Arg Thr Asn Pro Ile Glu Thr Ser Gly Ala
450                 455                 460

Arg Cys Ala Ser Pro Arg Arg Leu Ala Asn Lys Arg Ile Gly Gln Ile
465                 470                 475                 480

Lys Ser Lys Lys Phe Arg Cys Ser Ala Lys Glu Gln Tyr Phe Ile Pro
                485                 490                 495

Gly Thr Glu Asp Tyr Gln Leu Asn Ser Glu Cys Asn Ser Asp Val Val
            500                 505                 510

Cys Pro His Lys Cys Arg Cys Glu Ala Asn Val Val Glu Cys Ser Ser
        515                 520                 525

Leu Lys Leu Thr Lys Ile Pro Glu Arg Ile Pro Gln Ser Thr Ala Glu
            530                 535                 540

Leu Arg Leu Asn Asn Asn Glu Ile Ser Ile Leu Glu Ala Thr Gly Met
545                 550                 555                 560
```

```
Phe Lys Lys Leu Thr His Leu Lys Lys Ile Asn Leu Ser Asn Asn Lys
                565                 570                 575

Val Ser Glu Ile Glu Asp Gly Ala Phe Gly Ala Ala Ser Val Ser
            580                 585                 590

Glu Leu His Leu Thr Ala Asn Gln Leu Glu Ser Ile Arg Ser Gly Met
        595                 600                 605

Phe Arg Gly Leu Asp Gly Leu Arg Thr Leu Met Leu Arg Asn Asn Arg
    610                 615                 620

Ile Ser Cys Ile His Asn Asp Ser Phe Thr Gly Leu Arg Asn Val Arg
625                 630                 635                 640

Leu Leu Ser Leu Tyr Asp Asn Gln Ile Thr Thr Val Ser Pro Gly Ala
                645                 650                 655

Phe Asp Thr Leu Gln Ser Leu Ser Thr Leu Asn Leu Leu Ala Asn Pro
            660                 665                 670

Phe Asn Cys Asn Cys Gln Leu Ala Trp Leu Gly Gly Trp Leu Arg Lys
        675                 680                 685

Arg Lys Ile Val Thr Gly Asn Pro Arg Cys Gln Asn Pro Asp Phe Leu
    690                 695                 700

Arg Gln Ile Pro Leu Gln Asp Val Ala Phe Pro Asp Phe Arg Cys Glu
705                 710                 715                 720

Glu Gly Gln Glu Glu Gly Gly Cys Leu Pro Arg Pro Gln Cys Pro Gln
                725                 730                 735

Glu Cys Ala Cys Leu Asp Thr Val Val Arg Cys Ser Asn Lys His Leu
            740                 745                 750

Arg Ala Leu Pro Lys Gly Ile Pro Lys Asn Val Thr Glu Leu Tyr Leu
        755                 760                 765

Asp Gly Asn Gln Phe Thr Leu Val Pro Gly Gln Leu Ser Thr Phe Lys
    770                 775                 780

Tyr Leu Gln Leu Val Asp Leu Ser Asn Asn Lys Ile Ser Ser Leu Ser
785                 790                 795                 800

Asn Ser Ser Phe Thr Asn Met Ser Gln Leu Thr Thr Leu Ile Leu Ser
                805                 810                 815

Tyr Asn Ala Leu Gln Cys Ile Pro Pro Leu Ala Phe Gln Gly Leu Arg
            820                 825                 830

Ser Leu Arg Leu Leu Ser Leu His Gly Asn Asp Ile Ser Thr Leu Gln
        835                 840                 845

Glu Gly Ile Phe Ala Asp Val Thr Ser Leu Ser His Leu Ala Ile Gly
    850                 855                 860

Ala Asn Pro Leu Tyr Cys Asp Cys His Leu Arg Trp Leu Ser Ser Trp
865                 870                 875                 880

Val Lys Thr Gly Tyr Lys Glu Pro Gly Ile Ala Arg Cys Ala Gly Pro
                885                 890                 895

Gln Asp Met Glu Gly Lys Leu Leu Thr Thr Pro Ala Lys Lys Phe
            900                 905                 910

Glu Cys Gln Gly Pro Pro Thr Leu Ala Val Gln Ala Lys Cys Asp Leu
        915                 920                 925

Cys Leu Ser Ser Pro Cys Gln Asn Gln Gly Thr Cys His Asn Asp Pro
    930                 935                 940

Leu Glu Val Tyr Arg Cys Ala Cys Pro Ser Gly Tyr Lys Gly Arg Asp
945                 950                 955                 960

Cys Glu Val Ser Leu Asn Ser Cys Ser Ser Gly Pro Cys Glu Asn Gly
                965                 970                 975

Gly Thr Cys His Ala Gln Glu Gly Glu Asp Ala Pro Phe Thr Cys Ser
            980                 985                 990
```

-continued

```
Cys Pro Thr Gly Phe Glu Gly Pro Thr Cys Gly Val Asn Thr Asp Asp
        995                 1000                1005

Cys Val Asp His Ala Cys Ala Asn Gly Val Cys Val Asp Gly
    1010                1015                1020

Val Gly Asn Tyr Thr Cys Gln Cys Pro Leu Gln Tyr Glu Gly Lys
    1025                1030                1035

Ala Cys Glu Gln Leu Val Asp Leu Cys Ser Pro Asp Leu Asn Pro
    1040                1045                1050

Cys Gln His Glu Ala Gln Cys Val Gly Thr Pro Asp Gly Pro Arg
    1055                1060                1065

Cys Glu Cys Met Pro Gly Tyr Ala Gly Asp Asn Cys Ser Glu Asn
    1070                1075                1080

Gln Asp Asp Cys Arg Asp His Arg Cys Gln Asn Gly Ala Gln Cys
    1085                1090                1095

Met Asp Glu Val Asn Ser Tyr Ser Cys Leu Cys Ala Glu Gly Tyr
    1100                1105                1110

Ser Gly Gln Leu Cys Glu Ile Pro Pro His Leu Pro Ala Pro Lys
    1115                1120                1125

Ser Pro Cys Glu
    1130

<210> SEQ ID NO 37
<211> LENGTH: 1119
<212> TYPE: PRT
<213> ORGANISM: Homo sapiens

<400> SEQUENCE: 37

Met Arg Gly Val Gly Trp Gln Met Leu Ser Leu Ser Leu Gly Leu Val
1               5                   10                  15

Leu Ala Ile Leu Asn Lys Val Ala Pro Gln Ala Cys Pro Ala Gln Cys
                20                  25                  30

Ser Cys Ser Gly Ser Thr Val Asp Cys His Gly Leu Ala Leu Arg Ser
            35                  40                  45

Val Pro Arg Asn Ile Pro Arg Asn Thr Glu Arg Leu Asp Leu Asn Gly
        50                  55                  60

Asn Asn Ile Thr Arg Ile Thr Lys Thr Asp Phe Ala Gly Leu Arg His
65                  70                  75                  80

Leu Arg Val Leu Gln Leu Met Glu Asn Lys Ile Ser Thr Ile Glu Arg
                85                  90                  95

Gly Ala Phe Gln Asp Leu Lys Glu Leu Glu Arg Leu Arg Leu Asn Arg
            100                 105                 110

Asn His Leu Gln Leu Phe Pro Glu Leu Leu Phe Leu Gly Thr Ala Lys
        115                 120                 125

Leu Tyr Arg Leu Asp Leu Ser Glu Asn Gln Ile Gln Ala Ile Pro Arg
    130                 135                 140

Lys Ala Phe Arg Gly Ala Val Asp Ile Lys Asn Leu Gln Leu Asp Tyr
145                 150                 155                 160

Asn Gln Ile Ser Cys Ile Glu Asp Gly Ala Phe Arg Ala Leu Arg Asp
                165                 170                 175

Leu Glu Val Leu Thr Leu Asn Asn Asn Ile Thr Arg Leu Ser Val
            180                 185                 190

Ala Ser Phe Asn His Met Pro Lys Leu Arg Thr Phe Arg Leu His Ser
        195                 200                 205

Asn Asn Leu Tyr Cys Asp Cys His Leu Ala Trp Leu Ser Asp Trp Leu
    210                 215                 220
```

-continued

```
Arg Gln Arg Pro Arg Val Gly Leu Tyr Thr Gln Cys Met Gly Pro Ser
225                 230                 235                 240

His Leu Arg Gly His Asn Val Ala Glu Val Gln Lys Arg Glu Phe Val
            245                 250                 255

Cys Ser Gly His Gln Ser Phe Met Ala Pro Ser Cys Ser Val Leu His
            260                 265                 270

Cys Pro Ala Ala Cys Thr Cys Ser Asn Asn Ile Val Asp Cys Arg Gly
            275                 280                 285

Lys Gly Leu Thr Glu Ile Pro Thr Asn Leu Pro Glu Thr Ile Thr Glu
            290                 295                 300

Ile Arg Leu Glu Gln Asn Thr Ile Lys Val Ile Pro Pro Gly Ala Phe
305                 310                 315                 320

Ser Pro Tyr Lys Lys Leu Arg Arg Ile Asp Leu Ser Asn Asn Gln Ile
            325                 330                 335

Ser Glu Leu Ala Pro Asp Ala Phe Gln Gly Leu Arg Ser Leu Asn Ser
            340                 345                 350

Leu Val Leu Tyr Gly Asn Lys Ile Thr Glu Leu Pro Lys Ser Leu Phe
            355                 360                 365

Glu Gly Leu Phe Ser Leu Gln Leu Leu Leu Leu Asn Ala Asn Lys Ile
            370                 375                 380

Asn Cys Leu Arg Val Asp Ala Phe Gln Asp Leu His Asn Leu Asn Leu
385                 390                 395                 400

Leu Ser Leu Tyr Asp Asn Lys Leu Gln Thr Ile Ala Lys Gly Thr Phe
                405                 410                 415

Ser Pro Leu Arg Ala Ile Gln Thr Met His Leu Ala Gln Asn Pro Phe
                420                 425                 430

Ile Cys Asp Cys His Leu Lys Trp Leu Ala Asp Tyr Leu His Thr Asn
            435                 440                 445

Pro Ile Glu Thr Ser Gly Ala Arg Cys Thr Ser Pro Arg Arg Leu Ala
            450                 455                 460

Asn Lys Arg Ile Gly Gln Ile Lys Ser Lys Lys Phe Arg Cys Ser Ala
465                 470                 475                 480

Lys Glu Gln Tyr Phe Ile Pro Gly Thr Glu Asp Tyr Arg Ser Lys Leu
                485                 490                 495

Ser Gly Asp Cys Phe Ala Asp Leu Ala Cys Pro Glu Lys Cys Arg Cys
            500                 505                 510

Glu Gly Thr Thr Val Asp Cys Ser Asn Gln Lys Leu Asn Lys Ile Pro
            515                 520                 525

Glu His Ile Pro Gln Tyr Thr Ala Glu Leu Arg Leu Asn Asn Asn Glu
            530                 535                 540

Phe Thr Val Leu Glu Ala Thr Gly Ile Phe Lys Lys Leu Pro Gln Leu
545                 550                 555                 560

Arg Lys Ile Asn Phe Ser Asn Asn Lys Ile Thr Asp Ile Glu Glu Gly
                565                 570                 575

Ala Phe Glu Gly Ala Ser Gly Val Asn Glu Ile Leu Leu Thr Ser Asn
            580                 585                 590

Arg Leu Glu Asn Val Gln His Lys Met Phe Lys Gly Leu Glu Ser Leu
            595                 600                 605

Lys Thr Leu Met Leu Arg Ser Asn Arg Ile Thr Cys Val Gly Asn Asp
            610                 615                 620

Ser Phe Ile Gly Leu Ser Ser Val Arg Leu Leu Ser Leu Tyr Asp Asn
625                 630                 635                 640

Gln Ile Thr Thr Val Ala Pro Gly Ala Phe Asp Thr Leu His Ser Leu
```

```
                        645                 650                 655
Ser Thr Leu Asn Leu Leu Ala Asn Pro Phe Asn Cys Asn Cys Tyr Leu
            660                 665                 670

Ala Trp Leu Gly Glu Trp Leu Arg Lys Lys Arg Ile Val Thr Gly Asn
            675                 680                 685

Pro Arg Cys Gln Lys Pro Tyr Phe Leu Lys Glu Ile Pro Ile Gln Asp
            690                 695                 700

Val Ala Ile Gln Asp Phe Thr Cys Asp Asp Gly Asn Asp Asn Ser
705                 710                 715                 720

Cys Ser Pro Leu Ser Arg Cys Pro Thr Glu Cys Thr Cys Leu Asp Thr
                    725                 730                 735

Val Val Arg Cys Ser Asn Lys Gly Leu Lys Val Leu Pro Lys Gly Ile
            740                 745                 750

Pro Arg Asp Val Thr Glu Leu Tyr Leu Asp Gly Asn Gln Phe Thr Leu
            755                 760                 765

Val Pro Lys Glu Leu Ser Asn Tyr Lys His Leu Thr Leu Ile Asp Leu
            770                 775                 780

Ser Asn Asn Arg Ile Ser Thr Leu Ser Asn Gln Ser Phe Asn Met Thr
785                 790                 795                 800

Gln Leu Leu Thr Leu Ile Leu Ser Tyr Asn Arg Leu Arg Cys Ile Pro
            805                 810                 815

Pro Arg Thr Phe Asp Gly Leu Lys Ser Leu Arg Leu Leu Ser Leu His
            820                 825                 830

Gly Asn Asp Ile Ser Val Val Pro Glu Gly Ala Phe Asn Asp Leu Ser
            835                 840                 845

Ala Leu Ser His Leu Ala Ile Gly Ala Asn Pro Leu Tyr Cys Asp Cys
            850                 855                 860

Asn Met Gln Trp Leu Ser Asp Trp Val Lys Ser Glu Tyr Lys Glu Pro
865                 870                 875                 880

Gly Ile Ala Arg Cys Ala Gly Pro Gly Glu Met Ala Asp Lys Leu Leu
            885                 890                 895

Leu Thr Thr Pro Ser Lys Lys Phe Thr Cys Gln Gly Pro Val Asp Val
            900                 905                 910

Asn Ile Leu Ala Lys Cys Asn Pro Cys Leu Ser Asn Pro Cys Lys Asn
            915                 920                 925

Asp Gly Thr Cys Asn Ser Asp Pro Val Asp Phe Tyr Arg Cys Thr Cys
            930                 935                 940

Pro Tyr Gly Phe Lys Gly Gln Asp Cys Asp Val Pro Ile His Ala Cys
945                 950                 955                 960

Ile Ser Asn Pro Cys Lys His Gly Gly Thr Cys His Leu Lys Glu Gly
            965                 970                 975

Glu Glu Asp Gly Phe Trp Cys Ile Cys Ala Asp Gly Phe Glu Gly Glu
            980                 985                 990

Asn Cys Glu Val Asn Val Asp Asp Cys Glu Asp Asn Asp Cys Glu Asn
            995                 1000                1005

Asn Ser Thr Cys Val Asp Gly Ile Asn Asn Tyr Thr Cys Leu Cys
            1010                1015                1020

Pro Pro Glu Tyr Thr Gly Glu Leu Cys Glu Glu Lys Leu Asp Phe
            1025                1030                1035

Cys Ala Gln Asp Leu Asn Pro Cys Gln His Asp Ser Lys Cys Ile
            1040                1045                1050

Leu Thr Pro Lys Gly Phe Lys Cys Asp Cys Thr Pro Gly Tyr Val
            1055                1060                1065
```

-continued

```
Gly Glu His Cys Asp Ile Asp Phe Asp Asp Cys Gln Asp Asn Lys
    1070                1075                1080

Cys Lys Asn Gly Ala His Cys Thr Asp Ala Val Asn Gly Tyr Thr
    1085                1090                1095

Cys Ile Cys Pro Glu Gly Tyr Ser Gly Leu Phe Cys Glu Phe Ser
    1100                1105                1110

Pro Pro Met Val Leu Pro
    1115

<210> SEQ ID NO 38
<211> LENGTH: 1118
<212> TYPE: PRT
<213> ORGANISM: Homo sapiens

<400> SEQUENCE: 38

Met Ala Pro Gly Trp Ala Gly Val Gly Ala Ala Val Arg Ala Arg Leu
1               5                   10                  15

Ala Leu Ala Leu Ala Leu Ala Ser Val Leu Ser Gly Pro Pro Ala Val
            20                  25                  30

Ala Cys Pro Thr Lys Cys Thr Cys Ser Ala Ala Ser Val Asp Cys His
        35                  40                  45

Gly Leu Gly Leu Arg Ala Val Pro Arg Gly Ile Pro Arg Asn Ala Glu
    50                  55                  60

Arg Leu Asp Leu Asp Arg Asn Asn Ile Thr Arg Ile Thr Lys Met Asp
65                  70                  75                  80

Phe Ala Gly Leu Lys Asn Leu Arg Val Leu His Leu Glu Asp Asn Gln
                85                  90                  95

Val Ser Val Ile Glu Arg Gly Ala Phe Gln Asp Leu Lys Gln Leu Glu
            100                 105                 110

Arg Leu Arg Leu Asn Lys Asn Lys Leu Gln Val Leu Pro Glu Leu Leu
        115                 120                 125

Phe Gln Ser Thr Pro Lys Leu Thr Arg Leu Asp Leu Ser Glu Asn Gln
    130                 135                 140

Ile Gln Gly Ile Pro Arg Lys Ala Phe Arg Gly Ile Thr Asp Val Lys
145                 150                 155                 160

Asn Leu Gln Leu Asp Asn Asn His Ile Ser Cys Ile Glu Asp Gly Ala
                165                 170                 175

Phe Arg Ala Leu Arg Asp Leu Glu Ile Leu Thr Leu Asn Asn Asn Asn
            180                 185                 190

Ile Ser Arg Ile Leu Val Thr Ser Phe Asn His Met Pro Lys Ile Arg
        195                 200                 205

Thr Leu Arg Leu His Ser Asn His Leu Tyr Cys Asp Cys His Leu Ala
    210                 215                 220

Trp Leu Ser Asp Trp Leu Arg Gln Arg Arg Thr Val Gly Gln Phe Thr
225                 230                 235                 240

Leu Cys Met Ala Pro Val His Leu Arg Gly Phe Asn Val Ala Asp Val
                245                 250                 255

Gln Lys Lys Glu Tyr Val Cys Pro Ala Pro His Ser Glu Pro Pro Ser
            260                 265                 270

Cys Asn Ala Asn Ser Ile Ser Cys Pro Ser Pro Cys Thr Cys Ser Asn
        275                 280                 285

Asn Ile Val Asp Cys Arg Gly Lys Gly Leu Met Glu Ile Pro Ala Asn
    290                 295                 300

Leu Pro Glu Gly Ile Val Glu Ile Arg Leu Glu Gln Asn Ser Ile Lys
305                 310                 315                 320
```

```
Ala Ile Pro Ala Gly Ala Phe Thr Gln Tyr Lys Lys Leu Lys Arg Ile
            325                 330                 335

Asp Ile Ser Lys Asn Gln Ile Ser Asp Ile Ala Pro Asp Ala Phe Gln
            340                 345                 350

Gly Leu Lys Ser Leu Thr Ser Leu Val Leu Tyr Gly Asn Lys Ile Thr
            355                 360                 365

Glu Ile Ala Lys Gly Leu Phe Asp Gly Leu Val Ser Leu Gln Leu Leu
            370                 375                 380

Leu Leu Asn Ala Asn Lys Ile Asn Cys Leu Arg Val Asn Thr Phe Gln
385                 390                 395                 400

Asp Leu Gln Asn Leu Asn Leu Leu Ser Leu Tyr Asp Asn Lys Leu Gln
            405                 410                 415

Thr Ile Ser Lys Gly Leu Phe Ala Pro Leu Gln Ser Ile Gln Thr Leu
            420                 425                 430

His Leu Ala Gln Asn Pro Phe Val Cys Asp Cys His Leu Lys Trp Leu
            435                 440                 445

Ala Asp Tyr Leu Gln Asp Asn Pro Ile Glu Thr Ser Gly Ala Arg Cys
            450                 455                 460

Ser Ser Pro Arg Arg Leu Ala Asn Lys Arg Ile Ser Gln Ile Lys Ser
465                 470                 475                 480

Lys Lys Phe Arg Cys Ser Gly Ser Glu Asp Tyr Arg Ser Arg Phe Ser
            485                 490                 495

Ser Glu Cys Phe Met Asp Leu Val Cys Pro Glu Lys Cys Arg Cys Glu
            500                 505                 510

Gly Thr Ile Val Asp Cys Ser Asn Gln Lys Leu Val Arg Ile Pro Ser
            515                 520                 525

His Leu Pro Glu Tyr Val Thr Asp Leu Arg Leu Asn Asp Asn Glu Val
            530                 535                 540

Ser Val Leu Glu Ala Thr Gly Ile Phe Lys Lys Leu Pro Asn Leu Arg
545                 550                 555                 560

Lys Ile Asn Leu Ser Asn Asn Lys Ile Lys Glu Val Arg Glu Gly Ala
            565                 570                 575

Phe Asp Gly Ala Ala Ser Val Gln Glu Leu Met Leu Thr Gly Asn Gln
            580                 585                 590

Leu Glu Thr Val His Gly Arg Val Phe Arg Gly Leu Ser Gly Leu Lys
            595                 600                 605

Thr Leu Met Leu Arg Ser Asn Leu Ile Gly Cys Val Ser Asn Asp Thr
            610                 615                 620

Phe Ala Gly Leu Ser Ser Val Arg Leu Leu Ser Leu Tyr Asp Asn Arg
625                 630                 635                 640

Ile Thr Thr Ile Thr Pro Gly Ala Phe Thr Thr Leu Val Ser Leu Ser
            645                 650                 655

Thr Ile Asn Leu Leu Ser Asn Pro Phe Asn Cys Asn Cys His Leu Ala
            660                 665                 670

Trp Leu Gly Lys Trp Leu Arg Lys Arg Arg Ile Val Ser Gly Asn Pro
            675                 680                 685

Arg Cys Gln Lys Pro Phe Phe Leu Lys Glu Ile Pro Ile Gln Asp Val
            690                 695                 700

Ala Ile Gln Asp Phe Thr Cys Asp Gly Asn Glu Glu Ser Ser Cys Gln
705                 710                 715                 720

Leu Ser Pro Arg Cys Pro Glu Gln Cys Thr Cys Met Glu Thr Val Val
            725                 730                 735

Arg Cys Ser Asn Lys Gly Leu Arg Ala Leu Pro Arg Gly Met Pro Lys
            740                 745                 750
```

Asp Val Thr Glu Leu Tyr Leu Glu Gly Asn His Leu Thr Ala Val Pro
    755                 760                 765

Arg Glu Leu Ser Ala Leu Arg His Leu Thr Leu Ile Asp Leu Ser Asn
    770                 775                 780

Asn Ser Ile Ser Met Leu Thr Asn Tyr Thr Phe Ser Asn Met Ser His
785                 790                 795                 800

Leu Ser Thr Leu Ile Leu Ser Tyr Asn Arg Leu Arg Cys Ile Pro Val
                805                 810                 815

His Ala Phe Asn Gly Leu Arg Ser Leu Arg Val Leu Thr Leu His Gly
                    820                 825                 830

Asn Asp Ile Ser Ser Val Pro Glu Gly Ser Phe Asn Asp Leu Thr Ser
                835                 840                 845

Leu Ser His Leu Ala Leu Gly Thr Asn Pro Leu His Cys Asp Cys Ser
    850                 855                 860

Leu Arg Trp Leu Ser Glu Trp Val Lys Ala Gly Tyr Lys Glu Pro Gly
865                 870                 875                 880

Ile Ala Arg Cys Ser Ser Pro Glu Pro Met Ala Asp Arg Leu Leu Leu
                885                 890                 895

Thr Thr Pro Thr His Arg Phe Gln Cys Lys Gly Pro Val Asp Ile Asn
                900                 905                 910

Ile Val Ala Lys Cys Asn Ala Cys Leu Ser Ser Pro Cys Lys Asn Asn
                915                 920                 925

Gly Thr Cys Thr Gln Asp Pro Val Glu Leu Tyr Arg Cys Ala Cys Pro
    930                 935                 940

Tyr Ser Tyr Lys Gly Lys Asp Cys Thr Val Pro Ile Asn Thr Cys Ile
945                 950                 955                 960

Gln Asn Pro Cys Gln His Gly Gly Thr Cys His Leu Ser Asp Ser His
                965                 970                 975

Lys Asp Gly Phe Ser Cys Ser Cys Pro Leu Gly Phe Glu Gly Gln Arg
                980                 985                 990

Cys Glu Ile Asn Pro Asp Asp Cys Glu Asp Asn Asp Cys Glu Asn Asn
                995                 1000                1005

Ala Thr Cys Val Asp Gly Ile Asn Asn Tyr Val Cys Ile Cys Pro
    1010                1015                1020

Pro Asn Tyr Thr Gly Glu Leu Cys Asp Glu Val Ile Asp His Cys
    1025                1030                1035

Val Pro Glu Leu Asn Leu Cys Gln His Glu Ala Lys Cys Ile Pro
    1040                1045                1050

Leu Asp Lys Gly Phe Ser Cys Glu Cys Val Pro Gly Tyr Ser Gly
    1055                1060                1065

Lys Leu Cys Glu Thr Asp Asn Asp Asp Cys Val Ala His Lys Cys
    1070                1075                1080

Arg His Gly Ala Gln Cys Val Asp Thr Ile Asn Gly Tyr Thr Cys
    1085                1090                1095

Thr Cys Pro Gln Gly Phe Ser Gly Pro Phe Cys Glu His Pro Pro
    1100                1105                1110

Pro Met Val Leu Leu
    1115

<210> SEQ ID NO 39
<211> LENGTH: 1091
<212> TYPE: PRT
<213> ORGANISM: Homo sapiens

<400> SEQUENCE: 39

```
Gln Ala Cys Pro Ala Gln Cys Ser Cys Ser Gly Ser Thr Val Asp Cys
 1               5                  10                  15

His Gly Leu Ala Leu Arg Ser Val Pro Arg Asn Ile Pro Arg Asn Thr
                20                  25                  30

Glu Arg Leu Asp Leu Asn Gly Asn Asn Ile Thr Arg Ile Thr Lys Thr
                 35                  40                  45

Asp Phe Ala Gly Leu Arg His Leu Arg Val Leu Gln Leu Met Glu Asn
         50                  55                  60

Lys Ile Ser Thr Ile Glu Arg Gly Ala Phe Gln Asp Leu Lys Glu Leu
 65                  70                  75                  80

Glu Arg Leu Arg Leu Asn Arg Asn His Leu Gln Leu Phe Pro Glu Leu
                 85                  90                  95

Leu Phe Leu Gly Thr Ala Lys Leu Tyr Arg Leu Asp Leu Ser Glu Asn
            100                 105                 110

Gln Ile Gln Ala Ile Pro Arg Lys Ala Phe Arg Gly Ala Val Asp Ile
            115                 120                 125

Lys Asn Leu Gln Leu Asp Tyr Asn Gln Ile Ser Cys Ile Glu Asp Gly
130                 135                 140

Ala Phe Arg Ala Leu Arg Asp Leu Glu Val Leu Thr Leu Asn Asn Asn
145                 150                 155                 160

Asn Ile Thr Arg Leu Ser Val Ala Ser Phe Asn His Met Pro Lys Leu
                165                 170                 175

Arg Thr Phe Arg Leu His Ser Asn Asn Leu Tyr Cys Asp Cys His Leu
                180                 185                 190

Ala Trp Leu Ser Asp Trp Leu Arg Gln Arg Pro Arg Val Gly Leu Tyr
            195                 200                 205

Thr Gln Cys Met Gly Pro Ser His Leu Arg Gly His Asn Val Ala Glu
            210                 215                 220

Val Gln Lys Arg Glu Phe Val Cys Ser Gly His Gln Ser Phe Met Ala
225                 230                 235                 240

Pro Ser Cys Ser Val Leu His Cys Pro Ala Ala Cys Thr Cys Ser Asn
                245                 250                 255

Asn Ile Val Asp Cys Arg Gly Lys Gly Leu Thr Glu Ile Pro Thr Asn
                260                 265                 270

Leu Pro Glu Thr Ile Thr Glu Ile Arg Leu Glu Gln Asn Thr Ile Lys
            275                 280                 285

Val Ile Pro Pro Gly Ala Phe Ser Pro Tyr Lys Lys Leu Arg Arg Ile
290                 295                 300

Asp Leu Ser Asn Asn Gln Ile Ser Glu Leu Ala Pro Asp Ala Phe Gln
305                 310                 315                 320

Gly Leu Arg Ser Leu Asn Ser Leu Val Leu Tyr Gly Asn Lys Ile Thr
                325                 330                 335

Glu Leu Pro Lys Ser Leu Phe Glu Gly Leu Phe Ser Leu Gln Leu Leu
            340                 345                 350

Leu Leu Asn Ala Asn Lys Ile Asn Cys Leu Arg Val Asp Ala Phe Gln
            355                 360                 365

Asp Leu His Asn Leu Asn Leu Leu Ser Leu Tyr Asp Asn Lys Leu Gln
            370                 375                 380

Thr Ile Ala Lys Gly Thr Phe Ser Pro Leu Arg Ala Ile Gln Thr Met
385                 390                 395                 400

His Leu Ala Gln Asn Pro Phe Ile Cys Asp Cys His Leu Lys Trp Leu
                405                 410                 415

Ala Asp Tyr Leu His Thr Asn Pro Ile Glu Thr Ser Gly Ala Arg Cys
```

```
                420              425              430
Thr Ser Pro Arg Arg Leu Ala Asn Lys Arg Ile Gly Gln Ile Lys Ser
        435              440              445
Lys Lys Phe Arg Cys Ser Ala Lys Glu Gln Tyr Phe Ile Pro Gly Thr
    450              455              460
Glu Asp Tyr Arg Ser Lys Leu Ser Gly Asp Cys Phe Ala Asp Leu Ala
465              470              475              480
Cys Pro Glu Lys Cys Arg Cys Glu Gly Thr Thr Val Asp Cys Ser Asn
            485              490              495
Gln Lys Leu Asn Lys Ile Pro Glu His Ile Pro Gln Tyr Thr Ala Glu
        500              505              510
Leu Arg Leu Asn Asn Asn Glu Phe Thr Val Leu Glu Ala Thr Gly Ile
    515              520              525
Phe Lys Lys Leu Pro Gln Leu Arg Lys Ile Asn Phe Ser Asn Asn Lys
        530              535              540
Ile Thr Asp Ile Glu Glu Gly Ala Phe Glu Gly Ala Ser Gly Val Asn
545              550              555              560
Glu Ile Leu Leu Thr Ser Asn Arg Leu Glu Asn Val Gln His Lys Met
            565              570              575
Phe Lys Gly Leu Glu Ser Leu Lys Thr Leu Met Leu Arg Ser Asn Arg
        580              585              590
Ile Thr Cys Val Gly Asn Asp Ser Phe Ile Gly Leu Ser Ser Val Arg
    595              600              605
Leu Leu Ser Leu Tyr Asp Asn Gln Ile Thr Thr Val Ala Pro Gly Ala
    610              615              620
Phe Asp Thr Leu His Ser Leu Ser Thr Leu Asn Leu Leu Ala Asn Pro
625              630              635              640
Phe Asn Cys Asn Cys Tyr Leu Ala Trp Leu Gly Glu Trp Leu Arg Lys
            645              650              655
Lys Arg Ile Val Thr Gly Asn Pro Arg Cys Gln Lys Pro Tyr Phe Leu
        660              665              670
Lys Glu Ile Pro Ile Gln Asp Val Ala Ile Gln Asp Phe Thr Cys Asp
    675              680              685
Asp Gly Asn Asp Asp Asn Ser Cys Ser Pro Leu Ser Arg Cys Pro Thr
    690              695              700
Glu Cys Thr Cys Leu Asp Thr Val Val Arg Cys Ser Asn Lys Gly Leu
705              710              715              720
Lys Val Leu Pro Lys Gly Ile Pro Arg Asp Val Thr Glu Leu Tyr Leu
            725              730              735
Asp Gly Asn Gln Phe Thr Leu Val Pro Lys Glu Leu Ser Asn Tyr Lys
        740              745              750
His Leu Thr Leu Ile Asp Leu Ser Asn Asn Arg Ile Ser Thr Leu Ser
        755              760              765
Asn Gln Ser Phe Ser Asn Met Thr Gln Leu Leu Thr Leu Ile Leu Ser
        770              775              780
Tyr Asn Arg Leu Arg Cys Ile Pro Pro Arg Thr Phe Asp Gly Leu Lys
785              790              795              800
Ser Leu Arg Leu Leu Ser Leu His Gly Asn Asp Ile Ser Val Val Pro
            805              810              815
Glu Gly Ala Phe Asn Asp Leu Ser Ala Leu Ser His Leu Ala Ile Gly
        820              825              830
Ala Asn Pro Leu Tyr Cys Asp Cys Asn Met Gln Trp Leu Ser Asp Trp
        835              840              845
```

```
Val Lys Ser Glu Tyr Lys Glu Pro Gly Ile Ala Arg Cys Ala Gly Pro
    850                 855                 860

Gly Glu Met Ala Asp Lys Leu Leu Leu Thr Thr Pro Ser Lys Lys Phe
865                 870                 875                 880

Thr Cys Gln Gly Pro Val Asp Val Asn Ile Leu Ala Lys Cys Asn Pro
                885                 890                 895

Cys Leu Ser Asn Pro Cys Lys Asn Asp Gly Thr Cys Asn Ser Asp Pro
                900                 905                 910

Val Asp Phe Tyr Arg Cys Thr Cys Pro Tyr Gly Phe Lys Gly Gln Asp
                915                 920                 925

Cys Asp Val Pro Ile His Ala Cys Ile Ser Asn Pro Cys Lys His Gly
                930                 935                 940

Gly Thr Cys His Leu Lys Glu Gly Glu Asp Gly Phe Trp Cys Ile
945                 950                 955                 960

Cys Ala Asp Gly Phe Glu Gly Glu Asn Cys Glu Val Asn Val Asp Asp
                965                 970                 975

Cys Glu Asp Asn Asp Cys Glu Asn Asn Ser Thr Cys Val Asp Gly Ile
                980                 985                 990

Asn Asn Tyr Thr Cys Leu Cys Pro Pro Glu Tyr Thr Gly Glu Leu Cys
                995                1000                1005

Glu Glu Lys Leu Asp Phe Cys Ala Gln Asp Leu Asn Pro Cys Gln
   1010                1015                1020

His Asp Ser Lys Cys Ile Leu Thr Pro Lys Gly Phe Lys Cys Asp
   1025                1030                1035

Cys Thr Pro Gly Tyr Val Gly Glu His Cys Asp Ile Asp Phe Asp
   1040                1045                1050

Asp Cys Gln Asp Asn Lys Cys Lys Asn Gly Ala His Cys Thr Asp
   1055                1060                1065

Ala Val Asn Gly Tyr Thr Cys Ile Cys Pro Glu Gly Tyr Ser Gly
   1070                1075                1080

Leu Phe Cys Glu Phe Ser Pro Pro
   1085                1090

<210> SEQ ID NO 40
<211> LENGTH: 1506
<212> TYPE: PRT
<213> ORGANISM: Homo sapiens

<400> SEQUENCE: 40

Ile Leu Asn Lys Val Ala Pro Gln Ala Cys Pro Ala Gln Cys Ser Cys
1               5                  10                  15

Ser Gly Ser Thr Val Asp Cys His Gly Leu Ala Leu Arg Ser Val Pro
                20                  25                  30

Arg Asn Ile Pro Arg Asn Thr Glu Arg Leu Asp Leu Asn Gly Asn Asn
            35                  40                  45

Ile Thr Arg Ile Thr Lys Thr Asp Phe Ala Gly Leu Arg His Leu Arg
        50                  55                  60

Val Leu Gln Leu Met Glu Asn Lys Ile Ser Thr Ile Glu Arg Gly Ala
65                  70                  75                  80

Phe Gln Asp Leu Lys Glu Leu Glu Arg Leu Arg Leu Asn Arg Asn His
                85                  90                  95

Leu Gln Leu Phe Pro Glu Leu Leu Phe Leu Gly Thr Ala Lys Leu Tyr
            100                 105                 110

Arg Leu Asp Leu Ser Glu Asn Gln Ile Gln Ala Ile Pro Arg Lys Ala
        115                 120                 125
```

```
Phe Arg Gly Ala Val Asp Ile Lys Asn Leu Gln Leu Asp Tyr Asn Gln
130                 135                 140

Ile Ser Cys Ile Glu Asp Gly Ala Phe Arg Ala Leu Arg Asp Leu Glu
145                 150                 155                 160

Val Leu Thr Leu Asn Asn Asn Asn Ile Thr Arg Leu Ser Val Ala Ser
                165                 170                 175

Phe Asn His Met Pro Lys Leu Arg Thr Phe Arg Leu His Ser Asn Asn
                180                 185                 190

Leu Tyr Cys Asp Cys His Leu Ala Trp Leu Ser Asp Trp Leu Arg Gln
            195                 200                 205

Arg Pro Arg Val Gly Leu Tyr Thr Gln Cys Met Gly Pro Ser His Leu
210                 215                 220

Arg Gly His Asn Val Ala Glu Val Gln Lys Arg Glu Phe Val Cys Ser
225                 230                 235                 240

Gly His Gln Ser Phe Met Ala Pro Ser Cys Ser Val Leu His Cys Pro
                245                 250                 255

Ala Ala Cys Thr Cys Ser Asn Asn Ile Val Asp Cys Arg Gly Lys Gly
            260                 265                 270

Leu Thr Glu Ile Pro Thr Asn Leu Pro Glu Thr Ile Thr Glu Ile Arg
        275                 280                 285

Leu Glu Gln Asn Thr Ile Lys Val Ile Pro Pro Gly Ala Phe Ser Pro
290                 295                 300

Tyr Lys Lys Leu Arg Arg Ile Asp Leu Ser Asn Asn Gln Ile Ser Glu
305                 310                 315                 320

Leu Ala Pro Asp Ala Phe Gln Gly Leu Arg Ser Leu Asn Ser Leu Val
                325                 330                 335

Leu Tyr Gly Asn Lys Ile Thr Glu Leu Pro Lys Ser Leu Phe Glu Gly
                340                 345                 350

Leu Phe Ser Leu Gln Leu Leu Leu Asn Ala Asn Lys Ile Asn Cys
            355                 360                 365

Leu Arg Val Asp Ala Phe Gln Asp Leu His Asn Leu Asn Leu Leu Ser
        370                 375                 380

Leu Tyr Asp Asn Lys Leu Gln Thr Ile Ala Lys Gly Thr Phe Ser Pro
385                 390                 395                 400

Leu Arg Ala Ile Gln Thr Met His Leu Ala Gln Asn Pro Phe Ile Cys
                405                 410                 415

Asp Cys His Leu Lys Trp Leu Ala Asp Tyr Leu His Thr Asn Pro Ile
            420                 425                 430

Glu Thr Ser Gly Ala Arg Cys Thr Ser Pro Arg Arg Leu Ala Asn Lys
        435                 440                 445

Arg Ile Gly Gln Ile Lys Ser Lys Lys Phe Arg Cys Ser Ala Lys Glu
450                 455                 460

Gln Tyr Phe Ile Pro Gly Thr Glu Asp Tyr Arg Ser Lys Leu Ser Gly
465                 470                 475                 480

Asp Cys Phe Ala Asp Leu Ala Cys Pro Glu Lys Cys Arg Cys Glu Gly
                485                 490                 495

Thr Thr Val Asp Cys Ser Asn Gln Lys Leu Asn Lys Ile Pro Glu His
                500                 505                 510

Ile Pro Gln Tyr Thr Ala Glu Leu Arg Leu Asn Asn Asn Glu Phe Thr
        515                 520                 525

Val Leu Glu Ala Thr Gly Ile Phe Lys Lys Leu Pro Gln Leu Arg Lys
530                 535                 540

Ile Asn Phe Ser Asn Asn Lys Ile Thr Asp Ile Glu Glu Gly Ala Phe
545                 550                 555                 560
```

Glu Gly Ala Ser Gly Val Asn Glu Ile Leu Leu Thr Ser Asn Arg Leu
                565                 570                 575

Glu Asn Val Gln His Lys Met Phe Lys Gly Leu Glu Ser Leu Lys Thr
            580                 585                 590

Leu Met Leu Arg Ser Asn Arg Ile Thr Cys Val Gly Asn Asp Ser Phe
                595                 600                 605

Ile Gly Leu Ser Ser Val Arg Leu Leu Ser Leu Tyr Asp Asn Gln Ile
        610                 615                 620

Thr Thr Val Ala Pro Gly Ala Phe Asp Thr Leu His Ser Leu Ser Thr
625                 630                 635                 640

Leu Asn Leu Leu Ala Asn Pro Phe Asn Cys Asn Cys Tyr Leu Ala Trp
                645                 650                 655

Leu Gly Glu Trp Leu Arg Lys Lys Arg Ile Val Thr Gly Asn Pro Arg
                660                 665                 670

Cys Gln Lys Pro Tyr Phe Leu Lys Glu Ile Pro Ile Gln Asp Val Ala
            675                 680                 685

Ile Gln Asp Phe Thr Cys Asp Asp Gly Asn Asp Asp Asn Ser Cys Ser
        690                 695                 700

Pro Leu Ser Arg Cys Pro Thr Glu Cys Thr Cys Leu Asp Thr Val Val
705                 710                 715                 720

Arg Cys Ser Asn Lys Gly Leu Lys Val Leu Pro Lys Gly Ile Pro Arg
                725                 730                 735

Asp Val Thr Glu Leu Tyr Leu Asp Gly Asn Gln Phe Thr Leu Val Pro
            740                 745                 750

Lys Glu Leu Ser Asn Tyr Lys His Leu Thr Leu Ile Asp Leu Ser Asn
        755                 760                 765

Asn Arg Ile Ser Thr Leu Ser Asn Gln Ser Phe Ser Asn Met Thr Gln
        770                 775                 780

Leu Leu Thr Leu Ile Leu Ser Tyr Asn Arg Leu Arg Cys Ile Pro Pro
785                 790                 795                 800

Arg Thr Phe Asp Gly Leu Lys Ser Leu Arg Leu Leu Ser Leu His Gly
                805                 810                 815

Asn Asp Ile Ser Val Val Pro Glu Gly Ala Phe Asn Asp Leu Ser Ala
            820                 825                 830

Leu Ser His Leu Ala Ile Gly Ala Asn Pro Leu Tyr Cys Asp Cys Asn
        835                 840                 845

Met Gln Trp Leu Ser Asp Trp Val Lys Ser Glu Tyr Lys Glu Pro Gly
850                 855                 860

Ile Ala Arg Cys Ala Gly Pro Gly Glu Met Ala Asp Lys Leu Leu Leu
865                 870                 875                 880

Thr Thr Pro Ser Lys Lys Phe Thr Cys Gln Gly Pro Val Asp Val Asn
                885                 890                 895

Ile Leu Ala Lys Cys Asn Pro Cys Leu Ser Asn Pro Cys Lys Asn Asp
            900                 905                 910

Gly Thr Cys Asn Ser Asp Pro Val Asp Phe Tyr Arg Cys Thr Cys Pro
        915                 920                 925

Tyr Gly Phe Lys Gly Gln Asp Cys Asp Val Pro Ile His Ala Cys Ile
        930                 935                 940

Ser Asn Pro Cys Lys His Gly Gly Thr Cys His Leu Lys Glu Gly Glu
945                 950                 955                 960

Glu Asp Gly Phe Trp Cys Ile Cys Ala Asp Gly Phe Glu Gly Glu Asn
                965                 970                 975

Cys Glu Val Asn Val Asp Asp Cys Glu Asp Asn Asp Cys Glu Asn Asn

-continued

|  | 980 |  |  |  | 985 |  |  |  | 990 |  |  |
|---|---|---|---|---|---|---|---|---|---|---|---|
| Ser | Thr | Cys | Val | Asp | Gly | Ile | Asn | Asn | Tyr | Thr | Cys | Leu | Cys | Pro | Pro |
|  | 995 |  |  |  | 1000 |  |  |  | 1005 |  |  |
| Glu | Tyr | Thr | Gly | Glu | Leu | Cys | Glu | Glu | Lys | Leu | Asp | Phe | Cys | Ala |
|  | 1010 |  |  |  | 1015 |  |  |  | 1020 |  |  |
| Gln | Asp | Leu | Asn | Pro | Cys | Gln | His | Asp | Ser | Lys | Cys | Ile | Leu | Thr |
|  | 1025 |  |  |  | 1030 |  |  |  | 1035 |  |  |
| Pro | Lys | Gly | Phe | Lys | Cys | Asp | Cys | Thr | Pro | Gly | Tyr | Val | Gly | Glu |
|  | 1040 |  |  |  | 1045 |  |  |  | 1050 |  |  |
| His | Cys | Asp | Ile | Asp | Phe | Asp | Cys | Gln | Asp | Asn | Lys | Cys | Lys |
|  | 1055 |  |  |  | 1060 |  |  |  | 1065 |  |  |
| Asn | Gly | Ala | His | Cys | Thr | Asp | Ala | Val | Asn | Gly | Tyr | Thr | Cys | Ile |
|  | 1070 |  |  |  | 1075 |  |  |  | 1080 |  |  |
| Cys | Pro | Glu | Gly | Tyr | Ser | Gly | Leu | Phe | Cys | Glu | Phe | Ser | Pro | Pro |
|  | 1085 |  |  |  | 1090 |  |  |  | 1095 |  |  |
| Met | Val | Leu | Pro | Arg | Thr | Ser | Pro | Cys | Asp | Asn | Phe | Asp | Cys | Gln |
|  | 1100 |  |  |  | 1105 |  |  |  | 1110 |  |  |
| Asn | Gly | Ala | Gln | Cys | Ile | Val | Arg | Ile | Asn | Glu | Pro | Ile | Cys | Gln |
|  | 1115 |  |  |  | 1120 |  |  |  | 1125 |  |  |
| Cys | Leu | Pro | Gly | Tyr | Gln | Gly | Glu | Lys | Cys | Glu | Lys | Leu | Val | Ser |
|  | 1130 |  |  |  | 1135 |  |  |  | 1140 |  |  |
| Val | Asn | Phe | Ile | Asn | Lys | Glu | Ser | Tyr | Leu | Gln | Ile | Pro | Ser | Ala |
|  | 1145 |  |  |  | 1150 |  |  |  | 1155 |  |  |
| Lys | Val | Arg | Pro | Gln | Thr | Asn | Ile | Thr | Leu | Gln | Ile | Ala | Thr | Asp |
|  | 1160 |  |  |  | 1165 |  |  |  | 1170 |  |  |
| Glu | Asp | Ser | Gly | Ile | Leu | Leu | Tyr | Lys | Gly | Asp | Lys | Asp | His | Ile |
|  | 1175 |  |  |  | 1180 |  |  |  | 1185 |  |  |
| Ala | Val | Glu | Leu | Tyr | Arg | Gly | Arg | Val | Arg | Ala | Ser | Tyr | Asp | Thr |
|  | 1190 |  |  |  | 1195 |  |  |  | 1200 |  |  |
| Gly | Ser | His | Pro | Ala | Ser | Ala | Ile | Tyr | Ser | Val | Glu | Thr | Ile | Asn |
|  | 1205 |  |  |  | 1210 |  |  |  | 1215 |  |  |
| Asp | Gly | Asn | Phe | His | Ile | Val | Glu | Leu | Leu | Ala | Leu | Asp | Gln | Ser |
|  | 1220 |  |  |  | 1225 |  |  |  | 1230 |  |  |
| Leu | Ser | Leu | Ser | Val | Asp | Gly | Gly | Asn | Pro | Lys | Ile | Ile | Thr | Asn |
|  | 1235 |  |  |  | 1240 |  |  |  | 1245 |  |  |
| Leu | Ser | Lys | Gln | Ser | Thr | Leu | Asn | Phe | Asp | Ser | Pro | Leu | Tyr | Val |
|  | 1250 |  |  |  | 1255 |  |  |  | 1260 |  |  |
| Gly | Gly | Met | Pro | Gly | Lys | Ser | Asn | Val | Ala | Ser | Leu | Arg | Gln | Ala |
|  | 1265 |  |  |  | 1270 |  |  |  | 1275 |  |  |
| Pro | Gly | Gln | Asn | Gly | Thr | Ser | Phe | His | Gly | Cys | Ile | Arg | Asn | Leu |
|  | 1280 |  |  |  | 1285 |  |  |  | 1290 |  |  |
| Tyr | Ile | Asn | Ser | Glu | Leu | Gln | Asp | Phe | Gln | Lys | Val | Pro | Met | Gln |
|  | 1295 |  |  |  | 1300 |  |  |  | 1305 |  |  |
| Thr | Gly | Ile | Leu | Pro | Gly | Cys | Glu | Pro | Cys | His | Lys | Lys | Val | Cys |
|  | 1310 |  |  |  | 1315 |  |  |  | 1320 |  |  |
| Ala | His | Gly | Thr | Cys | Gln | Pro | Ser | Ser | Gln | Ala | Gly | Phe | Thr | Cys |
|  | 1325 |  |  |  | 1330 |  |  |  | 1335 |  |  |
| Glu | Cys | Gln | Glu | Gly | Trp | Met | Gly | Pro | Leu | Cys | Asp | Gln | Arg | Thr |
|  | 1340 |  |  |  | 1345 |  |  |  | 1350 |  |  |
| Asn | Asp | Pro | Cys | Leu | Gly | Asn | Lys | Cys | Val | His | Gly | Thr | Cys | Leu |
|  | 1355 |  |  |  | 1360 |  |  |  | 1365 |  |  |
| Pro | Ile | Asn | Ala | Phe | Ser | Tyr | Ser | Cys | Lys | Cys | Leu | Glu | Gly | His |
|  | 1370 |  |  |  | 1375 |  |  |  | 1380 |  |  |

-continued

Gly Gly Val Leu Cys Asp Glu Glu Asp Leu Phe Asn Pro Cys
1385                1390                1395

Gln Ala Ile Lys Cys Lys His Gly Lys Cys Arg Leu Ser Gly Leu
1400                1405                1410

Gly Gln Pro Tyr Cys Glu Cys Ser Ser Gly Tyr Thr Gly Asp Ser
1415                1420                1425

Cys Asp Arg Glu Ile Ser Cys Arg Gly Glu Arg Ile Arg Asp Tyr
1430                1435                1440

Tyr Gln Lys Gln Gln Gly Tyr Ala Ala Cys Gln Thr Thr Lys Lys
1445                1450                1455

Val Ser Arg Leu Glu Cys Arg Gly Gly Cys Ala Gly Gly Gln Cys
1460                1465                1470

Cys Gly Pro Leu Arg Ser Lys Arg Arg Lys Tyr Ser Phe Glu Cys
1475                1480                1485

Thr Asp Gly Ser Ser Phe Val Asp Glu Val Glu Lys Val Val Lys
1490                1495                1500

Cys Gly Cys
1505

<210> SEQ ID NO 41
<211> LENGTH: 1498
<212> TYPE: PRT
<213> ORGANISM: Homo sapiens

<400> SEQUENCE: 41

Ile Leu Asn Lys Val Ala Pro Gln Ala Cys Pro Ala Gln Cys Ser Cys
1               5                   10                  15

Ser Gly Ser Thr Val Asp Cys His Gly Leu Ala Leu Arg Ser Val Pro
            20                  25                  30

Arg Asn Ile Pro Arg Asn Thr Glu Arg Leu Asp Leu Asn Gly Asn Asn
        35                  40                  45

Ile Thr Arg Ile Thr Lys Thr Asp Phe Ala Gly Leu Arg His Leu Arg
    50                  55                  60

Val Leu Gln Leu Met Glu Asn Lys Ile Ser Thr Ile Glu Arg Gly Ala
65                  70                  75                  80

Phe Gln Asp Leu Lys Glu Leu Glu Arg Leu Arg Leu Asn Arg Asn His
                85                  90                  95

Leu Gln Leu Phe Pro Glu Leu Leu Phe Leu Gly Thr Ala Lys Leu Tyr
            100                 105                 110

Arg Leu Asp Leu Ser Glu Asn Gln Ile Gln Ala Ile Pro Arg Lys Ala
        115                 120                 125

Phe Arg Gly Ala Val Asp Ile Lys Asn Leu Gln Leu Asp Tyr Asn Gln
    130                 135                 140

Ile Ser Cys Ile Glu Asp Gly Ala Phe Arg Ala Leu Arg Asp Leu Glu
145                 150                 155                 160

Val Leu Thr Leu Asn Asn Asn Asn Ile Thr Arg Leu Ser Val Ala Ser
                165                 170                 175

Phe Asn His Met Pro Lys Leu Arg Thr Phe Arg Leu His Ser Asn Asn
            180                 185                 190

Leu Tyr Cys Asp Cys His Leu Ala Trp Leu Ser Asp Trp Leu Arg Gln
        195                 200                 205

Arg Pro Arg Val Gly Leu Tyr Thr Gln Cys Met Gly Pro Ser His Leu
    210                 215                 220

Arg Gly His Asn Val Ala Glu Val Gln Lys Arg Glu Phe Val Cys Ser
225                 230                 235                 240

```
Gly His Gln Ser Phe Met Ala Pro Ser Cys Ser Val Leu His Cys Pro
                245                 250                 255

Ala Ala Cys Thr Cys Ser Asn Asn Ile Val Asp Cys Arg Gly Lys Gly
            260                 265                 270

Leu Thr Glu Ile Pro Thr Asn Leu Pro Glu Thr Ile Thr Glu Ile Arg
        275                 280                 285

Leu Glu Gln Asn Thr Ile Lys Val Ile Pro Gly Ala Phe Ser Pro
    290                 295                 300

Tyr Lys Lys Leu Arg Arg Ile Asp Leu Ser Asn Asn Gln Ile Ser Glu
305                 310                 315                 320

Leu Ala Pro Asp Ala Phe Gln Gly Leu Arg Ser Leu Asn Ser Leu Val
                325                 330                 335

Leu Tyr Gly Asn Lys Ile Thr Glu Leu Pro Lys Ser Leu Phe Glu Gly
            340                 345                 350

Leu Phe Ser Leu Gln Leu Leu Leu Asn Ala Asn Lys Ile Asn Cys
        355                 360                 365

Leu Arg Val Asp Ala Phe Gln Asp Leu His Asn Leu Asn Leu Leu Ser
    370                 375                 380

Leu Tyr Asp Asn Lys Leu Gln Thr Ile Ala Lys Gly Thr Phe Ser Pro
385                 390                 395                 400

Leu Arg Ala Ile Gln Thr Met His Leu Ala Gln Asn Pro Phe Ile Cys
                405                 410                 415

Asp Cys His Leu Lys Trp Leu Ala Asp Tyr Leu His Thr Asn Pro Ile
            420                 425                 430

Glu Thr Ser Gly Ala Arg Cys Thr Ser Pro Arg Arg Leu Ala Asn Lys
        435                 440                 445

Arg Ile Gly Gln Ile Lys Ser Lys Lys Phe Arg Cys Ser Ala Lys Glu
    450                 455                 460

Gln Tyr Phe Ile Pro Gly Thr Glu Asp Tyr Arg Ser Lys Leu Ser Gly
465                 470                 475                 480

Asp Cys Phe Ala Asp Leu Ala Cys Pro Glu Lys Cys Arg Cys Glu Gly
                485                 490                 495

Thr Thr Val Asp Cys Ser Asn Gln Lys Leu Asn Lys Ile Pro Glu His
            500                 505                 510

Ile Pro Gln Tyr Thr Ala Glu Leu Arg Leu Asn Asn Asn Glu Phe Thr
        515                 520                 525

Val Leu Glu Ala Thr Gly Ile Phe Lys Lys Leu Pro Gln Leu Arg Lys
    530                 535                 540

Ile Asn Phe Ser Asn Asn Lys Ile Thr Asp Ile Glu Glu Gly Ala Phe
545                 550                 555                 560

Glu Gly Ala Ser Gly Val Asn Glu Ile Leu Leu Thr Ser Asn Arg Leu
                565                 570                 575

Glu Asn Val Gln His Lys Met Phe Lys Gly Leu Glu Ser Leu Lys Thr
            580                 585                 590

Leu Met Leu Arg Ser Asn Arg Ile Thr Cys Val Gly Asn Asp Ser Phe
        595                 600                 605

Ile Gly Leu Ser Ser Val Arg Leu Leu Ser Leu Tyr Asp Asn Gln Ile
    610                 615                 620

Thr Thr Val Ala Pro Gly Ala Phe Asp Thr Leu His Ser Leu Ser Thr
625                 630                 635                 640

Leu Asn Leu Leu Ala Asn Pro Phe Asn Cys Asn Cys Tyr Leu Ala Trp
                645                 650                 655

Leu Gly Glu Trp Leu Arg Lys Lys Arg Ile Val Thr Gly Asn Pro Arg
            660                 665                 670
```

```
Cys Gln Lys Pro Tyr Phe Leu Lys Glu Ile Pro Ile Gln Asp Val Ala
        675                 680                 685
Ile Gln Asp Phe Thr Cys Asp Asp Gly Asn Asp Asp Asn Ser Cys Ser
690                 695                 700
Pro Leu Ser Arg Cys Pro Thr Glu Cys Thr Cys Leu Asp Thr Val Val
705                 710                 715                 720
Arg Cys Ser Asn Lys Gly Leu Lys Val Leu Pro Lys Gly Ile Pro Arg
                725                 730                 735
Asp Val Thr Glu Leu Tyr Leu Asp Gly Asn Gln Phe Thr Leu Val Pro
                740                 745                 750
Lys Glu Leu Ser Asn Tyr Lys His Leu Thr Leu Ile Asp Leu Ser Asn
            755                 760                 765
Asn Arg Ile Ser Thr Leu Ser Asn Gln Ser Phe Ser Asn Met Thr Gln
770                 775                 780
Leu Leu Thr Leu Ile Leu Ser Tyr Asn Arg Leu Arg Cys Ile Pro Pro
785                 790                 795                 800
Arg Thr Phe Asp Gly Leu Lys Ser Leu Arg Leu Leu Ser Leu His Gly
                805                 810                 815
Asn Asp Ile Ser Val Val Pro Glu Gly Ala Phe Asn Asp Leu Ser Ala
                820                 825                 830
Leu Ser His Leu Ala Ile Gly Ala Asn Pro Leu Tyr Cys Asp Cys Asn
            835                 840                 845
Met Gln Trp Leu Ser Asp Trp Val Lys Ser Glu Tyr Lys Glu Pro Gly
850                 855                 860
Ile Ala Arg Cys Ala Gly Pro Gly Glu Met Ala Asp Lys Leu Leu Leu
865                 870                 875                 880
Thr Thr Pro Ser Lys Lys Phe Thr Cys Gln Gly Pro Val Asp Val Asn
                885                 890                 895
Ile Leu Ala Lys Cys Asn Pro Cys Leu Ser Asn Pro Cys Lys Asn Asp
                900                 905                 910
Gly Thr Cys Asn Ser Asp Pro Val Asp Phe Tyr Arg Cys Thr Cys Pro
            915                 920                 925
Tyr Gly Phe Lys Gly Gln Asp Cys Asp Val Pro Ile His Ala Cys Ile
930                 935                 940
Ser Asn Pro Cys Lys His Gly Gly Thr Cys His Leu Lys Glu Gly Glu
945                 950                 955                 960
Glu Asp Gly Phe Trp Cys Ile Cys Ala Asp Gly Phe Glu Gly Glu Asn
                965                 970                 975
Cys Glu Val Asn Val Asp Asp Cys Glu Asp Asn Asp Cys Glu Asn Asn
                980                 985                 990
Ser Thr Cys Val Asp Gly Ile Asn Asn Tyr Thr Cys Leu Cys Pro Pro
            995                 1000                1005
Glu Tyr Thr Gly Glu Leu Cys Glu Glu Lys Leu Asp Phe Cys Ala
    1010                1015                1020
Gln Asp Leu Asn Pro Cys Gln His Asp Ser Lys Cys Ile Leu Thr
    1025                1030                1035
Pro Lys Gly Phe Lys Cys Asp Cys Thr Pro Gly Tyr Val Gly Glu
    1040                1045                1050
His Cys Asp Ile Asp Phe Asp Asp Cys Gln Asp Asn Lys Cys Lys
    1055                1060                1065
Asn Gly Ala His Cys Thr Asp Ala Val Asn Gly Tyr Thr Cys Ile
    1070                1075                1080
Cys Pro Glu Gly Tyr Ser Gly Leu Phe Cys Glu Phe Ser Pro Pro
```

```
            1085                1090                1095
Met Val Leu Pro Arg Cys Gln Asn Gly Ala Gln Cys Ile Val Arg
   1100                1105                1110

Ile Asn Glu Pro Ile Cys Gln Cys Leu Pro Gly Tyr Gln Gly Glu
   1115                1120                1125

Lys Cys Glu Lys Leu Val Ser Val Asn Phe Ile Asn Lys Glu Ser
   1130                1135                1140

Tyr Leu Gln Ile Pro Ser Ala Lys Val Arg Pro Gln Thr Asn Ile
   1145                1150                1155

Thr Leu Gln Ile Ala Thr Asp Glu Asp Ser Gly Ile Leu Leu Tyr
   1160                1165                1170

Lys Gly Asp Lys Asp His Ile Ala Val Glu Leu Tyr Arg Gly Arg
   1175                1180                1185

Val Arg Ala Ser Tyr Asp Thr Gly Ser His Pro Ala Ser Ala Ile
   1190                1195                1200

Tyr Ser Val Glu Thr Ile Asn Asp Gly Asn Phe His Ile Val Glu
   1205                1210                1215

Leu Leu Ala Leu Asp Gln Ser Leu Ser Leu Ser Val Asp Gly Gly
   1220                1225                1230

Asn Pro Lys Ile Ile Thr Asn Leu Ser Lys Gln Ser Thr Leu Asn
   1235                1240                1245

Phe Asp Ser Pro Leu Tyr Val Gly Gly Met Pro Gly Lys Ser Asn
   1250                1255                1260

Val Ala Ser Leu Arg Gln Ala Pro Gly Gln Asn Gly Thr Ser Phe
   1265                1270                1275

His Gly Cys Ile Arg Asn Leu Tyr Ile Asn Ser Glu Leu Gln Asp
   1280                1285                1290

Phe Gln Lys Val Pro Met Gln Thr Gly Ile Leu Pro Gly Cys Glu
   1295                1300                1305

Pro Cys His Lys Lys Val Cys Ala His Gly Thr Cys Gln Pro Ser
   1310                1315                1320

Ser Gln Ala Gly Phe Thr Cys Glu Cys Gln Glu Gly Trp Met Gly
   1325                1330                1335

Pro Leu Cys Asp Gln Arg Thr Asn Asp Pro Cys Leu Gly Asn Lys
   1340                1345                1350

Cys Val His Gly Thr Cys Leu Pro Ile Asn Ala Phe Ser Tyr Ser
   1355                1360                1365

Cys Lys Cys Leu Glu Gly His Gly Gly Val Leu Cys Asp Glu Glu
   1370                1375                1380

Glu Asp Leu Phe Asn Pro Cys Gln Ala Ile Lys Cys Lys His Gly
   1385                1390                1395

Lys Cys Arg Leu Ser Gly Leu Gly Gln Pro Tyr Cys Glu Cys Ser
   1400                1405                1410

Ser Gly Tyr Thr Gly Asp Ser Cys Asp Arg Glu Ile Ser Cys Arg
   1415                1420                1425

Gly Glu Arg Ile Arg Asp Tyr Tyr Gln Lys Gln Gly Tyr Ala
   1430                1435                1440

Ala Cys Gln Thr Thr Lys Lys Val Ser Arg Leu Glu Cys Arg Gly
   1445                1450                1455

Gly Cys Ala Gly Gly Gln Cys Cys Gly Pro Leu Arg Ser Lys Arg
   1460                1465                1470

Arg Lys Tyr Ser Phe Glu Cys Thr Asp Gly Ser Ser Phe Val Asp
   1475                1480                1485
```

```
Glu Val Glu Lys Val Val Lys Cys Gly Cys
    1490                1495

<210> SEQ ID NO 42
<211> LENGTH: 244
<212> TYPE: PRT
<213> ORGANISM: Homo sapiens

<400> SEQUENCE: 42

Ile Leu Asn Lys Val Ala Pro Gln Ala Cys Pro Ala Gln Cys Ser Cys
1               5                   10                  15

Ser Gly Ser Thr Val Asp Cys His Gly Leu Ala Leu Arg Ser Val Pro
            20                  25                  30

Arg Asn Ile Pro Arg Asn Thr Glu Arg Leu Asp Leu Asn Gly Asn Asn
        35                  40                  45

Ile Thr Arg Ile Thr Lys Thr Asp Phe Ala Gly Leu Arg His Leu Arg
50                  55                  60

Val Leu Gln Leu Met Glu Asn Lys Ile Ser Thr Ile Glu Arg Gly Ala
65                  70                  75                  80

Phe Gln Asp Leu Lys Glu Leu Glu Arg Leu Arg Leu Asn Arg Asn His
                85                  90                  95

Leu Gln Leu Phe Pro Glu Leu Leu Phe Leu Gly Thr Ala Lys Leu Tyr
            100                 105                 110

Arg Leu Asp Leu Ser Glu Asn Gln Ile Gln Ala Ile Pro Arg Lys Ala
        115                 120                 125

Phe Arg Gly Ala Val Asp Ile Lys Asn Leu Gln Leu Asp Tyr Asn Gln
    130                 135                 140

Ile Ser Cys Ile Glu Asp Gly Ala Phe Arg Ala Leu Arg Asp Leu Glu
145                 150                 155                 160

Val Leu Thr Leu Asn Asn Asn Asn Ile Thr Arg Leu Ser Val Ala Ser
                165                 170                 175

Phe Asn His Met Pro Lys Leu Arg Thr Phe Arg Leu His Ser Asn Asn
            180                 185                 190

Leu Tyr Cys Asp Cys His Leu Ala Trp Leu Ser Asp Trp Leu Arg Gln
        195                 200                 205

Arg Pro Arg Val Gly Leu Tyr Thr Gln Cys Met Gly Pro Ser His Leu
    210                 215                 220

Arg Gly His Asn Val Ala Glu Val Gln Lys Arg Glu Phe Val Cys Ser
225                 230                 235                 240

Gly His Gln Ser

<210> SEQ ID NO 43
<211> LENGTH: 464
<212> TYPE: PRT
<213> ORGANISM: Homo sapiens

<400> SEQUENCE: 43

Ile Leu Asn Lys Val Ala Pro Gln Ala Cys Pro Ala Gln Cys Ser Cys
1               5                   10                  15

Ser Gly Ser Thr Val Asp Cys His Gly Leu Ala Leu Arg Ser Val Pro
            20                  25                  30

Arg Asn Ile Pro Arg Asn Thr Glu Arg Leu Asp Leu Asn Gly Asn Asn
        35                  40                  45

Ile Thr Arg Ile Thr Lys Thr Asp Phe Ala Gly Leu Arg His Leu Arg
50                  55                  60

Val Leu Gln Leu Met Glu Asn Lys Ile Ser Thr Ile Glu Arg Gly Ala
65                  70                  75                  80
```

-continued

Phe Gln Asp Leu Lys Glu Leu Glu Arg Leu Arg Leu Asn Arg Asn His
            85                  90                  95

Leu Gln Leu Phe Pro Glu Leu Leu Phe Leu Gly Thr Ala Lys Leu Tyr
            100                 105                 110

Arg Leu Asp Leu Ser Glu Asn Gln Ile Gln Ala Ile Pro Arg Lys Ala
            115                 120                 125

Phe Arg Gly Ala Val Asp Ile Lys Asn Leu Gln Leu Asp Tyr Asn Gln
    130                 135                 140

Ile Ser Cys Ile Glu Asp Gly Ala Phe Arg Ala Leu Arg Asp Leu Glu
145                 150                 155                 160

Val Leu Thr Leu Asn Asn Asn Ile Thr Arg Leu Ser Val Ala Ser
            165                 170                 175

Phe Asn His Met Pro Lys Leu Arg Thr Phe Arg Leu His Ser Asn Asn
            180                 185                 190

Leu Tyr Cys Asp Cys His Leu Ala Trp Leu Ser Asp Trp Leu Arg Gln
            195                 200                 205

Arg Pro Arg Val Gly Leu Tyr Thr Gln Cys Met Gly Pro Ser His Leu
    210                 215                 220

Arg Gly His Asn Val Ala Glu Val Gln Lys Arg Glu Phe Val Cys Ser
225                 230                 235                 240

Gly His Gln Ser Phe Met Ala Pro Ser Cys Ser Val Leu His Cys Pro
            245                 250                 255

Ala Ala Cys Thr Cys Ser Asn Asn Ile Val Asp Cys Arg Gly Lys Gly
            260                 265                 270

Leu Thr Glu Ile Pro Thr Asn Leu Pro Glu Thr Ile Thr Glu Ile Arg
    275                 280                 285

Leu Glu Gln Asn Thr Ile Lys Val Ile Pro Pro Gly Ala Phe Ser Pro
            290                 295                 300

Tyr Lys Lys Leu Arg Arg Ile Asp Leu Ser Asn Asn Gln Ile Ser Glu
305                 310                 315                 320

Leu Ala Pro Asp Ala Phe Gln Gly Leu Arg Ser Leu Asn Ser Leu Val
            325                 330                 335

Leu Tyr Gly Asn Lys Ile Thr Glu Leu Pro Lys Ser Leu Phe Glu Gly
            340                 345                 350

Leu Phe Ser Leu Gln Leu Leu Leu Asn Ala Asn Lys Ile Asn Cys
            355                 360                 365

Leu Arg Val Asp Ala Phe Gln Asp Leu His Asn Leu Asn Leu Leu Ser
    370                 375                 380

Leu Tyr Asp Asn Lys Leu Gln Thr Ile Ala Lys Gly Thr Phe Ser Pro
385                 390                 395                 400

Leu Arg Ala Ile Gln Thr Met His Leu Ala Gln Asn Pro Phe Ile Cys
            405                 410                 415

Asp Cys His Leu Lys Trp Leu Ala Asp Tyr Leu His Thr Asn Pro Ile
            420                 425                 430

Glu Thr Ser Gly Ala Arg Cys Thr Ser Pro Arg Arg Leu Ala Asn Lys
            435                 440                 445

Arg Ile Gly Gln Ile Lys Ser Lys Lys Phe Arg Cys Ser Ala Lys Glu
    450                 455                 460

<210> SEQ ID NO 44
<211> LENGTH: 687
<212> TYPE: PRT
<213> ORGANISM: Homo sapiens

<400> SEQUENCE: 44

-continued

```
Ile Leu Asn Lys Val Ala Pro Gln Ala Cys Pro Ala Gln Cys Ser Cys
1               5                   10                  15
Ser Gly Ser Thr Val Asp Cys His Gly Leu Ala Leu Arg Ser Val Pro
                20                  25                  30
Arg Asn Ile Pro Arg Asn Thr Glu Arg Leu Asp Leu Asn Gly Asn Asn
            35                  40                  45
Ile Thr Arg Ile Thr Lys Thr Asp Phe Ala Gly Leu Arg His Leu Arg
50                  55                      60
Val Leu Gln Leu Met Glu Asn Lys Ile Ser Thr Ile Glu Arg Gly Ala
65                      70                  75                  80
Phe Gln Asp Leu Lys Glu Leu Glu Arg Leu Arg Leu Asn Arg Asn His
                85                  90                  95
Leu Gln Leu Phe Pro Glu Leu Leu Phe Leu Gly Thr Ala Lys Leu Tyr
                100                 105                 110
Arg Leu Asp Leu Ser Glu Asn Gln Ile Gln Ala Ile Pro Arg Lys Ala
                115                 120                 125
Phe Arg Gly Ala Val Asp Ile Lys Asn Leu Gln Leu Asp Tyr Asn Gln
            130                 135                 140
Ile Ser Cys Ile Glu Asp Gly Ala Phe Arg Ala Leu Arg Asp Leu Glu
145                 150                 155                 160
Val Leu Thr Leu Asn Asn Asn Asn Ile Thr Arg Leu Ser Val Ala Ser
                165                 170                 175
Phe Asn His Met Pro Lys Leu Arg Thr Phe Arg Leu His Ser Asn Asn
                180                 185                 190
Leu Tyr Cys Asp Cys His Leu Ala Trp Leu Ser Asp Trp Leu Arg Gln
            195                 200                 205
Arg Pro Arg Val Gly Leu Tyr Thr Gln Cys Met Gly Pro Ser His Leu
210                 215                 220
Arg Gly His Asn Val Ala Glu Val Gln Lys Arg Glu Phe Val Cys Ser
225                 230                 235                 240
Gly His Gln Ser Phe Met Ala Pro Ser Cys Ser Val Leu His Cys Pro
                245                 250                 255
Ala Ala Cys Thr Cys Ser Asn Asn Ile Val Asp Cys Arg Gly Lys Gly
            260                 265                 270
Leu Thr Glu Ile Pro Thr Asn Leu Pro Glu Thr Ile Thr Glu Ile Arg
            275                 280                 285
Leu Glu Gln Asn Thr Ile Lys Val Ile Pro Pro Gly Ala Phe Ser Pro
290                 295                 300
Tyr Lys Lys Leu Arg Arg Ile Asp Leu Ser Asn Asn Gln Ile Ser Glu
305                 310                 315                 320
Leu Ala Pro Asp Ala Phe Gln Gly Leu Arg Ser Leu Asn Ser Leu Val
                325                 330                 335
Leu Tyr Gly Asn Lys Ile Thr Glu Leu Pro Lys Ser Leu Phe Glu Gly
            340                 345                 350
Leu Phe Ser Leu Gln Leu Leu Leu Asn Ala Asn Lys Ile Asn Cys
                355                 360                 365
Leu Arg Val Asp Ala Phe Gln Asp Leu His Asn Leu Asn Leu Leu Ser
            370                 375                 380
Leu Tyr Asp Asn Lys Leu Gln Thr Ile Ala Lys Gly Thr Phe Ser Pro
385                 390                 395                 400
Leu Arg Ala Ile Gln Thr Met His Leu Ala Gln Asn Pro Phe Ile Cys
                405                 410                 415
Asp Cys His Leu Lys Trp Leu Ala Asp Tyr Leu His Thr Asn Pro Ile
```

```
                420            425            430
Glu Thr Ser Gly Ala Arg Cys Thr Ser Pro Arg Arg Leu Ala Asn Lys
            435                440                445
Arg Ile Gly Gln Ile Lys Ser Lys Lys Phe Arg Cys Ser Ala Lys Glu
        450                455                460
Gln Tyr Phe Ile Pro Gly Thr Glu Asp Tyr Arg Ser Lys Leu Ser Gly
465                470                475                480
Asp Cys Phe Ala Asp Leu Ala Cys Pro Glu Lys Cys Arg Cys Glu Gly
                485                490                495
Thr Thr Val Asp Cys Ser Asn Gln Lys Leu Asn Lys Ile Pro Glu His
                500                505                510
Ile Pro Gln Tyr Thr Ala Glu Leu Arg Leu Asn Asn Asn Glu Phe Thr
                515                520                525
Val Leu Glu Ala Thr Gly Ile Phe Lys Lys Leu Pro Gln Leu Arg Lys
            530                535                540
Ile Asn Phe Ser Asn Asn Lys Ile Thr Asp Ile Glu Glu Gly Ala Phe
545                550                555                560
Glu Gly Ala Ser Gly Val Asn Glu Ile Leu Leu Thr Ser Asn Arg Leu
                565                570                575
Glu Asn Val Gln His Lys Met Phe Lys Gly Leu Glu Ser Leu Lys Thr
            580                585                590
Leu Met Leu Arg Ser Asn Arg Ile Thr Cys Val Gly Asn Asp Ser Phe
            595                600                605
Ile Gly Leu Ser Ser Val Arg Leu Leu Ser Leu Tyr Asp Asn Gln Ile
            610                615                620
Thr Thr Val Ala Pro Gly Ala Phe Asp Thr Leu His Ser Leu Ser Thr
625                630                635                640
Leu Asn Leu Leu Ala Asn Pro Phe Asn Cys Asn Cys Tyr Leu Ala Trp
                645                650                655
Leu Gly Glu Trp Leu Arg Lys Lys Arg Ile Val Thr Gly Asn Pro Arg
            660                665                670
Cys Gln Lys Pro Tyr Phe Leu Lys Glu Ile Pro Ile Gln Asp Val
            675                680                685

<210> SEQ ID NO 45
<211> LENGTH: 885
<212> TYPE: PRT
<213> ORGANISM: Homo sapiens

<400> SEQUENCE: 45

Ile Leu Asn Lys Val Ala Pro Gln Ala Cys Pro Ala Gln Cys Ser Cys
1               5                   10                  15
Ser Gly Ser Thr Val Asp Cys His Gly Leu Ala Leu Arg Ser Val Pro
            20                  25                  30
Arg Asn Ile Pro Arg Asn Thr Glu Arg Leu Asp Leu Asn Gly Asn Asn
        35                  40                  45
Ile Thr Arg Ile Thr Lys Thr Asp Phe Ala Gly Leu Arg His Leu Arg
    50                  55                  60
Val Leu Gln Leu Met Glu Asn Lys Ile Ser Thr Ile Glu Arg Gly Ala
65                  70                  75                  80
Phe Gln Asp Leu Lys Glu Leu Glu Arg Leu Arg Leu Asn Arg Asn His
                85                  90                  95
Leu Gln Leu Phe Pro Glu Leu Leu Phe Leu Gly Thr Ala Lys Leu Tyr
            100                 105                 110
Arg Leu Asp Leu Ser Glu Asn Gln Ile Gln Ala Ile Pro Arg Lys Ala
```

```
            115                 120                 125
Phe Arg Gly Ala Val Asp Ile Lys Asn Leu Gln Leu Asp Tyr Asn Gln
130                 135                 140
Ile Ser Cys Ile Glu Asp Gly Ala Phe Arg Ala Leu Arg Asp Leu Glu
145                 150                 155                 160
Val Leu Thr Leu Asn Asn Asn Ile Thr Arg Leu Ser Val Ala Ser
            165                 170                 175
Phe Asn His Met Pro Lys Leu Arg Thr Phe Arg Leu His Ser Asn Asn
            180                 185                 190
Leu Tyr Cys Asp Cys His Leu Ala Trp Leu Ser Asp Trp Leu Arg Gln
            195                 200                 205
Arg Pro Arg Val Gly Leu Tyr Thr Gln Cys Met Gly Pro Ser His Leu
210                 215                 220
Arg Gly His Asn Val Ala Glu Val Gln Lys Arg Glu Phe Val Cys Ser
225                 230                 235                 240
Gly His Gln Ser Phe Met Ala Pro Ser Cys Ser Val Leu His Cys Pro
            245                 250                 255
Ala Ala Cys Thr Cys Ser Asn Asn Ile Val Asp Cys Arg Gly Lys Gly
            260                 265                 270
Leu Thr Glu Ile Pro Thr Asn Leu Pro Glu Thr Ile Thr Glu Ile Arg
            275                 280                 285
Leu Glu Gln Asn Thr Ile Lys Val Ile Pro Pro Gly Ala Phe Ser Pro
            290                 295                 300
Tyr Lys Lys Leu Arg Arg Ile Asp Leu Ser Asn Asn Gln Ile Ser Glu
305                 310                 315                 320
Leu Ala Pro Asp Ala Phe Gln Gly Leu Arg Ser Leu Asn Ser Leu Val
            325                 330                 335
Leu Tyr Gly Asn Lys Ile Thr Glu Leu Pro Lys Ser Leu Phe Glu Gly
            340                 345                 350
Leu Phe Ser Leu Gln Leu Leu Leu Asn Ala Asn Lys Ile Asn Cys
            355                 360                 365
Leu Arg Val Asp Ala Phe Gln Asp Leu His Asn Leu Asn Leu Leu Ser
            370                 375                 380
Leu Tyr Asp Asn Lys Leu Gln Thr Ile Ala Lys Gly Thr Phe Ser Pro
385                 390                 395                 400
Leu Arg Ala Ile Gln Thr Met His Leu Ala Gln Asn Pro Phe Ile Cys
            405                 410                 415
Asp Cys His Leu Lys Trp Leu Ala Asp Tyr Leu His Thr Asn Pro Ile
            420                 425                 430
Glu Thr Ser Gly Ala Arg Cys Thr Ser Pro Arg Arg Leu Ala Asn Lys
            435                 440                 445
Arg Ile Gly Gln Ile Lys Ser Lys Lys Phe Arg Cys Ser Ala Lys Glu
            450                 455                 460
Gln Tyr Phe Ile Pro Gly Thr Glu Asp Tyr Arg Ser Lys Leu Ser Gly
465                 470                 475                 480
Asp Cys Phe Ala Asp Leu Ala Cys Pro Glu Lys Cys Arg Cys Glu Gly
            485                 490                 495
Thr Thr Val Asp Cys Ser Asn Gln Lys Leu Asn Lys Ile Pro Glu His
            500                 505                 510
Ile Pro Gln Tyr Thr Ala Glu Leu Arg Leu Asn Asn Asn Glu Phe Thr
            515                 520                 525
Val Leu Glu Ala Thr Gly Ile Phe Lys Lys Leu Pro Gln Leu Arg Lys
            530                 535                 540
```

Ile Asn Phe Ser Asn Asn Lys Ile Thr Asp Ile Glu Glu Gly Ala Phe
545                 550                 555                 560

Glu Gly Ala Ser Gly Val Asn Glu Ile Leu Leu Thr Ser Asn Arg Leu
                565                 570                 575

Glu Asn Val Gln His Lys Met Phe Lys Gly Leu Glu Ser Leu Lys Thr
            580                 585                 590

Leu Met Leu Arg Ser Asn Arg Ile Thr Cys Val Gly Asn Asp Ser Phe
        595                 600                 605

Ile Gly Leu Ser Ser Val Arg Leu Leu Ser Leu Tyr Asp Asn Gln Ile
610                 615                 620

Thr Thr Val Ala Pro Gly Ala Phe Asp Thr Leu His Ser Leu Ser Thr
625                 630                 635                 640

Leu Asn Leu Leu Ala Asn Pro Phe Asn Cys Asn Cys Tyr Leu Ala Trp
                645                 650                 655

Leu Gly Glu Trp Leu Arg Lys Lys Arg Ile Val Thr Gly Asn Pro Arg
            660                 665                 670

Cys Gln Lys Pro Tyr Phe Leu Lys Glu Ile Pro Ile Gln Asp Val Ala
        675                 680                 685

Ile Gln Asp Phe Thr Cys Asp Asp Gly Asn Asp Asn Ser Cys Ser
690                 695                 700

Pro Leu Ser Arg Cys Pro Thr Glu Cys Thr Cys Leu Asp Thr Val Val
705                 710                 715                 720

Arg Cys Ser Asn Lys Gly Leu Lys Val Leu Pro Lys Gly Ile Pro Arg
                725                 730                 735

Asp Val Thr Glu Leu Tyr Leu Asp Gly Asn Gln Phe Thr Leu Val Pro
            740                 745                 750

Lys Glu Leu Ser Asn Tyr Lys His Leu Thr Leu Ile Asp Leu Ser Asn
        755                 760                 765

Asn Arg Ile Ser Thr Leu Ser Asn Gln Ser Phe Ser Asn Met Thr Gln
770                 775                 780

Leu Leu Thr Leu Ile Leu Ser Tyr Asn Arg Leu Arg Cys Ile Pro Pro
785                 790                 795                 800

Arg Thr Phe Asp Gly Leu Lys Ser Leu Arg Leu Leu Ser Leu His Gly
                805                 810                 815

Asn Asp Ile Ser Val Val Pro Glu Gly Ala Phe Asn Asp Leu Ser Ala
            820                 825                 830

Leu Ser His Leu Ala Ile Gly Ala Asn Pro Leu Tyr Cys Asp Cys Asn
        835                 840                 845

Met Gln Trp Leu Ser Asp Trp Val Lys Ser Glu Tyr Lys Glu Pro Gly
850                 855                 860

Ile Ala Arg Cys Ala Gly Pro Gly Glu Met Ala Asp Lys Leu Leu Leu
865                 870                 875                 880

Thr Thr Pro Ser Lys
                885

<210> SEQ ID NO 46
<211> LENGTH: 1089
<212> TYPE: PRT
<213> ORGANISM: Homo sapiens

<400> SEQUENCE: 46

Ile Leu Asn Lys Val Ala Pro Gln Ala Cys Pro Ala Gln Cys Ser Cys
1               5                   10                  15

Ser Gly Ser Thr Val Asp Cys His Gly Leu Ala Leu Arg Ser Val Pro
            20                  25                  30

```
            Arg Asn Ile Pro Arg Asn Thr Glu Arg Leu Asp Leu Asn Gly Asn Asn
                         35                  40                  45

Ile Thr Arg Ile Thr Lys Thr Asp Phe Ala Gly Leu Arg His Leu Arg
             50                  55                  60

Val Leu Gln Leu Met Glu Asn Lys Ile Ser Thr Ile Glu Arg Gly Ala
             65                  70                  75                  80

Phe Gln Asp Leu Lys Glu Leu Glu Arg Leu Arg Leu Asn Arg Asn His
                             85                  90                  95

Leu Gln Leu Phe Pro Glu Leu Leu Phe Leu Gly Thr Ala Lys Leu Tyr
                            100                 105                 110

Arg Leu Asp Leu Ser Glu Asn Gln Ile Gln Ala Ile Pro Arg Lys Ala
                            115                 120                 125

Phe Arg Gly Ala Val Asp Ile Lys Asn Leu Gln Leu Asp Tyr Asn Gln
                        130                 135                 140

Ile Ser Cys Ile Glu Asp Gly Ala Phe Arg Ala Leu Arg Asp Leu Glu
            145                 150                 155                 160

Val Leu Thr Leu Asn Asn Asn Asn Ile Thr Arg Leu Ser Val Ala Ser
                            165                 170                 175

Phe Asn His Met Pro Lys Leu Arg Thr Phe Arg Leu His Ser Asn Asn
                        180                 185                 190

Leu Tyr Cys Asp Cys His Leu Ala Trp Leu Ser Asp Trp Leu Arg Gln
                        195                 200                 205

Arg Pro Arg Val Gly Leu Tyr Thr Gln Cys Met Gly Pro Ser His Leu
            210                 215                 220

Arg Gly His Asn Val Ala Glu Val Gln Lys Arg Glu Phe Val Cys Ser
            225                 230                 235                 240

Gly His Gln Ser Phe Met Ala Pro Ser Cys Ser Val Leu His Cys Pro
                            245                 250                 255

Ala Ala Cys Thr Cys Ser Asn Asn Ile Val Asp Cys Arg Gly Lys Gly
                        260                 265                 270

Leu Thr Glu Ile Pro Thr Asn Leu Pro Glu Thr Ile Thr Glu Ile Arg
                        275                 280                 285

Leu Glu Gln Asn Thr Ile Lys Val Ile Pro Pro Gly Ala Phe Ser Pro
                        290                 295                 300

Tyr Lys Lys Leu Arg Arg Ile Asp Leu Ser Asn Asn Gln Ile Ser Glu
            305                 310                 315                 320

Leu Ala Pro Asp Ala Phe Gln Gly Leu Arg Ser Leu Asn Ser Leu Val
                            325                 330                 335

Leu Tyr Gly Asn Lys Ile Thr Glu Leu Pro Lys Ser Leu Phe Glu Gly
                        340                 345                 350

Leu Phe Ser Leu Gln Leu Leu Leu Leu Asn Ala Asn Lys Ile Asn Cys
                        355                 360                 365

Leu Arg Val Asp Ala Phe Gln Asp Leu His Asn Leu Asn Leu Leu Ser
                        370                 375                 380

Leu Tyr Asp Asn Lys Leu Gln Thr Ile Ala Lys Gly Thr Phe Ser Pro
            385                 390                 395                 400

Leu Arg Ala Ile Gln Thr Met His Leu Ala Gln Asn Pro Phe Ile Cys
                            405                 410                 415

Asp Cys His Leu Lys Trp Leu Ala Asp Tyr Leu His Thr Asn Pro Ile
                        420                 425                 430

Glu Thr Ser Gly Ala Arg Cys Thr Ser Pro Arg Arg Leu Ala Asn Lys
                        435                 440                 445

Arg Ile Gly Gln Ile Lys Ser Lys Lys Phe Arg Cys Ser Ala Lys Glu
            450                 455                 460
```

-continued

```
Gln Tyr Phe Ile Pro Gly Thr Glu Asp Tyr Arg Ser Lys Leu Ser Gly
465                 470                 475                 480

Asp Cys Phe Ala Asp Leu Ala Cys Pro Glu Lys Cys Arg Cys Glu Gly
                485                 490                 495

Thr Thr Val Asp Cys Ser Asn Gln Lys Leu Asn Lys Ile Pro Glu His
            500                 505                 510

Ile Pro Gln Tyr Thr Ala Glu Leu Arg Leu Asn Asn Glu Phe Thr
        515                 520                 525

Val Leu Glu Ala Thr Gly Ile Phe Lys Lys Leu Pro Gln Leu Arg Lys
530                 535                 540

Ile Asn Phe Ser Asn Asn Lys Ile Thr Asp Ile Glu Glu Gly Ala Phe
545                 550                 555                 560

Glu Gly Ala Ser Gly Val Asn Glu Ile Leu Leu Thr Ser Asn Arg Leu
                565                 570                 575

Glu Asn Val Gln His Lys Met Phe Lys Gly Leu Glu Ser Leu Lys Thr
            580                 585                 590

Leu Met Leu Arg Ser Asn Arg Ile Thr Cys Val Gly Asn Asp Ser Phe
        595                 600                 605

Ile Gly Leu Ser Ser Val Arg Leu Leu Ser Leu Tyr Asp Asn Gln Ile
610                 615                 620

Thr Thr Val Ala Pro Gly Ala Phe Asp Thr Leu His Ser Leu Ser Thr
625                 630                 635                 640

Leu Asn Leu Leu Ala Asn Pro Phe Asn Cys Asn Cys Tyr Leu Ala Trp
                645                 650                 655

Leu Gly Glu Trp Leu Arg Lys Lys Arg Ile Val Thr Gly Asn Pro Arg
            660                 665                 670

Cys Gln Lys Pro Tyr Phe Leu Lys Glu Ile Pro Ile Gln Asp Val Ala
        675                 680                 685

Ile Gln Asp Phe Thr Cys Asp Asp Gly Asn Asp Asn Ser Cys Ser
690                 695                 700

Pro Leu Ser Arg Cys Pro Thr Glu Cys Thr Cys Leu Asp Thr Val Val
705                 710                 715                 720

Arg Cys Ser Asn Lys Gly Leu Lys Val Leu Pro Lys Gly Ile Pro Arg
                725                 730                 735

Asp Val Thr Glu Leu Tyr Leu Asp Gly Asn Gln Phe Thr Leu Val Pro
            740                 745                 750

Lys Glu Leu Ser Asn Tyr Lys His Leu Thr Leu Ile Asp Leu Ser Asn
        755                 760                 765

Asn Arg Ile Ser Thr Leu Ser Asn Gln Ser Phe Ser Asn Met Thr Gln
770                 775                 780

Leu Leu Thr Leu Ile Leu Ser Tyr Asn Arg Leu Arg Cys Ile Pro Pro
785                 790                 795                 800

Arg Thr Phe Asp Gly Leu Lys Ser Leu Arg Leu Leu Ser Leu His Gly
                805                 810                 815

Asn Asp Ile Ser Val Val Pro Glu Gly Ala Phe Asn Asp Leu Ser Ala
            820                 825                 830

Leu Ser His Leu Ala Ile Gly Ala Asn Pro Leu Tyr Cys Asp Cys Asn
        835                 840                 845

Met Gln Trp Leu Ser Asp Trp Val Lys Ser Glu Tyr Lys Glu Pro Gly
850                 855                 860

Ile Ala Arg Cys Ala Gly Pro Gly Glu Met Ala Asp Lys Leu Leu Leu
865                 870                 875                 880

Thr Thr Pro Ser Lys Lys Phe Thr Cys Gln Gly Pro Val Asp Val Asn
```

```
                       885                 890                 895
Ile Leu Ala Lys Cys Asn Pro Cys Leu Ser Asn Pro Cys Lys Asn Asp
                900                 905                 910

Gly Thr Cys Asn Ser Asp Pro Val Asp Phe Tyr Arg Cys Thr Cys Pro
            915                 920                 925

Tyr Gly Phe Lys Gly Gln Asp Cys Asp Val Pro Ile His Ala Cys Ile
        930                 935                 940

Ser Asn Pro Cys Lys His Gly Thr Cys His Leu Lys Glu Gly Glu
945                 950                 955                 960

Glu Asp Gly Phe Trp Cys Ile Cys Ala Asp Gly Phe Glu Gly Glu Asn
                965                 970                 975

Cys Glu Val Asn Val Asp Asp Cys Glu Asp Asn Asp Cys Glu Asn Asn
            980                 985                 990

Ser Thr Cys Val Asp Gly Ile Asn Asn Tyr Thr Cys Leu Cys Pro Pro
        995                1000                1005

Glu Tyr Thr Gly Glu Leu Cys Glu Glu Lys Leu Asp Phe Cys Ala
    1010                1015                1020

Gln Asp Leu Asn Pro Cys Gln His Asp Ser Lys Cys Ile Leu Thr
    1025                1030                1035

Pro Lys Gly Phe Lys Cys Asp Cys Thr Pro Gly Tyr Val Gly Glu
    1040                1045                1050

His Cys Asp Ile Asp Phe Asp Asp Cys Gln Asp Asn Lys Cys Lys
    1055                1060                1065

Asn Gly Ala His Cys Thr Asp Ala Val Asn Gly Tyr Thr Cys Ile
    1070                1075                1080

Cys Pro Glu Gly Tyr Ser
    1085

<210> SEQ ID NO 47
<211> LENGTH: 1163
<212> TYPE: PRT
<213> ORGANISM: Homo sapiens

<400> SEQUENCE: 47

Ile Leu Asn Lys Val Ala Pro Gln Ala Cys Pro Ala Gln Cys Ser Cys
1               5                  10                  15

Ser Gly Ser Thr Val Asp Cys His Gly Leu Ala Leu Arg Ser Val Pro
                20                  25                  30

Arg Asn Ile Pro Arg Asn Thr Glu Arg Leu Asp Leu Asn Gly Asn Asn
            35                  40                  45

Ile Thr Arg Ile Thr Lys Thr Asp Phe Ala Gly Leu Arg His Leu Arg
    50                  55                  60

Val Leu Gln Leu Met Glu Asn Lys Ile Ser Thr Ile Glu Arg Gly Ala
65                  70                  75                  80

Phe Gln Asp Leu Lys Glu Leu Glu Arg Leu Arg Leu Asn Arg Asn His
                85                  90                  95

Leu Gln Leu Phe Pro Glu Leu Leu Phe Leu Gly Thr Ala Lys Leu Tyr
            100                 105                 110

Arg Leu Asp Leu Ser Glu Asn Gln Ile Gln Ala Ile Pro Arg Lys Ala
        115                 120                 125

Phe Arg Gly Ala Val Asp Ile Lys Asn Leu Gln Leu Asp Tyr Asn Gln
    130                 135                 140

Ile Ser Cys Ile Glu Asp Gly Ala Phe Arg Ala Leu Arg Asp Leu Glu
145                 150                 155                 160

Val Leu Thr Leu Asn Asn Asn Asn Ile Thr Arg Leu Ser Val Ala Ser
```

-continued

```
                165                 170                 175
Phe Asn His Met Pro Lys Leu Arg Thr Phe Arg Leu His Ser Asn Asn
                180                 185                 190

Leu Tyr Cys Asp Cys His Leu Ala Trp Leu Ser Asp Trp Leu Arg Gln
                195                 200                 205

Arg Pro Arg Val Gly Leu Tyr Thr Gln Cys Met Gly Pro Ser His Leu
            210                 215                 220

Arg Gly His Asn Val Ala Glu Val Gln Lys Arg Glu Phe Val Cys Ser
225                 230                 235                 240

Gly His Gln Ser Phe Met Ala Pro Ser Cys Ser Val Leu His Cys Pro
                245                 250                 255

Ala Ala Cys Thr Cys Ser Asn Asn Ile Val Asp Cys Arg Gly Lys Gly
            260                 265                 270

Leu Thr Glu Ile Pro Thr Asn Leu Pro Glu Thr Ile Thr Glu Ile Arg
            275                 280                 285

Leu Glu Gln Asn Thr Ile Lys Val Ile Pro Pro Gly Ala Phe Ser Pro
            290                 295                 300

Tyr Lys Lys Leu Arg Arg Ile Asp Leu Ser Asn Asn Gln Ile Ser Glu
305                 310                 315                 320

Leu Ala Pro Asp Ala Phe Gln Gly Leu Arg Ser Leu Asn Ser Leu Val
                325                 330                 335

Leu Tyr Gly Asn Lys Ile Thr Glu Leu Pro Lys Ser Leu Phe Glu Gly
                340                 345                 350

Leu Phe Ser Leu Gln Leu Leu Leu Leu Asn Ala Asn Lys Ile Asn Cys
                355                 360                 365

Leu Arg Val Asp Ala Phe Gln Asp Leu His Asn Leu Asn Leu Leu Ser
            370                 375                 380

Leu Tyr Asp Asn Lys Leu Gln Thr Ile Ala Lys Gly Thr Phe Ser Pro
385                 390                 395                 400

Leu Arg Ala Ile Gln Thr Met His Leu Ala Gln Asn Pro Phe Ile Cys
                405                 410                 415

Asp Cys His Leu Lys Trp Leu Ala Asp Tyr Leu His Thr Asn Pro Ile
            420                 425                 430

Glu Thr Ser Gly Ala Arg Cys Thr Ser Pro Arg Arg Leu Ala Asn Lys
            435                 440                 445

Arg Ile Gly Gln Ile Lys Ser Lys Lys Phe Arg Cys Ser Ala Lys Glu
            450                 455                 460

Gln Tyr Phe Ile Pro Gly Thr Glu Asp Tyr Arg Ser Lys Leu Ser Gly
465                 470                 475                 480

Asp Cys Phe Ala Asp Leu Ala Cys Pro Glu Lys Cys Arg Cys Glu Gly
                485                 490                 495

Thr Thr Val Asp Cys Ser Asn Gln Lys Leu Asn Lys Ile Pro Glu His
                500                 505                 510

Ile Pro Gln Tyr Thr Ala Glu Leu Arg Leu Asn Asn Asn Glu Phe Thr
            515                 520                 525

Val Leu Glu Ala Thr Gly Ile Phe Lys Lys Leu Pro Gln Leu Arg Lys
            530                 535                 540

Ile Asn Phe Ser Asn Asn Lys Ile Thr Asp Ile Glu Glu Gly Ala Phe
545                 550                 555                 560

Glu Gly Ala Ser Gly Val Asn Glu Ile Leu Leu Thr Ser Asn Arg Leu
                565                 570                 575

Glu Asn Val Gln His Lys Met Phe Lys Gly Leu Glu Ser Leu Lys Thr
            580                 585                 590
```

```
Leu Met Leu Arg Ser Asn Arg Ile Thr Cys Val Gly Asn Asp Ser Phe
        595                 600                 605

Ile Gly Leu Ser Ser Val Arg Leu Leu Ser Leu Tyr Asp Asn Gln Ile
        610                 615                 620

Thr Thr Val Ala Pro Gly Ala Phe Asp Thr Leu His Ser Leu Ser Thr
625                 630                 635                 640

Leu Asn Leu Leu Ala Asn Pro Phe Asn Cys Asn Cys Tyr Leu Ala Trp
                645                 650                 655

Leu Gly Glu Trp Leu Arg Lys Lys Arg Ile Val Thr Gly Asn Pro Arg
            660                 665                 670

Cys Gln Lys Pro Tyr Phe Leu Lys Glu Ile Pro Ile Gln Asp Val Ala
        675                 680                 685

Ile Gln Asp Phe Thr Cys Asp Asp Gly Asn Asp Asn Ser Cys Ser
690                 695                 700

Pro Leu Ser Arg Cys Pro Thr Glu Cys Thr Cys Leu Asp Thr Val Val
705                 710                 715                 720

Arg Cys Ser Asn Lys Gly Leu Lys Val Leu Pro Lys Gly Ile Pro Arg
                725                 730                 735

Asp Val Thr Glu Leu Tyr Leu Asp Gly Asn Gln Phe Thr Leu Val Pro
            740                 745                 750

Lys Glu Leu Ser Asn Tyr Lys His Leu Thr Leu Ile Asp Leu Ser Asn
        755                 760                 765

Asn Arg Ile Ser Thr Leu Ser Asn Gln Ser Phe Ser Asn Met Thr Gln
770                 775                 780

Leu Leu Thr Leu Ile Leu Ser Tyr Asn Arg Leu Arg Cys Ile Pro Pro
785                 790                 795                 800

Arg Thr Phe Asp Gly Leu Lys Ser Leu Arg Leu Leu Ser Leu His Gly
                805                 810                 815

Asn Asp Ile Ser Val Val Pro Glu Gly Ala Phe Asn Asp Leu Ser Ala
            820                 825                 830

Leu Ser His Leu Ala Ile Gly Ala Asn Pro Leu Tyr Cys Asp Cys Asn
        835                 840                 845

Met Gln Trp Leu Ser Asp Trp Val Lys Ser Glu Tyr Lys Glu Pro Gly
        850                 855                 860

Ile Ala Arg Cys Ala Gly Pro Gly Glu Met Ala Asp Lys Leu Leu Leu
865                 870                 875                 880

Thr Thr Pro Ser Lys Lys Phe Thr Cys Gln Gly Pro Val Asp Val Asn
                885                 890                 895

Ile Leu Ala Lys Cys Asn Pro Cys Leu Ser Asn Pro Cys Lys Asn Asp
            900                 905                 910

Gly Thr Cys Asn Ser Asp Pro Val Asp Phe Tyr Arg Cys Thr Cys Pro
        915                 920                 925

Tyr Gly Phe Lys Gly Gln Asp Cys Asp Val Pro Ile His Ala Cys Ile
        930                 935                 940

Ser Asn Pro Cys Lys His Gly Gly Thr Cys His Leu Lys Glu Gly Glu
945                 950                 955                 960

Glu Asp Gly Phe Trp Cys Ile Cys Ala Asp Gly Phe Glu Gly Glu Asn
                965                 970                 975

Cys Glu Val Asn Val Asp Asp Cys Glu Asp Asn Asp Cys Glu Asn Asn
            980                 985                 990

Ser Thr Cys Val Asp Gly Ile Asn Asn Tyr Thr Cys Leu Cys Pro Pro
        995                 1000                1005

Glu Tyr Thr Gly Glu Leu Cys Glu Glu Lys Leu Asp Phe Cys Ala
        1010                1015                1020
```

```
Gln Asp Leu Asn Pro Cys Gln His Asp Ser Lys Cys Ile Leu Thr
1025                1030                1035

Pro Lys Gly Phe Lys Cys Asp Cys Thr Pro Gly Tyr Val Gly Glu
    1040                1045                1050

His Cys Asp Ile Asp Phe Asp Asp Cys Gln Asp Asn Lys Cys Lys
    1055                1060                1065

Asn Gly Ala His Cys Thr Asp Ala Val Asn Gly Tyr Thr Cys Ile
    1070                1075                1080

Cys Pro Glu Gly Tyr Ser Gly Leu Phe Cys Glu Phe Ser Pro Pro
    1085                1090                1095

Met Val Leu Pro Arg Thr Ser Pro Cys Asp Asn Phe Asp Cys Gln
    1100                1105                1110

Asn Gly Ala Gln Cys Ile Val Arg Ile Asn Glu Pro Ile Cys Gln
    1115                1120                1125

Cys Leu Pro Gly Tyr Gln Gly Glu Lys Cys Glu Lys Leu Val Ser
    1130                1135                1140

Val Asn Phe Ile Asn Lys Glu Ser Tyr Leu Gln Ile Pro Ser Ala
    1145                1150                1155

Lys Val Arg Pro Gln
    1160
```

COMPOSITIONS AND METHODS FOR INHIBITING VASCULAR PERMEABILITY

RELATED APPLICATIONS

This application is a continuation of U.S. application Ser. No. 12/518,730, filed on Nov. 19, 2009, which is a National Stage Filing under 35 U.S.C. 37 of International Application No. PCT/US2007/25354, filed Dec. 11, 2007, which designated the United States and which claims the benefit of U.S. Provisional Application No. 60/869,526, filed Dec. 11, 2006. This application hereby incorporates by reference the U.S. and international priority applications enumerated herein.

STATEMENT REGARDING FEDERALLY SPONSORED RESEARCH

This invention was made with government support under Grant 1R01 HL77671-01 awarded by the National Institutes of Health. The government has certain rights in the invention.

BACKGROUND OF THE INVENTION

Though, the formation of the vertebrate vasculature of any organ system is a complex process that is orchestrated by a constellation of growth factors and guidance cues (Jain et al., 2003), recent studies have dramatically increased our understanding of the signaling cascades that regulate angiogenesis. For example, it is increasingly clear that molecular programs, which direct trajectory of axons and the formation of the neural network, have important roles in generating the highly stereotypical pattern of the mature vascular network (Carmeliet et al., 2005; Urness et al., 2004; and Jones et al., 2007).

During the initial phase of vascular development in mammals, which is referred to as vasculogenesis, endothelial cells differentiate, migrate and coalesce to form the central axial vessels, the dorsal aortae and cardinal veins. The second phase, called angiogenesis, is characterized by the sprouting of new vessels from the nascent plexus to form a mature circulatory system. VEGF (or VPF) is critical for both of these first two phases: the differentiation and survival of endothelial cells during vasculogenesis as well as proliferation and permeability during angiogenesis. Following this angiogenic remodeling, the endothelium secretes platelet-derived growth factor (PDGF), which induces the recruitment and differentiation of vascular smooth muscle cells. Subsequently, the vascular smooth muscle cells secrete angiopoietins, which ensure proper interaction between endothelial and vascular smooth muscle cells. Finally, the vascular smooth muscle cells deposit matrix proteins, such as elastin, that inhibit vascular smooth muscle cell proliferation and differentiation, thereby stabilizing the mature vessel. Thus, to establish and maintain a mature vascular network, the endothelial and smooth muscle compartments of a vessel must interact via autocrine and paracrine signaling. The gaps between endothelial cells (cell junctions) forming the vascular endothelium are strictly regulated depending on the type and physiological state of the tissue. For example, in a mature vascular bed, endothelial cells do not behave independently of one another; rather, they form a monolayer that prevents the movement of protein, fluid and cells from the endothelial lumen into the surrounding tissue.

Even after development, the vascular system is continually exposed to events, conditions or pathogens that cause injury, ischemia, and inflammation, which typically result in the release of cytokines and angiogenic factors, such as vascular endothelial growth factor (VEGF). Initially, VEGF was described, purified and cloned as vascular permeability factor (VPF), based on its ability to induce blood vessels to leak. VEGF destabilizes endothelial cell-cell junctions, leading to endothelial permeability, stimulates endothelial proliferation and migration, and promotes vascular sprouting and edema. These functions serve to deconstruct a stable vascular network producing leaky new blood vessels. In many contexts, the release of cytokines and angiogenic factors in response to injury, ischemia and inflammation is desirable, in that such a response leads initiates a restorative or healing processes. However, excessive angiogenesis and vascular leak (e.g., endothelial hyperpermeability) underscore the pathologies of several diseases and pathologic conditions.

For example, in the developed world, pathologic angiogenesis and endothelial hyperpermeability in the retinal or choroidal vascular beds are the most common causes of catastrophic vision loss. New and dysfunctional blood vessels leak, bleed or stimulate fibrosis that in turn precipitates edema, hemorrhage, or retinal detachment compromising vision. The major diseases sharing this pathogenesis include proliferative diabetic retinopathy (DR), non-proliferative diabetic macular edema (DME), and age-related macular degeneration (AMD) (Dorrell et al., 2007; Afzal et al., 2007). Approximately 15 million Americans over the age of 65 suffer from AMD, and 10% of these patients will experience visual loss as a result of choroidal neovascularization. Further, more than 16 million Americans are diabetic, and over 400,000 new patients suffer from retinal edema or neovascularization. Given that the current number of 200 million diabetics worldwide is likely to double in the next 20 years, and that over 8% of such patients suffer from microvascular complications, the number of patients that will experience vision loss from diabetic eye disease is unfortunately set to increase rapidly. Though less prevalent than DR, DME and AMD, retinopathy of prematurity (ROP) and ischemic retinal vein occlusion (IRVO) are also associated with pathologic angiogenesis and endothelial hyperpermeability in the retinal or choroidal vascular beds and lack effective treatment.

In addition to diseases of the eye, pathologic angiogenesis is also associated with tumor formation and growth. Tumor angiogenesis is the proliferation of a network of blood vessels that penetrates into cancerous growths, supplying nutrients and oxygen and removing waste products. With angiogenesis tumor growth proceeds, without it, it stops. Tumor angiogenesis actually starts with cancerous tumor cells releasing molecules that send signals to surrounding normal host tissue. This signaling activates certain genes in the host tissue that, in turn, make proteins to encourage growth of new blood vessels. Angiogenesis is regulated by both activator and inhibitor molecules. Under normal conditions, the inhibitors predominate, blocking growth. However, during tumor formation and growth, tumor cells release angiogenesis activators, causing such activators to increase in number/concentration. Such an increase in angiogenesis activators results in the growth and division of vascular endothelial cells and, ultimately, the formation of new blood vessels.

More than a dozen different proteins, as well as several smaller molecules, have been identified as "angiogenic." Among these molecules, two proteins appear to be the most important for sustaining tumor growth: vascular endothelial growth factor (VEGF) and basic fibroblast growth factor (bFGF). VEGF and bFGF are produced by many kinds of cancer cells and by certain types of normal cells. VEGF and bFGF are first synthesized inside tumor cells and then secreted into the surrounding tissue. When they encounter endothelial cells, they bind to specific proteins, called receptors, sitting on the outer surface of the cells. The binding of either VEGF or bFGF to its appropriate receptor activates a series of relay proteins that transmits a signal into the nucleus of the endothelial cells. The nuclear signal ultimately prompts a group of genes to make products needed for new endothelial cell growth. The activation of endothelial cells by VEGF or bFGF sets in motion a series of steps toward the creation of new blood vessels. First, the activated endothelial cells produce matrix metalloproteinases (MMPs), a special class of degradative enzymes. These enzymes are then released from the endothelial cells into the surrounding tissue. The MMPs break down the extracellular matrix—support material that fills the spaces between cells and is made of proteins and polysaccharides. Breakdown of this matrix permits the migration of endothelial cells. As they migrate into the surrounding tissues, activated endothelial cells begin to divide and organize into hollow tubes that evolve gradually into a mature network of blood vessels.

Additional diseases and disorders characterized by undesirable vascular permeability include, for example, edema associated with brain tumors, ascites associated with malignancies, Meigs' syndrome, lung inflammation, nephrotic syndrome, pericardial effusion, pleural effusion, acute lung injury, inflammatory bowel disease, ischemia/reperfusion injury in stroke, myocardial infarction, and infectious and non-infectious diseases that result in a cytokine storm. Though a cytokine storm is the systemic expression of a healthy and vigorous immune system, it is an exaggerated immune response caused by rapidly proliferating and highly activated T-cells or natural killer (NK) cells and results in the release of more than 150 inflammatory mediators (cytokines, oxygen free radicals, and coagulation factors). Both pro-inflammatory cytokines (such as Tumor Necrosis Factor-alpha, InterLeukin-1, and InterLeukin-6) and anti-inflammatory cytokines (such as interleukin 10, and interleukin 1 receptor antagonist) are elevated in the serum, and it is the fierce and often lethal interplay of these cytokines is referred to as a "cytokine storm."

Cytokine storms can occur in a number of infectious and non-infectious diseases including, for example, graft versus host disease (GVHD), adult respiratory distress syndrome (ARDS), sepsis, avian influenza, smallpox, and systemic inflammatory response syndrome (SIRS). In the absence of prompt intervention, a cytokine storm can result in permanent lung damage and, in many cases, death. Many patients will develop ARDS, which is characterized by pulmonary edema that is not associated with volume overload or depressed left ventricular function. The end stage symptoms of a disease precipitating the cytokine storm may include one or more of the following: hypotension; tachycardia; dyspnea; fever; ischemia or insufficient tissue perfusion; uncontrollable hemorrhage; severe metabolism dysregulation; and multisystem organ failure. Deaths from infections that precipitate a cytokine storm are often attributable to the symptoms resulting from the cytokine storm and are, therefore, not directly caused by the relevant pathogen. For example, deaths in severe influenza infections, such as by avian influenza or "bird flu," are typically the result of ARDS, which results from a cytokine storm triggered by the viral infection.

Because of its involvement in angiogenesis and vascular permeability, much attention has been focused on vascular endothelial growth factor (VEGF). Products that that reduce VEGF mediated angiogenesis and vascular edema are now marketed and available to patients. For example, the anti-VEGF antibody Ranibizumab (Lucentis), an antibody fragment of Bevacizumab (Avastin), which is itself a VEGF antibody (Rosenfeld et al., 2006; Brown et al., 2006) is commercially available for the treatment of AMD. The development and success of this product has triggered enormous commercial interest in alternative strategies for the treatment of diseases and conditions associated with pathologic angiogenesis or enthothelial hyperpermeability. Other approaches for inhibiting VEGF signaling include, for example, anti-VEGF aptamer, a soluble VEGF receptor ectodomain, receptor tyrosine kinase inhibitors, and siRNA against either VEGF or its receptors. With respect to AMD, such strategies have shown promise. However, there remains tremendous interest in a similar approaches for treating other conditions associated with pathologic angiogenesis and vascular leak. Moreover, as VEGF is only one of many angiogenic, permeability and inflammatory factors that contribute to angiogenesis and vascular permeability, there is continued value in identifying pathways and developing methods that affect VEGF functionality as well as the functionality of other angiogenic, permeability, or inflammatory factors.

SUMMARY

Generally, compounds, compositions and methods for inhibiting vascular permeability and pathologic angiogenesis are described herein. Methods for producing and screening compounds and compositions capable of inhibiting vascular permeability and pathologic angiogenesis are also described herein. Pharmaceutical compositions are included in the compositions described herein.

Compositions according to the present description can be used in, for example, methods of inhibiting vascular permeability and pathologic angiogenesis, including methods of inhibiting vascular permeability and pathologic angiogenesis induced by specific angiogenic, permeability and inflammatory factors, such as, for example VEGF, bFGF and thrombin. Methods for treating specific diseases and conditions are also provided herein.

Additional aspects of the specification provided herein will become apparent by reference to the Detailed Description, including the Examples and Materials and Methods, the Claims, and the Figures, including the Brief Description of the Drawings.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions. As it is used herein, the term "Mock" indicates a sham preparation that does not include active Slit protein.

FIG. 1E shows model of defective vascular guidance in robo4 morphant embryos. 5× and 20× images are shown in the left and right panels, respectively. DLAV=dorsal longitudinal anastomosing vessel. PAV=parachordal vessel. DA=dorsal aorta. PCV=posterior cardinal vein.

FIG. 2 shows Robo4-dependent inhibition of haptotaxis requires the aminoterminal half of the cytoplasmic tail.

HA=hemagglutinin epitope.

FIG. 3 shows Robo4 interacts with Hic-5 and paxillin in HEK 293 cells.

FIG. 4 shows paxillin interacts with Robo4 through a novel motif that is required for Robo4-dependent inhibition of haptotaxis.

FIG. 6 shows a paxillinΔLim4 mutant does not interact with Robo4, or support Slit2-Robo4-mediated inhibition of cell spreading.

FIG. 7 shows the paxillin interaction motif is required for repulsive vascular guidance.

FIG. 8 shows splice-blocking morpholinos suppress expression of robo4 in zebrafish embryos.

FIG. 9 shows Hic-5 is a Robo4-interacting protein.

FIG. 11 shows the Robo4 cytoplasmic tail does not inhibit Cdc42 activation nor interact with srGAP1.

FIG. 12 shows slit reduces retinopathy of prematurity, which is an FDA standard for factors that affect diabetic retinopathy, retinopathy of prematurity, and age related macular degeneration.

FIG. 17A shows the results of immunoprecipitation of cell lysates from untransfected human embryonic kidney cells (HEK), HEK cells transfected with Slit tagged with a myc epitope (Slit-myc), HEK cells transfected with Robo4 tagged with a HA epitope (Robo-4-HA) and HEK cells transfected with a control vector (Control-HEK). Western blot analysis of the Slit-myc cell lysates serves as a control and demonstrates that the Slit protein has a mass of approximately 210 kD, as previously reported (lane 1). Slit-myc protein is also detected by Western blot with an anti-myc antibody after Slit-myc and Robo4-HA cell lysates were combined and immunoprecipitated with an anti-HA antibody (lane 6). The specificity of this interaction is confirmed by the absence of detectable Slit protein with all other combinations of lysates. The same amount of lysate was used in each experiment. The lower bands in lanes 2-6 correspond to immunoglobulin heavy chains. FIG. 17B shows the results of immunoprecipitation of conditioned media from untransfected HEK cells (HEK CM), HEK cells transfected with Slit tagged with a myc epitope (Slit-myc CM), HEK cells transfected with the N-terminal soluble ectodomain of Robo4 tagged with the HA epitope (NRobo4-HA CM) and HEK cells transfected with control vector (Control-HEK CM). The full-length Slit-myc protein (210 KD) and its C-terminal proteolytic fragment (70 KD) are detected in Slit-myc CM by an anti-myc antibody (lane 1). As in FIG. 17A, Slit-myc protein is also detected by Western blot after Slit-myc and Robo4-HA conditioned media are combined and immunoprecipitated with an anti-HA antibody (lane 6). The specificity of this interaction is confirmed by the absence of Slit protein with all other combinations of conditioned media. As shown in FIG. 17C-FIG. 17F, Slit protein binds to the plasma membrane of cells expressing Robo4. Binding of Slit-myc protein was detected using an anti-myc antibody and an Alexa 594 conjugated anti-mouse antibody. Binding is detected on the surface of Robo4-HEK cells (FIG. 17F) but not Control-HEK cells (FIG. 17D).

FIG. 18A illustrates retinal flatmounts prepared from P5 Robo4$^{+/AP}$ mice and stained for Endomucin (endothelial cells), NG2 (pericytes) and Alkaline Phosphatase (AP; Robo4). The top-most arrow pointing to the right in the upper left panel indicates a tip cell, and the remaining arrows indicate pericytes (NG2-positive). "T" also indicates tip cells. FIG. 18B illustrates retinal flatmounts prepared from adult Robo4$^{+/AP}$ mice and stained for NG2 (pericytes) and AP (Robo4), with the arrows included in FIG. 18B indicating pericytes (NG2-positive). FIG. 18C shows the results of quantitative RT-PCR (qPCR) performed on the indicated samples using primers specific for PECAM, Robo1 and Robo4. As used in FIG. 18C: "HAEC" represents Human Aortic Endothelial Cells; "HMVEC" represents Human Microvascular Endothelial Cells; and "HASMC" represents Human Aortic Smooth Muscle Cells. FIG. 18D illustrates the results of probing total cell lysates from HMVEC and HASMC with antibodies to Robo4, VE-Cadherin, Smooth Muscle Actin and ERK1/2.

In FIG. 23A, different constructs for the Slit protein are depicted. The four leucine rich domains (LRR), the epidermal growth factor homology region (EGF) and the c-terminal tags (MYC/HIS) are indicated. Inhibition of VEGF mediated endothelial cell migration by the different Slit construts (2 nM) is shown in FIG. 23B.

FIG. 24 shows the effect of administering Slit protein on the survival of mice infected with Avian Flu Virus in accordance with a mouse model of avian flu.

Figure 1:
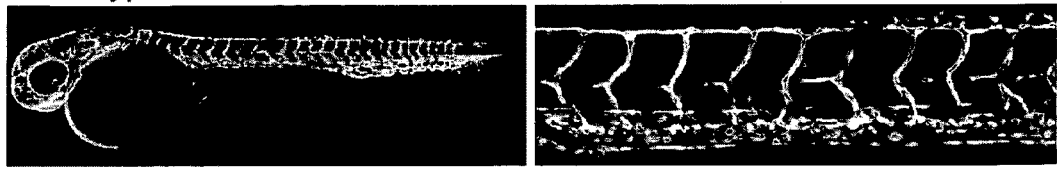
FIG. 1 shows Robo4-mediated vascular guidance requires the cytoplasmic tail of the receptor. Shown is the results of confocal microscopy of 48 hpf TG(fli: egfp)y1 embryos (A) un-injected, (B) injected with robo4 morpholino, (C) robo4 morpholino and wild-type murine robo4 RNA, and (D) robo4 morpholino and robo4Δtail RNA. Quantification is shown in FIG. 7.
Figure 1:
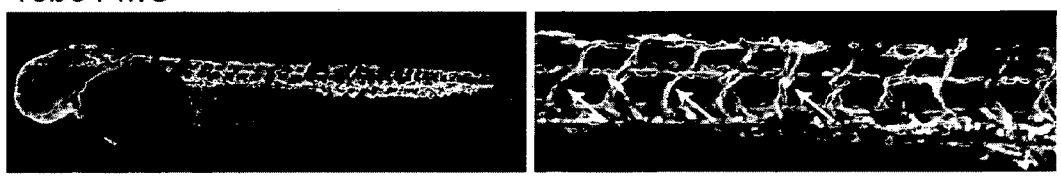
Figure 1:
Figure 1:
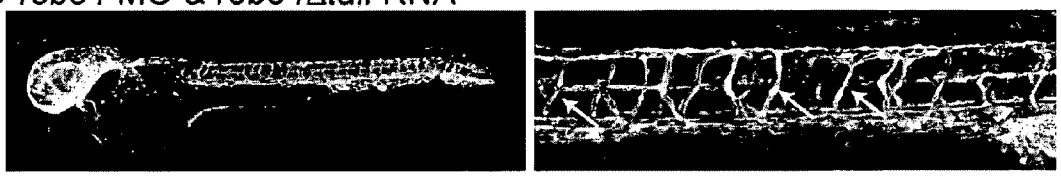
Figure 1:
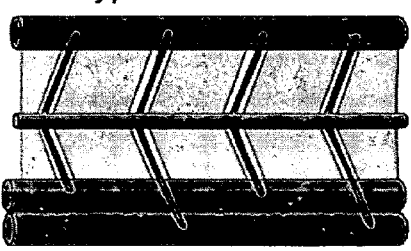
Figure 1:
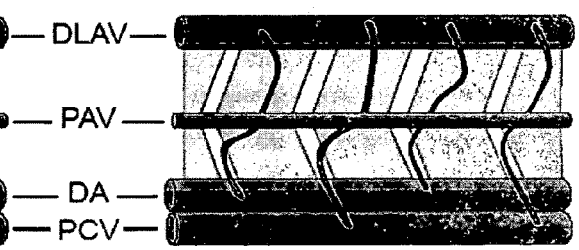

DETAILED DESCRIPTION OF THE INVENTION

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a polypeptide is disclosed and discussed and a number of modifications that can be made to a number of molecules including the polypeptide are discussed, each and every combination and permutation of polypeptide and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Those skilled in the art will recognize, or be able to ascertain using no more than routine experimentation, many equivalents to the specific embodiments of the method and compositions described herein. Such equivalents are intended to be encompassed by the following claims.

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the meanings that would be commonly understood by one of skill in the art in the context of the present specification.

It must be noted that as used herein and in the appended claims, the singular forms "a," "an," and "the" include plural reference unless the context clearly dictates otherwise. Thus, for example, reference to "a polypeptide" includes a plurality of such polypeptides, reference to "the polypeptide" is a reference to one or more polypeptides and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, the term "subject" means any target of administration. The subject can be a vertebrate, for example, a mammal. Thus, the subject can be a human. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between the specifically recited percentages, as compared to native or control levels.

"Promote," "promotion," and "promoting" refer to an increase in an activity, response, condition, disease, or other biological parameter. This can include but is not limited to the initiation of the activity, response, condition, or disease. This may also include, for example, a 10% increase in the activity, response, condition, or disease as compared to the native or control level. Thus, the increase in an activity, response, condition, disease, or other biological parameter can be a 10, 20, 30, 40, 50, 60, 70, 80, 90, 100%, or more, including any amount of increase in between the specifically recited percentages, as compared to native or control levels.

The term "therapeutically effective" means that the amount of the composition used is of sufficient quantity to ameliorate one or more causes or symptoms of a disease or disorder. Such amelioration only requires a reduction or alteration, not necessarily elimination.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "regulatory sequences" refers to those sequences normally within 100-1000 kilobases (kb) of the coding region of a locus, but they may also be more distant from the coding region, which affect the expression of the gene. Such regulation of expression comprises transcription of the gene, and translation, splicing, and stability of the messenger RNA.

The term "operably linked" refers to a juxtaposition wherein the components so described are in a relationship permitting them to function in their intended manner. For instance, a promoter is operably linked to a coding sequence if the promoter affects its transcription or expression. The term "operably linked" may refer to functional linkage between a nucleic acid expression control sequence (e.g., a promoter, enhancer, or array of transcription factor binding sites) and a second nucleic acid sequence, wherein the expression control sequence directs transcription of the nucleic acid corresponding to the second sequence.

"Isolated," when used to describe biomolecules disclosed herein, means, e.g., a peptide, protein, or nucleic acid that has been identified and separated and/or recovered from a component of its natural environment. Contaminant components of its natural environment are materials that would typically interfere with diagnostic or therapeutic uses for the isolated molecule(s), and may include enzymes, hormones, and other proteinaceous or non-proteinaceous materials. Methods for isolation and purification of biomolecules described herein are known and available in the art, and one of ordinary skill in the art can determine suitable isolation and purification methods in light of the material to be isolated or purified. Though isolated biomolecules will typically be prepared using at least one purification step, as it is used herein, "isolated" additionally refers to, for example, peptide, protein, antibody, or nucleic acid materials in-situ within recombinant cells, even if expressed in a homologous cell type.

Further, where the terms "isolated", "substantially pure", and "substantially homogeneous" are used to describe a monomeric protein they are used interchangeably herein. A monomeric protein is substantially pure when at least about 60 to 75% of a sample exhibits a single polypeptide sequence. A substantially pure protein can typically comprise about 60 to 90% W/W of a protein sample, and where desired, a substantially pure protein can be greater than about 90%, about 95%, or about 99% pure. Protein purity or homogeneity can be indicated by a number of means well known in the art, such as polyacrylamide gel electrophoresis of a protein sample, followed by visualizing a single polypeptide band upon staining the gel. For certain purposes, higher resolution can be provided by using HPLC or other means well known in the art which are utilized for purification.

Throughout the description and claims of this specification, the word "comprise" and variations of the word, such as "comprising" and "comprises," means "including but not limited to," and is not intended to exclude, for example, other additives, components, integers or steps.

As used herein, "vascular permeability" refers to the capacity of small molecules (e.g., ions, water, nutrients), large molecules (e.g., proteins and nucleic acids) or even whole cells (lymphocytes on their way to the site of inflammation) to pass through a blood vessel wall.

The terms "pathologic" or "pathologic conditions" refer to any deviation from a healthy, normal, or efficient condition which may be the result of a disease, condition, event or injury.

Proteins & Peptides

As the terms are used herein, "protein" and "peptide" are simply refer to polypeptide molecules generally and are not used to refer to polypeptide molecules of any specific size, length or molecular weight. Protein variants and derivatives are well understood to those of skill in the art and can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Table 1 and are referred to as conservative substitutions.

TABLE 1

Amino Acid Substitutions
Original Residue Exemplary Conservative
Substitutions, others are known in the art.

| Original Residue | Exemplary Conservative Substitutions |
|---|---|
| Ala | Ser |
| Arg | Lys; Gln |
| Asn | Gln; His |
| Asp | Glu |
| Cys | Ser |
| Gln | Asn, Lys |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, Proteins: Structure and Molecular Properties, W. H. Freeman & Co., San Francisco pp 79-86 [1983]), acetylation of the N-terminal amine and, in some instances, amidation of the C-terminal carboxyl.

It is understood that one way to define the variants and derivatives of the proteins and peptides disclosed herein is through defining the variants and derivatives in terms of homology/identity to specific known sequences. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e., all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence.

It is understood that there are numerous amino acid and peptide analogs which can be incorporated into the disclosed compositions. For example, there are numerous D amino acids or amino acids which have a different functional substituent then the amino acids shown in Table 1. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Enginerring Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include —$CH_2NH$—, —$CH_2S$—, —$CH_2$—$CH_2$—, —CH=CH—(cis and trans), —$COCH_2$—, —CH(OH)$CH_2$—, and —$CHH_2SO$— (These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appin, EP 45665 CA (1982): 97:39405 (1982) (—CH(OH)$CH_2$—); Holladay et al. Tetrahedron. Lett 24:4401-4404 (1983) (—C(OH)$CH_2$—); and Hruby Life Sci 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

Nucleic Acids

There are a variety of molecules disclosed herein that are nucleic acid based. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantagous that the antisense molecule be made up of nucleotide analogs that reduce the degradation of the antisense molecule in the cellular environment.

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl (.psi.), hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Often time base modifications can be combined with for example a sugar modifcation, such as 2'-O-methoxyethyl, to achieve unique properties such as increased duplex stability. There are numerous United States patents such as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxy ribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$, alkyl or $C_2$ to $C_{10}$ alkenyl and alkynyl. 2' sugar modifications also include but are not limited to —O[(CH$_2$)$_n$O]$_m$CH$_3$, —O(CH$_2$)$_n$ OCH$_3$, —O(CH$_2$)$_n$ NH$_2$, —O(CH$_2$)$_n$CH$_3$, —O(CH$_2$)$_n$—ONH$_2$, and —O(CH$_2$)$_n$ON[(CH$_2$)$_n$CH$_3$)]$_2$, where n and m are from 1 to about 10.

Other modifications at the 2' position include but are not limited to: $C_1$ to $C_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkage between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH$_2$ component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science, 1991, 254, 1497-1500).

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety (Letsinger et al., Proc. Natl. Acad. Sci. USA, 1989, 86:6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., dodecandiol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937. Numerous United States patents teach the preparation of such conjugates and include, but are not limited to U.S. Pat. Nos. 4,828,979; 4,948,882; 5,218,105; 5,525, 465; 5,541,313; 5,545,730; 5,552,538; 5,578,717, 5,580,731;

5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, N1, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

i. Nucleic Acid Sequences

A variety of sequences are provided herein, with some of these sequences available from Genbank at www.pubmed.gov. Those of skill in the art understand how to resolve sequence discrepancies and differences and to adjust the compositions and methods relating to a particular sequence to other related sequences. Primers and/or probes can be designed for any sequence given the information disclosed herein and known in the art.

ii. Hybridization/selective hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., Molecular Cloning: A Laboratory Manual, 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

iii. Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, RNAi, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA, genomic DNA, or polypeptide for any of the herein disclosed guidance cues or receptors therefor. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, Science 238:407-409 (1990)).

Similarly, eukaryotic EGS/RNAse P-directed cleavage of RNA can be utilized to cleave desired targets within eukarotic cells. (Yuan et al., Proc. Natl. Acad. Sci. USA 89:8006-8010 (1992); WO 93/22434 by Yale; WO 95/24489 by Yale; Yuan and Altman, EMBO J. 14:159-168 (1995), and Carrara et al., Proc. Natl. Acad. Sci. (USA) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

Gene expression can also be effectively silenced in a highly specific manner through RNA interference (RNAi). This silencing was originally observed with the addition of double stranded RNA (dsRNA) (Fire, A., et al. (1998) Nature, 391, 806 811) (Napoli, C., et al. (1990) Plant Cell 2, 279 289) (Hannon, G. J. (2002) Nature, 418, 244 251). Once dsRNA enters a cell, it is cleaved by an RNase III-like enzyme, Dicer, into double stranded small interfering RNAs (siRNA) 21-23 nucleotides in length that contains 2 nucleotide overhangs on the 3' ends (Elbashir, S. M., et al. (2001) Genes Dev., 15:188-200) (Bernstein, E., et al. (2001) Nature, 409, 363 366) (Hammond, S. M., et al. (2000) Nature, 404:293-296). In an ATP dependent step, the siRNAs become integrated into a multi-subunit protein complex, commonly known as the RNAi induced silencing complex (RISC), which guides the siRNAs to the target RNA sequence (Nykanen, A., et al. (2001) Cell, 107:309 321). At some point the siRNA duplex unwinds, and it appears that the antisense strand remains bound to RISC and directs degradation of the complementary mRNA sequence by a combination of endo and exonucleases (Martinez, J., et al. (2002) Cell, 110:563-574). However, the effect of siRNA or siRNA or their use is not limited to anytype of mechanism.

Also disclosed are nucleic acids can be used for RNAi or RNA interference. It is thought that RNAi involves a two-step mechanism for RNA interference (RNAi): an initiation step and an effector step. For example, in the first step, input double-stranded (ds) RNA (siRNA) is processed into small fragments, such as 21-23-nucleotide 'guide sequences'. RNA amplification appears to be able to occur in whole animals. Typically then, the guide RNAs can be incorporated into a protein RNA complex which is cable of degrading RNA, the nuclease complex, which has been called the RNA-induced silencing complex (RISC). This RISC complex acts in the second effector step to destroy mRNAs that are recognized by the guide RNAs through base-pairing interactions. RNAi involves the introduction by any means of double stranded RNA into the cell which triggers events that cause the degradation of a target RNA. RNAi is a form of post-transcriptional gene silencing. Disclosed are RNA hairpins that can act in RNAi. For description of making and using RNAi molecules see See, e.g., Hammond et al., Nature Rev Gen 2: 110-119 (2001); Sharp, Genes Dev 15: 485-490 (2001), Waterhouse et al., Proc. Natl. Acad. Sci. USA 95(23): 13959-13964 (1998) all of which are incorporated herein by reference in their entireties and at least form material related to delivery and making of RNAi molecules.

RNAi has been shown to work in a number of cells, including mammalian cells. For work in mammalian cells it is preferred that the RNA molecules which will be used as targeting sequences within the RISC complex are shorter. For example, less than or equal to 50 or 40 or 30 or 29, 28, 27, 26, 25, 24, 23, 22, 21, 20, 19, 18, 17, 16, 15, 14, 13, 12, 11, or nucleotides in length. These RNA molecules can also have overhangs on the 3' or 5' ends relative to the target RNA which is to be cleaved. These overhangs can be at least or less than or equal to 1, 2, 3, 4, 5, 6, 7, 8, 9, 10, 15, or 20 nucleotides long. RNAi works in mammalian stem cells, such as mouse ES cells.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, S. M., et al. (2001) Nature, 411:494 498) (Ui-Tei, K., et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Tex.), ChemGenes (Ashland, Mass.), Dharmacon (Lafayette, Colo.), Glen Research (Sterling, Va.), MWB Biotech (Esbersberg, Germany), Proligo (Boulder, Colo.), and Qiagen (Vento, The Netherlands). siRNA can also be synthesized in vitro using kits such as Ambion's SILENCER siRNA Construction Kit. Disclosed herein are any siRNA designed as described above based on the sequences for the herein disclosed inflammatory mediators.

The production of siRNA from a vector is more commonly done through the transcription of a shRNA. Kits for the production of vectors comprising shRNA are available, such as for example Imgenex's GeneSuppressor Construction Kits and Invitrogen's BLOCK-iT inducible RNAi plasmid and lentivirus vectors. Disclosed herein are any shRNA designed as described above based on the sequences for the herein disclosed inflammatory mediators.

iv. Vectors

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as those encoding scFvs into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

v. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

vi. Adenoviral Vectors

The construction of replication-defective adenoviruses has been described (Berkner et al., J. Virology 61:1213-1220 (1987); Massie et al., Mol. Cell. Biol. 6:2872-2883 (1986); Haj-Ahmad et al., J. Virology 57:267-274 (1986); Davidson et al., J. Virology 61:1226-1239 (1987); Zhang "Generation and identification of recombinant adenovirus by liposome-mediated transfection and PCR analysis" BioTechniques 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580-1586 (1993); Kirshenbaum, J. Clin. Invest. 92:381-387 (1993); Roessler, J. Clin. Invest. 92:1085-1092 (1993); Moullier, Nature Genetics 4:154-159 (1993); La Salle, Science 259:988-990 (1993); Gomez-Foix, J. Biol. Chem. 267:25129-25134 (1992); Rich, Human Gene Therapy 4:461-476 (1993); Zabner, Nature Genetics 6:75-83 (1994); Guzman, Circulation Research 73:1201-1207 (1993); Bout, Human Gene Therapy 5:3-10 (1994); Zabner, Cell 75:207-216 (1993); Caillaud, Eur. J. Neuroscience 5:1287-1291 (1993); and Ragot, J. Gen. Virology 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462-477 (1970); Brown and Burlingham, J. Virology 12:386-396 (1973); Svensson and Persson, J. Virology 55:442-449 (1985); Seth, et al., J. Virol. 51:650-655 (1984); Seth, et al., Mol. Cell. Biol. 4:1528-1533 (1984); Varga et al., J. Virology 65:6061-6070 (1991); Wickham et al., Cell 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

vii. Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19.

Adeno-associated virus (AAV) is a member of the Parvoviridae, a virus family characterized by a single stranded linear DNA genome and a small icosahedral shaped capsid measuring about 20 nm in diameter. AAV was first described as a contamination of tissue culture grown simian virus 15, a simian adenovirus and was found dependent on adenovirus for measurable replication. This lead to its name, adeno-associated virus, and its classification in the genus Dependovirus (reviewed in Hoggan, M.D. Prog Med Virol 12 (1970) 211-39). AAV is a common contaminant of adenovirus samples and has been isolated from human virus samples (AAV2, AAV3, AAV5), from samples of simian virus-15 infected cells (AAV1, AAV4) as well as from stocks of avian (AAAV) (Bossis, I. and Chiorini, J. A. J Virol 77 (2003) 6799-810), bovine, canine and ovine adenovirus and laboratory adenovirus type 5 stock (AAV6). DNA spanning the entire rep-cap ORFs of AAV7 and AAV8 was amplified by PCR from heart tissue of rhesus monkeys (Gao, G. P., et al. Proc Natl Acad Sci USA 99 (2002) 11854-9). With the exception of AAVs 1 and 6, all cloned AAV isolates appear to be serologically distinct. Nine isolates have been cloned, and recombinant viral stocks have been generated from each isolated virus.

AAV2 is the best characterized adeno-associated virus and will be discussed as an AAV prototype. The AAV2 genome consists of a linear single stranded DNA of 4,780 nucleotides. Both polarities of DNA are encapsulated by AAV with equal efficiency. The AAV2 genome contains 2 open reading frames (ORF) named rep and cap. The rep ORF encodes the non-structural proteins that are essential for viral DNA replication, packaging and AAV integration. The cap ORF encodes the capsid proteins. The rep ORF is transcribed from promoters at map units P5 and P19. The rep transcripts contain an intron close to the 3' end of the rep ORF and can be alternatively spliced. The rep ORF is therefore expressed as 4 partially overlapping proteins, which were termed according to their molecular weight Rep78, 68, 52 and 40. The cap ORF is expressed from a single promoter at P40. By alternative splicing and utilization of an alternative ACG start codon, cap is expressed into the capsid proteins VP1-3 which range in size from 65-86 kDa. VP3 is the most abundant capsid protein and constitutes 80% of the AAV2 capsid. All viral transcripts terminate at a polyA signal at map unit 96.

During a productive AAV2 infection, unspliced mRNAs from the p5 promoter encoding Rep78 are the first detectable viral transcripts. In the course of infection, expression from P5, P19 and P40 increase to 1:3:18 levels respectively. The levels of spliced transcripts increased to 50% for P5, P19 products and 90% of P40 expressed RNA (Mouw, M. B. and Pintel, D. J. J Virol 74 (2000) 9878-88).

The AAV2 genome is terminated on both sides by inverted terminal repeats (ITRs) of 145 nucleotides (nt). 125 nt of the ITR constitute a palindrome which contains 2 internal palindromes of 21 nt each. The ITR can fold back on itself to generate a T-shaped hairpin with only 7 non-paired bases. The stem of the ITR contains a Rep binding site (RBS) and a sequence that is site and strand specifically cleaved by Rep—the terminal resolution site (TRS). The ITR is essential for AAV2 genome replication, integration and contains the packaging signals.

The single-stranded AAV2 genome is packaged into a non-enveloped icosahedral shaped capsid of about 20-25 nm diameter. The virion consists of 26% DNA and 74% protein and has a density of 1.41 g/cm3. AAV2 particles are extremely stable and can withstand heating to 60° C. for 1 hour, extreme ph, and extraction with organic solvents.

Rep proteins are involved in almost every step of AAV2 replication including AAV2 genome replication, integration, and packaging. Rep78 and Rep68 possess ATPase, 3'-5' helicase, ligase and nicking activities and bind specifically to DNA. Rep52 and Rep40 appear to be involved in the encapsidation process and encode ATPase and 3'-5' helicase activities. Mutational analysis suggests a domain structure for Rep78. The N-terminal 225 aa are involved in DNA binding, DNA nicking and ligation. Rep78 and Rep68 recognize a GCTC repeat motif in the ITR as well as in a linear truncated form of the ITR (Chiorini, J. A., et al. J Virol 68 (1994) 7448-57) with similar efficiencies. Rep78 and Rep68 possess a sequence and strand specific endonuclease activity, which cleaves the ITR at the terminal resolution site (TRS). Rep endonuclease activity is dependent on nucleoside triphosphate hydrolysis and presence of metal cations. Rep 78 and 68 can also bind and cleave single stranded DNA in a NTP independent matter. In addition, Rep78 catalyzes rejoining of single stranded DNA substrates originating from the AAV2 origin of replication—i.e., sequences containing a rep binding and terminal resolution element.

The central region of AAV2 Rep78, which represents the N-terminus of Rep52 and Rep40, contains the ATPase and 3'-5' helicase activities as well as nuclear localization signals. The helicase activity unwinds DNA-DNA and DNA-RNA duplexes, but not RNA-RNA. The ATPase activity is constitutive and independent of a DNA substrate. The C-terminus of Rep78 contains a potential zinc-finger domain and can inhibit the cellular serine/threonine kinase activity of PKA as well as its homolog PRKX by pseudosubstrate inhibition. Rep68 which is translated from a spliced mRNA that encodes the N-terminal 529 amino acids (aa) of Rep78 fused to 7 aa unique for Rep68, doesn't inhibit either PKA or PRKX. In addition to these biochemical activities, Rep can affect intracellular conditions by protein-protein interactions. Rep78 binds to a variety of cellular proteins including transcription factors like SP-1, high-mobility-group non-histone protein 1 (HMG-1) and the oncosuppressor p53. Overexpression of Rep results in pleiotrophic effects. Rep78 disrupts cell cycle progression and inhibits transformation by cellular and viral oncogenes. In susceptible cell lines, overexpression of Rep resulted in apoptosis and cell death. Several of Rep78 activities contribute to cytotoxicity, including its constitutive ATPase activity, interference with cellular gene expression and protein interactions.

The first step of an AAV infection is binding to the cell surface. Receptors and coreceptors for AAV2 include heparan sulfate proteoglycan, fibroblast growth factor receptor-1, and $\alpha v \beta 5$ integrins whereas N-linked 2,3-linked sialic acid is required for AAV5 binding and transduction (Walters, R. W., et al. J Biol Chem 276 (2001) 20610-6). In HeLa cells, fluorescently labeled AAV2 particles appear to enter the cell via receptor-mediated endocytosis in clathrin coated pits. More than 60% of bound virus was internalized within 10 min after infection. Labeled AAV particles are observed to have escaped from the endosome, been trafficked via the cytoplasm to the cell nucleus and accumulated perinuclear, before entering the nucleus, probably via nuclear pore complex (NPC). AAV2 particles have been detected in the nucleus, suggesting that uncoating takes place in the nucleus (Bartlett, et al. J Virol 74 (2000) 2777-85; Sanlioglu et al. J Virol 74 (2000) 9184-96). AAV5 is internalized in HeLa cells predominantly by clathrin coated vesicles, but to a lesser degree also in noncoated pits. AAV particles can also be trafficked intercellularly via the Golgi apparatus (Bantel-Schaal, U., et al. J Virol 76 (2002) 2340-9). At least partial uncoating of AAV5 was suggested to take place before entering the nucleus since intact AAV5 particles could not be detected in the nucleus (Bantel-Schaal et al., 2002) After uncoating, the single stranded genome is converted into duplex DNA either by leading strand synthesis or annealing of input DNA of opposite polarity. AAV replication takes place within the nucleus.

During a co-infection with a helper virus such as Adenovirus, herpes simplex virus or cytomegalovirus, AAV is capable of an efficient productive replication. The helper functions provided by Adenovirus have been studied in great detail. In human embryonic kidney 293 cells, which constitutively express the Adenovirus E1A and E1B genes, the early Adenovirus gene products of E2A, E4 and VA were found sufficient to allow replication of recombinant rAAV. Allen et al. reported that efficient production of rAAV is possible in 293 cells transfected with only an E4orf6 expression plasmid (Allen, J. M., et al. Mol Ther 1 (2000) 88-95). E1A stimulates S phase entry and induces unscheduled DNA synthesis by inactivating the pRB checkpoint at the G1/S border by interaction with pRB family proteins which results in the release of E2F (reviewed in (Ben-Israel, H. and Kleinberger, T. Front Biosci 7 (2002) D1369-95). This leads to either induction or activation of enzymes involved in nucleotide synthesis and DNA replication. Since unscheduled DNA synthesis is a strong apoptotic signal, anti-apoptotic functions are required. E1B-19k is a Bcl-2 homolog and E1B-55k is a p53 antagonist. Both proteins have anti-apoptotic functions. E4orf6 forms a complex with E1B-55k and results in degradation of p53. It is also reported to cause S-phase arrest (Ben-Israel and Kleinberger, 2002). E2A encodes a single strand DNA binding protein, which appears to be non-essential for DNA replication but effects gene expression (Chang and Shenk. J Virol 64 (1990) 2103-9). The VA transcription unit affects AAV2 RNA stability and translation (Janik et al., Virology 168 (1989) 320-9). E1A has a more direct effect on AAV2 gene expression. The cellular transcription factor YY-1 binds and inhibits the viral P5 promoter. E1A relieves this transcriptional block. None of the late Ad gene products have been found to be essential for AAV2 replication. The main function of the helper virus appears to be the generation of a cellular environment with active DNA replication machinery and blocked pro-apoptotic functions that allows high-level AAV replication rather than a direct involvement in AAV replication.

viii. Large Payload Viral Vectors

Molecular genetic experiments with large human herpes viruses have provided a means whereby large heterologous DNA fragments can be cloned, propagated and established in cells permissive for infection with herpesviruses (Sun et al., Nature genetics 8: 33-41, 1994; Cotter and Robertson, Curr Opin Mol Ther 5: 633-644, 1999). These large DNA viruses (herpes simplex virus (HSV) and Epstein-Barr virus (EBV), have the potential to deliver fragments of human heterologous DNA>150 kb to specific cells. EBV recombinants can maintain large pieces of DNA in the infected B-cells as episomal DNA. Individual clones carried human genomic inserts up to 330 kb appeared genetically stable The maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA>220 kb and to infect cells that can stably maintain DNA as episomes.

Other useful systems include, for example, replicating and host-restricted non-replicating vaccinia virus vectors.

iX. Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, for example, the compositions can comprise lipids, such as liposomes, such as cationic liposomes (e.g., DOTMA, DOPE, DC-cholesterol) or anionic liposomes. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. Am. J. Resp. Cell. Mol. Biol. 1:95-100 (1989); Felgner et al. Proc. Natl. Acad. Sci. USA 84:7413-7417 (1987); U.S. Pat. No. 4,897,355. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). These techniques can be used for a variety of other speciifc cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

x. In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

xi. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355-360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell. Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell. Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTR.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b. Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR-cells and mouse LTK-cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Guidance Cues

Cell migration is involved in diverse morphogenetic programs, including patterning of the vascular and neural networks (Lauffenburger and Horwitz, 1996, Ridley et al., 2003). To execute these developmental programs, a migrating cell must reorganize its actin cytoskeleton in response to positive and negative guidance cues present in the extracellular milieu. The influence of these cues on cell migration is dictated by the complement of transmembrane receptors on the surface of the cell, and the diverse intracellular signal transduction cascades that are activated by specific cues.

The formation of neural and vascular networks share common molecular cues that reduce the complex task of projecting long distances to the simpler task of navigating a series of short segments based on these specific cues in the extracellular environment. Guidance cues come in four varieties: attractants and repellents, which may act either at short range (being cell- or matrix-associated) or at longer range (being diffusible). Intermediate targets are often the source of long-range attractive signals that lure axons, and of short- or long-range repellent signals that expel axons that have entered the target, or prevent their entry altogether. In between intermediate targets, axons and vessels are often guided through tissue corridors by attractive cues made by cells along the corridors, and by repulsive signals that prevent them from entering surrounding tissues.

As used herein, a "guidance cue" is a molecule that can act to attract or repulse neuron or blood vessel navigation or formation. Guidance cues, such as axonal guidance cues, are often categorized as "attractive" or "repulsive." However, this is a simplification, as different axons will respond to a given cue differently. Furthermore, the same axonal growth cone can alter its responses to a given cue based on timing, previous experience with the same or other cues, and the context in which the cue is found. Thus, in one aspect, the guidance cue can be an attractive guidance cue for a specific cell. In another aspect, the guidance cue can be a repulsive guidance cue for a specific cell. As disclosed herein, "guidance cues" can be proteins that act extracellularly on cell receptors. However, also disclosed are molecules, including nucleic acids and small molecules, that can act either extracellularly or intracellularly to attract or repulse neuron or blood vessel navigation. Thus, as an example, where a ligand of a guidance cue receptor is disclosed herein, also disclosed are molecules that can modulate the activity or expression of said receptor. Thus, for example, disclosed are compositions, such as functional nucleic acids, that can alter gene expression of a receptor of a guidance cue disclosed herein or signaling molecule thereof. In one aspect, these molecules affect the same cell receptors and intracellular signaling pathways as the traditional protein guidance cues disclosed herein. In another aspect, these molecules can be identified by the screening methods disclosed herein.

Guidance cues can be identified based on the ability to guide axons. Growing axons have a highly motile structure at the growing tip called the growth cone, which "sniffs out" the extracellular environment for signals that instruct the axon which way to grow. These signals, called guidance cues, can be fixed in place or diffusible; they can attract or repel axons. With respect to axons, growth cones contain receptors that recognize these guidance cues and interpret the signal into a chemotropic response. The general theoretical framework is that when a growth cone "senses" a guidance cue, the receptors activate various signaling molecules in the growth cone that eventually affect the cytoskeleton. If the growth cone of the axon senses a gradient of guidance cue, the intracellular signaling in the growth cone happens asymmetrically, so that cytoskeletal changes happen asymmetrically and the growth cone turns toward or away from the guidance cue.

A combination of genetic and biochemical methods has led to the discovery of several important classes of guidance molecules and their receptors. Netrins and their receptors, DCC and UNC5, are secreted molecules that can act to attract or repel axons. Slits are secreted proteins that normally repel neural growth cones by engaging Robo (Roundabout) class receptors. Ephrins are cell surface molecules that activate Eph receptors on the surface of other cells. This interaction can be attractive or repulsive. In some cases, Ephrins can also act as receptors by transducing a signal into the expressing cell, while Ephs act as the ligands. Signaling into both the Ephrin- and Eph-bearing cells is called "bi-directional signaling." The many types of Semaphorins are primarily axonal repellents, and activate complexes of cell-surface receptors called Plexins and Neuropilins. In addition, many other classes of extracellular molecules are used by growth cones to navigate properly, including developmental morphogens, such as BMPs, Wnts, Hedgehogs, and FGFs; extracellular matrix and adhesion molecules, such as NCAM, L1, and laminin; growth factors like NGF; and neurotransmitters and modulators like GABA. Thus, as disclosed herein, a repulsive cue can be, for example, a ligand of a roundabout receptor or a ligand of a netrin receptor.

xii. Unc5 and Netrin

Netrins were identified as chemoattractants that guide axons to the midline by binding receptors of the DCC (deleted in colorectal carcinoma) family. Netrins have also been implicated in axon repulsion, an effect mediated by receptors of the Unc5 family acting alone or with DCC receptors. In addition, DCC-Unc5 heterodimers can mediate repulsion at longer range than Unc5 receptors alone. Netrin1 and Unc5b, one of four mammalian Unc5 receptors, also regulate blood vessel guidance. Unc5b is expressed in endothelial tip cells. Loss of Unc5b in mice results in aberrant extension of tip cell filopodia and excessive branching of many vessels. Treatment of cultured endothelial cells or growing vessels in vivo with netrin1 induces filopodial retraction. A role for Unc5b in mediating endothelial cell repulsion was confirmed by analysis of the developing intersegmental vessels (ISV) in zebrafish embryos.

Netrins comprise a phylogenetically conserved family of guidance cues related to the extracellular matrix molecule laminin. Four secreted netrins have been identified in vertebrates: netrin-1 in chickens, mice, zebrafish and humans; netrin-2 in chickens; netrin-3 in mice and humans; and netrin-4 in mice and humans. All netrins are structurally related to the short arms of laminin and contain the laminin VI and V domains. All netrins also contain positively charged C-terminal domains, termed NTR modules. Netrin-1, -2, and -3 are more closely related to the laminin gamma chain. In contrast, netrin-4 is more closely related to the laminin beta chain.

Two families of netrin receptors have been identified that dictate the direction of migration. Both families belong to the immunoglobulin (Ig) superfamily of receptors. In vertebrates, the Deleted in Colorectal Cancer (DCC) family has two members, DCC and neogenin, that contain six, extracellular fibronectin type III repeats in addition to four Ig domains and three regions of intracellular homology (P1, P2 and P3) that mediate interactions with other receptors such as UNC5b (P1) and Robo1 (P3). The UNC5 family has four members, UNC5a (UNC5H1), UNC5b (UNC5H2), UNC5c (UNC5H3), that contain two Ig and two thrombospondin type I (TspI) domains extracellularlly and ZU-5, DCC binding and C-terminal death domains intracellularly. Functionally, the DCC family mediates attraction to netrin-1 while the UNC5 family mediates repulsion by forming a netrin-1 dependent complex with DCC. Members of both families have been shown to act as dependence receptors and induce apoptosis in the absence and not the presence of ligand.

xiii. Semaphorins and Neuropilins/Plexins

As disclosed herein, some semaphorins can act through plexins to increase vascular permeability. Thus, in some aspects of the disclosed compositions and methods, the repulsive guidance cue is not a semaphorin. In some aspects of the disclosed compositions and methods, the repulsive guidance cue is not a ligand of a plexin or neuropilin.

However, as disclosed herein, semaphorin 3E acts through plexin D1 to inhibit vascular permeability. Thus, in some aspects, the repulsive guidance cue can be semaphorin 3E. In some aspects, the repulsive guidance cue can be a ligand of plexin D1.

Semaphorins are guidance signals that are secreted and capable of long range diffusion (class 3) but can, in some contexts, have restricted diffusion, or are membrane-bound and function as short range guidance cues. Semaphorins are best known as repellents, but semaphorin 3A (Sema3A) can also function as a chemoattractant, depending on the intracellular level of cyclic nucleotides. Semaphorins signal through multimeric receptor complexes: membrane-bound semaphorins bind plexins, whereas secreted class 3 semaphorins bind neuropilins, which function as non-signalling co-receptors with plexins. An exception to this rule is the secreted Sema3E, which binds plexinD1 (Plxnd1) directly. Furthermore, the membrane-anchored Sema7A stimulates axon extension by activating integrins. Semaphorins and their receptors also regulate vessel guidance and branching. Endothelial cells express various neuropilin and plexin receptors. Sema3A inhibits formation of endothelial lamellipodia and vessels. Neuropilin2 is expressed in veins and lymph vessels, and Neuropilin1 is expressed widely in the developing vasculature. Neuropilins have also been implicated in vessel patterning, but this can reflect their role in modulating VEGF rather than semaphorin signaling, since neuropilins are also receptors for specific VEGF isoforms (VEGF165) and modulate the activity of VEGF receptors. Moreover, VEGF165 competes with Sema3A for binding to neuropilins.

As disclosed herein, semaphorin 3E acts through plexin D1 to inhibit vascular permeability. Thus, in some aspects, the repulsive guidance cue can be semaphorin 3E. In some aspects, the repulsive guidance cue can be a ligand of plexin D1.

xiv. Ephrins and Ephs

Another principal class of shortrange axon guidance molecules is the Eph receptor tyrosine kinases and their ephrin ligands. The 13 Eph receptors in mammals are categorized into A (EphA1-8) and B (EphB1-4 and EphB6) subfamilies. The eight ephrin ligands comprise ephrinA1-5, which are tethered to the membrane via a glycosyl-phosphatidylinositol anchor, and ephrinB1-3, which contain transmembrane and cytoplasmic regions. EphrinA ligands bind EphA receptors, and ephrinB ligands bind EphB receptors; only a modest degree of cross-reactivity between the families has been observed; for example, EphA4 binds some B class ephrins. Eph receptors and ephrins initiate bidirectional signaling in cells expressing Eph receptors (forward signaling) or ephrinB ligands (reverse signalling). Ephrins were first identified as repellent axon guidance molecules through studies on topographic retinotectal projections, and subsequently have been implicated as both negative and positive cues in other wiring processes. Eph-ephrin signals also control vascular development. Some of these guidance molecules were among the first factors found to be expressed selectively in either arteries or veins. Historically, haemodynamic pressure differences were presumed to regulate the differentiation of high-pressure vessels into arteries and low-pressure vessels into veins. Expression analysis and loss-of-function studies in mice indicated, however, that EphB4 and ephrinB2 are expressed in developing veins and arteries, respectively, and are critical for their maintenance. These studies indicated that repulsive ephrinB2-EphB4 signaling—both forward and reverse—can prevent intermixing of venous and arterial endothelial cells, secure assembly of 'like' endothelial cells and demarcate arterial-venous cell boundaries. Repulsive ephrin-Eph signals provide short-range guidance cues for vessels to navigate through tissue boundaries. For instance, ephrinB2 repels EphB3/EphB4-expressing ISVs from entering somites. However, ephrin-Eph interactions can also provide attractive cues and induce capillary sprouting in other contexts. For instance, juxtacrine expression of ephrinB ligands and EphBs on adjacent endothelial cells or smooth muscle cells in the same vessel may provide bidirectional signals for establishing contact-dependent communication, and promote vessel assembly, sprouting and maturation. For example, EphrinA ligands may also function as positive regulators of vascular morphogenesis.

EphA2/ephrinA1 signaling has been shown to inhibit VEGF-induced retinal vascular permeability and has been implicated in the treatment of neovascularization and vasopermeability abnormalities in diabetic retinopathy (Ojima et al, 2006). Thus, in some aspects of the disclosed compositions and methods for inhibiting vascular permeability, the repulsive cue is not a ligand of an Eph or ephrin receptor. In other aspects, the disclosed compositions comprise at least one guidance cue in addition to a ligand of an Eph or ephrin receptor.

xv. Slits and Roundabouts

A well-known example of a repulsive guidance cue is the Slit family of extracellular matrix proteins. Slit was originally identified in a genetic screen for axon guidance defects at the midline of Drosophila embryos (Seeger et al., 1993; Kidd et al, 1998; Battye et al., 1999; Kidd et al., 1999). Subsequently, three evolutionarily conserved Slit genes were cloned in vertebrates and their encoded proteins repel axons (Brose et al., 1999; Li et al., 1999) and promote sensory axon arborization (Wang et al., 1999).

Genetic and biochemical studies have demonstrated that the Robo family of transmembrane proteins function as receptors for Slit proteins. Like slit, robo was discovered in a genetic screen for defective axon guidance in Drosophila (Seeger et al., 1993). Four Robos have been identified in vertebrates, and Robo1-3 are predominantly expressed in the nervous system (Marillat et al., 2002). In contrast, Robo4, also known as Magic Roundabout, is exclusively expressed in the vasculature of embryonic mice (Park et al., 2003), placental arteries (Huminiecki et al., 2002) and in the tumor endothelium of a variety of human malignancies (Huminiecki et al., 2002; Seth et al., 2005). Robo4 is further distinguished from Robo1-3 by its divergent sequence: the ectodomain of the neuronal Robos contains five immunoglobulin (Ig) domains and three fibronectin type III (FNIII) repeats, while Robo4 contains two Ig domains and two FNIII repeats (Huminiecki et al., 2002; Park et al., 2003). In addition, Robo1-3 possess four conserved cytoplasmic (CC) motifs, CC0, CC1, CC2 and CC3 (Kidd et al., 1998; Zallen et al., 1998), of which, only CC0 and CC2 are present in Robo4 (Huminiecki et al., 2002; Park et al., 2003).

The ability of Robo to facilitate guidance decisions in the nervous system is dependent upon activation of specific biochemical programs downstream of the Slit-stimulated receptor. Analysis of Slit-dependent repulsion in Drosophila, C. elegans, and mammals has identified key mediators of Robo signaling in the nervous system. In Drosophila, the Abelson (Abl) tyrosine kinase and the actin binding protein Enabled (Ena) are involved in regulating Robo's repulsive activity (Bashaw et al., 2000). Additional studies in Drosophila identified a Rac GTPase activating protein (GAP) that is involved in Robo-mediated repulsion of tracheal cells and axons (Lundstrom et al., 2004; Hu et al., 2005). In C. elegans, a direct role for Ena in modulating Slit signaling has emerged from genetic analyses (Yu et al., 2002). In mammalian neurons, the Robo1-interacting protein srGAP1 is essential for Slit-dependent repulsion of precursor cells migrating from the anterior subventricular zone (Wong et al., 2001). Not only have these mechanistic studies begun to elucidate the signaling pathways downstream of neuronal Robos, but such studies have provided an explanation for the receptor's repulsive activity.

In contrast to the nervous system, little is known about Slit-Robo signal transduction in the vasculature, and despite the preponderance of evidence that Slit-Robo signaling inhibits the migration of both neuronal and non-neuronal cell types, including endothelial cells (Wu et al., 1999; Zhu et al., 1999; Wu et al., 2001; Park et al., 2003; Seth et al., 2005), several recent reports have proposed that Robos can promote angiogenesis in both Slit-dependent and Slit-independent ways. For example, it was reported that Slit2 stimulation of Robo1 induced migration and tube formation in vitro, and promoted tumor angiogenesis in vivo (Feng et al., 2004). Moreover, a recent study showed blocking Robo4 activity with a soluble Robo4 ectodomain inhibited migration and tube formation in vitro, consistent with a positive role for Robo4 during angiogenesis. Further, this study reported that Slit proteins do not bind to Robo4, thereby implicating an unknown ligand for the receptor (Suchting et al., 2004). The notion that Robo4 is proangiogenic has also emerged from recent data showing that overexpression of Robo4 augments endothelial cell adhesion and migration independently of Slit (Kaur et al., 2006). These seemingly incongruous observations emphasize the need to define both the functional significance and mechanism of Slit-Robo signaling in endothelial cells.

As disclosed herein, Slit2 is a ligand of Robo4, and Slit2-Robo4 signaling negatively regulates cell motility and inhibits vascular permeability. In particular, the teachings provided herein establish that Slit2 elicits a repulsive cue in the endothelium via activation of Robo4, defining a novel signal transduction cascade responsible for such activity. As described herein Slit2 activation of Robo4 inhibits Rac activation and, hence, Rac initiated or mediated cell motility and cell spreading. The teachings provided herein further establish a Slit2-dependent association between Robo4 and the adaptor protein paxillin, with the experimental data detailed herein providing biochemical and cell biological evidence that this interaction is critical for Robo4-dependent inhibition of cell migration, spreading and Rac activation. In particular, as is taught herein, Robo4 activation initiates paxillin activation of GIT1 and, in turn, GIT1 inhibition of ARF6. Robo4 activation preserves endothelial barrier function, blocks VEGF signaling downstream of the VEGF receptor, and reduces vascular leak and pathologic angiogenesis. Of significance, Robo4 activation not only blocks VEGF signaling, but inhibits signaling from multiple angiogenic, permeability and inflammatory factors, including thrombin and bFGF. As is also disclosed herein, Robo4-paxillin signaling is essential for proper embryonic vascular development in zebrafish.

These disclosed relationships and results associated with Robo4 activation allow for new targets for modulation and for cellular manipulation as discussed herein. "Modulation" as used herein includes changing the activity of a target, and "manipulation" as used herein includes a change in the cellular state.

Vascular Permeability

Diseases and disorders characterized by undesirable vascular permeability include, for example, edema associated with brain tumors, ascites associated with malignancies, Meigs' syndrome, lung inflammation, nephrotic syndrome, pericardial effusion and pleural effusion. Thus, provided is a method of treating or preventing these or any other disease associated with an increase in vascular permeability or edema. For example, inhibiting edema formation should be beneficial to overall patient outcome in situations such as inflammation, allergic diseases, cancer, cerebral stroke, myocardial infarction, pulmonary and cardiac insufficiency, renal failure, and retinopathies, to name a few. Furthermore, as edema is a general consequence of tissue hypoxia, it can also be concluded that inhibition of vascular leakage represents a potential approach to the treatment of tissue hypoxia. For example, interruption of blood flow by pathologic conditions (such as thrombus formation) or medical intervention (such as cardioplegia, organ transplantation, and angioplasty) could be treated both acutely and prophylactically using inhibitors of vascular leakage.

Ischemia/reperfusion injury following stroke and myocardial infarction is also characterized by vascular permeability and edema. A deficit in tissue perfusion leads to persistent post-ischemic vasogenic edema, which develops as a result of increased vascular permeability. Tissue perfusion is a measure of oxygenated blood reaching the given tissue due to the patency of an artery and the flow of blood in an artery. Tissue vascularization may be disrupted due to blockage, or alternatively, it may result from the loss of blood flow resulting from blood vessel leakage or hemorrhage upstream of the affected site. The deficit in tissue perfusion during acute myocardial infarction, cerebral stroke, surgical revascularization procedures, and other conditions in which tissue vascularization has been disrupted, is a crucial factor in outcome of the patient's condition. Edema can cause various types of damage including vessel collapse and impaired electrical function, particularly in the heart. Subsequent reperfusion, however, can also cause similar damage in some patients, leading to a treatment paradox. While it is necessary, to unblock an occluded blood vessel or to repair or replace a damaged blood vessel, the ensuing reperfusion can, in some cases, lead to further damage. Likewise, during bypass surgery, it is necessary to stop the heart from beating and to have the patient hooked to a heart pump. Some patients who undergo bypass surgery, for example, may actually experience a worsening of condition ("post-pump syndrome"), which may be the result of ischemia during cessation of cardiac function during surgery. An arterial blockage may cause a reduction in the flow of blood, but even after the blockage is removed and the artery is opened, if tissue reperfusion fails to occur, further tissue damage may result. For example, disruption of a clot may trigger a chain of events leading to loss of tissue perfusion, rather than a gain of perfusion.

Additional diseases and disorders characterized by undesirable vascular permeability include, for example, infectious and non-infectious diseases that may result in a cytokine storm. A cytokine storm can be precipitated by a number of infectious and non-infectious diseases including, for example, graft versus host disease (GVHD), adult respiratory distress syndrome (ARDS), sepsis, avian influenza, smallpox, and systemic inflammatory response syndrome (SIRS).

Pathologic Angiogenesis

Angiogenesis and angiogenesis related diseases are closely affected by cellular proliferation. As used herein, the term "angiogenesis" means the generation of new blood vessels into a tissue or organ. Under normal physiological conditions, humans or animals undergo angiogenesis only in very specific restricted situations. For example, angiogenesis is normally observed in wound healing, fetal and embryonal development and formation of the corpus luteum, endometrium and placenta. The term "endothelium" is defined herein as a thin layer of flat cells that lines serous cavities, lymph vessels, and blood vessels. These cells are defined herein as "endothelial cells." The term "endothelial inhibiting activity" means the capability of a molecule to inhibit angiogenesis in general. The inhibition of endothelial cell proliferation also results in an inhibition of angiogenesis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

New blood vessels may also form in part by vasculogenesis. Vasculogenesis is distinguished from angiogenesis by the source of the endothelial cells. Vasculogenesis involves the recruitment of endothelial progenitor cells known as angioblasts. These angioblasts can come from the circulation or from the tissue. Vasculogenesis is regulated by similar signaling pathways as angiogenesis. Thus, the term "angiogenesis" is used herein interchangeably with vasculogenesis such that a method of modulating angiogenesis can also modulate vasculogenesis.

Pathologic angiogenesis, which may be characterized as persistant, dysregulated or unregulated angiogenesis, occurs in a multiplicity of disease states, tumor metastasis and abnormal growth by endothelial cells and supports the pathological damage seen in these conditions. The diverse disease states in which pathologic angiogenesis is present have been grouped together as angiogenic-dependent, angiogenic-associated, or angiogenic-related diseases. These diseases are a result of abnormal or undesirable cell proliferation, particularly endothelial cell proliferation.

Diseases and processes mediated by abnormal or undesirable endothelial cell proliferation, including, but not limited to, hemangioma, solid tumors, leukemia, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy (DR), retrolental fibroplasia, non-proliferative diabetic macular edema (DME), arthritis, diabetic neovascularization, age-related macular degeneration (AMD), retinopathy of prematurity (ROP), ischemic retinal vein occlusion (IRVO), wound healing, peptic ulcer, fractures, keloids, vasculogenesis, hematopoiesis, ovulation, menstruation, and placentation.

Compositions

Provided herein are compositions for inhibiting vascular permeability and pathologic angiogenesis in a tissue.

In one embodiment, such a composition comprises a ligand of a Unc5 or Deleted in Colorectal Cancer (DCC) receptor. In one such embodiment, a ligand of Unc5 or DCC can be any composition or molecule that can act through an Unc5 or DCC receptor to inhibit Rac activation by VEGF. As it is used herein the term "act through" a receptor refers to the binding of a composition to a receptor that promotes an activity by the receptor. For example, the composition may comprise a ligand of Unc5 or DCC that acts through an Unc5 or DCC receptor to activate Git1 inhibition of ARF6. In another example, the composition may comprise a ligand of Unc5 or DCC that acts through an Unc5 or DCC receptor to activate paxillin activation of Git1. In yet another example, the composition described herein may comprise a composition or molecule that mimics an Unc5 or DCC receptor to activate paxillin activation of Git1.

In one embodiment, the composition described herein includes a ligand of Unc5, wherein the ligand is a netrin, such as human netrin1, netrin2, netrin4, netrin G1, or netrin G2 and rodent (e.g., mouse or rat) netrin1, netrin3, netrin4, netrin G1, or netrin G2, or a fragment or variant thereof that binds and activates Unc5b inhibition of ARF6. For example, the netrin ligan can comprise an amino acid sequence selected from SEQ ID NO:17, SEQ ID NO: 19, SEQ ID NO: 21, SEQ ID NO: 23, SEQ ID NO: 25 or a variant or fragment of such amino acid sequences that binds Unc5b. A fragment of such amino acid sequences can be at least about 5, 10, 15, 20, 25, 30, 40, 50, 60, 70, 80, 90, or 100 amino acids long. In another embodiment, the netrin ligand of Unc5b can comprise an amino acid sequence having at least about 70%, at least about 75%, at least about 80%, at least about 85%, at least about 90%, at least about 95%, or at least about 100% sequence identity to an amino acid sequence selected from SEQ ID NO:17, SEQ ID NO: 19, SEQ ID NO: 21, SEQ ID NO: 23, SEQ ID NO: 25, or a fragment thereof that binds Unc5b.

In another embodiment, a composition as described herein may include a ligand of Eph. In one such embodiment, the composition comprises a ligand of Eph that can act through an Eph receptor to inhibit Rac activation by VEGF. In another such embodiment, the composition comprises a ligand of Eph that can act through an Eph receptor to activate Git1 inhibition of ARF6. In yet another embodiment, a composition according to the present description may comprise any composition or molecule that can act through an Eph receptor to activate Eph activation of Git1. In still a further embodiment, a composition as described herein may include any composition or molecule that mimics an Eph receptor to activate Paxillin activation of Git1.

In another embodiment, the composition provided herein comprises a ligand of a Robo4 receptor. In one such embodiment, the ligand of Robo4 can be any composition or molecule that can act through Robo4 to negatively regulate cell motility. In another such embodiment, the ligand of Robo4 can be any composition or molecule that can act through Robo4 to inhibit vascular permeability. In yet another such embodiment, the ligand of Robo4 can be any composition or molecule that can act through Robo4 to inhibit Rac activation by VEGF. In still a further embodiment, a composition as described herein includes a ligand of a Robo4 receptor, wherein the ligand can act through Robo4 to initiate paxillin activation of GIT1. In another embodiment, a composition as described herein includes a ligand of a Robo4 receptor, wherein the ligand can act through Robo4 to activate Git1 inhibition of ARF6. In a further embodiment, a composition as described herein includes a ligand of a Robo4 receptor, wherein the ligand can act through Robo4 in a manner that results in one or more of the following preservation of endothelial barrier function, blocking of VEGF signaling downstream of the VEGF receptor, inhibition of vascular leak, inhibition of pathologic angiogenesis, signal inhibition of multiple angiogenic, permeability and inflammatory factors.

Where the composition of the present invention includes a ligand of Robo4, the ligand be any composition or molecule that binds the extracellular domain of Robo4. Alternatively, a ligand of Robo4 can be any composition or molecule that acts through the Robo4 receptor to inhibit Rac activation by VEGF. Even further, a ligand of Robo4 can be any composition or molecule that acts through the Robo4 receptor to activate Git1 inhibition of ARF6. Still further, a ligand of Robo4 can be any composition or molecule that acts through the Robo4 receptor to activate Paxillin activation of Git1. In another aspect, a ligand of Robo4 can be any composition or molecule that mimics the Robo4 receptor to activate Paxillin activation of Git1. In one embodiment, a ligand of Robo4 included in a composition according to the present description comprises an isolated polypeptide of about 5, 10, 15, 20, 25, 30, 40, 50, 60, 70, 80, 90, 100, 200, 300, 400 amino acids in length.

Where a composition as described herein includes a ligand of Robo4, such ligand can be a Slit, such as Slit2, or a fragment or variant thereof that binds and activates Robo4. In specific embodiments, the Slit ligand, or fragment or variant thereof, binds to and activates Robo4 in a manner that results in one or more of the following: inhibition of ARF6; preservation of endothelial barrier function; blocking of VEGF signaling downstream of the VEGF receptor; inhibition of vascular leak; inhibition of pathologic angiogenesis; and signal inhibition of multiple angiogenic, permeability and inflammatory factors. For example, the ligand of Robo4 can comprise an amino acid sequence selected from SEQ ID NO: 3, SEQ ID NO: 5, SEQ ID NO: 7, and any of SEQ ID NO: 36 through SEQ ID NO: 47 or a fragment thereof that binds Robo4. For example, a fragment of such amino acid sequences can be at least about 5, 10, 15, 20, 25, 30, 40, 50, 60, 70, 80, 90, or 100 amino acids long. The ligand of Robo4 can comprise an amino acid sequence having at least about 70%, at least about 75%, at least about 80%, at least about 85%, at least about 90%, at least about 95%, or at least about 100% sequence identity to and amino acid sequence selected from an amino acid sequence selected from SEQ ID NO: 3, SEQ ID NO: 5, SEQ ID NO: 7, and any of SEQ ID NO: 36 through SEQ ID NO: 47, or a fragment thereof that binds Robo4. The fragment of Slit can comprise the N-terminal region of a Slit. For example, the ligand of Robo4 can comprise amino acids 1-1132 of Slit1 (SEQ ID NO:36), amino acids 1-1121 of Slit2 (SEQ ID NO:37), amino acids 1-1118 of Slit3 (SEQ ID NO:38), or any of the n-terminal fragments illustrated in FIG. 23 and detailed SEQ ID NO: 39 through SEQ ID NO: 47. In particular embodiments, the ligand of Robo4 can comprise a polypeptide consisting essentially of an amino acid sequence selected from any one of SEQ ID NO: 36 through SEQ ID NO: 47. In some embodiments, as reflected in the amino acid sequences of SEQ ID NO: 39 through SEQ ID NO: 47, a Slit fragment included in a composition of the present invention does not comprise the N-terminal most amino acids. For example, the amino acid sequence may lack about 5, 10, 15, 20, 25, 30, 40, 50, 60, 70, 80, 90, or 100 N-terminal amino acids of a natural Slit. In other embodiments, the Slit fragment may not comprise the C-terminal most about 5, 10, 15, 20, 25, 30, 40, 50, 60, 70, 80, 90, or 100 amino acids of a natural Slit.

For example, the ligand of Robo4 can comprise a polypeptide consisting essentially of amino acids 281-511 (SEQ ID NO:15) of Slit1 or amino acids 271-504 of Slit2 (SEQ ID NO:16). Thus, the ligand of Robo4 can comprise SEQ ID NO:15 or SEQ ID NO: 16 or a fragment thereof that binds Robo4. The ligand of Robo4 can comprise an amino acid sequence having at least about 70%, at least about 75%, at least about 80%, at least about 85%, at least about 90%, at least about 95%, or at least about 100% sequence identity to SEQ ID NO:15 or SEQ ID NO:16 or a fragment thereof that binds Robo4.

In yet another embodiment, a composition according to the present invention may include a fragment of Robo4 that can activate Paxillin activation of Git1. Thus, provided herein is an isolated polypeptide comprising the paxillin binding sequence of Robo4, wherein the polypeptide does not comprise full-length Robo4. In one such embodiment, the paxillin binding sequence may comprise the amino acid sequence SEQ ID NO:27 or a fragment or variant thereof of that binds paxillin. For example the fragment can be at least about 5, 10, 15, 20, 25, 30, 40, 50, 60, 70, 80, 90, or 100 amino acids long. A fragment or variant of the amino acid sequence of SEQ ID NO:27 can comprise an amino acid sequence having at least about 70%, at least about 75%, at least about 80%, at least about 85%, at least about 90%, at least about 95%, or at least about 100% sequence identity to SEQ ID NO:27 or a fragment thereof that binds paxillin.

In yet a further embodiment, a composition as described herein comprises and isolated polypeptide comprising the paxillin binding sequence (PBS) of Robo4, wherein the polypeptide is defined by the formula:

$$R^1\text{-PBS-}R^2$$

wherein $R^1$ and $R^2$ are, independently, H, acyl, $NH_2$, an amino acid or a peptide, wherein the polypeptide does not comprise full-length Robo4. The PBS can consist of an amino acid sequence having at least 80% sequence homology to SEQ ID NO:27 or a fragment thereof of at least 10 residues in length.

Also provided herein is an isolated nucleic acid encoding any of the herein disclosed polypeptides. Thus, provided is an isolated nucleic acid encoding a polypeptide comprising the paxillin binding sequence of Robo4, wherein the polypeptide does not comprise full-length Robo4. Also provided is an isolated nucleic acid comprising SEQ ID NO: 2 or a fragment thereof of at least 30 residues in length, wherein the nucleic acid does not encode full-length Robo4.

Pharmaceutical Compositions

The compositions disclosed herein, e.g, the ligands, proteins and peptides disclosed herein, can be formulated in a pharmaceutical composition. For example, such compositions can be combined with a pharmaceutically acceptable carrier to provide a formulation that is suitable for therapeutic administration. As used herein, "pharmaceutically acceptable" refers to a material that is not biologically or otherwise undesirable, i.e., the material may be administered to a subject, along with the desired composition (e.g., a desired ligand, protein, peptide, nucleic acid, small molecule therapeutic, etc.), without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., Bioconjugate Chem., 2:447-451, (1991); Bagshawe, K. D., Br. J. Cancer, 60:275-281, (1989); Bagshawe, et al., Br. J. Cancer, 58:700-703, (1988); Senter, et al., Bioconjugate Chem., 4:3-9, (1993); Battelli, et al., Cancer Immunol. Immunother., 35:421-425, (1992); Pietersz and McKenzie, Immunolog. Reviews, 129: 57-80, (1992); and Roffler, et al., Biochem. Pharmacol, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., Cancer Research, 49:6214-6220, (1989); and Litzinger and Huang, Biochimica et Biophysica Acta, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, DNA and Cell Biology 10:6, 399-409 (1991)).

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

Methods

Methods of screening for, or evaluating, an agent that inhibits vascular permeability or pathologic angiogenesis are provided herein. In one embodiment, the method comprises determining the ability of said agent to affect Robo4-mediated activation of Git1. For example, Robo4-mediated activation of Git1 can be determined by the steps comprising: contacting a first cell expressing Robo4 with a candidate agent, contacting a second cell essentially identical to the first cell but substantially lacking Robo4 with the candidate agent, and assaying for Git1 activation in the first and second cells, wherein detectably higher Git1 activation in the first cell as compared to the second cell indicates Robo4-mediated Git1 activation by said agent.

As disclosed herein, Robo4-mediated Git1 activation results in ARF6 inactivation. ARF6 is involved in VEGF-mediated activation of Rac, which activates Pak, which activates MEK, which activates ERK, which promotes vascular permeability. Thus, as disclosed herein Git1 activation can be assayed by detecting any of the components of the signaling pathway that is either activated or inactivated. Thus, Robo4-mediated Git1 activation can be assayed by detecting ARF6 inactivation, Rac inactivation, Pak inactivation, MEK inactivation, or ERK inactivation. It is understood that any other known or newly discovered method of monitoring this signaling pathway can be used in the disclosed methods.

Also provided is a method of screening for, or evaluating, an agent that inhibits vascular permeability, comprising determining the ability of said agent to inhibit ARF6, Rac, Pak, MEK, or ERK. For example, Robo4-mediated inhibition of ARF6, Rac, Pak, MEK, or Erk is determined by the steps comprising: contacting a first cell expressing Robo4 with a candidate agent, contacting a second cell essentially identical to the first cell but substantially lacking Robo4 with the candidate agent, assaying for inhibition of ARF6, Rac, Pak, MEK, ERK, or a combination thereof, in the first and second cells, wherein detectably lower ARF6, Rac, Pak, MEK, or ERK activation in the first cell as compared to the second cell indicates Robo4-mediated ARF6, Rac, Pak, MEK, or ERK inhibition by said agent.

Activation of signaling proteins such as Rac, Pak, MEK, ERK can be assayed by detecting the phosphorylation of said proteins. Cell-based and cell-free assays for detecting phosphorylation of proteins are well known in the art and include the use of antibodies, including, for example, anti-Phosphoserine (Chemicon® AB1603) (Chemicon, Temecula, Calif.), anti-Phosphothreonine (Chemicon® AB 1607), and anti-Phosphotyrosine (Chemicon®AB1599). Site-specific antibodies can also be generated specific for the phosphorylated form of DDX-3. The methods of generating and using said antibodies are well known in the art.

The herein disclosed assay methods can be performed in the substantial absence of VEGF, TNF, thrombin, or histamine. Alternatively, the disclosed assay methods can be performed in the presence of a biologically active amount of VEGF, TNF, thrombin, or histamine.

"Activities" of a protein include, for example, transcription, translation, intracellular translocation, secretion, phosphorylation by kinases, cleavage by proteases, homophilic and heterophilic binding to other proteins, ubiquitination.

In one embodiment, the method of screening described herein is a screening assay, such as a high-throughput screening assay. Thus, the contacting step can be in a cell-based or cell-free assay. For example, vascular endothelial cells can be contacted with a candidate agent either in vivo, ex vivo, or in vitro. The cells can be on in monolayer culture but preferably constitute an epithelium. The cells can be assayed in vitro or in situ or the protein extract of said cells can be assayed in vitro for the detection of activated (e.g., phosphorylated) Rac, Pak, MEK, ERK. Endothelial cells can also be engineered to express a reporter construct, wherein the cells are contacted with a candidate agents and evaluated for reporter expression. Other such cell-based and cell-free assays are contemplated for use herein.

For example, the effect of small molecule, amino acid or nucleic acid mimetics on vascular permeability or pathologic angiogenesis can be evaluated in endothelial cells expressing Robo4 and compared to endothelial cells lacking Robo4.

In general, candidate agents can be identified from large libraries of natural products or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the exemplary methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, polypeptide- and nucleic acid-based compounds. Synthetic compound libraries are commercially available, e.g., from Brandon Associates (Merrimack, N. H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods. In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their effect should be employed whenever possible.

When a crude extract is found to have a desired activity, further fractionation of the positive lead extract is necessary to isolate chemical constituents responsible for the observed effect. Thus, the goal of the extraction, fractionation, and purification process is the careful characterization and identification of a chemical entity within the crude extract having an activity that stimulates or inhibits vascular permeability. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art. Compounds identified as being of therapeutic value may be subsequently analyzed using animal models for diseases or conditions in which it is desirable to regulate vascular permeability.

Methods for inhibiting vascular permeability in a subject are also provided herein. As is detailed herein, activation of Robo4 inhibits vascular permeability, inhibits Rac activation by VEGF, preserves endothelial cell barrier function, blocks of VEGF signaling downstream of the VEGF receptor, inhibits vascular leak, and inhibits multiple angiogenic, permeability and inflammatory factors. As determined herein, activation of Robo4 signaling achieves such effects through initiation of paxillin activation of GIT1, which, in turn, leads to GIT1 inhibition of ARF6. Therefore, in one embodiment, the method for inhibiting vascular permeability provided herein comprises administering a therapeutically effective amount of a ligand of Robo4, wherein such ligand results in GIT1 inhibition of ARF6. In another embodiment, the ligand administered is a Slit protein as described herein. In specific embodiments, the vascular permeability experienced by the subject and treated by administration of a therapeutically effective amount of a ligand of Robo4 is associated with a disease state selected from infectious and non-infectious diseases that may result in a cytokine storm, including, for example, graft versus host disease (GVHD), adult respiratory distress syndrome (ARDS), sepsis, avian influenza, smallpox, and systemic inflammatory response syndrome (SIRS), ischemia/reperfusion injury following stroke or myocardial infarction, edema associated with brain tumors, ascites associated with malignancies, Meigs' syndrome, lung inflammation, nephrotic syndrome, pericardial effusion and pleural effusion, inflammation, allergic diseases, cancer, cerebral stroke, myocardial infarction, pulmonary and cardiac insufficiency, renal failure, and retinopathies.

Methods for inhibiting pathologic angiogenesis in a subject are provided herein. As is detailed herein, activation of Robo4 inhibits the effect of multiple inflammatory, permeability and angiogenic factors. Again, as determined herein, activation of Robo4 signaling initiates paxillin activation of GIT1, which, in turn, leads to GIT1 inhibition of ARF6. Therefore, in one embodiment, the method for inhibiting pathologic angiogenesis provided herein comprises administering a therapeutically effective amount of a ligand of Robo4, wherein such ligand results in GIT1 inhibition of ARF6. In another embodiment, the ligand administered is a Slit protein as described herein. In specific embodiments, the pathologic angiogenesis experienced by the subject and treated by administration of a therapeutically effective amount of a ligand of Robo4 is associated with a disease state selected from hemangioma, solid tumors, leukemia, metastasis, telangiectasia psoriasis scleroderma, pyogenic granuloma, myocardial angiogenesis, plaque neovascularization, coronary collaterals, ischemic limb angiogenesis, corneal diseases, rubeosis, neovascular glaucoma, diabetic retinopathy (DR), retrolental fibroplasia, non-proliferative diabetic macular edema (DME), arthritis, diabetic neovascularization, age-related macular degeneration (AMD), retinopathy of prematurity (ROP), ischemic retinal vein occlusion (IRVO), wound healing, peptic ulcer, fractures, keloids, vasculogenesis, hematopoiesis, ovulation, menstruation, and placentation.

In another embodiment, a method of treating or preventing avian flu is provided, wherein the method comprises identifying a subject having or at risk of having said avian flu, and administering to the subject a therapeutically effective amount of a ligand of roundabout-4 (Robo4) receptor.

In another embodiment, a method of treating or preventing adult respiratory distress syndrome (ARDS) is provided, wherein the method comprises identifying a subject having or at risk of having said ARDS, and administering to the subject a therapeutically effective amount of a ligand of roundabout-4 (Robo4) receptor.

In another embodiment, a method of treating or preventing systemic inflammatory response syndrome (SIRS) is provided, wherein the method comprises identifying a subject having or at risk of having said SIRS, and administering to the subject a therapeutically effective amount of a ligand of roundabout-4 (Robo4) receptor.

In another embodiment, a method of treating or preventing graft versus host disease (GVHD) is provided, wherein the method comprises identifying a subject having or at risk of having said RDS, and administering to the subject a therapeutically effective amount of a ligand of roundabout-4 (Robo4) receptor.

In another embodiment, a method of treating or preventing tumor formation or growth is provided, wherein the method comprises identifying a subject having or at risk of having said tumor formation or growth, and administering to the subject a therapeutically effective amount of a ligand of roundabout-4 (Robo4) receptor.

In another embodiment, a method of treating or preventing respiratory distress syndrome (RDS) is provided, wherein the method comprises identifying a subject having or at risk of having said RDS, and administering to the subject a therapeutically effective amount of a ligand of roundabout-4 (Robo4) receptor.

In another embodiment, a method of treating or preventin ischemic retinal vein occlusion (IRVO) in a subject is provided, wherein the method comprises identifying a subject having or at risk of having said IRVO, and administering to the subject a therapeutically effective amount of a ligand of roundabout-4 (Robo4) receptor.

In another embodiment, a method of treating or preventing non-proliferative diabetic macular edema (DME) in a subject is provided, wherein the method comprises identifying a subject having or at risk of having said DME, and administering to the subject a therapeutically effective amount of a ligand of roundabout-4 (Robo4) receptor.

In another embodiment, a method of treating or preventing retinopathy of pre-maturity (ROP) is provided, wherein the method comprises identifying a subject having or at risk of having said ROP, and administering to the subject a therapeutically effective amount of a ligand of roundabout-4 (Robo4) receptor.

In another embodiment, a method of treating or preventing diabetic retinopathy (DR) in a subject is provided, wherein the method comprises identifying a subject having or at risk of having said DR, and administering to the subject a therapeutically effective amount of a ligand of roundabout-4 (Robo4) receptor.

In another embodiment, a method of treating or preventing wet macular degeneration (AMD) in a subject is provided, wherein the method comprises identifying a subject having or at risk of having said AMD, and administering to the subject a therapeutically effective amount of a ligand of roundabout-4 (Robo4) receptor.

In another embodiment, a method of treating or preventing ischemia in a subject is provided, wherein the method comprises identifying a subject having or at risk of having said ischemia, and administering to the subject a therapeutically effective amount of a ligand of roundabout-4 (Robo4) receptor.

In another embodiment, a method of treating or preventing hemorrhagic stroke in a subject is provided, wherein the methods comprises identifying a subject having or at risk of having said hemorrhagic stroke, and administering to the subject a therapeutically effective amount of a ligand of roundabout-4 (Robo4) receptor.

In another embodiment, a method of treating or preventing reperfusion injury, such as that observed in myocardial infarction and stroke, in a subject is provided, wherein the method comprises identifying a subject having or at risk of having said reperfusion injury, and administering to the subject a therapeutically effective amount of a ligand of roundabout-4 (Robo4) receptor.

In another embodiment, a method of treating or preventing a dermal vascular blemish or malformation in a subject is provided, wherein the method comprises identifying a subject having or at risk of having said blemish, and administering to the skin of the subject a therapeutically effective amount of a ligand of roundabout-4 (Robo4) receptor.

In another embodiment, a method of treating or preventing avian flu is provided, wherein the method comprises identifying a subject having or at risk of having said avian flu, and administering to the subject a therapeutically effective amount of a repulsive guidance cue, such as ligand of roundabout-4 (Robo4) receptor.

In another embodiment, a method of treating or preventing adult respiratory distress syndrome (ARDS) is provided, wherein the method comprises identifying a subject having or at risk of having said ARDS, and administering to the subject a therapeutically effective amount of a repulsive guidance cue, such as ligand of roundabout-4 (Robo4) receptor.

In another embodiment, a method of treating or preventing systemic inflammatory response syndrome (SIRS) is provided, wherein the method comprises identifying a subject having or at risk of having said SIRS, and administering to the subject a therapeutically effective amount of a repulsive guidance cue, such as ligand of roundabout-4 (Robo4) receptor.

In another embodiment, a method of treating or preventing graft versus host disease (GVHD) is provided, wherein the method comprises identifying a subject having or at risk of having said RDS, and administering to the subject a therapeutically effective amount of a repulsive guidance cue, such as ligand of roundabout-4 (Robo4) receptor.

In another embodiment, a method of treating or preventing tumor formation or growth is provided, wherein the method comprises identifying a subject having or at risk of having said tumor formation or growth, and administering to the subject a therapeutically effective amount of a repulsive guidance cue, such as ligand of roundabout-4 (Robo4) receptor.

In another embodiment, a method of treating or preventing respiratory distress syndrome (RDS) is provided, wherein the method comprises identifying a subject having or at risk of having said RDS, and administering to the subject a therapeutically effective amount of a repulsive guidance cue, such as ligand of roundabout-4 (Robo4) receptor.

In another embodiment, a method of treating or preventing ischemic retinal vein occlusion (IRVO) in a subject is provided, wherein the method comprises identifying a subject having or at risk of having said IRVO, and administering to the subject a therapeutically effective amount of a repulsive guidance cue, such as ligand of roundabout-4 (Robo4) receptor.

In another embodiment, a method of treating or preventing non-proliferative diabetic macular edema (DME) in a subject is provided, wherein the method comprises identifying a subject having or at risk of having said DME, and administering to the subject a therapeutically effective amount of a repulsive guidance cue, such as ligand of roundabout-4 (Robo4) receptor.

In another embodiment, a method of treating or preventing retinopathy of pre-maturity (ROP) is provided, wherein the method comprises identifying a subject having or at risk of having said ROP, and administering to the subject a therapeutically effective amount of a repulsive guidance cue, such as ligand of roundabout-4 (Robo4) receptor.

In another embodiment, a method of treating or preventing diabetic retinopathy (DR) in a subject is provided, wherein the method comprises identifying a subject having or at risk of having said DR, and administering to the subject a therapeutically effective amount of a repulsive guidance cue, such as ligand of roundabout-4 (Robo4) receptor.

In another embodiment, a method of treating or preventing wet macular degeneration (AMD) in a subject is provided, wherein the method comprises identifying a subject having or at risk of having said AMD, and administering to the subject a therapeutically effective amount of a repulsive guidance cue, such as ligand of roundabout-4 (Robo4) receptor.

In another embodiment, a method of treating or preventing ischemia in a subject is provided, wherein the method comprises identifying a subject having or at risk of having said ischemia, and administering to the subject a therapeutically effective amount of a repulsive guidance cue, such as ligand of roundabout-4 (Robo4) receptor.

In another embodiment, a method of treating or preventing hemorrhagic stroke in a subject is provided, wherein the methods comprises identifying a subject having or at risk of having said hemorrhagic stroke, and administering to the subject a therapeutically effective amount of a repulsive guidance cue, such as ligand of roundabout-4 (Robo4) receptor.

In another embodiment, a method of treating or preventing reperfusion injury, such as that observed in myocardial infarction and stroke, in a subject is provided, wherein the method comprises identifying a subject having or at risk of having said reperfusion injury, and administering to the subject a therapeutically effective amount of a repulsive guidance cue, such as ligand of roundabout-4 (Robo4) receptor.

In another embodiment, a method of treating or preventing a dermal vascular blemish or malformation in a subject is provided, wherein the method comprises identifying a subject having or at risk of having said blemish, and administering to the skin of the subject a therapeutically effective amount of a repulsive guidance cue, such as ligand of roundabout-4 (Robo4) receptor.

Ligands suitable for use in conjunction with the methods described herein include, for example, those ligands described herein. For example, in particular embodiments, the compositions described herein in relation to Robo receptors, including the Robo4 receptor, and in relation to the Unc5 or Deleted in Colorectal Cancer (DCC) receptor may be used as ligands in the methods of the present invention. Even more specifically, for example, the slit compounds described herein may be used as ligands for activating Robo4 and achieving the therapeutic benefits of the methods described herein.

In some aspects, subjects are identified by medical diagnosis. For example, subjects with diabetic retinopathy and macular degeneration can be identified by visualization of excess blood vessels in the eyes. Acute lung injury can be diagnosed by lung edema in the absence of congetive heart failure. Ischemic stroke can be diagnosed by neurologic presentation and imaging (MRI and CT). Other known or newly discovered medical determinations can be used to identify subjects for use in the disclosed methods.

In addition, subjects can be identified by genetic predisposition. For example, genes that predispose patients to age related macular degeneration have been identified (Klein R J, et al, 2005; Yang Z, et al. 2006; Dewan A, et al. 2006). Likewise, genetic mutations that predispose patients to vascular malformations in the brain have been identified (Plummer N R, et al., 2005). Other known or newly discovered genetic determinations can be used to identify subjects for use in the disclosed methods.

The nucleic acid and polypeptide molecules disclosed herein, as well as any compositions necessary to perform the disclosed methods, can be made using any method known to those of skill in the art for that particular reagent or compound unless otherwise specifically noted.

For example, the nucleic acids, such as, the oligonucleotides to be used as primers can be made using standard chemical synthesis methods or can be produced using enzymatic methods or any other known method. Such methods can range from standard enzymatic digestion followed by nucleotide fragment isolation (see for example, Sambrook et al., Molecular Cloning: A Laboratory Manual, 2nd Edition (Cold Spring Harbor Laboratory Press, Cold Spring Harbor, N.Y., 1989) Chapters 5, 6) to purely synthetic methods, for example, by the cyanoethyl phosphoramidite method using a Milligen or Beckman System 1Plus DNA synthesizer (for example, Model 8700 automated synthesizer of Milligen-Biosearch, Burlington, Mass. or ABI Model 380B). Synthetic methods useful for making oligonucleotides are also described by Ikuta et al., Ann. Rev. Biochem. 53:323-356 (1984), (phosphotriester and phosphite-triester methods), and Narang et al., Methods Enzymol., 65:610-620 (1980), (phosphotriester method). Protein nucleic acid molecules can be made using known methods such as those described by Nielsen et al., Bioconjug. Chem. 5:3-7 (1994).

One method of producing the disclosed proteins described herein is to link two or more peptides or polypeptides together by protein chemistry techniques. For example, peptides or polypeptides can be chemically synthesized using currently available laboratory equipment using either Fmoc (9-fluorenylmethyloxycarbonyl) or Boc (tert-butyloxycarbonoyl) chemistry. (Applied Biosystems, Inc., Foster City, Calif.). One skilled in the art can readily appreciate that a peptide or polypeptide corresponding to the disclosed proteins, for example, can be synthesized by standard chemical reactions. For example, a peptide or polypeptide can be synthesized and not cleaved from its synthesis resin whereas the other fragment of a peptide or protein can be synthesized and subsequently cleaved from the resin, thereby exposing a terminal group which is functionally blocked on the other fragment. By peptide condensation reactions, these two fragments can be covalently joined via a peptide bond at their carboxyl and amino termini, respectively, to form an antibody, or fragment thereof. (Grant G A (1992) Synthetic Peptides: A User Guide. W.H. Freeman and Co., N.Y. (1992); Bodansky M and Trost B., Ed. (1993) Principles of Peptide Synthesis. Springer-Verlag Inc., NY (which is herein incorporated by reference at least for material related to peptide synthesis). Alternatively, the peptide or polypeptide is independently synthesized in vivo as described herein. Once isolated, these independent peptides or polypeptides may be linked to form a peptide or fragment thereof via similar peptide condensation reactions.

For example, enzymatic ligation of cloned or synthetic peptide segments allow relatively short peptide fragments to be joined to produce larger peptide fragments, polypeptides or whole protein domains (Abrahmsen L et al., Biochemistry, 30:4151 (1991)). Alternatively, native chemical ligation of synthetic peptides can be utilized to synthetically construct large peptides or polypeptides from shorter peptide fragments. This method consists of a two step chemical reaction (Dawson et al. Synthesis of Proteins by Native Chemical Ligation. Science, 266:776-779 (1994)). The first step is the chemoselective reaction of an unprotected synthetic peptide—thioester with another unprotected peptide segment containing an amino-terminal Cys residue to give a thioester-linked intermediate as the initial covalent product. Without a change in the reaction conditions, this intermediate undergoes spontaneous, rapid intramolecular reaction to form a native peptide bond at the ligation site (Baggiolini M et al. (1992) FEBS Lett. 307:97-101; Clark-Lewis I et al., J. Biol. Chem., 269:16075 (1994); Clark-Lewis I et al., Biochemistry, 30:3128 (1991); Rajarathnam K et al., Biochemistry 33:6623-30 (1994)).

Alternatively, unprotected peptide segments are chemically linked where the bond formed between the peptide segments as a result of the chemical ligation is an unnatural (non-peptide) bond (Schnolzer, M et al. Science, 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Disclosed are processes for making nucleic acids disclosed herein as well as for making nucleic acids useful for expressing the protein and peptide moledules described herein. There are a variety of methods that can be used for making these compositions, such as synthetic chemical methods and standard molecular biology methods. It is understood that the methods of making these and the other disclosed compositions are specifically disclosed.

Disclosed are nucleic acid molecules produced by the process comprising linking in an operative way a nucleic acid comprising the sequence set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, or SEQ ID NO: 28 and a sequence controlling the expression of the nucleic acid.

Also disclosed are nucleic acid molecules produced by the process comprising linking in an operative way a nucleic acid molecule comprising a sequence having 80% identity to a sequence set forth in SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, or SEQ ID NO: 28, and a sequence controlling the expression of the nucleic acid.

Disclosed are nucleic acid molecules produced by the process comprising linking in an operative way a nucleic acid molecule comprising a sequence that hybridizes under stringent hybridization conditions to a sequence set forth SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, or SEQ ID NO: 28 and a sequence controlling the expression of the nucleic acid.

Disclosed are nucleic acid molecules produced by the process comprising linking in an operative way a nucleic acid molecule comprising a sequence encoding a peptide set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or any of SEQ ID NO: 36 through SEQ ID NO: 47 and a sequence controlling an expression of the nucleic acid molecule.

Disclosed are nucleic acid molecules produced by the process comprising linking in an operative way a nucleic acid molecule comprising a sequence encoding a peptide having 80% identity to a peptide set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or any of SEQ ID NO: 36 through SEQ ID NO: 47 and a sequence controlling an expression of the nucleic acid molecule.

Disclosed are nucleic acids produced by the process comprising linking in an operative way a nucleic acid molecule comprising a sequence encoding a peptide having 80% identity to a peptide set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, or any of SEQ ID NO: 36 through SEQ ID NO: 47, wherein any change is a conservative changes and a sequence controlling an expression of the nucleic acid molecule.

Therapeutic Administration

The herein disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, transdermally orally, parenterally (e.g., intravenously), intratracheally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained. See, e.g., U.S. Pat. No. 3,610,795, which is incorporated by reference herein.

The compositions disclosed herein may be administered prophylactically to patients or subjects who are at risk for vascular permeability or pathologic angiogenesis. Thus, the method can further comprise identifying a subject at risk for vascular permeability or pathologic angiogenesis prior to administration of the herein disclosed compostions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. For example, effective dosages and schedules for administering the compositions may be determined empirically, and making such determinations is within the skill in the art. The dosage ranges for the administration of the compositions are those large enough to produce the desired effect in which the symptoms disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of a peptide or protein therapeutic used alone might range from about 1 µg/kg to up to 100 mg/kg of body weight or more per day, depending on the factors mentioned above. For example, the concentration of the herein disclosed ligands, proteins, peptides and guidance cues can be in the range of about 1 pM to 100 µM, including about 1 pM, 2 pM, 3 pM, 4 pM, 5 pM, 6 pM, 7 pM, 8 pM, 9 pM, about 10 pM, about 20 nM, about 30 nM, about 40 nM, about 50 nM, about 60 nM, about 70 nM, about 80 nM, about 90 nM, or about 100 nM, about 1 µM, 2 µM, 3 µM, 4 µM, 5 µM, 6 µM, 7 µM, 8 µM, 9 µM, about 10 µM, about 20 µM, about 30 µM, about 40 µM, about 50 µM, about 60 µM, about 70 µM, about 80 µM, about 90 µM, or about 100 µM in the body of the subject.

EXAMPLES

The Examples that follow are offered for illustrative purposes only and are not intended to limit the scope of the compositions and methods described herein in any way. In each instance, unless otherwise specified, standard materials and methods were used in carrying out the work described in the Examples provided. All patent and literature references cited in the present specification are hereby incorporated by reference in their entirety.

The practice of the present invention employs, unless otherwise indicated, conventional techniques of chemistry, molecular biology, microbiology, recombinant DNA, genetics, immunology, cell biology, cell culture and transgenic biology, which are within the skill of the art (See, e.g., Maniatis, T., et al. (1982) Molecular Cloning: A Laboratory Manual (Cold Spring Harbor Laboratory, Cold Spring Harbor, N.Y.); Sambrook, J., et al. (1989) Molecular Cloning: A Laboratory Manual, $2^{nd}$ Ed. (Cold Spring Harbor Laboratory, Cold Spring Harbor, N.Y.); Ausubel, F. M., et al. (1992) Current Protocols in Molecular Biology, (J. Wiley and Sons, NY); Glover, D. (1985) DNA Cloning, I and II (Oxford Press); Anand, R. (1992) Techniques for the Analysis of Complex Genomes, (Academic Press); Guthrie, G. and Fink, G. R. (1991) Guide to Yeast Genetics and Molecular Biology (Academic Press); Harlow and Lane (1988) Antibodies: A Laboratory Manual (Cold Spring Harbor Laboratory, Cold Spring Harbor, N.Y.); Jakoby, W. B. and Pastan, I. H. (eds.) (1979) Cell Culture. Methods in Enzymology, Vol. 58 (Academic Press, Inc., Harcourt Brace Jovanovich (NY); Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); Hogan et al. (eds) (1994) Manipulating the Mouse Embryo. A Laboratory Manual, $2^{nd}$ Edition, Cold Spring Harbor Laboratory Press, Cold Spring Harbor, N.Y. A general discussion of techniques and materials for human gene mapping, including mapping of human chromosome 1, is provided, e.g., in White and Lalouel (1988) Ann. Rev. Genet. 22:259 279. The practice of the present invention employs, unless otherwise indicated, conventional techniques of chemistry, molecular biology, microbiology, recombinant DNA, genetics, and immunology. (See, e.g., Maniatis et al., 1982; Sambrook et al., 1989; Ausubel et al., 1992; Glover, 1985; Anand, 1992; Guthrie and Fink, 1991).

Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Example 1

Figure 8A:
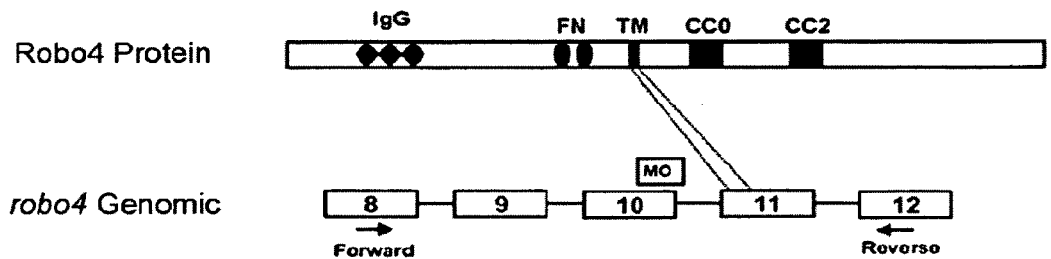
FIG. 8A shows a schematic representation of the robo4 locus in Danio rerio and the encoded Robo4 protein. The exon targeted with the splice-blocking morpholino is indicated, as is the location of the primers used to amplify robo4 cDNA.
Figure 8B:
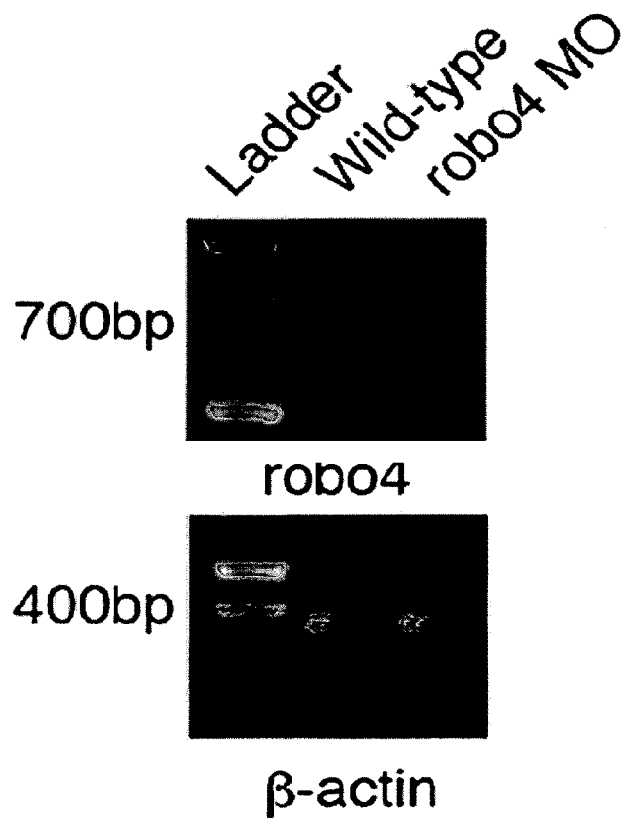
FIG. 8B shows RNA from uninjected embryos and embryos injected with robo4 spliceblocking morpholinos was isolated and used to reverse transcribe cDNA. The cDNA was then used to amplify robo4 and the resulting fragments were separated by agarose gel electrophoresis and visualized by ethidium bromide staining.

Robo4 is Required for Vascular Guidance in vivo: During the past decade, the zebrafish has become an attractive model for analysis of vascular development (Weinstein, 2002), and was chosen to investigate the biological importance of Robo4 in vivo. To suppress Robo4 gene expression, a previously described splice-blocking morpholino that targets the exon10-intron10 boundary of Robo4 pre-mRNA (Bedell et al., 2005) was used. To verify the efficacy of the Robo4 morpholino, RNA was isolated from un-injected and morpholino-injected embryos, and analyzed by RT-PCR with primers flanking the targeted exon (FIG. 8A). Injection of the Robo4 morpholino resulted in complete loss of wild-type RNA when compared to the un-injected control, indicating that morphant zebrafish are functionally null for Robo4 (FIG. 8B).

TG(fli1:egfp)$^{y1}$ zebrafish embryos, which express green fluorescent protein under the control of the endothelialspecific fli1 promoter, and permit detailed visualization of the developing endothelium in vivo were utilized to evaluate the consequence of morpholino-mediated knockdown of Robo4 on vascular development (FIG. 1A; Lawson and Weinstein, 2002). At 48 hpf, Robo4 MO-injected embryos exhibited wild-type formation of the primary axial vessels (dorsal aorta and posterior cardinal vein), as well as the dorsal longitudinal anastomotic vessel and parachordal vessel, indicating that vasculogenesis and angiogenesis, respectively, are not affected by reduction of Robo4 levels (FIG. 1B, right panel). However, a striking degree of abnormality was observed in the architecture of the intersegmental vessels in Robo4 morphants. In wild-type embryos, the intersegmental vessels arise form the dorsal aorta and grow toward the dorsal surface of the embryo, tightly apposed to the somitic boundary. It is this precise trajectory between the somites that defines the characteristic chevron shape of the intersegmental vessels (FIG. 1A, right panel). Rather than adopting this stereotypical pattern, the intersegmental vessels of Robo4 morphant embryos grew the wrong direction (FIG. 1B, right panel: white arrows indicate abnormal vessels). At 48 hpf, 60% of embryos injected with the Robo MO exhibited this defect, compared to 5% in wild-type embryos. Importantly, Robo4 morphants were indistinguishable from control embryos by phase microscopy, indicating that the observed vascular patterning defects were not a result of gross morphological perturbation. Together, these data demonstrate a requirement for Robo4 during zebrafish vascular development and suggest that functional output from the receptor elicits a repulsive guidance cue.

Example 2

The Robo4 Cytoplasmic Tail is required for Vascular Guidance in vivo: It was next determined whether the vascular defects observed in Robo4 morphants could be suppressed by reconstitution of robo4. robo4 MO and wildtype murine Robo4 RNA, which is refractory to the morpholino, were injected into TG(fli1:egfp)y1 embryos and vascular patterning was analyzed at 48 hpf. Robo4 RNA restored the stereotypic patterning of the trunk vessels in approximately 60% of morphant embryos, confirming the specificity of gene knockdown (FIGS. 1B and C, right panels).

The ability of the robo4 to regulate vascular development is likely a consequence of its ability to transmit cytoplasmic signals. To substantiate this notion, Robo4 MO and a mutant form of murine Robo4 lacking the portion of the receptor that interacts with cytoplasmic components (robo4Δtail) were co-injected and vessel architecture evaluated at 48 hpf. Unlike wild-type Robo4 RNA, robo4Δtail was unable to rescue patterning defects in morphant embryos (FIGS. 1B and D, right panels). These data demonstrate that information contained in the cytoplasmic tail of Robo4 is critical for vascular guidance during zebrafish embryogenesis. All together, these in vivo analyses indicate that Robo4 activity is required for precisely defining the trajectory of the intersegmental vessels during vertebrate vascular development (FIG. 1E).

Example 3

Figure 2A:
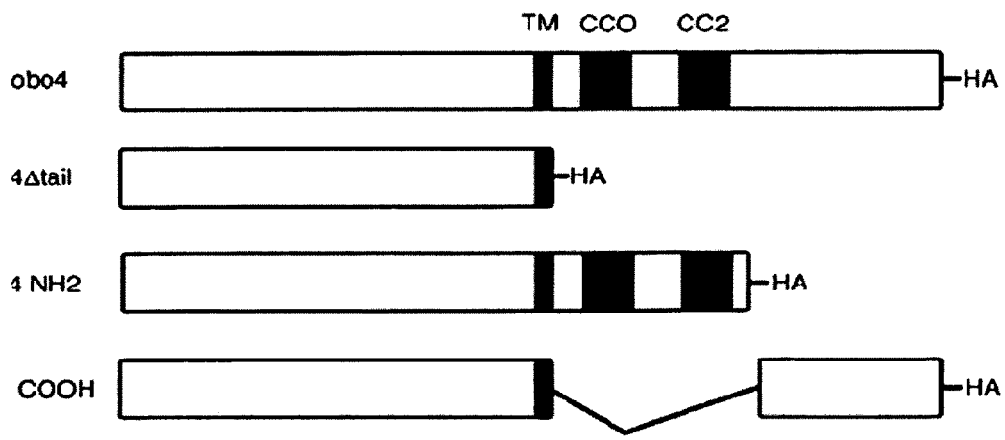
FIG. 2A shows schematic representation of cDNA constructs used in the haptotaxis migration assays. TM represents the transmembrane domain. CC0 and CC2 are conserved cytoplasmic signaling motifs found in Robo family members.
Figure 2B:
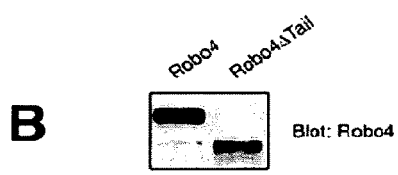
FIG. 2B and FIG. 2C show HEK 293 cells were co-transfected with GFP and the indicated constructs and 36 hours later subjected to haptotaxis migration on membranes coated with 5 µg/ml fibronectin and either Mock preparation or Slit2. Expression of Robo4 constructs was verified by Western blotting (Inset). Results are presented as the mean±SE.
Figure 2B:
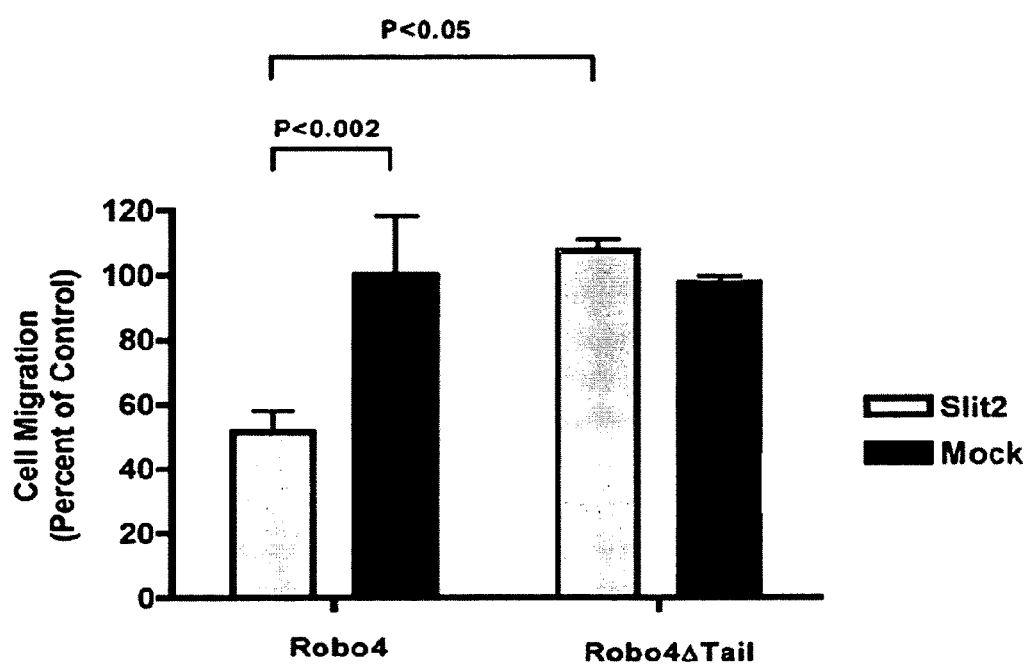

The Robo4 Cytoplasmic Tail is required for Inhibition of Haptotaxis: Slit2-Robo4 signaling inhibits migration of primary endothelial cells towards a gradient of VEGF, and of HEK 293 cells ectopically expressing Robo4 towards serum (Park et al., 2003; Seth et al., 2005). In addition to soluble growth factors, immobilized extracellular matrix proteins such as fibronectin play a critical role in cellular motility (Ridley et al., 2003), and gradients of fibronectin can direct migration in a process called haptotaxis. Indeed it was recently shown that fibronectin is deposited adjacent to migrating endothelial cells in the early zebrafish embryo (Jin et al., 2005). The observation that Robo4 is required for proper endothelial cell migration in vivo (FIG. 1), indicated the ability of Slit2-Robo4 signaling to modulate fibronectin-induced haptotaxis. HEK 293 cells were transfected with Robo4 or Robo4ΔTail (FIG. 2A) and subjected to haptotaxis migration assays on membranes coated with a mixture of fibronectin and Slit2. Slit2 inhibited fibronectin-induced migration of cells expressing Robo4, but not Robo4ΔTail, demonstrating that the Robo4 cytoplasmic tail is critical for repulsive activity of the receptor (FIG. 2B).

Figure 2C:
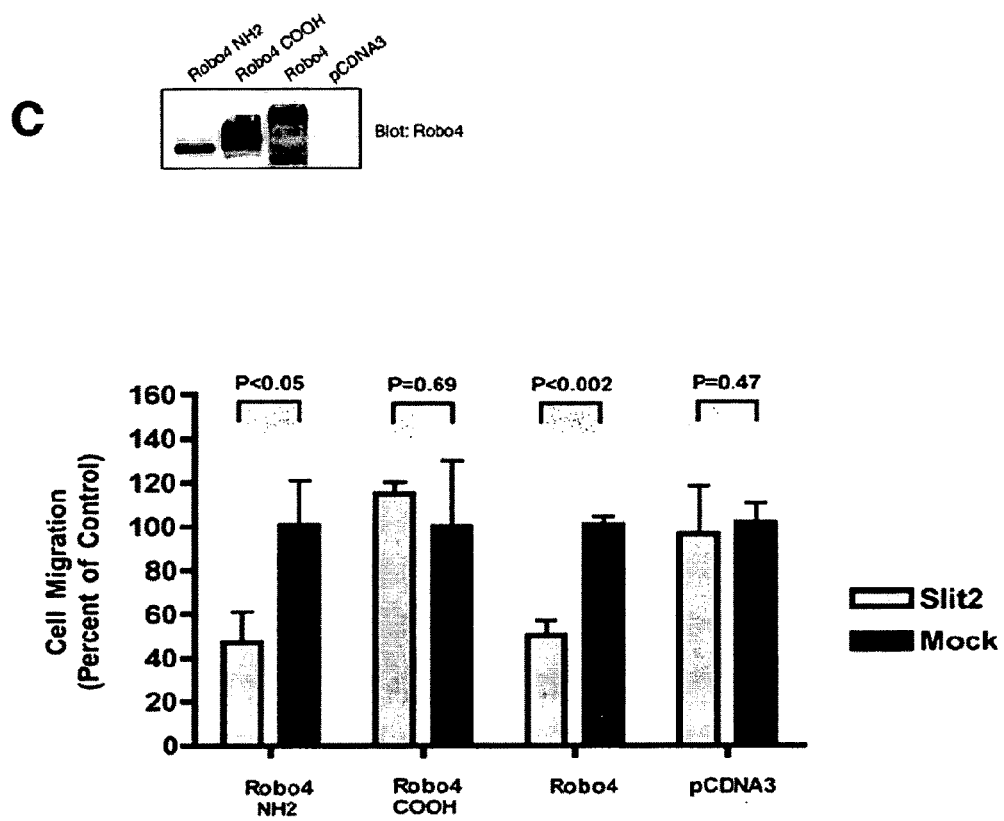

The region of the Robo4 cytoplasmic tail that is required for inhibition of cell migration was next defined. HEK 293 cells were transfected with Robo4 deletion constructs (FIG. 2A) and subjected to haptotaxis migration assays. Fibronectin-dependent migration of cells expressing Robo4-NH2, but not Robo4-COOH was inhibited by Slit2 (FIG. 2C), demonstrating that the N-terminal half of the Robo4 cytoplasmic tail is necessary and sufficient for modulation of cell motility.

Example 4

Figure 3A:
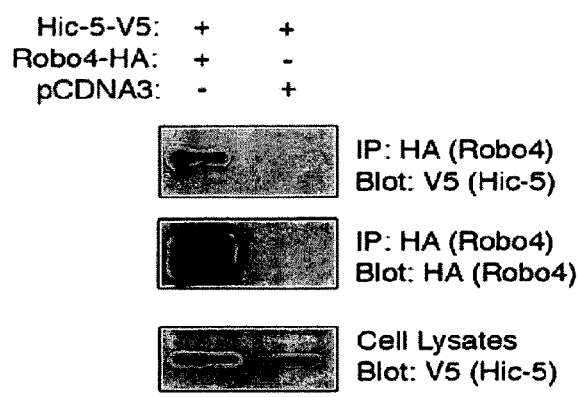
FIG. 3A shows HEK 293 cells were co-transfected with the Robo4 cytoplasmic tail-HA and Hic-5-V5, or empty vector (pcDNA3) and Hic-5-V5. Robo4 was immunoprecipitated with HA antibodies and Hic-5 was detected by western blotting with V5 antibodies.

Paxillin Family Members are Robo4-interacting Proteins: Identification of the region of the Robo4 cytoplasmic tail that confers functional activity allowed the search for cytoplasmic components that might regulate Robo4 signal transduction. Using the N-terminal half of the Robo4 tail as a bait, a yeast two-hybrid screen of a human aortic cDNA library was performed, which identified a member of the paxillin family of adaptor proteins, Hic-5, as a potential Robo4-interacting protein (FIG. 8). To verify this interaction, Hic-5 plasmids were isolated and re-transformed into yeast with Robo4 or empty vector. Only strains co-expressing Robo4 and Hic-5 were competent to grow on nutrient deficient medium and induce robust betagalactosidase activity (FIG. 8B). To further confirm this interaction, co-immunoprecipitation experiments were performed using mammalian cells co-transfected with Hic-5 and the Robo4 cytoplasmic tail. Hic-5 was found in anti-Robo4 immunoprecipitates of HEK 293 cells expressing Robo4 and Hic-5, but not Hic-5 alone (FIG. 3A). Collectively, these data demonstrate that Hic-5 specifically interacts with the Robo4 cytoplasmic tail in both yeast and mammalian cells.

Figure 3B:
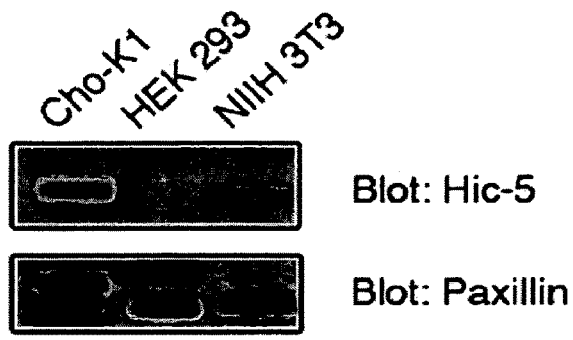
FIG. 3B shows total cell lysates from Cho-K1, HEK 293 and NIH 3T3 cells were probed with antibodies to Hic-5 and paxillin.
Figure 3C:
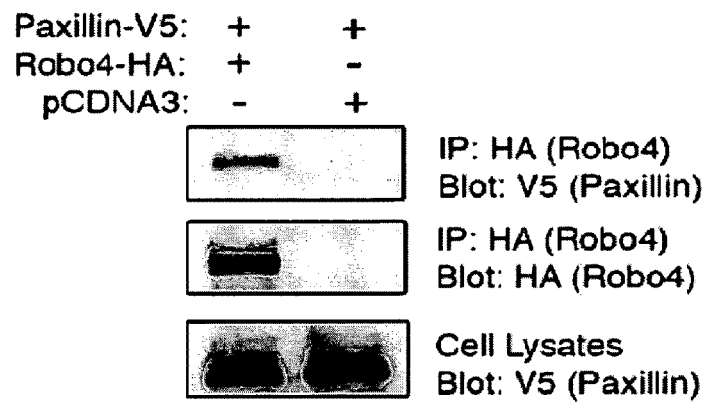
FIG. 3C shows HEK 293 cells were co-transfected with paxillin-V5 and Robo4 cytoplasmic tail-HA or empty vector (pcDNA3). Robo4 was immunoprecipitated from cell lysates with HA antibodies and paxillin was detected by western blotting with V5 antibodies.
Figure 3D:
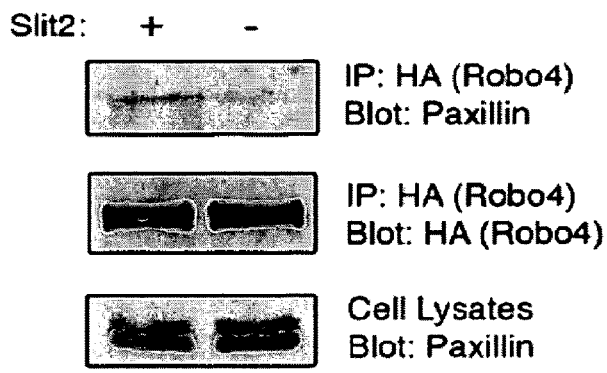
FIG. 3D shows HEK 293 cells were transfected with full length Robo4-HA and paxillin-V5, and stimulated with Slit2 for 5 minutes. Robo4 was immunoprecipitated from cell lysates with HA antibodies and paxillin was detected by western blotting with V5 antibodies.

Hic-5 and its paralog, paxillin, can exhibit cell-type specific expression (Turner, 2000; Yuminamochi et al., 2003). For this reason, it was determined which of these proteins were expressed in HEK 293 cells, the cell line used in the haptotaxis migration assays. Western blotting of cell lysates from CHO-K1, HEK 293 and NIH3T3 cells with antibodies to Hic-5 or paxillin detected paxillin in all cell lines, whereas Hic-5 was only found in CHO-K1 and NIH3T3 cells (FIG. 3B). This not only suggested that Hic-5 and paxillin could interact with Robo4 to regulate cell migration, but that paxillin was the likely binding partner in HEK 293 cells. With this latter idea in mind, co-immunoprecipitation experiments were performed using mammalian cells expressing paxillin and the Robo4 cytoplasmic tail. As was observed with Hic-5, paxillin was identified in anti-Robo4 immunoprecipitates of HEK 293 cells expressing paxillin and Robo4, but not paxillin alone (FIG. 3C).

Since Slit2 is a physiological ligand of Robo4 (Park et al., 2003; Hohenester et al., 2006), it was determined whether Slit2 stimulation regulated the interaction between Robo4 and paxillin. HEK 293 cells expressing Robo4 were incubated in the presence or absence of Slit2. In the presence of Slit2, endogenous paxillin was detected in Robo4 immunoprecipitates. In sharp contrast, in the absence of Slit2, no paxillin was detected in the immunoprecipitates (FIG. 3E). Thus, engagement of Robo4 by Slit2 stimulated its association with paxillin.

Example 5

Figure 4A:
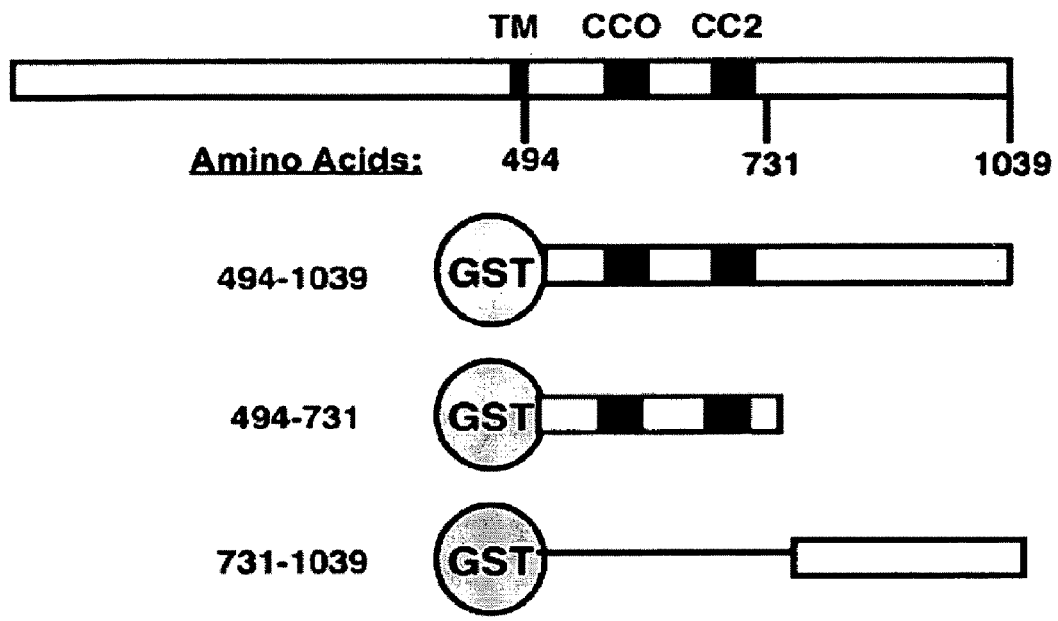
FIG. 4A shows schematic representation of GST-Robo4 fusion proteins used in pull down assays shown in panel B.
Figure 4B:
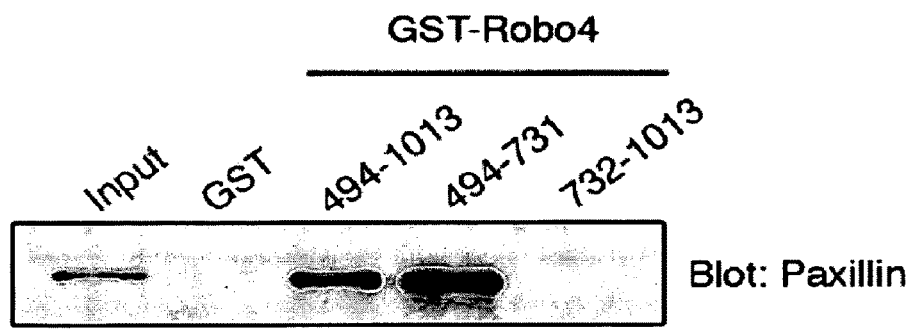
FIG. 4B shows GST-Robo4 fusion proteins were purified form E. coli and incubated with recombinant purified paxillin. Paxillin was detected by western blotting with paxillin-specific monoclonal antibodies.
Figure 4C:
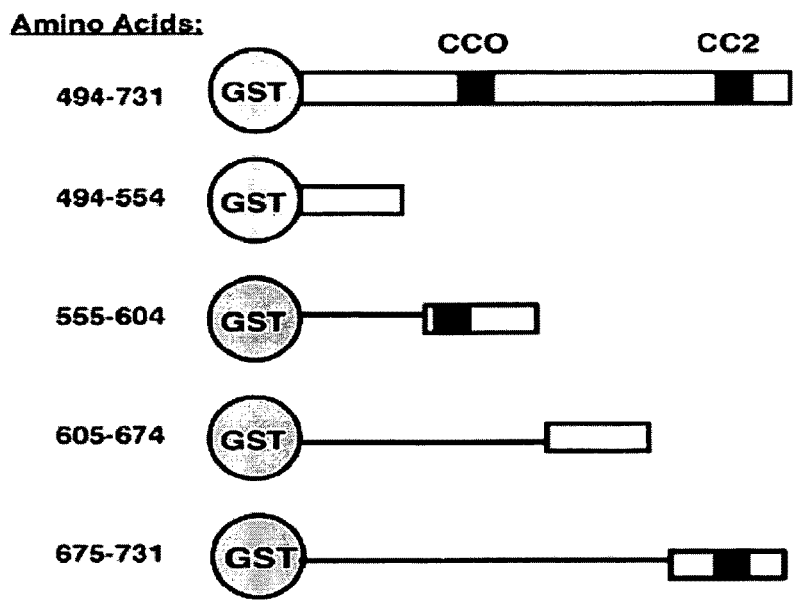
FIG. 4C shows schematic representation of GST-Robo4 fusion proteins used in pull down assays described in panel D.
Figure 4D:
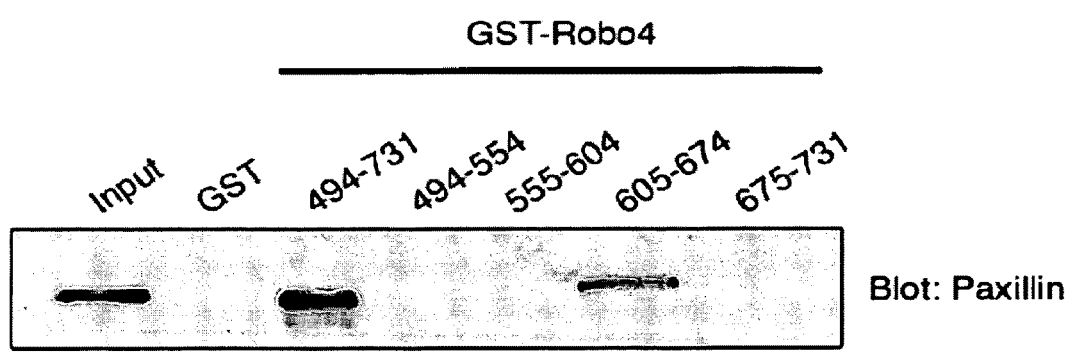
FIG. 4D shows GST-Robo4 fusion proteins were purified form E. coli and incubated with recombinant purified paxillin. Paxillin was detected by western blotting with a paxillin-specific monoclonal antibodies.
Figure 4E:
FIG. 4E shows GST-Robo4 wild-type or GST-Robo4ΔPIM were purified from E. coli and incubated with recombinant purified paxillin or in vitro transcribed/translated Mena-V5. Paxillin and Mena were detected with paxillin-specific monoclonal antibodies and V5 antibodies, respectively.
Figure 9A:
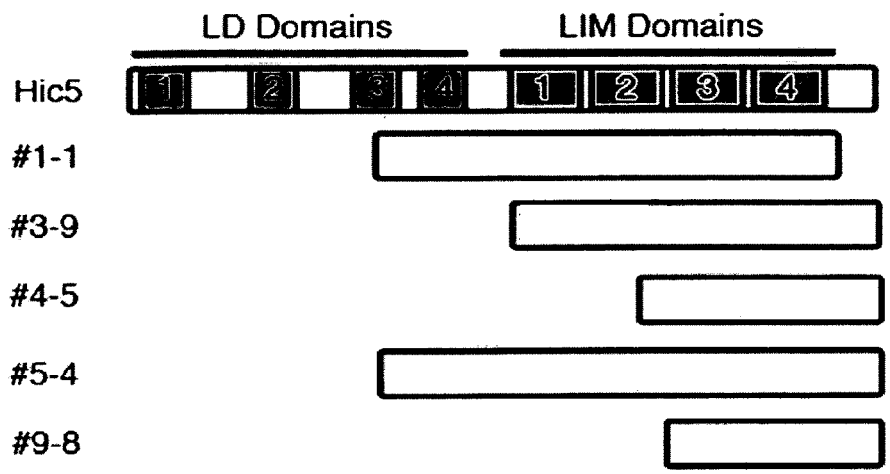
FIG. 9A shows a schematic representation of full-length Hic-5 and the cDNA clones recovered from the yeast two-hybrid screen.
Figure 9B:
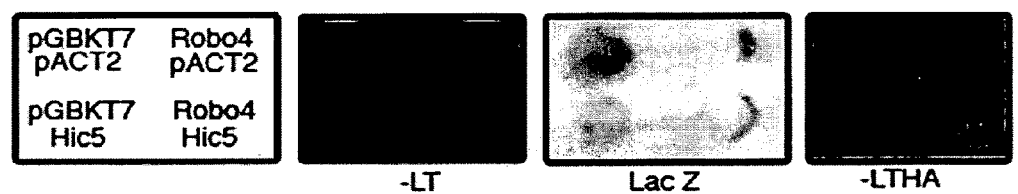
FIG. 9B shows S. cerevisiae strain PJ694-A was transformed with the indicated plasmids and plated to synthetic media lacking Leucine and Tryptophan, or Leucine, Tryptophan, Histidine and Alanine. Colonies capable of growing on nutrient deficient media were spotted onto the same media, replica plated, and either photographed or used for the beta-galactosidase assay.
Figure 10:
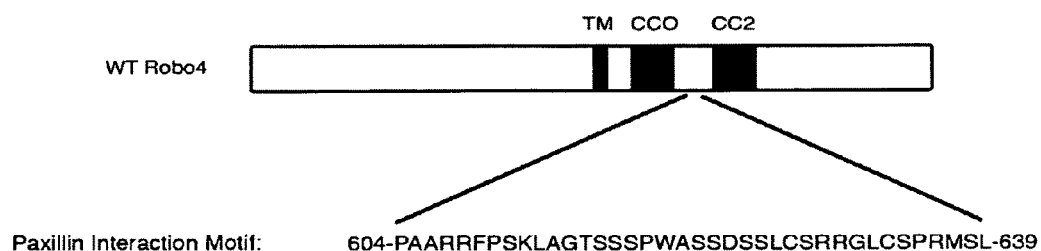
FIG. 10 shows the paxillin interaction motif lies between CC0 and CC2 in the Robo4 cytoplasmic tail. Schematic representation of the murine Robo4 protein and identification of the amino acids comprising the paxillin interaction motif.

Identification of the Paxillin Interaction Motif of Robo4: To precisely define the region of Robo4 that is required for interaction with paxillin a series of GST-Robo4 fusion proteins spanning the entire length of the cytoplasmic tail were created (FIG. 4A). In vitro binding assays with purified recombinant paxillin demonstrated that the amino terminal half of the Robo4 tail (494-731) is necessary and sufficient for direct interaction with paxillin (FIG. 4B). Four additional GST-Robo4 fusion proteins encompassing approximately 70 amino acid fragments of the amino terminal half of the cytoplasmic tail were then generated (FIG. 4C). In vitro binding assays revealed that paxillin selectively interacts with a fragment of the Robo4 tail residing between the CC0 and CC2 motifs (604-674; FIG. 4D). To determine whether this region of Robo4 was necessary for interaction with paxillin amino acids 604-674 were deleted from the cytoplasmic tail and this mutant GST-Robo4 fusion protein subjected to in vitro binding assays. While interaction with paxillin was attenuated, so was interaction with a known Robo4-binding protein, Mena, indicating that elimination of amino acids 604-674 affects the conformation of the Robo4 tail. To circumvent this issue, smaller deletions were created within this 70 amino acid stretch and additional in vitro binding assays performed. Using this approach a mutant GST-Robo4 fusion protein was identified lacking 36 amino acids (604-639; FIG. 9) that lost binding to paxillin, but retained binding to Mena (FIG. 4E). This region of Robo4 is heretofore referred to as the paxillin interaction motif (PIM).

Example 6

Figure 4F:
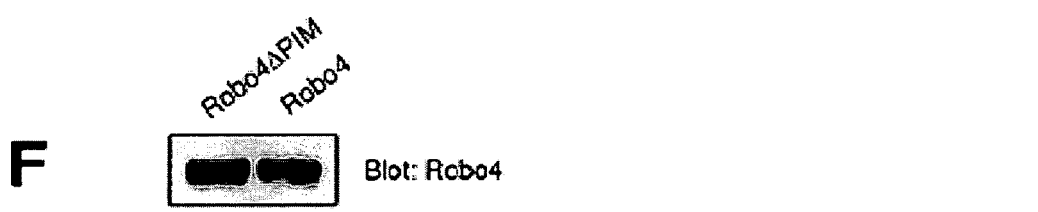
FIG. 4F shows HEK 293 cells were transfected with GFP and the indicated constructs and 36 hours later subjected to haptotaxis migration on membranes coated with 5 µg/ml fibronectin and either Mock preparation or Slit2. Expression of Robo4 constructs was verified by western blotting (Inset). Results are presented as the mean±SE.
Figure 4F:
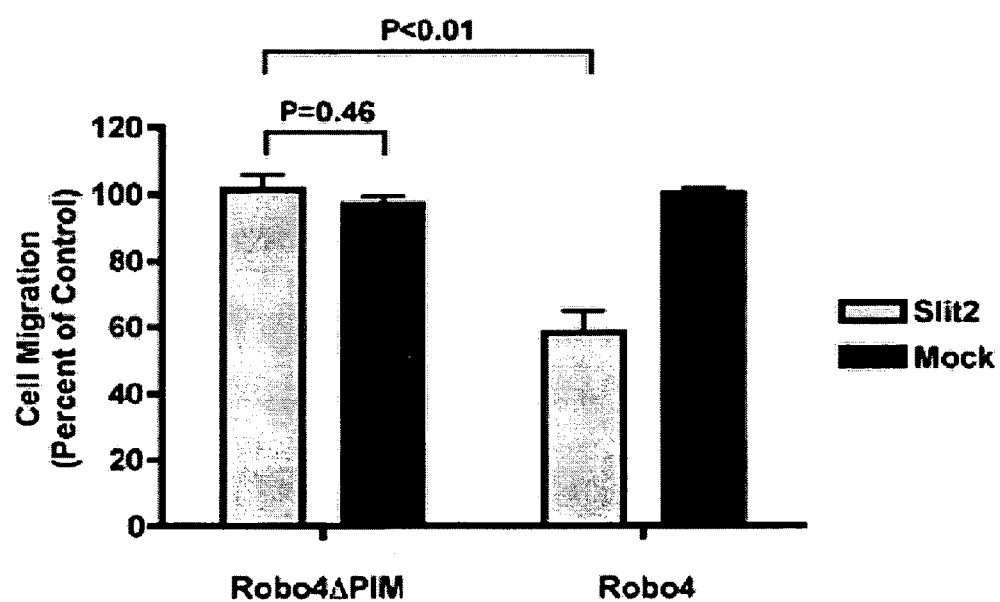

The Paxillin Interaction Motif is required for Robo4-dependent Inhibition of Haptotaxis: It was next determined whether the paxillin interaction motif of Robo4 is important for functional activity of the receptor. A mutant form of full length Robo4 lacking amino acids 604-639 (Robo4ΔPIM) was generated by site directed mutagenesis and used in haptotaxis migration assays. Robo4ΔPIM failed to mediate Slit2-directed inhibition of migration towards a gradient of fibronectin (FIG. 4F), demonstrating that the region of the Robo4 tail necessary for paxillin binding is likewise required for Robo4-dependent inhibition of cell migration.

Example 7

Figure 5A:
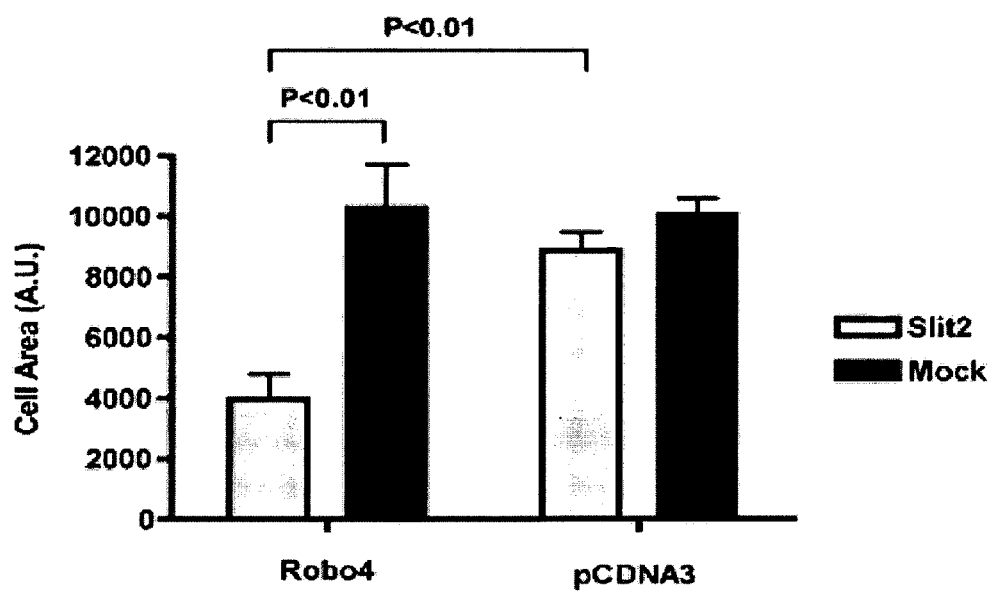
FIG. 5A, FIG. 5D, and FIG. 5G show HEK 293 cells were transfected with GFP and the indicated constructs and 36 hours later subjected to cell spreading assays on coverslips coated with 5 µg/ml fibronectin and either Mock preparation or Slit2. Results are presented as the mean±SE.

Slit2-Robo4 Signaling Inhibits Cell Spreading and Adhesion-dependent Rac Activation: The ability of immobilized Slit2 to inhibit the migration of cells expressing Robo4 on fibronectin could potentially result from negative regulation of adhesion and/or spreading on this ECM protein. To determine whether Slit2-Robo4 signaling influences these processes, HEK 293 cells were transfected with Robo4 or empty vector (pcDNA3) and subjected to adhesion and spreading assays on fibronectin. Although cells expressing Robo4 adhered normally to coverslips coated with fibronectin and Slit2, they were significantly less spread than cells transfected with pcDNA3 (FIG. 5A). These data indicate that Slit2-Robo4 signaling modulates intracellular pathways that control cell spreading.

Figure 5B:
FIG. 5B and FIG. 5E show HEK 293 cells were transfected with the indicated constructs and 36 hours later plated onto dishes coated with 5 µg/ml fibronectin and either Mock preparation or Slit2. Following a 5-minute incubation, cells were lysed and GTP-Rac was precipitated with GST-PBD. Rac was detected by western blotting with a Racspecific monoclonal antibody.
Figure 5C:
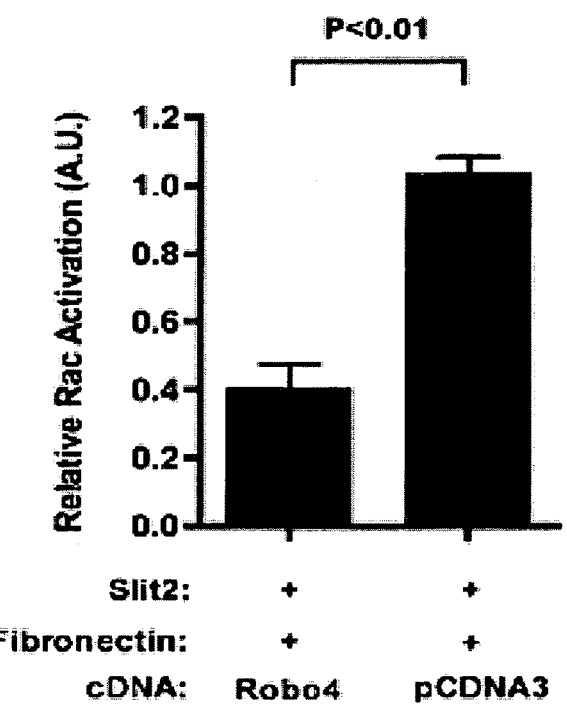
FIG. 5 shows Robo4 suppresses cell spreading through inactivation of Rac.
FIG. 5H shows HUVEC were incubated for 60 minutes with Slit2, stimulated with 25 ng/ml VEGF for 5 minutes, lysed and GTP-Rac was precipitated with GST-PBD. Rac was detected by western blotting with a Rac-specific monoclonal antibody. Slit2-dependent inhibition of (C) and (F) adhesion induced- and (I) VEGF-induced Rac activation was quantified by densitometry. Results are presented as mean±SE.
Figure 11A:
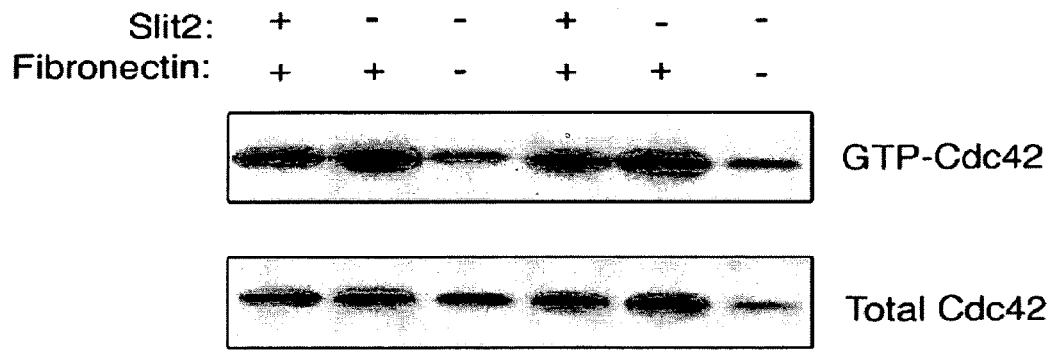
FIG. 11A shows HEK 293 cells expressing Robo4 were plated onto bacterial Petri dishes coated with 5 µg/ml fibronectin and either Mock preparation or Slit2. Following a 5-minute incubation, cells were lysed, and GTP-Cdc42 was precipitated with GST-PBD. Cdc42 was detected by western blotting with a Cdc42-specific monoclonal antibody.
Figure 11B:
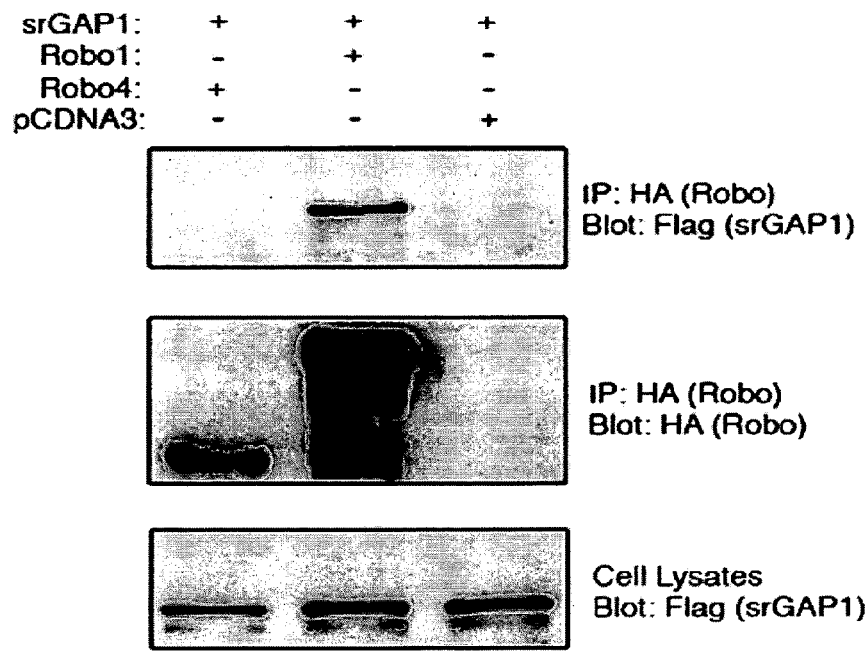
FIG. 11B shows HEK 293 cells were transfected with the indicated plasmids, and Robo1/Robo4 were immunoprecipitated with HA antibodies. srGAP1 was detected by western blotting with Flag M2 antibodies.
Figure 12A:
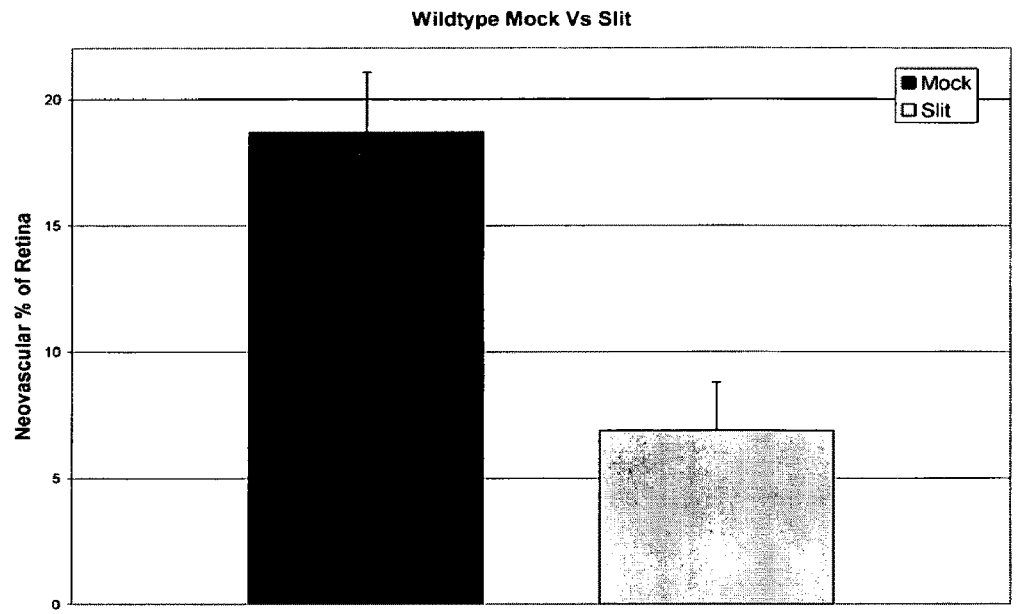
FIG. 12A shows percent neovascularization of the retina in wildtype mice receiving Mock preparation compared to those receiving Slit protein. There was a 63% reduction in neovascularization in mice treated with Slit treated mice as compared to wildtype mice. N=6, P<0.003.
Figure 12B:
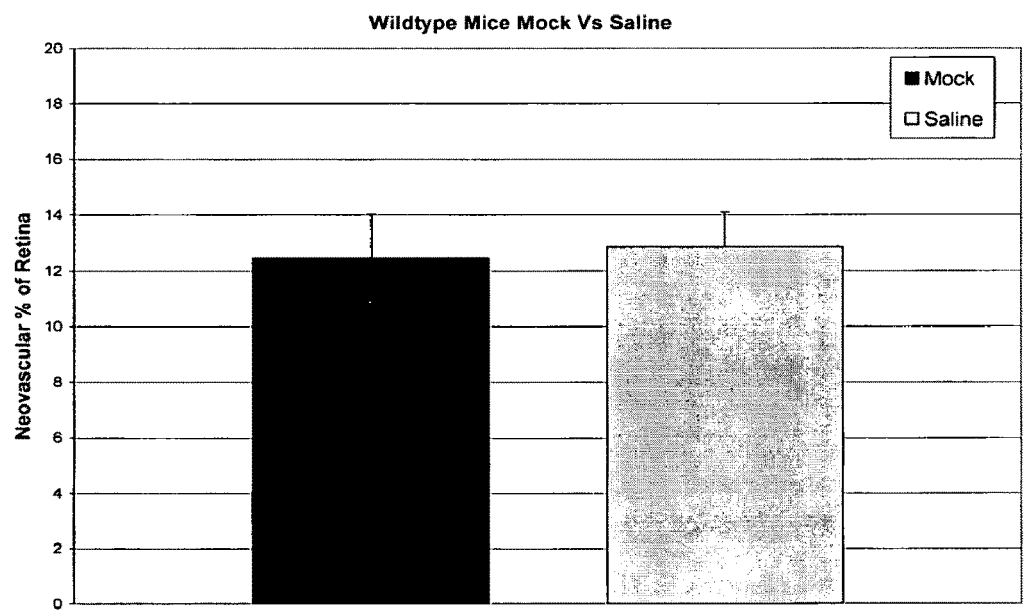
FIG. 12B shows percent neovascularization of the retina in wildtype mice receiving Mock preparation compared to those receiving saline control. N=5, P<0.85.
Figure 12C:
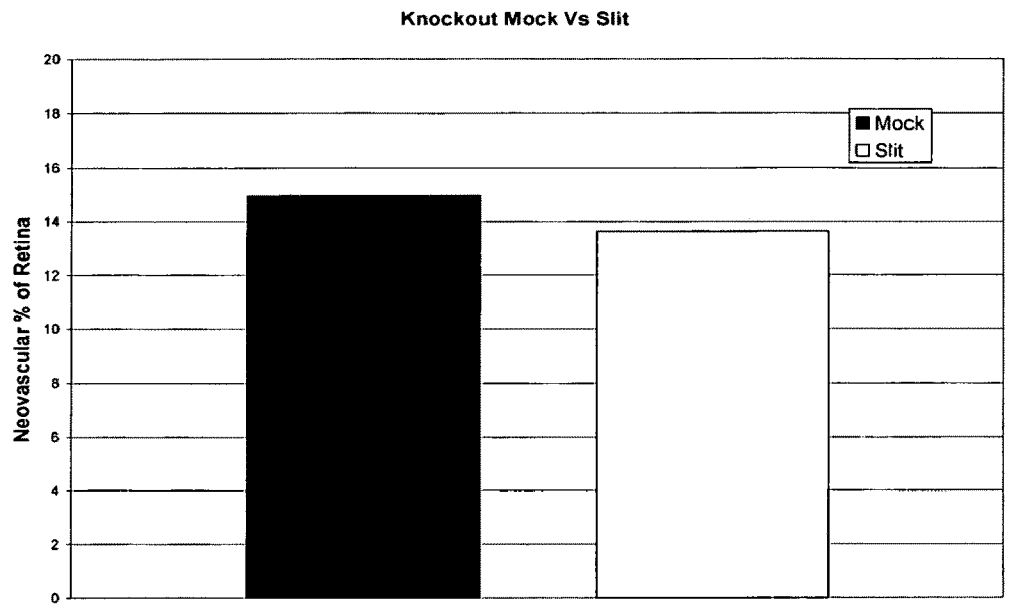
FIG. 12C shows percent neovascularization of the retina in knockout mice compared to slit. N=1.
Figure 13:
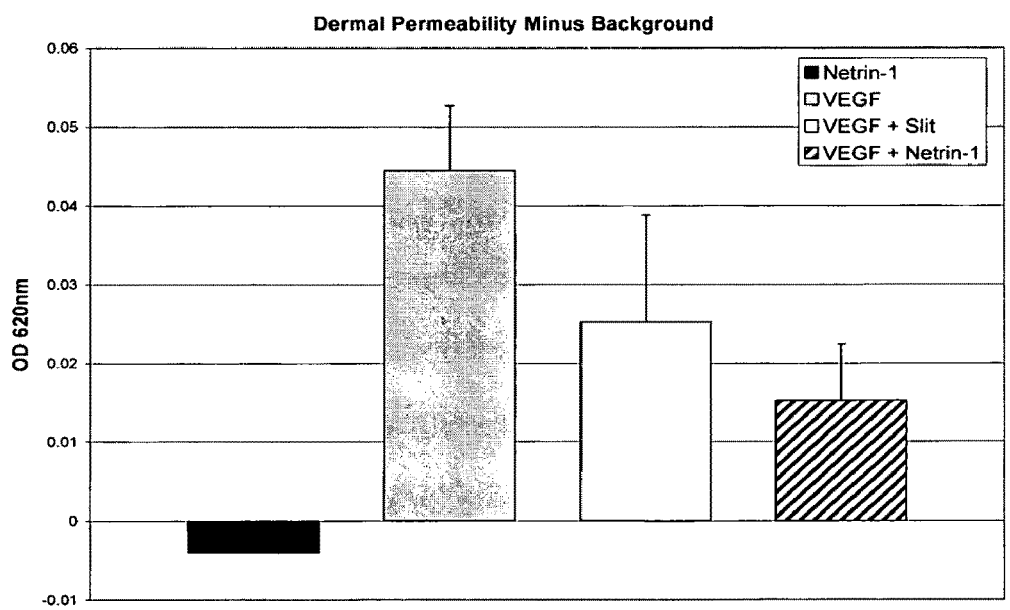
FIG. 13 shows slit and netrin can reduce VEGF-induced dermal permeability.
Figure 14:
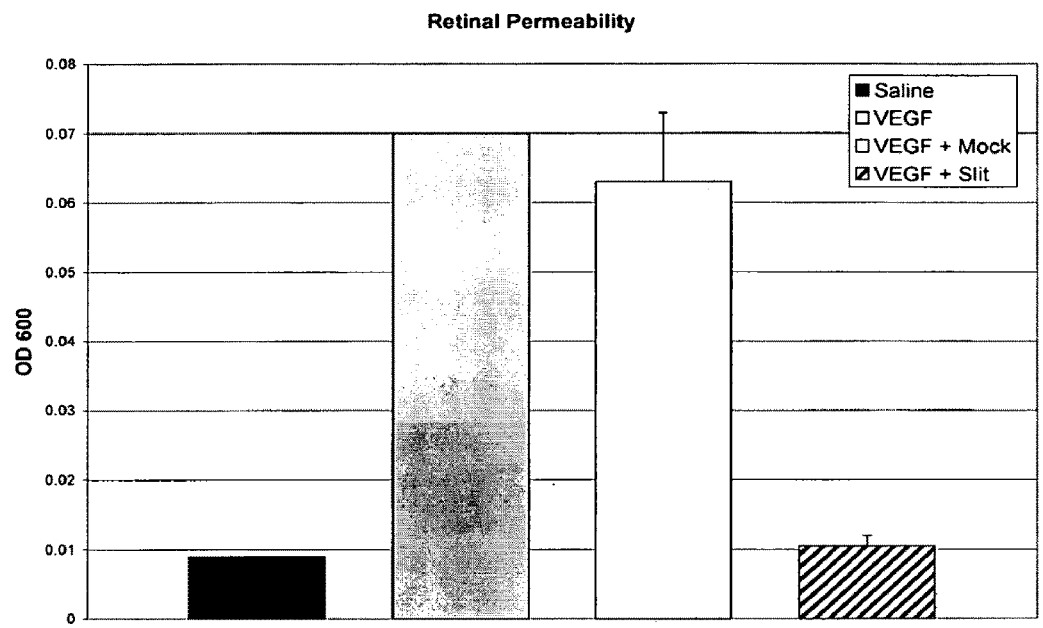
FIG. 14 shows slit can reduce VEGF mediated retinal permeability.
Figure 15:
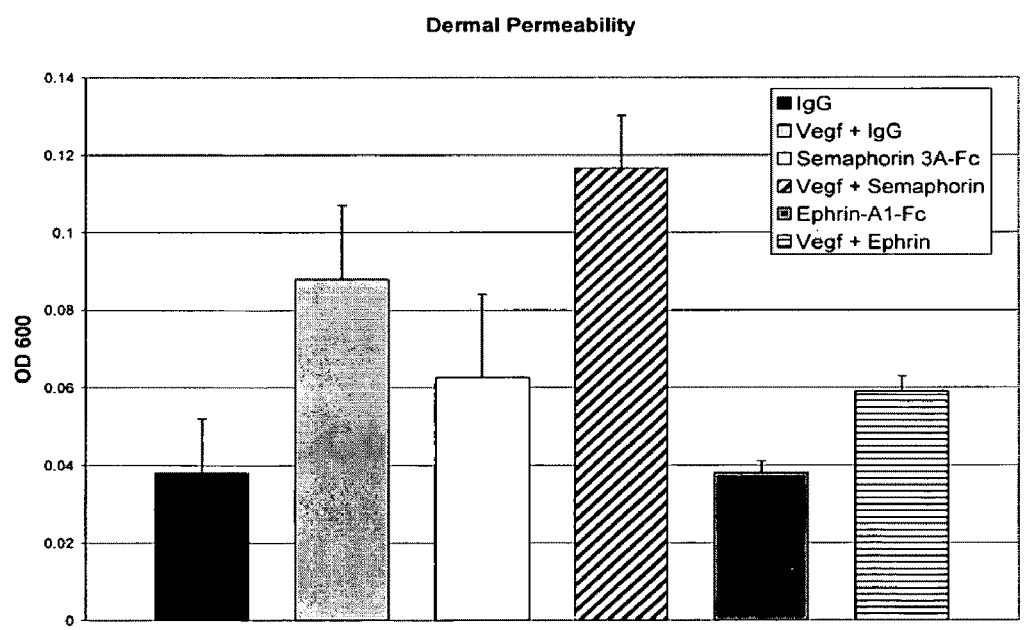
FIG. 15 shows semaphorin like VEGF increases dermal permeability.

The ability of a cell to spread on an ECM protein, such as fibronectin, is regulated by activation of the Rho family of small GTPases, which include Rho, Cdc42 and Rac migration (Nobes and Hall, 1995; Nobes and Hall, 1998). Of these proteins, Rac plays an essential role in promoting the actin polymerization that leads to cell spreading and migration (Nobes and Hall, 1995; Nobes and Hall, 1998). This established relationship between Rac and cell spreading indicated that Slit2-Robo4 signaling might inhibit adhesion-dependent activation of Rac. To evaluate this possibility, HEK 293 cells were transfected with Robo4 or pcDNA3, plated onto dishes coated with fibronectin and Slit2 and Rac-GTP levels were assayed using GST-PBD pull down assays. Cells expressing Robo4 exhibited significantly less adhesion-stimulated Rac activation when compared to cells transfected with pcDNA3 (FIGS. 5B and C). To confirm the specificity of this effect, Cdc42 activation was also examined in cells expressing Robo4, which was unaltered by exposure to Slit2 (FIG. 11A). This result is supported by the observation that Robo4 does not interact with the Robo1 binding-protein srGAP1, a known GTPase activating protein for Cdc42 (FIG. 11B). Together, these data demonstrate that Slit2-Robo4 signaling specifically inhibits adhesion-induced activation of Rac.

Example 8

Figure 5D:
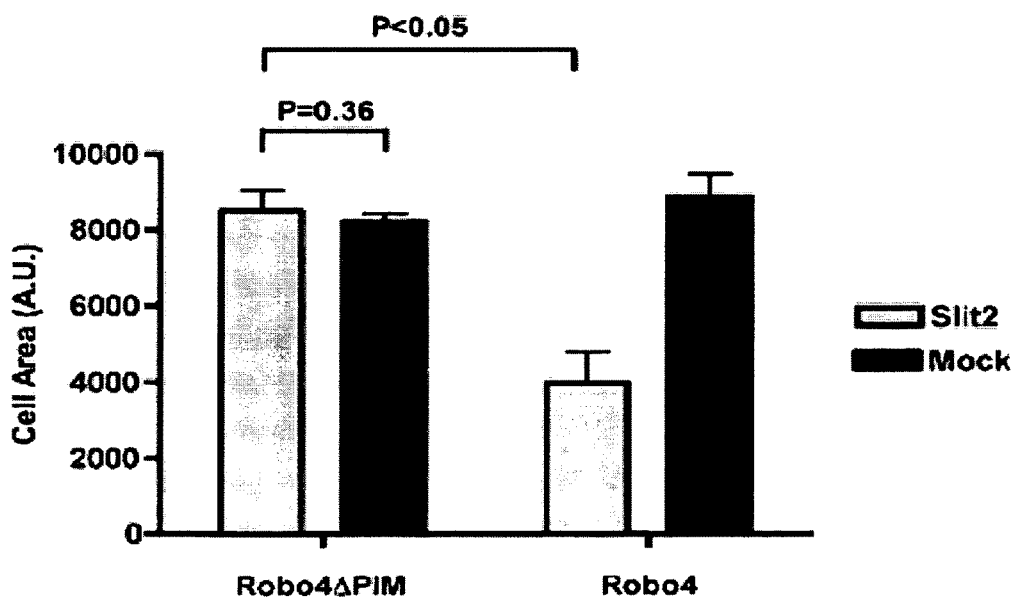
Figure 5E:
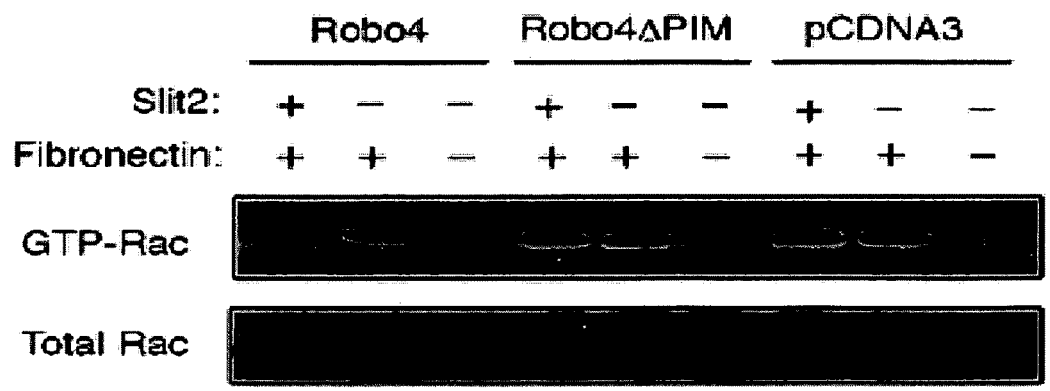
Figure 5F:
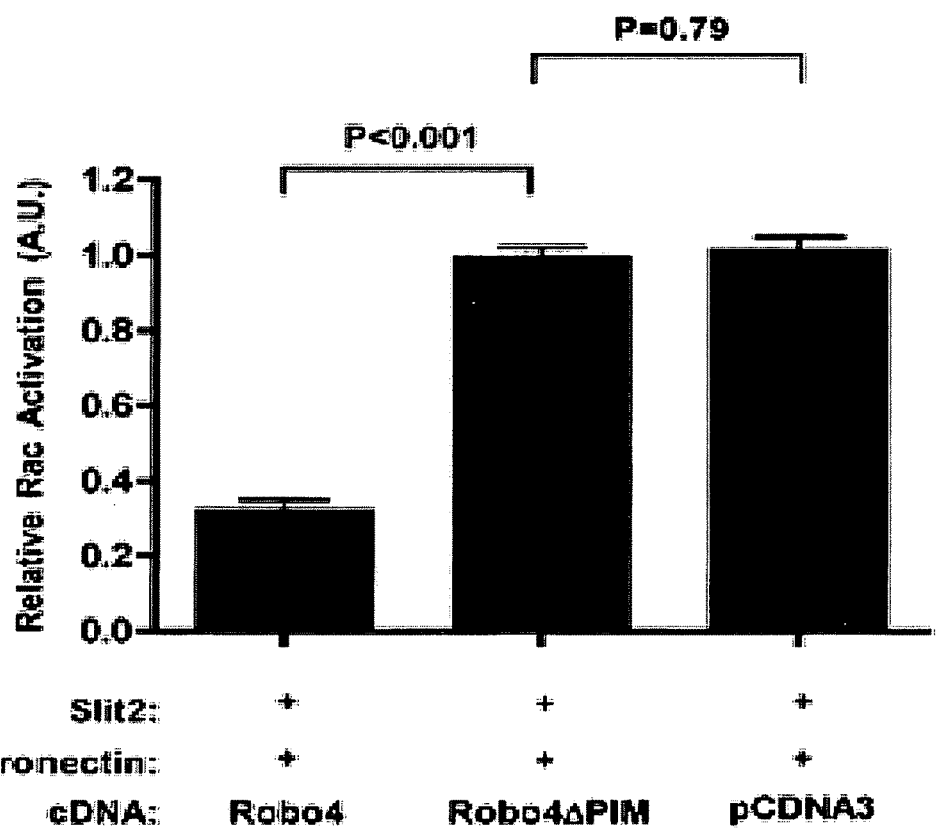

The Paxillin Interaction Motif is required for Robo4-dependent Inhibition of Cell Spreading and Rac Activation: Whether Robo4ΔPIM was competent to inhibit fibronectin-induced cell spreading and Rac activation was next evaluated. HEK 293 cells were transfected with Robo4ΔPIM, plated onto fibronectin and Slit2 coated surfaces and subjected to spreading or Rac assays. This mutant form of the receptor was incapable of inhibiting cell spreading and adhesion-dependent Rac activation (FIGS. 5D, E and F), demonstrating that the paxillin interaction motif is essential for functional activity of Robo4 in vitro.

Figure 5G:
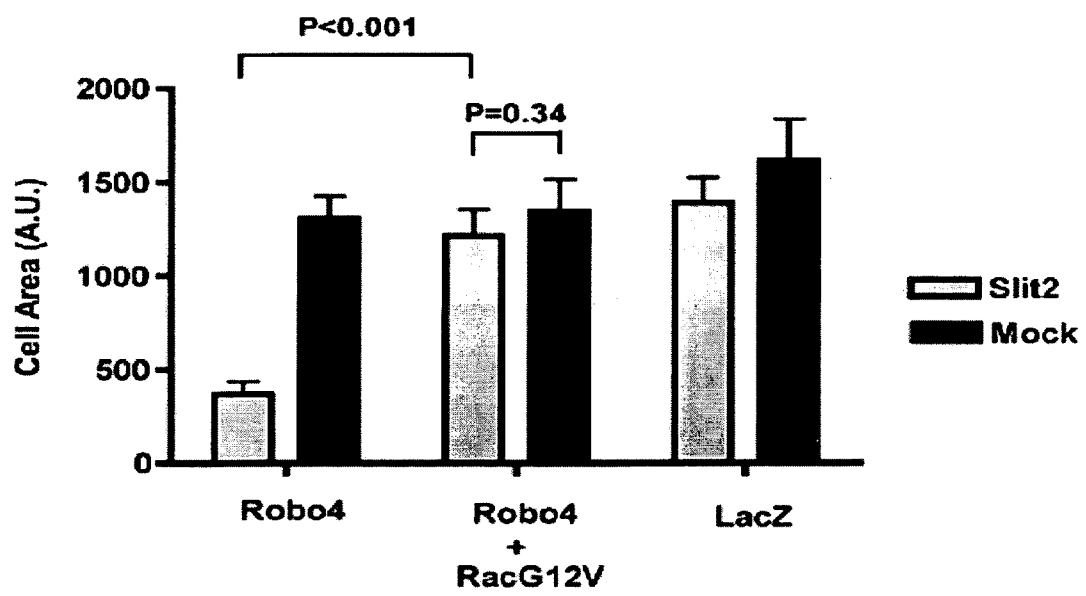

To confirm that Robo4-dependent inhibition of cell spreading was due principally to suppression of Rac activation, HEK 293 cells were co-transfected with Robo4 and a dominant active form of Rac, Rac (G12V), and subjected to spreading assays. Cells expressing Rac (G12V) were refractory to Robo4-dependent inhibition of cell spreading (FIG. 5G), demonstrating that Slit2-Robo4 signaling blocks spreading by inhibiting Rac activity.

Example 9

Figure 5H:
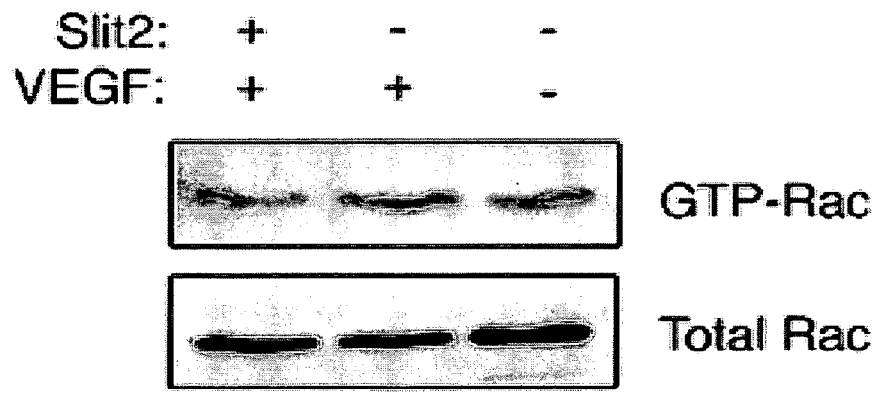
Figure 5I:
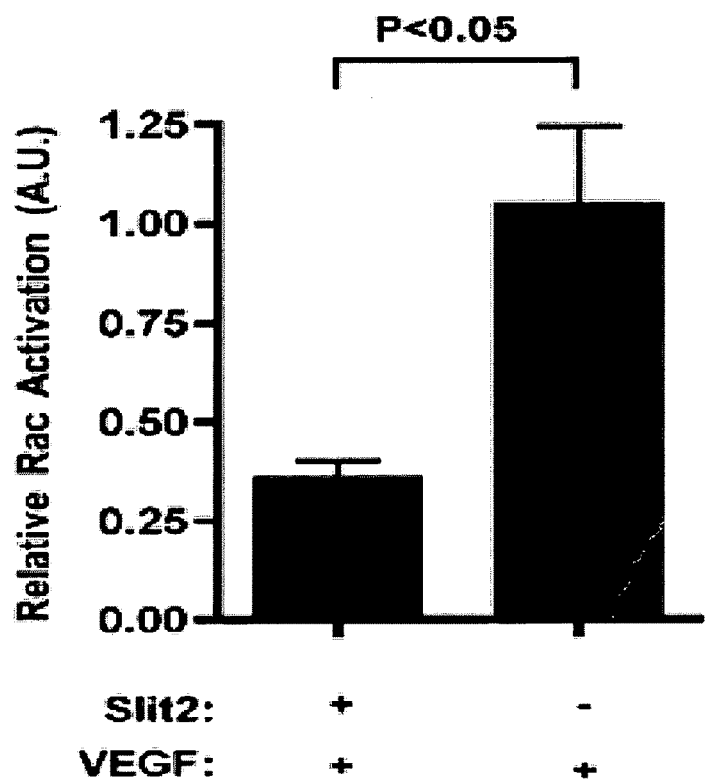

Slit2 Inhibits VEGF-induced Rac Activation in Primary Human Endothelial Cells: Slit2 inhibits VEGF-stimulated migration of several primary human endothelial cell lines (Park et al., 2003), and Rac plays an essential role for in VEGF-induced cell motility (Soga et al., 2001a; Soga et al., 2001b). It was therefore determined whether Slit2-Robo4 signaling could inhibit Rac activation in an endogenous setting. Human Umbilcal Vein Endothelial Cells (HUVEC) were stimulated with VEGF in the presence and absence of Slit2, and GTP-Rac levels were analyzed using GST-PBD pull down assays. Slit2 treatment completely suppressed VEGF-stimulated Rac activation (FIGS. 5H and I), demonstrating that endogenous Slit2-Robo4 signaling modulates Rac activation.

Example 10

Figure 6A:
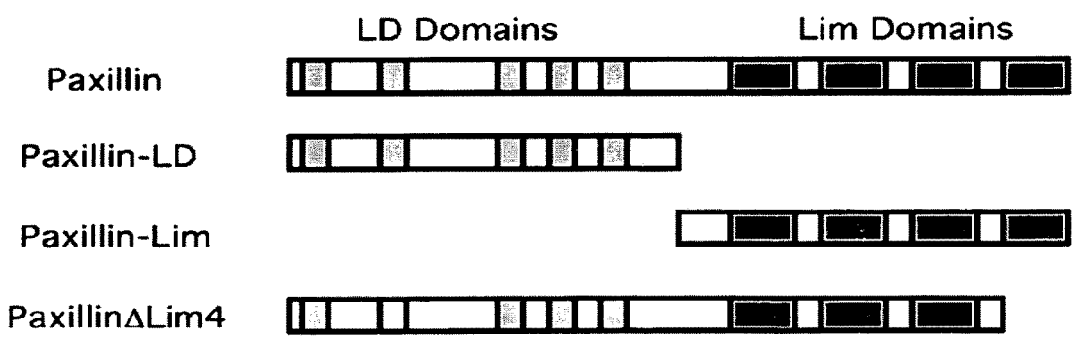
FIG. 6A shows a schematic representation of paxillin constructs used in panels B, C and D.
Figure 6B:
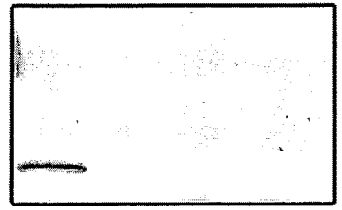
FIG. 6B shows HEK 293 cells were co-transfected with the Robo4 cytoplasmic tail-HA and paxillin-V5, or empty vector (pcDNA3) and paxillin-V5. Robo4 was immunoprecipitated from cell lysates with HA antibodies, and paxillin was detected by western blotting with V5 antibodies.
Figure 6B:
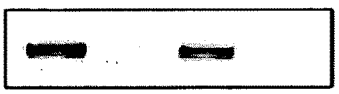
Figure 6B:
Figure 6C:
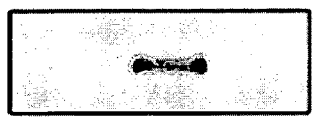
FIG. 6C shows HEK 293 cells were co-transfected with the Robo4 cytoplasmic tail-HA and either wild-type paxillin-V5 or paxillinΔLim4-V5. Robo4 was immunoprecipitated with HA antibodies, and paxillin was detected by western blotting with V5 antibodies.
Figure 6C:
Figure 6C:

Lim4 of Paxillin is required for Interaction with Robo4 and Robo4-dependent Inhibition of Cell Spreading: Although Robo4APIM maintains its interaction with Mena (FIG. 4E), it is possible that this mutation perturbed interaction of Robo4 with proteins other than paxillin. To address this issue definitively, paxillin mutants were generated that disrupt association with Robo4. Paxillin is a modular protein composed of N-terminal leucine/aspartic acid (LD) repeats and C-terminal Lim domains (FIG. 6A). Analysis of the clones recovered from the yeast two-hybrid screen (see FIG. 9A) indicated that the Lim domains, particularly Lim3 and Lim4, are important for interaction with Robo4. To validate this notion, co-immunoprecipitation experiments were performed using HEK 293 cells co-transfected with the Robo4 tail and either paxillin-LD or paxillin-Lim. Paxillin-Lim, but not paxillin-LD was found in Robo4 immunoprecipitates (FIG. 6B), demonstrating that the Lim domains of paxillin are necessary and sufficient for interaction with Robo4. To clarify which Lim domain is required for binding to Robo4, serial deletions were made from the carboxy terminus of paxillin, cotransfected with the Robo4 tail into HEK 293 cells, and coimmunoprecipitation experiments performed. Deletion of the Lim4 domain of paxillin completely abrogated binding to Robo4 (FIG. 6C), demonstrating that this region of paxillin is critical for its ability to interact with Robo4.

Figure 6D:
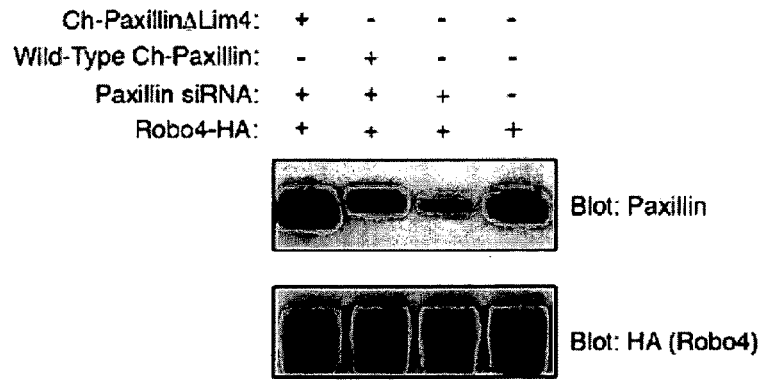
FIG. 6D shows Endogenous paxillin was knocked down in HEK 293 cells using siRNA and reconstituted with either wild-type chicken paxillin or chicken paxillinΔLim4. Knock down and reconstitution were visualized by western blotting with paxillin antibodies and quantified by densitometry. Paxillin expression was determined to be 35% of wild-type levels.
Figure 6E:
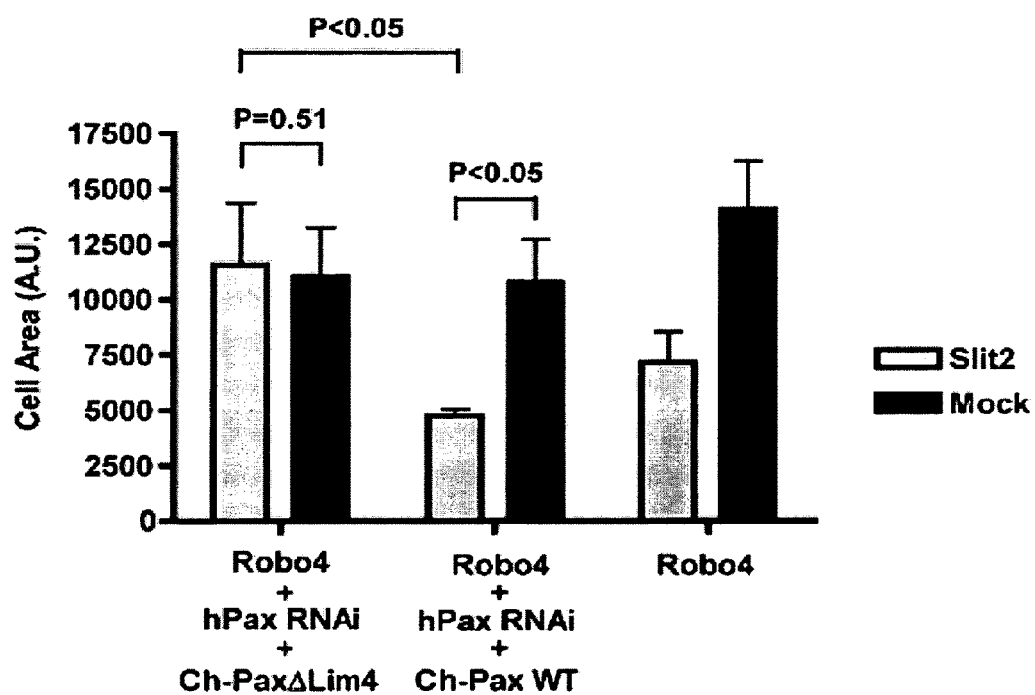
FIG. 6E shows HEK 293 cells subjected to knock down/reconstitution were subjected to spreading assays on coverslips coated with 5 µg/ml fibronectin and either Mock preparation or Slit2. Results are presented as the mean±SE.

Delineation of the Robo4 binding site on paxillin allowed direct evaluation of the role of paxillin in Robo4-dependent inhibition of cell spreading. Endogenous paxillin was knocked-down in HEK 293 cells using siRNA and reconstituted with wild type chicken paxillin (Ch-paxillin) or Ch-paxillin ΔLim4 (FIG. 6D). These cells were then subjected to spreading assays on coverslips coated with fibronectin and Slit2. Cells expressing Ch-paxillin ΔLim4 were refractory to Robo4-dependent inhibition of cell spreading, while cells expressing Ch-paxillin exhibited the characteristic reduction in cell area (FIG. 6E). These data confirm that interaction of paxillin with the Robo4 enables Slit2-Robo4 signaling to suppress cell spreading.

Example 11

Figure 7A:
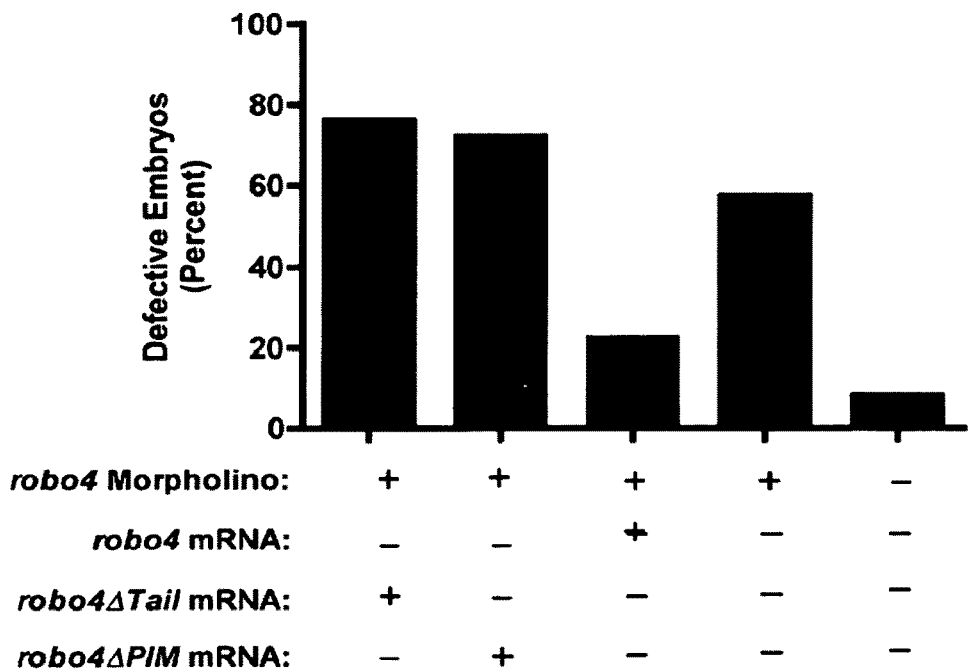
FIG. 7A shows Quantification of vascular patterning defects in uninjected (n=66), robo4 morpholino (n=56), robo4 morpholino and wild-type murine robo4 RNA (n=60), robo4 morpholino and robo4Δtail RNA (n=17), and robo4 morpholino and robo4ΔPIM RNA (n=45) injected TG(fli:egfp)y1 embryos. Representative images are shown in FIG. 1.
Figure 7B:
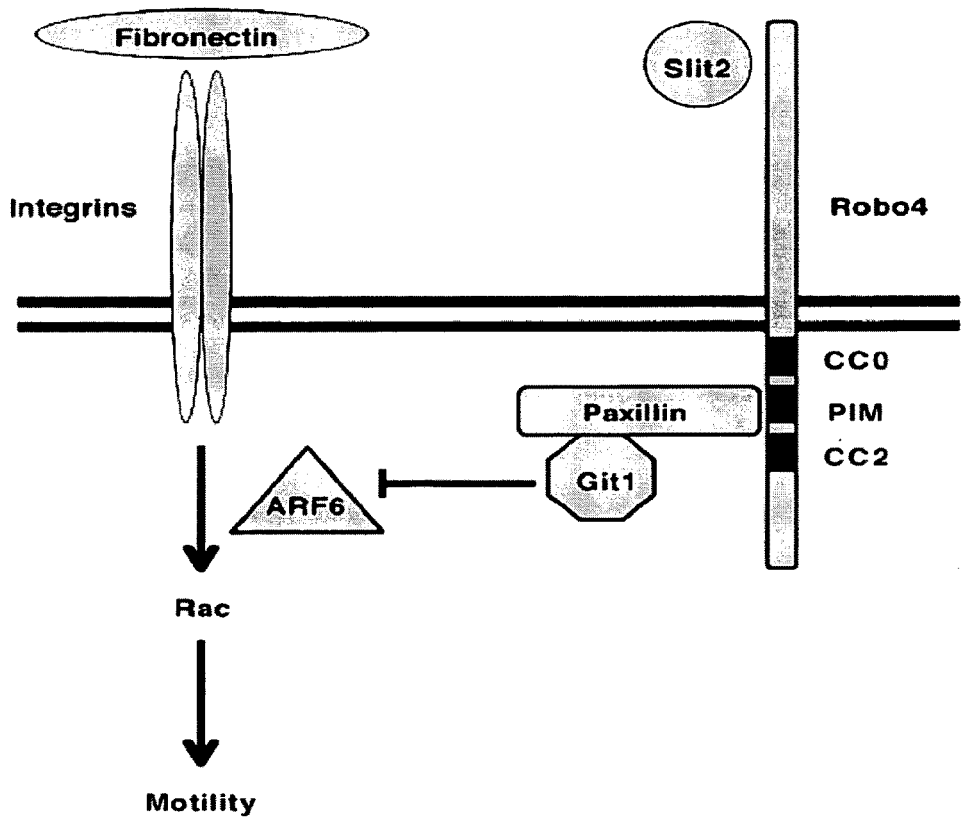
FIG. 7B shows a model of a Slit2-Robo4 signaling axis that inhibits cell migration, spreading and Rac activation.

The Paxillin Interaction Motif is required for Vascular Guidance in vivo: The requirement of the paxillin interaction motif of Robo4 during zebrafish vascular development was assessed. As described previously, injection of robo4 MO into TG (fli1:egfp)$^{y1}$ embryos caused disorganization of the inter-segmental vessels (see FIG. 1B). Co-injection of robo4ΔPIM RNA exacerbated the defects caused by the robo4 MO, while wild-type robo4 RNA suppressed these defects (FIG. 7A). The inability of both robo4Δtail and robo4ΔPIM RNA to rescue vascular patterning defects in morphant embryos demonstrates that the 36 amino acid paxillin interaction motif is a critical signal transduction module in the Robo4 cytoplasmic tail. Further, these data indicate that the interaction between paxillin and Robo4 is essential for proper patterning of the zebrafish vasculature.

Example 12

Figure 16:
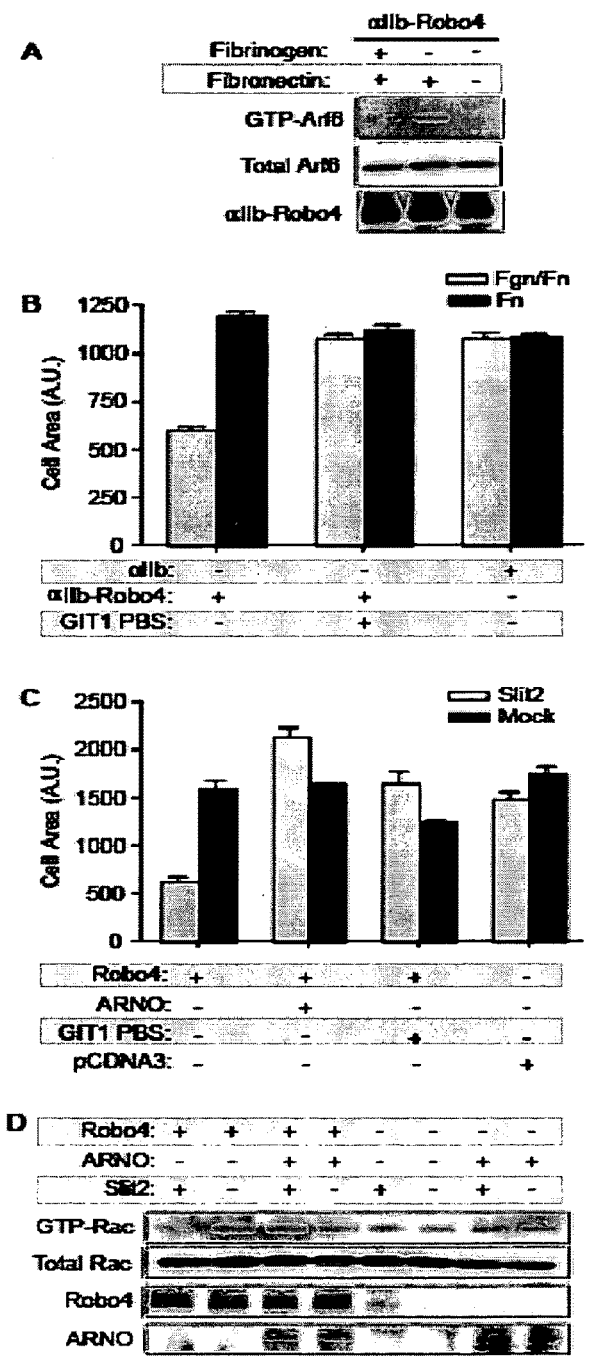
FIG. 16 shows that Robo4 blocks Rac-dependent protrusive activity through inhibition of Arf6. CHO-K1 cells stably expressing αIIb or αIIb-Robo4 cytoplasmic tail were plated on dishes coated with fibronectin or fibronectin and fibrinogen, lysed and GTP-Arf6 was precipitated with GST-GGA3. Arf6 was detected by western blotting with an Arf6-specific monoclonal antibody (See, FIG. 16A). CHO-K1 cells stably expressing αIIb or αIIb-Robo4 cytoplasmic tail were cotransfected with GFP and either an empty vector or the GIT1-PBS, and subjected to spreading assays on coverslips coated with fibronectin or fibronectin and fibrinogen. The area of GFP-positive cells was determined using ImageJ, with error bars indicating SEM (See, FIG. 16B). HEK 293 cells were co-transfected with GFP and the indicated constructs and 36 h later were subjected to spreading assays on fibronectin and either Mock preparation or a Slit2 protein (See, FIG. 16C). In all panels, error bars indicate mean±SE. Expression of Robo4 and ARNO was verified by western blotting (data not shown). HEK 293 cells were co-transfected with GFP and the indicated constructs and 36 h later were plated on dishes coated with fibronectin and either Mock preparation or a Slit2 protein. GTP-Rac was precipitated with GST-PBD and Rac was detected with a Rac1-specific monoclonal antibody (See, FIG. 16D).

Our determination that Robo4 interacts with paxillin and inhibits protrusive activity prompted us to determine whether Robo4 impinges upon the Arf6 pathway. Cells expressing αIIb-Robo4:β3 were plated on fibronectin alone, or fibronectin and fibrinogen, and Arf6-GTP levels were analyzed using a GST-GGA3 affinity precipitation technique. While fibronectin stimulated activation of Arf6, fibrinogen reduced Arf6-GTP levels in cells expressing αIIb-Robo4:β3 (FIG. 16A). This result demonstrated that Robo4 signaling inhibits Arf6 activation and suggested that Robo4's ability to block Rac activity stems from its regulation of Arf6.

Next we analyzed the requirement of a paxillin-GIT1 complex in Robo4-dependent inhibition of protrusive activity. The paxillin binding sequence (PBS) on GIT1 is found at the carboxy-terminus of the protein and has been shown to prevent interaction of GIT1 and paxillin (Uemura et al., 2006). Cells were transfected with αIIb-Robo4:β3 and either an empty vector or the GIT1-PBS and subjected to spreading assays on fibronectin or fibronectin and fibrinogen. As described previously, cells expressing αIIb-Robo4:β3 displayed a decrease in cell area when plated on fibrinogen, but this was lost in cells transfected with the GIT1-PBS (FIG. 16B). We repeated this experiment in cells expressing full length Robo4 plated on fibronectin or fibronectin and Slit2, and similar to the chimeric receptor experiment, the GIT1-PBS prevented the Slit2-dependent decrease in cell area (FIG. 16C). These data demonstrate that a functional paxillin-GIT1 complex is required for Slit2-Robo4 signaling.

To determine whether Slit2-Robo4 signaling inhibits protrusive activity by inactivating Arf6, we co-expressed the Arf6 guanine nucleotide exchange factor ARNO with Robo4 and performed spreading assays. Overexpression of ARNO blocked the ability of Slit2 to reduce cell area, indicating that a principal effect of Slit2-Robo4 signaling is to prevent GTP-loading of Arf6 (FIG. 16C). If ARNO restored the ability of Robo4-expressing cells to spread on Slit2, we reasoned that it should likewise re-establish Rac activation in response to fibronectin. Indeed, overexpression of ARNO led to normal levels of GTP-Rac in cells plated on fibronectin and Slit2 (FIG. 16D). Together these experiments demonstrate that Slit2-Robo4 signaling inactivates Arf6, which leads to the local blockade of Rac activation and the subsequent inhibition of the membrane protrusion necessary for cell spreading and migration.

Example 13

Figure 17:
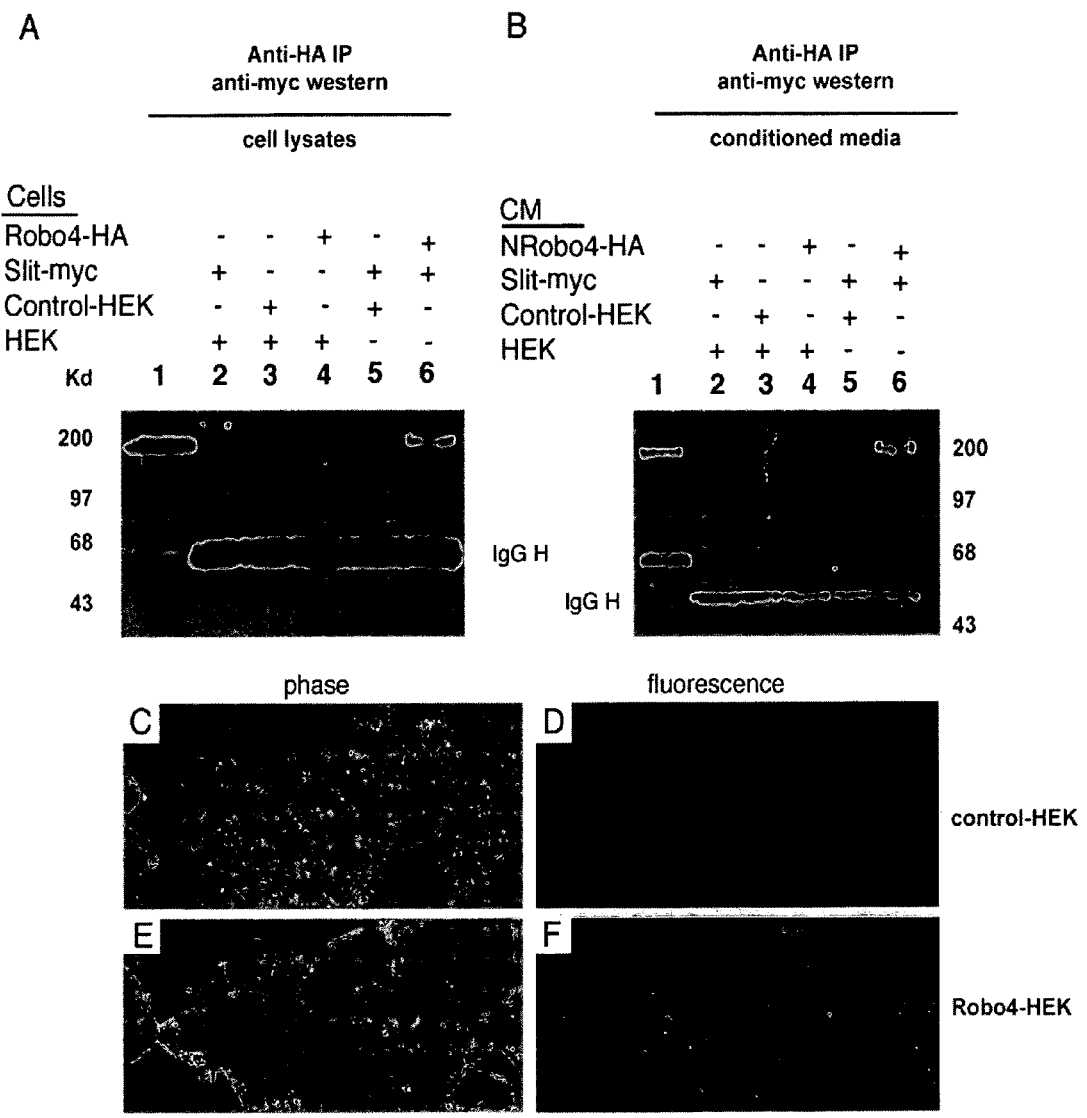
FIG. 17 illustrates the results of immunoprecipitation reactions that demonstrate the Robo4 receptor binds to the Slit ligand.
Figure 18:
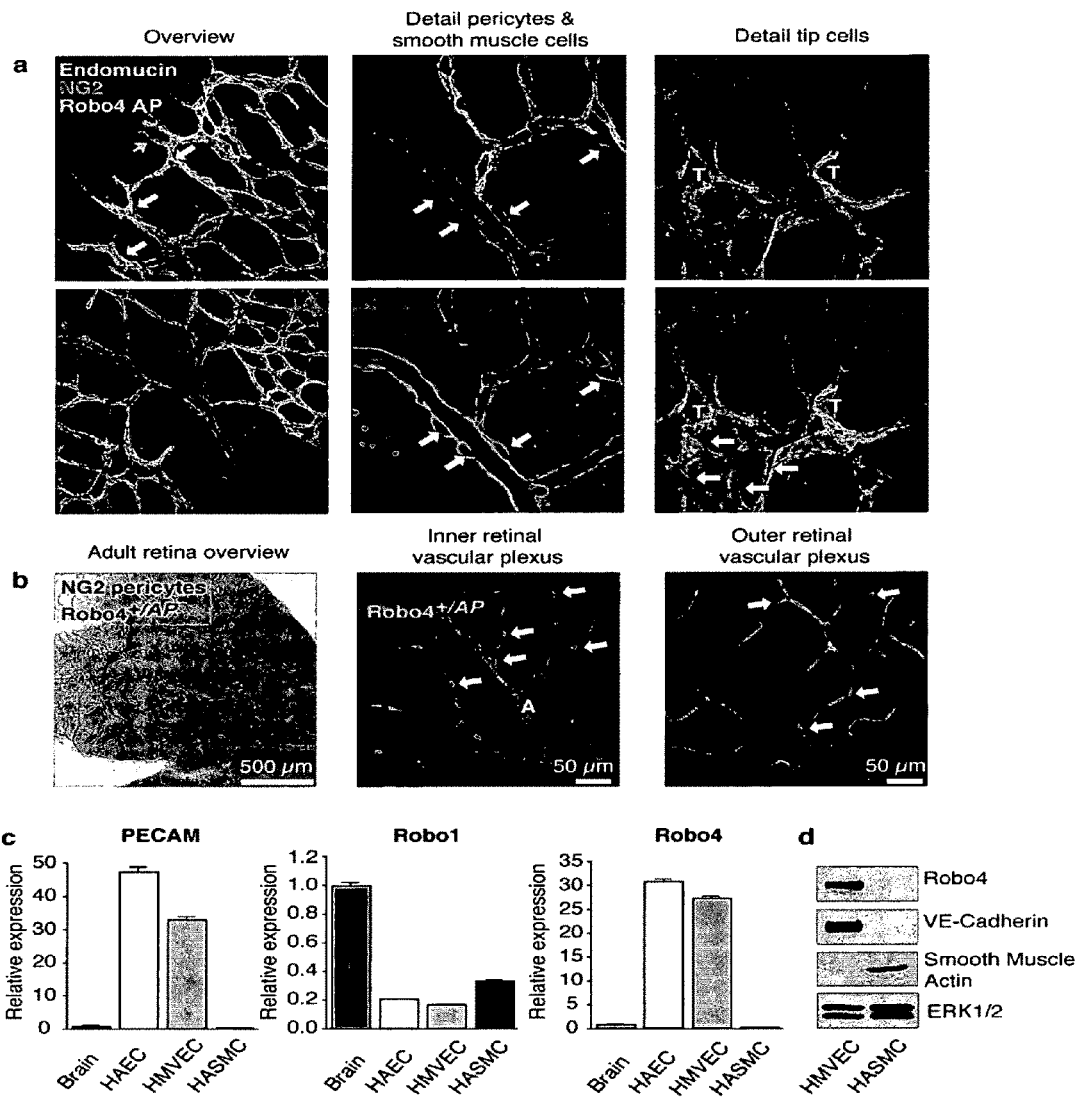
FIG. 18 illustrates that Robo4 expression is endothelial-specific and stalk-cell centric.

Immunoprecipitation Demonstrates Interaction Between Slit Ligand and Robo4 Receptor: Cell lysates from untransfected human embryonic kidney cells (HEK), HEK cells transfected with Slit tagged with a myc epitope (Slit-myc), HEK cells transfected with Robo4 tagged with a HA epitope (Robo4-HA) and HEK cells transfected with a control vector (Control-HEK) were immunopreciptated. Slit-myc protein was detected by Western blot with an anti-myc antibody after Slit-myc and Robo4-HA cell lysates were combined and immunoprecipitated with an anti-HA antibody (FIG. 17A, lane 6). The specificity of this interaction was confirmed by the absence of detectable Slit protein with all other combinations of lysates (FIG. 17A, lanes 2-5). The same amount of lysate was used in each experiment. A Western blot analysis of the Slit-myc cell lysates served as a control and demonstrated that the Slit protein has a mass of approximately 210 kD in accordance with previous reports (FIG. 17A, lane 1). The lower bands shown in lanes 2-6 of FIG. 17A correspond to immunoglobulin heavy chains.

Conditioned media from untransfected HEK cells (HEK CM), HEK cells transfected with Slit tagged with a myc epitope (Slit-myc CM), HEK cells transfected with the N-terminal soluble ectodomain of Robo4 tagged with the HA epitope (NRobo4-HA CM) and HEK cells transfected with control vector (Control-HEK CM) was also immunoprecipitated. The full-length Slit-myc protein (210 KD) and its C-terminal proteolytic fragment (70 KD) were detected in Slit-myc CM by an anti-myc antibody (FIG. 17B, lane 1). Slit-myc protein was also detected by Western blot after Slit-myc and Robo4-HA conditioned media were combined and immunoprecipitated with an anti-HA antibody (FIG. 17B, lane 6). The specificity of this interaction was confirmed by the absence of Slit protein with all other combinations of conditioned media.

As is shown in FIG. 17C through FIG. 17F, Slit protein binds to the plasma membrane of cells expressing Robo4. Binding of Slit-myc protein was detected using an anti-myc antibody and an Alexa 594 conjugated anti-mouse antibody. As can be seen in FIG. 17D and FIG. 17F, binding was detected on the surface of Robo4-HEK cells (FIG. 17F) but not Control-HEK cells (FIG. 17D).

Example 14

Figure 25:
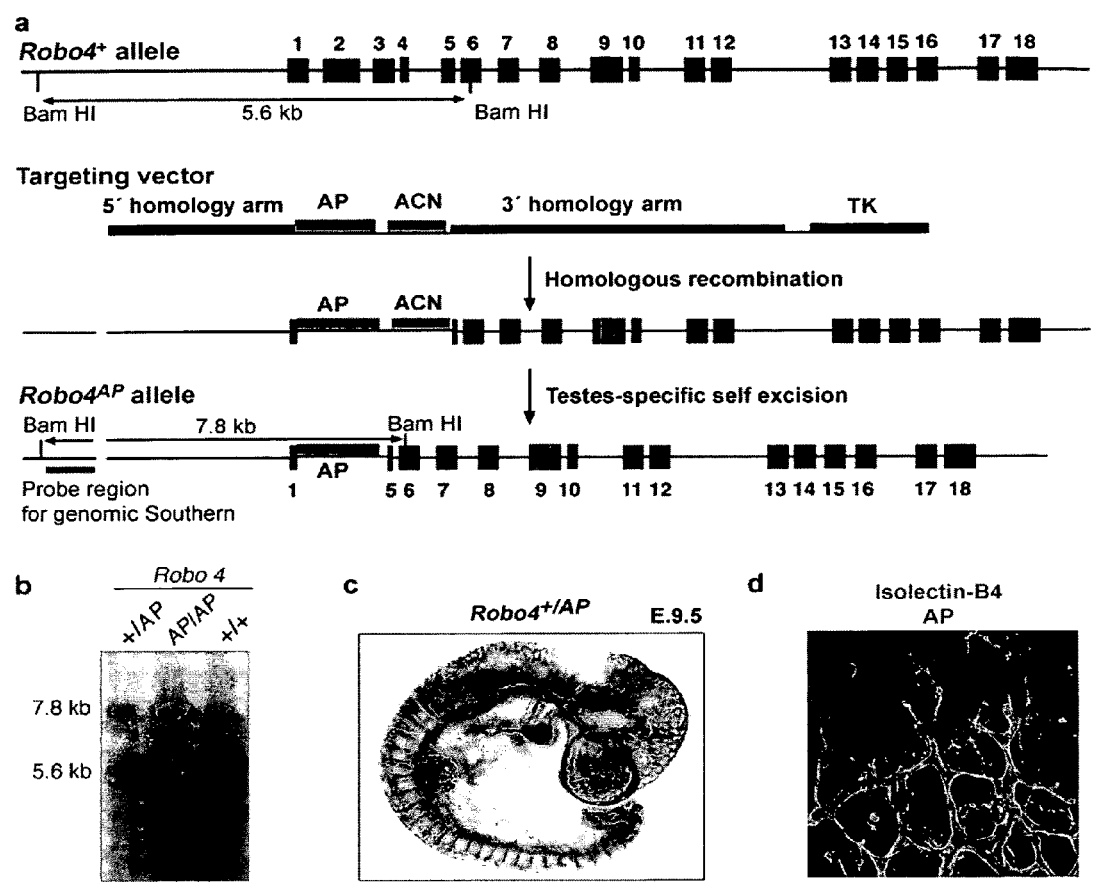
FIG. 25 illustrates the genomic traits of knockout mice described in Example 14.

Robo4 Knockout Mouse: To ascertain the functional significance of Robo4 in vivo, knockout mice were produced using standard techniques. To produce the knockout mice, exons one through five of the gene expressing Robo4 were replaced with an alkaline phosphatase (AP) reporter gene using homologous recombination. This allele, Robo4$^{AP}$, lacked the exons encoding the immunoglobulin (IgG) repeats of the Robo4 ectodomain, which are predicted to be required for interaction with Slit proteins. The Robo4$^{+/AP}$ animals were intercrossed to generate mice that were homozygous for the targeted allele. An illustration of the genomic structure of the mice is provided in FIG. 25. Robo4$^{AP/AP}$ animals were viable and fertile, and exhibited normal patterning of the vascular system. These data indicate that Robo4 is not required for sprouting angiogenesis in the developing mouse, and point to an alternate function for Robo4 signaling in the mammalian endothelium. Alkaline phosphatase activity was detected in these animals throughout the endothelium of all vascular beds in the developing embryos and in the adult mice, which confirmed that the Robo4$^{AP}$ allele is a valid marker of Robo4 expression.

Example 15

Robo4 Activation Stabilizes Mature Vessels: The central region of the murine retinal vascular plexus, comprised specifically of stalk cells, is an example of the differentiated/stabilized phenotype characteristic of a mature, lumenized vascular tube. We reasoned, therefore, that Robo4 expression in the stalk might maintain this phenotype by inhibiting processes that are stimulated by pro-angiogenic factors, such as VEGF-A. The effect of Robo4 signaling on processes stimulated by VEGF-A was evaluated using a VEGF-A endothelial cell migration assay and a VEGF-A tube formation assay. Both such assays are routinely used to investigate angiogenesis in vitro.

Figure 19:
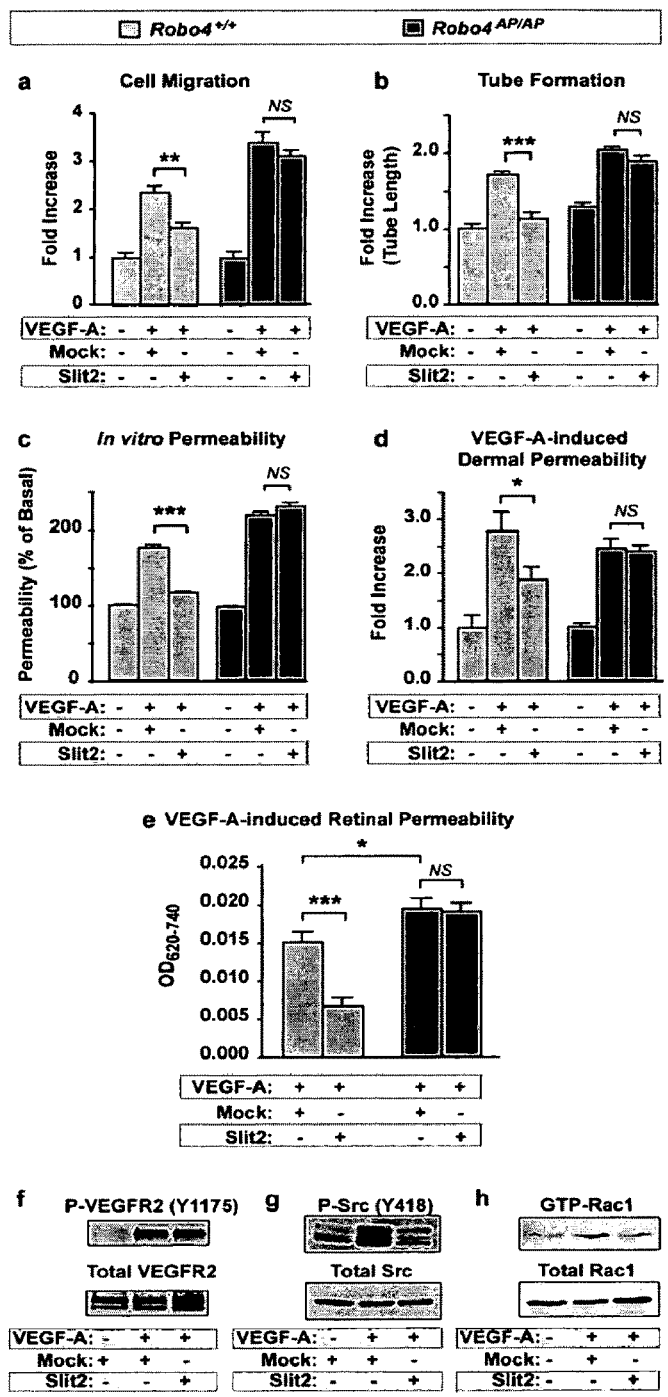
FIG. 19 illustrates that Robo4 signaling inhibits VEGF-A-induced migration, tube formation, permeability and Src family kinase (SFK) activation. Lung endothelial cells (ECs) isolated from Robo4$^{+/+}$ and Robo4$^{AP/AP}$ mice were used in endothelial cell migration (FIG. 19A), tube formation (FIG. 19B), in vitro permeability (FIG. 19C), Miles assay (FIG. 19D) and retinal permeability assay (FIG. 19E). Human microvascular endothelial cells were stimulated with VEGF-A in the presence of a Mock preparation or a Slit2 protein for 5 minutes, lysed and subjected to western blotting with phospho-VEGFR2 antibodies (FIG. 19F), western blotting with phospho-Src antibodies (FIG. 19G) and Rac activation assays (FIG. 19H). In all panels, * represents p<0.05,  represents p<0.005, * represents p<0.0005, NS indicates "not significant" and error bars represent SEM.

In order to conduct the endothelial cell migration and tube formation assays, endothelial cells from the lungs of Robo4$^{+/+}$ and Robo4$^{AP/AP}$ mice were isolated and their identity confirmed using immunocytochemistry and flow cytometry. These cells were then utilized in VEGF-A-dependent endothelial cell migration and tube formation assays. The Slit2 molecule used in these assays was Slit2N (SEQ ID NO: 39). As is shown in FIG. 19A and FIG. 19B, Slit2 inhibited both migration and tube formation of Robo4$^{+/+}$ endothelial cells. However, the inhibitory activity of Slit2 was lost in Robo4$^{AP/AP}$ endothelial cells. These results demonstrate that Slit2 inhibits endothelial cell migration and tube formation in a Robo4-dependent manner, and indicate that activation of Robo4 by Slit2 serves to stabilize the vascular endothelium of mature vessels.

Example 16

Robo4 Activation Preserves Endothelial Barrier Function: In a mature vascular bed, endothelial cells do not behave independently of one another; rather they form a monolayer that prevents the movement of protein, fluid and cells from the endothelial lumen into the surrounding tissue. This barrier function was modeled in vitro using a Transwell assay to analyze the transport of horseradish peroxidase (HRP), across confluent cell monolayers of endothelial cells taken from the lungs of Robo4$^{+/+}$ and Robo4$^{AP/AP}$ mice. Stimulation of Robo4$^{+/+}$ and Robo4$^{AP/AP}$ endothelial cells with VEGF-A, a known permeability-inducing factor, enhanced the accumulation of HRP in the lower chamber of the Transwell. As is shown in FIG. 19C, however, pre-treatment of the cell monolayers with a Slit2 protein (Slit2N (SEQ ID NO: 39)) prevented this effect in Robo4$^{+/+}$, but not Robo4$^{AP/AP}$ endothelial cells.

Next, the influence of Slit2 on endothelial barrier function in vivo was evaluated. A Miles assay was performed by injecting Evans Blue into the tail vein of Robo4$^{+/+}$ and Robo4$^{AP/AP}$ mice. VEGF-A in the absence and presence of a Slit2 protein (Slit2N (SEQ ID NO: 39)) was subsequently injected into the dermis. Analogous to the in vitro assay, VEGF-A-stimulated leak of Evans Blue into the dermis could be prevented by concomitant administration of Slit2 protein in Robo4$^{+/+}$, but not in Robo4$^{AP/AP}$ mice (shown in FIG. 19D). These observations were extended by evaluating the ability of Slit2 to suppress VEGF-A induced hyperpermeability of the retinal endothelium. In particular, it was found that intravitreal injection VEGF-A in Robo4$^{+/+}$ mice induced leak of Evans Blue from retinal blood vessels. However, such VEGF-A induced leak of Evans Blue from the retinal blood vessels was suppressed in Robo4$^{+/+}$ mice by co-injection of the Slit2 protein Slit2N (SEQ ID NO: 39) (FIG. 19E). This experiment was repeated in retinas of Robo4$^{AP/AP}$ mice, and it was found that Robo4$^{AP/AP}$ were refractory to treatment with Slit2N (SEQ ID NO: 39). These data demonstrate that Robo4 mediates Slit2-dependent inhibition of VEGF-A-induced endothelial hyperpermeability in vitro and in vivo.

Example 17

Robo4 Blocks VEGF Signaling Downstream of the VEGF Receptor: The ability of VEGF-A to promote angiogenesis and permeability is dependent upon activation of VEGFR2, which occurs by autophosphorylation following ligand binding. Subsequently, a number of non-receptor tyrosine kinases, serine/threonine kinases and small GTPases are activated to execute VEGF-A signaling in a spatially and temporally specific manner. To determine where Slit2-Robo4 signaling intersects the VEGF-A-VEGFR2 pathway, VEGFR2 phosphorylation following stimulation with VEGF-A and Slit2 was analyzed using Slit2N (SEQ ID NO: 39). Slit2N (SEQ ID NO: 39) had no effect on VEGF-A-induced VEGFR2 phosphorylation (FIG. 19F), indicating that the Slit2-Robo4 pathway must intersect VEGF-A signaling downstream of the receptor. Attention was then focused on the Src family of non-receptor tyrosine kinases, Fyn Yes and Src, due to their well-documented role in mediating VEGF-A-induced angiogenesis and permeability (Eliceiri et al., 2002; Eliceiri et al., 1999). Treatment of endothelial cells with Slit2N (SEQ ID NO: 39) reduced VEGF-A-stimulated phosphorylation of c-Src (FIG. 19G). Recently, several reports have shown that Src-dependent activation of the Rho family small GTPase, Rac1, is essential for VEGF-A-induced endothelial cell migration and permeability (Gavard et al., 2006; Garrett et al., 2007). Treatment of endothelial cell monolayers with Slit2N (SEQ ID NO: 39) prevented VEGF-A-dependent Rac1 activation (FIG. 19H). These biochemical experiments indicate that the Slit2-Robo4 pathway suppresses VEGF-A-induced endothelial migration and hyperpermeability via inhibition of an Src-Rac1 signaling axis.

Example 18

Figure 20:
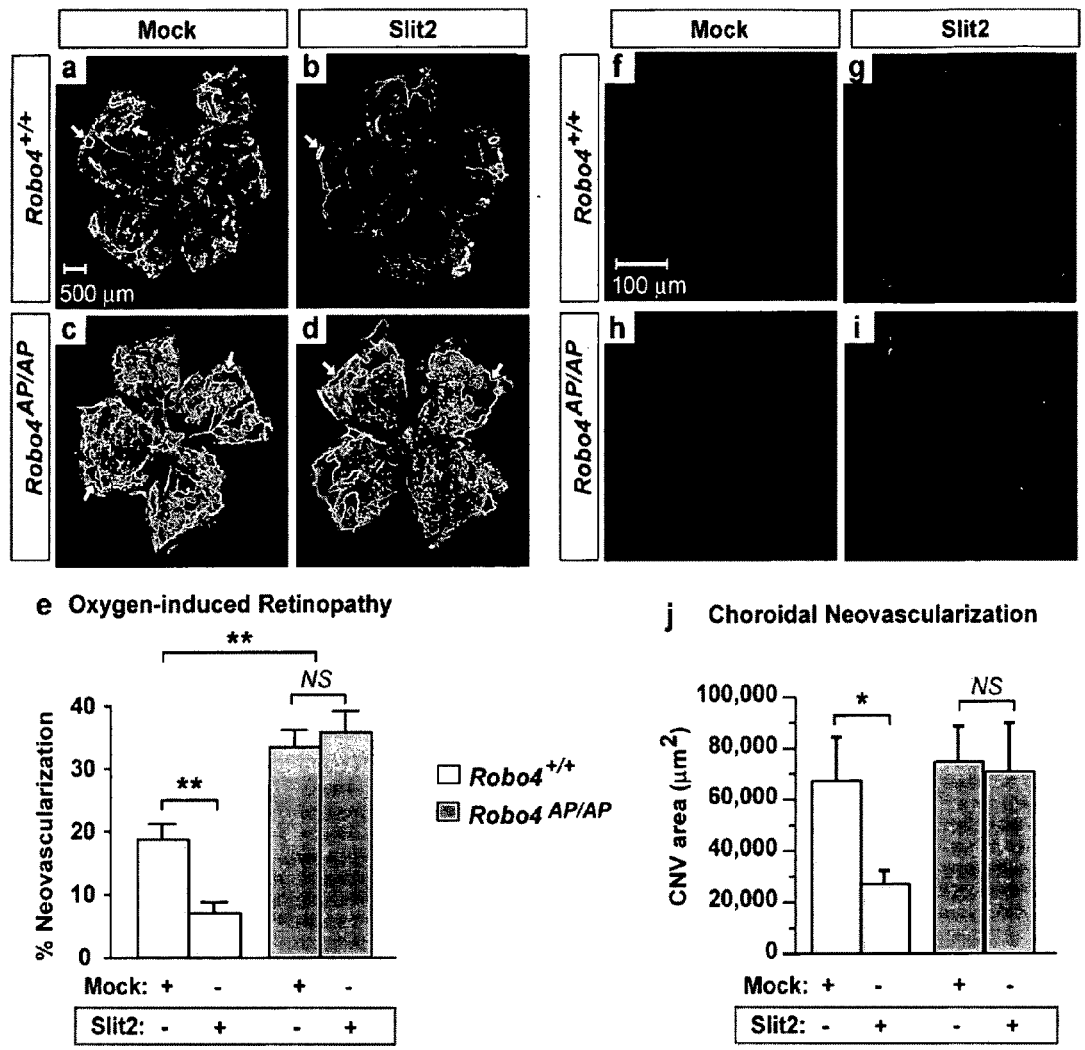
FIG. 20 illustrates that Robo4 signaling inhibits pathologic angiogenesis in an animal model of oxygen-induced retinopathy ("OIR") and in an animal model of choroidal neovascularization ("CNV"). Neonatal Robo4$^{+/+}$ and Robo4$^{AP/AP}$ mice were subjected to oxygen-induced retinopathy and perfused with fluorescein isothiocyanate (FITC)-dextran (green). Retinal flatmounts were prepared for each condition and analyzed by fluorescence microscopy. Arrows indicate areas of pathological angiogenesis (FIG. 20A through FIG. 20D). Quantification of pathologic angiogenesis observed in FIG. 20A through FIG. 20D is provided in FIG. 20 E. In the CNV model, 2-3 month old Robo4$^{+/+}$ and Robo4$^{AP/AP}$ mice were subjected to laser-induced choroidal neovascularization. Choroidal flatmounts were prepared, stained with isolectin and analyzed by confocal microscopy (FIG. 20F through FIG. 20I). Quantification of pathologic angiogenesis observed in FIG. 20F through FIG. 20I is provided in FIG. 20J. In all panels, * represents p<0.05,  represents p<0.005, * represents p<0.0005, NS indicates "not significant" and error bars represent SEM.

Activation of Robo4 Reduces Vascular Leak and Pathologic Angiogenesis in CNV and OIR Models: A murine model of oxygen-induced retinopathy (OIR) that mimics the ischemia-induced angiogenesis observed in both diabetic retinopathy and retinopathy of prematurity was used to investigate the effect of Robo4 signaling on retinal vascular disease. In this model, P7 mice were maintained in a 75% oxygen environment for five days and then returned to 25% oxygen for an additional five days. The perceived oxygen deficit initiates a rapid increase in VEGF-A expression in the retina, leading to pathological angiogenesis (Ozaki et al., 2000; Werdich et al., 2004. Robo4$^{+/+}$ mice and Robo4$^{AP/AP}$ mice were evaluated using this model. Intravitreal administration of Slit2N (SEQ ID NO: 39). markedly reduced angiogenesis in Robo4$^{+/+}$ mice, but not in Robo4$^{AP/AP}$ mice (FIG. 20A-FIG. 20E, where arrows indicate areas of pathological angiogenesis). Furthermore, Robo4$^{AP/AP}$ mice displayed more aggressive angiogenesis than Robo4$^{+/+}$ mice following exposure to hyperoxic conditions (See, e.g., FIGS. 20A and 20C).

In addition to the described OIR model, laser-induced choroidal neovascularization, which mimics age-related macular degeneration, is commonly used to study pathological angiogenesis in the mouse (Lima et al., 2005). In this model, a laser is used to disrupt Bruch's membrane, which allows the underlying choroidal vasculature to penetrate into the subretinal pigment epithelium. To discern the effect of Robo4 signaling on this pathological process, 8-12 week old Robo4$^{+/+}$ and Robo4$^{AP/AP}$ mice were subjected to laser-induced choroidal neovascularization followed by intravitreal injection of Slit2N (SEQ ID NO: 39). Similar to the results achieved in the mouse model of oxygen-induced retinopathy, intravitreal administration of Slit2N reduced angiogenesis in Robo4$^{+/+}$ mice, but not in Robo4$^{AP/AP}$ mice (See FIG. 20F-FIG. 20J). Together, the oxygen-induced retinopathy and choroidal neovascularization models indicate that two vascular beds with distinct characteristics, one a tight blood-brain barrier and the other a fenestrated endothelium, are protected from pathological insult by activation of Slit2-Robo4 signaling.

Example 19

Figure 21:
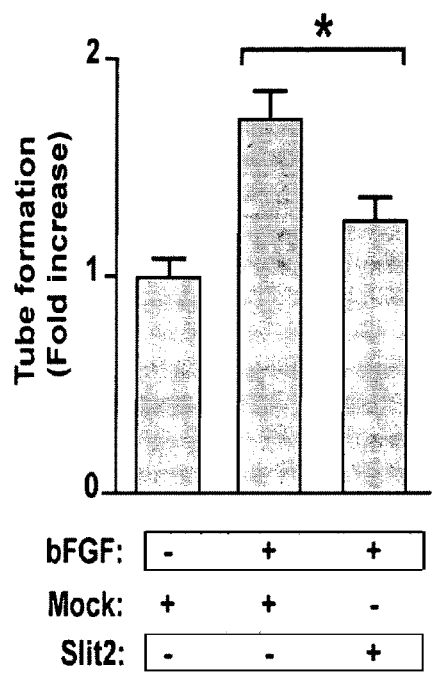
FIG. 21 illustrates that Robo4 signaling inhibits bFGF-induced angiogenesis and thrombin-stimulated endothelial hyperpermeability. In carrying out the experiments that provided the results illustrated in FIG. 21A, murine lung endothelial cells were subjected to tube formation assays on matrigel in the presence of bFGF and Mock preparation or a Slit2 protein. In carrying out the experiments that provided the results illustrated in FIG. 21B, muring lung endothelial cells were subjected to thrombin-induced permeability assays on fibronectin-coated Transwells.
Figure 21:
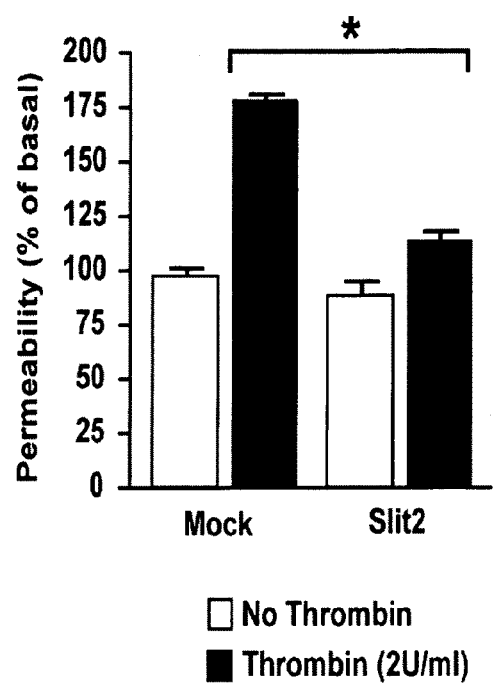

Robo4 Inhibits Signaling From Multiple Factors That Destabilize the Mature Vessel: The effect of Robo4 activation by a Slit2 molecule on the activity of bFGF, and angiogenic factor, and thrombin, the endothelial permeability factor, was evaluated. As shown in FIG. 21, Slit2N (SEQ ID NO: 39) blocked bFGF-induced endothelial tube formation and thrombin-induced permeability. These studies demonstrate that Slit-Robo4 signaling is capable of inhibiting the signaling induced by multiple angiogenic and permeability factors and support the concept that the Slit-Robo4 pathway protects the mature vascular beds from multiple angiogenic, permeability and cytokine factors.

Figure 22:
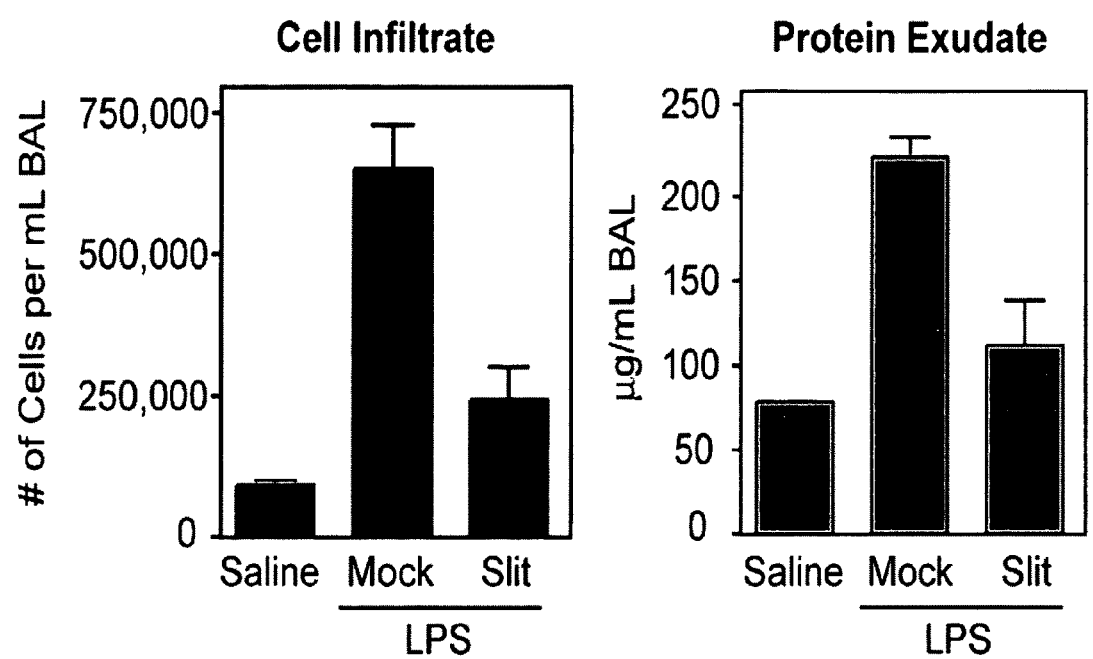
FIG. 22 illustrates that Robo4 signaling reduces injury and inflammation in a model of acute lung injury. Mice were exposed to intratracheal LPS and treated with either Slit protein or a Mock preparation. The concentrations of inflammatory cells and protein in bronchoalveolar lavages (BAL) were significantly reduced by treatment with Slit protein.

To reinforce that Robo4 signalizing protects vasculature from multiple angiogenic, permeability and cytokine factors, the effect of Robo4 activation by Slit2N (SEQ ID NO: 39) was evaluated in a mouse model of acute lung injury. In this model, the bacterial endotoxin LPS was dosed to the mice via intratracheal administration. Exposure to the bacterial endotoxin leads to a cytokine storm that causes catastrophic destabilization of the pulmonary vascular bed and results in non-cardiogenic pulmonary edema (Matthay et al., 2005). Following intratracheal administration of LPS, the mice were treated with Slit2N (SEQ ID NO: 39) or Mock preparation, which was a sham protein extract that served as a control. As shown in FIG. 22, the concentrations of inflammatory cells and protein in bronchoalveolar lavages (BAL) from mice treated with Slit2N (SEQ ID NO: 39) were significantly lower than in the mice treated with the Mock preparation. These results demonstrate that activating Robo4 under these circumstances provides potent vascular stabilization and suggest that Slit2-Robo4 is a potent vascular stabilization pathway that works to preserve the integrity of the mature endothelium and maintain vascular homeostasis against an extreme form of cytokine storm.

Example 20

Administration of Slit2 Protein Reduces Mortality in Mouse Model of Avian Flu: In the following example, the effect of Slit protein on the survival of mice infected with Avian Flu Virus was analyzed. A total of 120 female BALB/c mice were inoculated intranasally with 50 µl of a 1:400 dilution of the Avian Flu Virus, strain H5N1/Duck/Mn/1525/81. The mice used in this example were obtained from Charles River and had an average weight ranging from 18-20 grams. With reference to Table 2, the mice were randomly divided into 6 cages of 20 mice each, and each group were subjected to daily treatments for 5 days. Survivorship (death) and body weight were observed during and after treatment.

TABLE 2

| # mice/Cage | Group # | Infected y or n | Compound | Dosage | Treatment Schedule |
|---|---|---|---|---|---|
| 20 | 1 | Y | PSS | 50 μl volume | Qd X 4 or 5 (5 if possible) beg −4 before virus exposure, IV. |
| 20 | 2 | Y | SLIT "Mock" 1 | 15.625 μl SLIT/Mock + 34.375 μl PSS per mouse | Same as # 1 |
| 20 | 3 | Y | SLIT "Mock" 2 | 1.5625 μl SLIT/Mock + 48.44 μl PSS per mouse | Same as # 1 |
| 20 | 4 | Y | SLIT - Conc. 1 | 15.625 μl of 800 μg/ml SLIT + 34.375 μl PSS per mouse | Same as # 1 |
| 20 | 5 | Y | SLIT - Conc. 2 | 1.5625 μl of 800 μg/ml SLIT + 48.44 μl PSS per mouse | Same as # 1 |
| 20 | 6 | Y | Ribavirin | 75 mg/kg/day | 0.1 ml I.P. BID X 5 days |

Briefly, as shown in Table 2, Group 1 was treated with physiological saline solution (PSS) a negative control. Groups 2 and 3 were treated with a Mock preparation. Groups 4 and 5 were treated with different concentrations of a Slit protein (Slit2N (SEQ ID NO: 39)). As a positive control, the 20 mice of group 6 were treated with intraperitoneally with 75 mg/kg/day of Ribavirin brought up in a total volume of 0.1 mL PSS.

Figure 24:
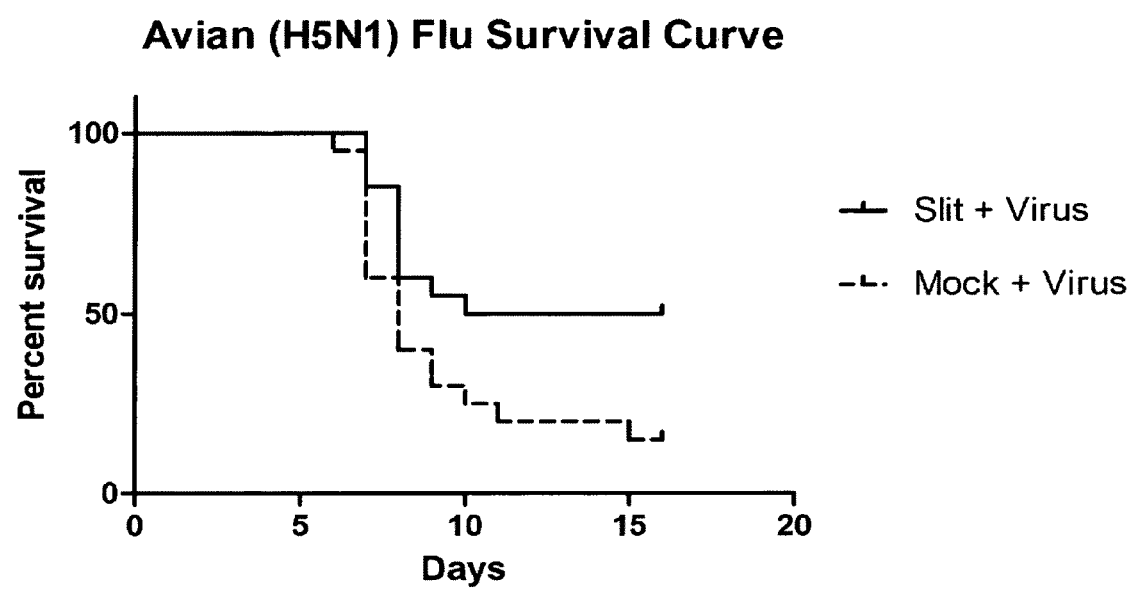

The results of the analysis are illustrated in FIG. 24 and detailed in Table 3. After 23 days, the mice treated with Slit protein in Groups 4 and 5 had a lower mortality than those mice that did not receive Slit protein in Groups 1, 2, and 3. The Group 4 mice, treated with 12.5 μg of Slit per dose, had a 25% survivability rate. The Group 5 mice, treated with 1.25 μg of Slit per dose, had a 50% survivability rate. In contrast to the survivorship of Groups 4 and 5, only 5% (1/20) of the negative control mice in Group 1, treated with PSS, survived past 23 days.

Table 3 shows that at 14 days after inoculation, the average body weights of the survivors in Groups 1, 2, and 3 were significantly lower than the Slit treated survivors in Groups 4 and 5. Moreover, 10/20 mice in Group 5, which was the lower of the Slit treatment concentrations, survived with body weights averaging 17.6 grams at 21 days, nearly as high as the starting average body weight of 17.7 grams. Therefore, those infected mice treated with Slit protein were able to maintain their body weights better than the untreated mice.

TABLE 3

| | Day | 0 | 1 | 2 | 3 | 4 | 5 | 6 | 7 | 8 | 9 |
|---|---|---|---|---|---|---|---|---|---|---|---|
| Cage #1 | Alive | 20 | 20 | 20 | 20 | 20 | 19 | 17 | 11 | 8 | 3 |
| | Total | 20 | 20 | 20 | 20 | 20 | 20 | 20 | 20 | 20 | 20 |
| | Av. Wt. | 17.6 | | | | | | | | | |
| Cage #2 | Alive | 20 | 20 | 20 | 20 | 20 | 20 | 19 | 14 | 7 | 3 |
| | Total | 20 | 20 | 20 | 20 | 20 | 20 | 20 | 20 | 20 | 20 |
| | Av. Wt. | 17.6 | | | | | | | | | |
| Cage #3 | Alive | 20 | 20 | 20 | 20 | 20 | 20 | 19 | 12 | 8 | 6 |
| | Total | 20 | 20 | 20 | 20 | 20 | 20 | 20 | 20 | 20 | 20 |
| | Av. Wt. | 17.6 | | | | | | | | | |
| Cage #4 | Alive | 20 | 20 | 20 | 20 | 20 | 20 | 17 | 13 | 10 | 7 |
| | Total | 20 | 20 | 20 | 20 | 20 | 20 | 20 | 20 | 20 | 20 |
| | Av. Wt. | 17.4 | | | | | | | | | |
| Cage #5 | Alive | 20 | 20 | 20 | 20 | 20 | 20 | 20 | 17 | 12 | 11 |
| | Total | 20 | 20 | 20 | 20 | 20 | 20 | 20 | 20 | 20 | 20 |
| | Av. Wt. | 17.7 | | | | | | | | | |
| Cage #6 | Alive | 20 | 20 | 20 | 20 | 20 | 20 | 20 | 20 | 20 | 20 |
| | Total | 20 | 20 | 20 | 20 | 20 | 20 | 20 | 20 | 20 | 20 |
| | Av.Wt. | 17.5 | | | | | | | | | |

| | | 10 | 11 | 12 | 13 | 14 | 15 | 16 | 17 | 18 | 19 | 20 | 21 | 22 | 23 |
|---|---|---|---|---|---|---|---|---|---|---|---|---|---|---|---|
| Cage #1 | Alive | 2 | 2 | 1 | 1 | 1 | 1 | 1 | 1 | 1 | 1 | 1 | 1 | 1 | 1 |
| | Total | 20 | 20 | 20 | 20 | 20 | 20 | 20 | 20 | 20 | 20 | 20 | 20 | 20 | 20 |
| | Av. Wt. | | | | | 12.5 | | | | | | | 16.0 | | |
| Cage #2 | Alive | 2 | 2 | 2 | 2 | 2 | 2 | 2 | 2 | 2 | 2 | 2 | 2 | 2 | 2 |
| | Total | 20 | 20 | 20 | 20 | 20 | 20 | 20 | 20 | 20 | 20 | 20 | 20 | 20 | 20 |
| | Av. Wt. | | | | | 12.5 | | | | | | | 15.3 | | |
| Cage #3 | Alive | 5 | 4 | 4 | 4 | 4 | 3 | 3 | 3 | 3 | 3 | 3 | 3 | 3 | 3 |
| | Total | 20 | 20 | 20 | 20 | 20 | 20 | 20 | 20 | 20 | 20 | 20 | 20 | 20 | 20 |
| | Av. Wt. | | | | | 13.0 | | | | | | | 16.1 | | |

TABLE 3-continued

| | | | | | | | | | | | | | | | |
|---|---|---|---|---|---|---|---|---|---|---|---|---|---|---|---|
| Cage #4 | Alive | 6 | 5 | 5 | 5 | 5 | 5 | 5 | 5 | 5 | 5 | 5 | 5 | 5 | 5 |
| | Total | 20 | 20 | 20 | 20 | 20 | 20 | 20 | 20 | 20 | 20 | 20 | 20 | 20 | 20 |
| | Av. Wt. | | | | | 16.0 | | | | | | | 18.5 | | |
| Cage #5 | Alive | 10 | 10 | 10 | 10 | 10 | 10 | 10 | 10 | 10 | 10 | 10 | 10 | 10 | 10 |
| | Total | 20 | 20 | 20 | 20 | 20 | 20 | 20 | 20 | 20 | 20 | 20 | 20 | 20 | 20 |
| | Av. Wt. | | | | | 15.4 | | | | | | | 17.6 | | |
| Cage #6 | Alive | 20 | 20 | 20 | 20 | 20 | 20 | 20 | 20 | 20 | 20 | 20 | 20 | 20 | 20 |
| | Total | 20 | 20 | 20 | 20 | 20 | 20 | 20 | 20 | 20 | 20 | 20 | 20 | 20 | 20 |
| | Av.Wt. | | | | | 17.2 | | | | | | | 18.3 | | |

Example 21

Figure 23:
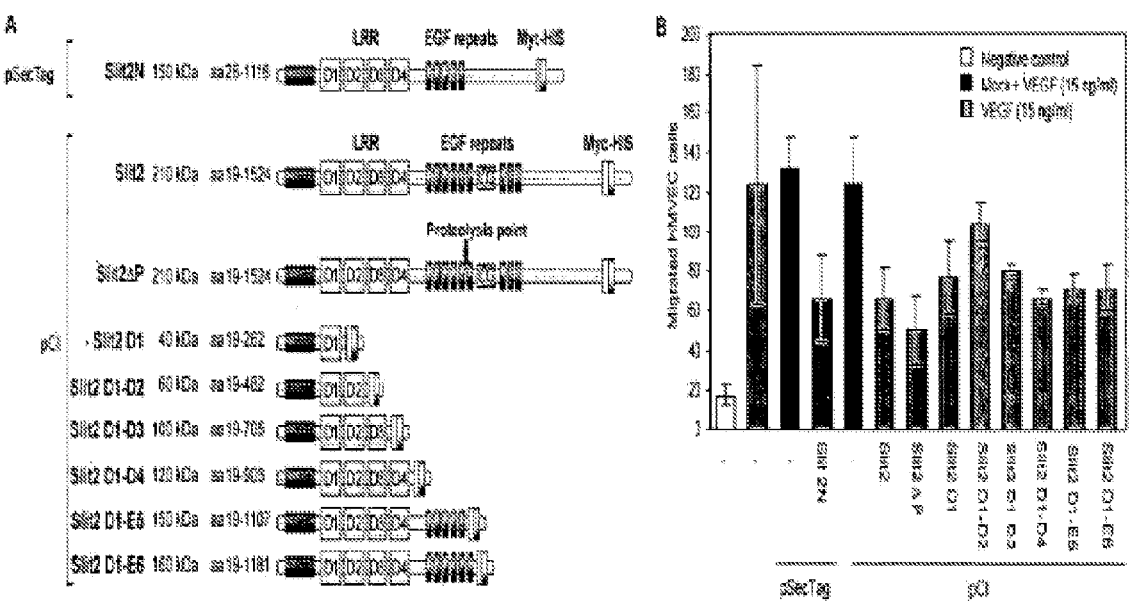
FIG. 23 illustrates different constructs for Slit proteins and shows that recombinant Slit peptides as small as Slit2-D1 (40 kD) are active.

Fragments of Slit Proteins Work to Activate Robo4: FIG. 23 illustrates various constructs of the Slit2 protein. As has already been described herein, the 150 kD protein Slit2N (SEQ ID NO: 39), has been found to be effective in in vitro and in vivo models, including Miles assays, assays for retinal permeability, tube formation and endothelial cell migration and in OIR and CNV models of ocular disease. Moreover, as is shown in FIG. 23, the (40 kD) protein SlitD1 (SEQ ID NO: 42) and Slit2N (SEQ ID NO: 39) constructs exhibits similar activity to full length Slit2 (SEQ ID NO: 40) in a VEGF-induced endothelial cell migration assay.

Materials and Methods

Reagents: HEK 293 and COS-7 cells, and all IMAGE clones were from ATCC. SP6 and T7 Message Machine kits were from Ambion. HUVEC, EBM-2 and bullet kits were from Cambrex. Yeast two-hybrid plasmids and reagents were from Clontech. FBS was from Hyclone. Anti-HA affinity matrix, Fugene6 and protease inhibitor cocktail were from Roche. Goat Anti-Mouse-HRP and Goat Anti-Rabbit-HRP secondary antibodies were from Jackson ImmunoResearch. Anti-V5 antibody, DAPI, DMEM, Lipofectamine 2000, Penicillin-Streptomycin, Superscript III kit, Trizol and TrypLE Express were from Invitrogen. Anti-Flag M2, Phosphatase Inhibitor Cocktails, Soybean Trypsin Inhibitor and Fatty acid-free Bovine Serum Albumin (BSA) were from Sigma. Human fibronectin was from Biomedical Technologies and Invitrogen. Costar Transwells and Amicon Ultra-15 Concentrator Columns were from Fisher. Rosetta2 *E. coli* were from Novagen. Glutathione-Sepharose 4B, parental pGEX-4T1 and ECL PLUS were from Amersham-Pharmacia. Coomassie Blue and PVDF were from BioRad. Quick change site-directed mutagenesis kit was from Stratagene. Normal Rat IgGagarose conjugate was from Santa Cruz. Robo4 morpholinos were from Gene Tools. Oligonucleotides for PCR were from the University of Utah Core Facility. Alexa564-Phalloidin, Anti-GFP and Goat Anti-Rabbit Alex488 were from Molecular Probes. Low melt agarose was from NuSieve. T7 in vitro transcription/translation kit was form Promega.

Molecular Biology: The Robo4-HA, Slit2-Myc-His and chicken paxillin plasmids have been previously described (Park et al., 2003; Nishiya et al., 2005). Robo4-NH2 was amplified from Robo4-HA and cloned into EcoRV/NotI of pcDNA3-HA. Robo4-COOH was amplified from Robo4-HA by overlap-extension PCR and cloned into EcoRV/NotI of pcDNA3-HA. The amino terminal half of the human Robo4 cytoplasmic tail (AA 465-723) was amplified by PCR and cloned into (EcoRI/BamHI) of pGBKT7. Murine Robo4 fragments were amplified by PCR and cloned into BamHI/EcoRI of pGEX-4T1. Murine Hic-5, Mena and paxillin (including deletions) were amplified from IMAGE clones by PCR and cloned into EcoRV/NotI of pcDNA3-V5. GST-Robo4ΔPIM and full-length Robo4ΔPIM were generated by site-directed mutagenesis of relevant wild-type constructs using Quick Change. The integrity of all constructs was verified by sequencing at the University of Utah Core Facility.

Embryo Culture and Zebrafish Stocks: Zebrafish, Danio rerio, were maintained according to standard methods (Westerfield, 2000). Developmental staging was carried out using standard morphological features of embryos raised at 28.5° C. (Kimmel et al., 1995). The Tg (fli:EGFP)$^{y1}$ transgenic zebrafish line used in this study was described in Lawson and Weinstein, 2002. Imaged embryos were treated with 0.2 mM 1-phenyl-2-thio-urea (PTU) after 24 hpf to prevent pigment formation.

Antisense Depletion of robo4: Antisense morpholino oligonucleotides (MO) directed against the exon 10/intron 10 splice site of robo4 (5'-tttttagcgtacctatgagcagtt-3', SEQ ID NO:28) were dissolved in 1× Danieau's Buffer at a concentration of 5 ng/nl, respectively. Before injection, the morpholino was heated at 65° C. for 5 minutes, cooled briefly, mixed with a negligible amount of dye to monitor injection efficiency, and approximately 1 nl was injected into the streaming yolk of 1-2 cell stage embryos.

Reverse Transcription (RT) PCR: RNA was extracted from 20 uninjected and 20 robo4 MO-injected embryos using Trizol, reagent and subsequent cDNA synthesis was performed using Superscript III primed by a mixture of both random hexamers and oligo dT primers. robo4 was amplified from cDNA by PCR with a forward primer in exon 8 (5'-caacacca-gacacttacgagtgcc-3', SEQ ID NO:29) and a reverse primer in exon 12 (5'-ttcgaaggccagaattctcctggc-3', SEQ ID NO:30) using the following parameters: (94° C. for 4', 94° C. for 30", 58° C. for 30", 68° C. for 45", 68° C. for 1'). To identify the linear range of the PCR reaction, cDNA was amplified for 23, 25, 27 and 30 cycles. β-actin was amplified using a forward primer (5'-cccaaggccaacagggaaaa, SEQ ID NO:31) and a reverse primer (5'-ggtgcccatctcctgctcaa-3', SEQ ID NO:32) from all samples to control for cDNA input.

Whole-Mount Indirect Immunofluorescence: Briefly, age-matched 24 and 48 hpf embryos were dechorionated and fixed in 4% PFA/4% sucrose/PBS overnight at 4° C. The embryos were then washed in PBS/0.1% Tween-20, dehydrated to absolute methanol, re-hydrated back to PBS-Tween 20, further permeabilized in PBS/1% Triton-X, rinsed in PBS/1% Triton-X/2% BSA, blocked at room temperature in PBS/1% Triton-X/2% BSA/10% Sheep Serum/1% DMSO, then incubated in IgG purified anti-GFP (1:400) in blocking solution overnight at 4° C. The following day embryos were washed vigorously in PBS/1% Triton-X/2% BSA, then incubated in goat-anti-Rabbit Alexa 488 conjugated secondary antibody (1:200) in blocking solution overnight at 4° C. The following day the embryos were washed extensively in PBS/1% Triton-X/2% BSA, then embedded in 1% low melt agarose in PBS and photographed on Leica confocal microscope and processed using Adobe Photoshop software.

Cell Culture: HEK 293 and COS-7 cells were cultured in DMEM supplemented with 10% FBS and 1% penicillin/ streptomycin. Human umbilical vein endothelial cells (HUVEC) were cultured in EGM-2 supplemented with 10% FBS. HUVEC were routinely used between passages 2 and 5.

Transfection: HEK293 and COS-7 cells were transfected with Fugene6 or Lipofectamine-2000 according to the manufacturer's protocol.

Preparation of Concentrated Slit2 Protein: COS-7 cells were transiently transfected with empty pSECTAG2 or pSECTAG2::hSlit2. Forty-eight hours later, the cells were washed twice with PBS and incubated with 6 ml salt extraction buffer (10 mM HEPES, pH 7.5, 1M NaCl and 1× protease inhibitors) for 15 minutes at 25° C. Salt extraction was repeated and the samples were centrifuged at 10,000 rpm for 20 minutes to pellet cell debris. The supernatant was loaded on Amicon Ultra-15 concentrator columns/100 kDa cutoff and centrifuged until 12 ml of salt extracts was reduced to approximately 500 µl. The concentrated protein preparations were analyzed by Coomassie Blue staining, and stored at 4° C. for up to one week. Using this protocol, Slit2 concentrations of 20-50 µg/ml were routinely obtained. In addition to preparing concentrated protein from cells transfected with Slit2 plasmid, the identical protocol was performed on cells transfected with an empty vector (pSECTAG2). This resulting preparation was referred to as a "Mock" preparation, and it was used as a control in all experiments analyzing the effect of Slit2.

Haptotaxis Migration Assay: Transfected HEK 293 cells were removed from tissue culture dishes with TrypLE Express, washed once with 0.1% trypsin inhibitor, 0.2% fatty acid-free BSA in DMEM or EBM-2, and twice with 0.2% BSA in the relevant media. The washed cells were counted and resuspended at $0.3 \times 10^5$ cells/ml. $1.5 \times 10^5$ were loaded into the upper chamber of 12 µm Costar transwells pre-coated on the lower surface with 5 µg/ml fibronectin. The effect of Slit2 on haptotaxis was analyzed by co-coating with 0.5 µg/ml Slit2 or an equivalent amount of Mock preparation. Cell migration was allowed to proceed for 6 hours, after which cells on the upper surface of the transwell were removed with a cotton swab. The cells on the lower surface were fixed with 4% formaldehyde for 5 minutes and washed three times with PBS. For HEK 293 cells, the number of GFP-positive cells (HEK 293) on the lower surface was enumerated by counting six 10× fields on an inverted fluorescence microscope. The number of migrated cells on fibronectin/Mock-coated membranes was considered 100% for data presentation and subsequent statistical analysis. At least two independent experiments in duplicate were performed.

Yeast Two Hybrid Assay: pGBKT7::hRobo4 465-723 was transformed into the yeast strain PJ694A, creating PJ694A-Robo4. A human aortic cDNA library was cloned into the prey plasmid pACT2 and then transformed into PJ694A-Robo4. Co-transformed yeast strains were plated onto SD-Leu-Trp (-LT) to analyze transformation efficiency and SD-Leu-Trp-His-Ade (-LTHA) to identify putative interacting proteins. Yeast strains competent to grow on SD-LTHA were then tested for expression of β-galactosidase by the filter lift assay. Prey plasmids were isolated from yeast strains capable of growing on SD-LTHA and expressing β-galactosidase, and sequenced at the University of Utah Core Facility.

Immunoprecipitation: Cell lysates were prepared in 50 mM Tris-Cl, pH 7.4, 50 mM NaCl, 1 mM DTT, 0.5% Triton X-100, phosphatase and protease inhibitors, centrifuged at 14K for 20 minutes to pellet insoluble material, cleared with normal IgG coupled to agarose beads for 60 minutes, and incubated for 2 hours at 4° C. with relevant antibodies coupled to agarose beads. The precipitates were washed extensively in lysis buffer and resuspended in 2× sample buffer (125 mM Tris-Cl, pH 6.8, 4% SDS, 20% Glycerol, 0.04% bromophenol blue and 1.4M 2-mercaptoethanol).

GST Pull Down Assay: Rosetta2 $E.$ $coli$ harboring pGEX-4T1::mRobo4 were grown to OD600 of 0.6 and induced with 0.3 mM IPTG. After 3-4 hours at 30° C., 220 rpm, the cells were lysed by sonication in 20 mM Tris-Cl pH 7.4, 1% Triton X-100, 1 µg/ml lysozyme, 1 mM DTT and protease inhibitors. The GST-fusion proteins were captured on glutathione-Sepharose 4B, washed once with lysis buffer without lysozyme and then twice with binding/wash buffer (50 mM Tris-Cl, pH 7.4, 150 mM NaCl, 1 mM DTT, 1% Triton X-100, 0.1% BSA and protease inhibitors). The GST-fusion proteins were incubated with 60 nM purified recombinant paxillin overnight at 4° C., washed extensively in binding/wash buffer, and resuspended in 2× sample buffer.

Western Blotting: Immunoprecipitates and GST-fusion proteins were incubated for 2 minutes at 100° C., separated by SDS polyacrylamide gel electrophoresis (SDS-PAGE) and transferred to a polyvinyldifluoride (PVDF) membrane. PVDF membranes were incubated with 5% nonfat dry milk in PBS+0.1% Tween20 (PBST) (PBST-M) for 60 minutes at 25° C. Blocked membranes were incubated with primary antibody (anti-Flag M2 at 1:2000; anti-HA at 1:10,000; anti-Hic-5 at 1:500; anti-paxillin at 1:10,000; anti-Rac at 1:1,000 and anti-Cdc42 at 1:500) in PBST-M for 60 minutes at 25° C., or overnight at 4° C. Membranes were washed 3×10 minutes in PBST and then incubated with secondary antibody (goat anti-mouse or goat anti-rabbit horseradish peroxidase at 1:10, 000) for 60 minutes at 25° C. Membranes were washed 3×10 minutes in PBST and visualized with ECL PLUS.

In vitro Transcription/Translation: Mena-V5 was synthesized with the T7 Quick Coupled in vitro Transcription/Translation system according to the manufacturer's protocol.

Spreading Assay: Transfected HEK 293 cells were plated onto coverslips coated with 5 µg/ml fibronectin. Following a 30 minute incubation at 5% $CO_2$ and 37° C., the cells were washed three times with ice-cold PBS and fixed with 3.7% formaldehyde for 10 minutes at room temperature. The cells were then peremabilized with 0.2% Triton X-100 for three minutes, washed three times with PBS+0.1% Tween20 (PBST) and incubated with 10 µg/ml Rhodamine-Phalloidin for one hour at room temperature. Following three more washes in PBS-T, the coverslips were mounted in Pro-Long Gold and analyzed by confocal microscopy. The total area of 150 cells in three independent experiments was determined using ImageJ.

siRNA-mediated knockdown of paxillin: HEK 293 cells were transfected with 100 nM siRNA duplexes (5'-CCCUGACGAAAGAGAAGCCUAUU-3', SEQ ID NO:33 and 5'-UAGGCUUCUCUUUCGUCAGGGUU-3', SEQ ID NO:34) using LipofectAMINE 2000, according to the manufacturer's instructions. 48 h after transfection, cells were processed for biochemical analysis or cell spreading assays. Paxillin reconstitution was accomplished by transfection with an expression vector encoding chicken paxillin, which has the nucleotide sequence 5'-CCCCTACAAAAGAAAAACCAA-3' (SEQ ID NO:35) within the siRNA target site. Knockdown and reconstitution were visualized by western blotting with paxillin antibodies and quantified by densitometry.

Rac and Cdc42 Activation Assay: Transfected HEK 293 cells were detached from cell culture dishes, held in suspension for one hour in DMEM+0.2% BSA, and plated onto bacterial Petri dishes coated with 5 µg/ml fibronectin for five minutes. The cells were then washed twice with ice-cold PBS and lysed in 50 mM Tris pH 7.0, 500 mM NaCl, 1 mM MgCl2, 1 mM EGTA, 1 mM DTT, 0.5% NP-40, 1× protease inhibitors, 1× phosphatase inhibitors and 20 µg/ml GST- PBD. The lysate was centrifuged for five minutes at 14,000 rpm and the supernatant was incubated with 30 μl of glutathione agarose for 30 minutes at 4° C. Following three washes with lysis buffer, bound proteins were eluted with 2× sample buffer. Rac and Cdc42 were detected by western blotting with antibodies specific to each protein. Rac activation levels were normalized to total Rac and the highest value in each experiment was assigned a value of 1.

Generation of Robo4$^{AP/AP}$ mice and genotyping: The Robo4 targeting vector was electroporated into embryonic stem (ES) cells. ES cells heterozygous for the targeted allele were injected into blastocysts and then transferred to pseudopregnant females. Chimeric males were identified by the presence of agouti color and then mated to C57BL/6 females to produce ES-cell derived offspring. Genotype was confirmed by Southern blot analysis of tail DNA. Genomic DNA from ear punch or tail samples was used for PCR genotyping under the following conditions; denaturation at 94° C. for 30 seconds, annealing at 60° C. for 30 seconds, and extension at 72° C. for 60 seconds, 40 cycles. The following two primers were used for genotyping of Robo4: 5' cccttcacagacagactctcgtatttcc 3' (forward) and 5' cccagacctacattacctttttgccg 3'(reverse) and for AP: 5' ggcaacttccagaccattggcttg 3'(forward) and 5' ggttaccactcccactgacttccctg 3' (reverse).

Embryos and expression analysis: Staging of embryos, in situ hybridization, paraffin sectioning and whole-mount PECAM-1 immunohistochemistry were performed as previously described[1]. For Northern Blot analysis, 20 μg of total RNA was loaded per lane after isolation with TRIZOL. $^{32}$P-labelled probe was generated using prime It II Random-Primer labeling kit (Stratagene). Lung lysates were prepared with lysis buffer [1% NP-40, 150 mM NaCl, 50 mM Tris-Cl (pH 7.5), 1 mM EDTA and protease inhibitor cocktail (Roche)]. Robo4 protein from the lung lysates was detected by Western blot analysis using a polyclonal anti-Robo4 antibody as previously described.

Alkaline phosphatase (AP) staining: Embryos or tissues were fixed in 4% paraformaldehyde and 2 mM $MgCl_2$ in PBS overnight at 4° C. with shaking Samples were washed three times for 15 min in PBST (PBS, 0.5% Tween 20). Endogenous alkaline phosphatase was inactivated at 65° C. for 90 min in PBS with 2 mM $MgCl_2$, then washed in AP buffer (100 mM Tris-Cl, pH9.5, 100 mM NaCl, 50 mM $MgCl_2$, 0.1% Tween 20, 2 mM Levamisole) twice for 15 minutes. Staining was carried out in BM purple substrate (Boehringer Mannheim) for embryos (Boehringer Mannheim) or NBT/BCIP for adult tissues. Staining was stopped in PBS, with 5 mM EDTA.

Whole mount immunohistochemistry after AP staining: Alkaline phosphatase (AP) staining on fixed and dissected retinas was performed as described above. Staining was stopped in PBS −5 mM EDTA. Retinas were washed twice in PBS and post-fixed 5 minutes in 4% paraformaldehyde, phosphate-buffered saline at RT, then washed twice in PBS. After 2 h hours incubation in PBlec (PBS, pH 6.8, 1% Triton-X100, 0.1 mM CaCl 0.1 mM MgCl 0.1 mM MnCl), retinas were incubated with antibodies overnight at 4° C. Pericytes were labeled using rabbit anti-NG2 antibody (1:200; Chemicon) and endothelial cells were labeled using rat anti-endomucin (Clone V.7C7 kindly provided by Dietmar Vestweber; diluted 1:20). After 3 washes in PBS-T (PBS, pH 7.4, 1% Triton-X100), samples were incubated with secondary antibodies conjugated with the appropriate fluorochrome—Alexa Fluor 488 or 568 (Molecular Probes; Invitrogen) in PBS. After washing and a brief postfixation in 4% PFA, the retinas were flat mounted and coversliped using Mowiol/DABCO (Sigma-Aldrich) Samples were analyzed by conventional light and fluorescence microscopy using a Zeiss Stereomicroscope Stemi SV 11 Bioquad equipped with a Zeiss Axiocam HRc digital camera and by confocal laser scanning microscopy using a Zeiss LSM Meta 510. AP staining was visualized using the 633 nm HeNe laser and reflection settings. Digital images were processed using Volocity (4.0 Improvision) and compiled in Adobe Photoshop CS2.

Immunohistochemistry: Whole-mount triple immunofluorescence confocal microscopy was performed as previously described[3]. Briefly, antibodies to PECAM, NP1, CX40, 2H3, BFABP and aSMA were used to label the limb skin of Robo4+/+ or Robo4−/− embryos at E15.5.

Construction of expression vectors for recombinant Slit fragments: The proposed expression vectors are depicted in FIG. 23. DNA encoding all fragments was cloned into the pSECTAG2 vector (Invitrogen) and shared the following features: a CMV promoter, a Kozak consensus sequence, a myc/his tag in-frame fusion, and a bovine growth hormone polyA sequence. The Fc fusions were generated by replacing the myc/his epitope with a recombinant form of the Fc domain of human IgG1 in which the complement activating and effector cell interaction domains have been replaced with IgG4 and IgG2 sequences respectively (Katoh et al., 2005; Armour et al., 1999). The recombinant Slit fragments and Slit fragment-Fc fusion proteins were isolated from transiently transfected cells. The desired construct was stably transfected into CHO cells by selection for Zeocin resistance.

Binding and activity of Robo4 agonists on Robo4 expressing HEK cells: Stable cell lines expressing Robo4-HA (Robo4-HEK), or the pcDNA3 vector alone (Control-HEK), were seeded in 6-well culture dishes precoated with 100 μg/ml poly-L-lysine. Cells were incubated with HEK CM or Slit-myc CM at 37° C. After 1 hr incubation with conditioned media, followed by three washes in PBS, cells were fixed in 4% paraformaldehyde for 20 min. Cells were then washed three times with PBS and incubated with mouse anti-myc antibody (Santa Cruz Biotech) and anti-mouse Alexa 594-conjugated secondary antibody (Molecular Probes). The ability of those agonists, which bind to Robo4 to inhibit migration, was performed according to Park K W, Morrison C M, Sorensen L K, et al., "Robo4 is a vascular-specific receptor that inhibits endothelial migration," Dev Biol 2003; 261(1): 251-67.

Isolation of murine lung endothelial cells: Isolation of murine endothelial cells has been previously described[4]. Sheep anti-rat IgG Dynal beads (Dynal Biotech) were conjugated with either anti-PECAM-1 or anti-ICAM-2 monoclonal antibody (BD Pharmingen) at 5 μg of antibody per 100 μL of beads. The beads were precoated and stored at 4° C. ($4 \times 10^8$ beads/mL of PBS with 0.1% BSA) for up to 2 weeks. The lungs from three adult mice were harvested. The lung lobes were dissected from visible bronchi and mediastinal connective tissue. The lungs were washed in 50 mL cold isolation medium (20% FBS-DMEM) to remove erythrocytes, minced with scissors and digested in 25 mL of pre-warmed Collagenase (2 mg/mL, Worthington) at 37° C. for 45 minutes with gentle agitation. The digested tissue was dissociated by triturating 12 times through a 60 cc syringe attached to a 14 gauge metal cannula and then filtered through sterile 70 μm disposable cell strainer (Falcon). The suspension was centrifuged at 400×g for 10 minutes at 4° C. The cell pellet was resuspended in 2 ml cold PBS and then incubated with PECAM-1 coated beads (15 μL/mL of cells) at room temperature for 10 minutes. A magnetic separator was used to recover the bead-bound cells, which were washed in isolation medium, and then resuspended in complete medium (EGM-2 MV, Lonza). The cells were plated in a single fibronectin-coated 75-cm² tissue culture flask and nonadherent cells were removed after overnight incubation. The adherent cells were washed with PBS and 15 ml of complete medium was added. Cultured cells were fed on alternate days with complete medium. When the cultures reached 70 to 80% confluency, they were detached with trypsin-EDTA, resuspended in 2 ml PBS and sorted for a second time using ICAM-2 conjugated beads (15 µL/mL of cells). The cells were washed and plated as above. Passages 2 to 5 were used for functional assays.

Cell Culture: Human dermal microvascular endothelial cells (HMVEC, Cambrex) were grown in EGM-2 MV, and used between passages 3 and 6.

Immunocytochemistry: 8 well chamber slides (Lab-Tek) were coated with 1.5 µg/cm² fibronectin for two hours prior to plating cells. Murine lung endothelial cells were plated overnight at 37° C. (100,000 cells/well) in complete medium, EGM-2 MV. The cells were then washed three times in PBS, and fixed in 4% paraformaldehyde for 10 minutes at room temperature. After three additional washes in PBS, the cells were washed in 1% Triton X-100 in PBS for 15 minutes at room temperature followed by three washes in PBST (0.1% Triton X-100 in PBS). The cells were then blocked in 2% BSA in PBS for 20 minutes at room temperature and incubated with primary antibody in 2% BSA: rat anti-PECAM-1 (Pharmigen), rabbit anti-Von Willebrand Factor (vWF) (DAKO) for 1 hour at room temperature. After incubation with primary antibody, the cells were washed in PBST and incubated with secondary antibody in 2% BSA: Alexa Fluor 488 donkey anti-rat IgG and Alexa Fluor 594 donkey anti-rabbit IgG (Molecular Probes) for 1 hour at room temperature. The cells were washed once in PBST, once in PBS, mounted in Vectashield mounting media (Vector Laboratories), and photographed by a confocal microscopy.

Fluorescence-Activated Cell Sorting (FACS): Murine lung endothelial cells were detached from the culture dish by brief trypsinization (no more than 2 minutes) at 37° C. Proteolysis was arrested by the addition of trypsin inhibitor in EBM-2+ 0.1% BSA. The cells were washed twice in FACS buffer (PBS without Ca2+ and Mg2++0.1% BSA) and then resuspended in 1 mL FACS buffer. Analysis of the expression of cell surface markers was performed with two-step immunofluorescence staining. The cells were incubated for 30 minutes at 4° C. with purified monoclonal antibodies: rat anti-PECAM-1, rabbit anti-vWF. The cells were then washed two times in FACS buffer and resuspended in 1 mL FACS buffer. The cells were then incubated for 30 minutes at 4° C. with fluorescent secondary antibody: Alexa Fluor 488 donkey anti-rat IgG and Alexa Fluor 594 donkey anti-rabbit IgG (Molecular Probes). The cells were again washed twice, resuspended in 1 mL FACS buffer and analyzed with the FACS.

Cell migration assay: Cells were labeled with CellTracker Green CMFDA (Molecular Probes) for 1 hour, washed and then starved overnight in EBM-2 supplemented with 0.1% BSA. Cells were trypsinized, washed and resuspended to 300,000 cells/mL. 100 µL of cell suspension (30,000 cells) was loaded onto 8-µm HTS FluoroBlock filters (BD Falcon) that had been previously coated on both sides with 5 µg/mL human fibronectin. Test factors were diluted in EBM-2/0.1% BSA and placed in the lower chamber. After incubation at 37° C. for 3 hours, two 5× fields from each well were photographed on an inverted fluorescence microscope (Axiovert 200). The number of migrated cells was enumerated by counting fluorescent cells. Basal migration of Robo4$^{+/+}$ cells was set at 1. Data are presented as mean±S.E. of three independent experiments in triplicate.

Tube formation assay: Tube formation was performed as previously described[5]. In brief, lung endothelial cells isolated from Robo4$^{+/+}$ and Robo4$^{AP/AP}$ mice were plated onto matrigel-coated wells of a 48-well dish, and starved overnight in 0.5% serum. The cells were then stimulated with 0.48 nM VEGF-A in the absence or presence of Slit2 for 3.5 hours, and then photographed. Average tube length was determined using ImageJ software. Data are presented as mean±S.E. of three independent experiments in duplicate.

In vitro permeability assay: Lung endothelial cells (ECs) isolated from Robo4$^{+/+}$ and Robo4$^{AP/AP}$ mice were plated onto 3.0 µm Costar transwells pre-coated with 1.5 µg/cm² human fibronectin and grown to confluency. Cells were starved overnight, pre-treated with 0.3 nM Slit2 for 30-60 minutes and then stimulated with 2.4 nM VEGF-A for 3.5 hours. Horseradish peroxidase (HRP) was added to the top chamber at a final concentration of 100 µg/ml, and 30 minutes later the media was removed from the lower chamber. Aliquots were incubated with 0.5 mM guaiacol, 50 mM $Na_2HPO_4$, and 0.6 mM $H_2O_2$, and formation of O-phenylenediamine was determined by measure of absorbance at 470 nm. Basal permeability of monolayers was set at 100%. The data is presented as mean±S.E. of three independent experiments in triplicate.

VEGF Induced Retinal Permeability: Retinal permeability was assessed as described in[53]. In brief, 8-10 week old mice were anesthetized with Avertin (2-2-2 Tribromoethanol, 0.4 mg/g; Acros Organics, Morris Plains, N.J.). Mice were given an intraocular injection of 1.4 uL of 35.7 ug/mL VEGF-A (R&D Systems Inc. Minneapolis, Minn.) with 50 ng Slit2N (SEQ ID NO: 39). An injection with equivalent volume of Mock preparation was given in the contralateral eye. As indicated, other conditions of 1.4 uL of saline, Mock preparation, or slit were administered. Six hours later, mice were given an I.V. injection via the tail vein of 50 uL Evans Blue 60 mg/mL. After two hours, mice were sacrificed and perfused with citrate-buffered para-formaldehyde to remove intravenous Evans Blue. Eyes were enucleated and retinas dissected. Evans Blue dye was eluted in 0.3 mL formamide for 18 hours at 70° C. The extract was ultra-centrifuged through a 5 kD filter for 2 hours. Absorbance was measured at 620 nm. Background absorbance was measured at 740 nm and subtracted out.

Adenoviral expression of Robo4: Robo4 was expressed via adenovirus as previously described.

Miles Assay: Evans Blue was injected into the tail vein of 6-8 week old mice, and thirty minutes later either saline, or 10 ng of VEGF-A in the absence and presence of 100 ng Slit2 was injected into the dermis. After an additional thirty minutes, punch biopsies were preformed and Evans Blue was eluted from the dermal tissue in formamide for 18 hours at 60° C. Following centrifugation, the absorbance was measured at 620 nm. The amount of dermal permeability observed in saline injected animals was set at 1. Data are presented as mean±S.E. of five individual mice with each treatment in duplicate (six total injections per animal).

Retinal permeability: Retinal permeability was assessed as previously described[8]. In brief, 8-10 week old mice were anesthetized with Avertin (2-2-2 Tribromoethanol, 0.4 mg/g; Acros Organics, Morris Plains, N.J.). Mice were given an intraocular injection of 1.44 of 35.7 µg/mL VEGF-A (R&D Systems Inc. Minneapolis, Minn.) with 50 ng Slit2. An equivalent volume of Mock was injected into the contralateral eye. As indicated, other conditions were administered. Six hours later, 50 µL of 60 mg/mL Evans Blue solution was administered via the femoral vein. After two hours, mice were sacrificed and perfused with citrate-buffered formaldehyde to remove intravenous Evans Blue. Eyes were enucleated and retinas dissected. Evans Blue dye was eluted in 0.4 mL formamide for 18 hours at 70° C. The extract was ultra-centrifuged through a 5 kD filter for 2 hours. Absorbance was measured at 620 nm. Background absorbance was measured at 740 nm and subtracted out. Data are presented as mean±S.E. of five individual mice per genotype.

Biochemical assays: HMVEC were grown to confluence on fibronectin-coated dishes and starved overnight in EBM-2+0.2% BSA. The next day, the cells were stimulated with 50 ng/mL VEGF-A for 5 minutes, washed twice with ice-cold PBS and lysed in 50 mM Tris pH 7.4, 150 mM NaCl, 10 mM $MgCl_2$, 1 mM DTT, 10% Glycerol, 1% NP-40, 0.5% Sodium Deoxycholate, 0.1% SDS, 1× protease inhibitors, 1× phosphatase inhibitors. Lysates were combined with 2× sample buffer, separated by SDS-PAGE and probed with antibodies to phospho-VEGFR2, phospho-p42/44 and phospho-Src (Cell Signaling) at 1:1000. For Rac activation assays, crude membrane preps were generated[9] and GTP-Rac was precipitated with 20 μg/ml GST-PBD. Following three washes with lysis buffer, bound proteins were eluted with 2× sample buffer. Rac1 was detected by western blotting with monoclonal antibodies (BD Biosciences).

Oxygen Induced Retinopathy: In brief, P7 pups along with nursing mothers were placed in 75% oxygen, which was maintained by a Pro-OX oxygen controller (BioSpherix, Redfield, N.Y.). Pups were removed on P12 and given an intraocular injection of Slit2N (SEQ ID NO: 39) agonist or Mock preparation, which served as a control condition. Mice were sacrificed on P17 and perfused via the left ventricle with 1 ml 50 mg/ml FITC-Dextran (Sigma, St. Louis, Mo.). Eyes were enucleated, fixed for 30 minutes in 4% paraformaldehyde, and retinal flatmounts generated. Images were taken using Axiovert 200 fluorescence microscopy (Carl Zeiss, Thornwood, N.Y.). Neovascularization was quantified using AxioVision software, which calculates the amount of vascularization per area (Carl Zeiss, Thornwood, N.Y.). Data are presented as mean±S.E. of five individual mice per genotype.

Laser Induced Choroidal Neovascularization: Two-three month old mice were anesthetized with Avertin (2-2-2 Tribromoethanol, 0.4 mg/g; Acros Organics, Morris Plains, N.J.) and the pupils dilated with 1% tropicamide (Alcon, Fort Worth, Tex.). An Iridex OcuLight GL 532 nm laser photocoagulator (Iridex, Mountain View, Calif.) with slit lamp delivery system was used to create three burns 3 disc diameters from the optic disc at 3, 6, and 9 o'clock with the following parameters: 150 mW power, 75 um spot size, and 0.1 second duration. Production of a bubble at the time of laser indicating rupture of Bruch's membrane was an important factor in obtaining CNV; therefore, only burns in which a bubble was produced were included in this study. Immediately after laser treatment and 3 days later, mice were given an intravitreal injection of 50 ng Slit2N (SEQ ID NO: 39). An equal volume of Mock preparation was given by intravitreal injection in the other eye. One week after laser treatment, mice were sacrificed and choroidal flat mounts generated. Biotin conjugated isolectin (Sigma, St. Louis, Mo.) and Texas red conjugated streptavidin (Sigma, St. Louis, Mo.) were used to stain CNV. Flat mounts were examined using a Zeiss LSM 510 confocal microscope (Zeiss, Thornwood, N.Y.) and CNV quantified using ImageJ software (NIH, Bethesda, Md.).

References

Afzal A, Shaw L C, Ljubimov A V, Boulton M E, Segal M S, Grant M B. Retinal and choroidal microangiopathies: Therapeutic opportunities. Microvasc Res 2007.

Armour K L, Clark M R, Hadley A G, Williamson L M. Recombinant human IgG molecules lacking Fcgamma receptor I binding and monocyte triggering activities. Eur J Immunol 1999; 29(8):2613-24.

Bashaw, G. J., Kidd, T., Murray, D., Pawson, T., and Goodman, C. S. (2000). Repulsive axon guidance: Abelson and Enabled play opposing roles downstream of the roundabout receptor. Cell 101, 703-715.

Battye, R., Stevens, A., and Jacobs, J. R. (1999). Axon repulsion from the midline of the *Drosophila* CNS requires slit function. Development 126, 2475-2481.

Battye R, Stevens A, Perry R L, Jacobs J R. Repellent signaling by Slit requires the leucine-rich repeats. J Neurosci 2001; 21(12):4290-8.

Bedell, V. M., Yeo, S. Y., Park, K. W., Chung. J., Seth, P., Shivalingappa, V., Zhao, J., Obara, T., Sukhatme, V. P., Drummond, I. A., Li, D. Y., and Ramchandran, R. (2005). roundabout 4 is essential for angiogenesis in vivo. Proc. Natl. Acad. Sci. U.S.A. 102, 6373-6378.

Brooks, P. C., Clark, R. A., and Cheresh, D. A. (1994). Requirement of vascular integrin alpha v beta 3 for angiogenesis. Science 264, 569-571.

Brooks, P. C., Montgomery, A. M., Rosenfeld, M., Reisfeld, R. A., Hu, T., Klier, G., and Cheresh, D. A. (1994). Integrin alpha v beta 3 antagonists promote tumor regression by inducing apoptosis of angiogenic blood vessels. Cell 30, 1157-1164.

Brose, K., Bland, K. S., Wang, K. H., Arnott, D., Henzel, W., Goodman, C. S., Tessier-Lavigne, M., and Kidd, T. (1999). Slit proteins bind Robo receptors and have an evolutionarily conserved role in repulsive axon guidance. Cell 19, 795-806.

Brown D M, Kaiser P K, Michels M, Soubrane G, Heier J S, Kim R Y, Sy J P, Schneider S; ANCHOR Study Group. Ranibizumab versus verteporfin for neovascular age-related macular degeneration. N Engl J. Med. 2006 355(14):1432-44.

Brown, M. C., and Turner, C. E. (2004). Paxillin: adapting to change. Physiol. Rev. 84, 1315-1339.

Byzova, T. V., Goldman, C. K., Pampori, N., Thomas, K. A., Bett, A., Shattil, S. J., and Plow, E. F. (2000). A mechanism for modulation of cellular responses to VEGF: activation of the integrins. Mol. Cell. 6, 851-860.

Carmeliet P, Tessier-Lavigne M. Common mechanisms of nerve and blood vessel wiring. Nature 2005; 436(7048):193-200.

Cheng H J, Nakamoto M, Bergemann A D, Flanagan J G. Complementary gradients in expression and binding of ELF-1 and Mek4 in development of the topographic retinotectal projection map. Cell 1995; 82(3):371-81.

Chun D W, Heier J S, Topping T M, Duker J S, Bankert J M. A pilot study of multiple intravitreal injections of ranibizumab in patients with center-involving clinically significant diabetic macular edema. Ophthalmology 2006; 113(10):1706-12.

Cross M J, Dixelius J, Matsumoto T, Claesson-Welsh L. VEGF-receptor signal transduction. Trends in biochemical sciences 2003; 28(9):488-94.

Culotti J G, Merz D C. DCC and netrins. Curr Opin Cell Biol 1998; 10(5):609-13.

Diabetic Retinopathy Clinical Research Network, Scott I U, Edwards A R, Beck R W, Bressler N M, Chan C K, Elman M J, Friedman S M, Greven C M, Maturi R K, Pieramici D J, Shami M, Singerman L J, Stockdale C R. A phase II randomized clinical trial of intravitreal bevacizumab for diabetic macular edema. Ophthalmology. 2007 114(10):1860-7.

Dickson B J. Molecular mechanisms of axon guidance. Science 2002; 298(5600):1959-64.

Dong Q G, Bernasconi S, Lostaglio S, et al. A general strategy for isolation of endothelial cells from murine tissues. Characterization of two endothelial cell lines from the murine lung and subcutaneous sponge implants. Arterioscler Thromb Vasc Biol 1997; 17(8):1599-604.

Dorrell M, Uusitalo-Jarvinen H, Aguilar E, Friedlander M. Ocular neovascularization: basic mechanisms and therapeutic advances. Sury Ophthalmol. 2007 52 Suppl 1:S3-19.

Drescher U, Kremoser C, Handwerker C, Loschinger J, Noda M, Bonhoeffer F. In vitro guidance of retinal ganglion cell axons by RAGS, a 25 kD tectal protein related to ligands for Eph receptor tyrosine kinases. Cell 1995; 82(3):359-70.

D'Souza-Schorey, C., and Chavrier, P. (2006). ARF proteins: roles in membrane traffic and beyond. Nat. Rev. Mol. Cell. Biol. 7, 347-358.

Eliceiri B P, Cheresh D A. (2000). Role of alpha v integrins during angiogenesis. Cancer J. 6, S245-249.

Eliceiri B P, Paul R, Schwartzberg P L, Hood J D, Leng J, Cheresh D A. Selective requirement for Src kinases during VEGF-induced angiogenesis and vascular permeability. Molecular cell 1999; 4(6):915-24.

Eliceiri B P, Puente X S, Hood J D, et al. Src-mediated coupling of focal adhesion kinase to integrin alpha(v) beta5 in vascular endothelial growth factor signaling. The Journal of cell biology 2002; 157(1):149-60.

Francis, S. E., Goh, K. L., Hodivala-Dilke, K., Bader, B. L., Stark, M., Davidson, D., and Hynes, R. O. (2002). Central roles of alpha5beta1 integrin and fibronectin in vascular development in mouse embryos and embryoid bodies. Arterioscler. Thromb. Vasc. Biol. 22, 927-933.

Garrett T A, Van Buul J D, Burridge K. VEGF-induced Rac1 activation in endothelial cells is regulated by the guanine nucleotide exchange factor Vav2. Experimental cell research 2007; 313(15):3285-97.

Gavard J, Gutkind J S. VEGF controls endothelial-cell permeability by promoting the beta-arrestin-dependent endocytosis of VE-cadherin. Nature cell biology 2006; 8(11): 1223-34.

Gerhardt H, Golding M, Fruttiger M, et al. VEGF guides angiogenic sprouting utilizing endothelial tip cell filopodia. The Journal of cell biology 2003; 161(6):1163-77.

Goldfinger, L. E., Han, J., Kiosses, W. B., Howe, A. K., and Ginsberg, M. H. (2003). Spatial restriction of alpha4 integrin phosphorylation regulates lamellipodial stability and alpha4beta1-dependent cell migration. J. Cell Biol. 162, 731-741.

Hagel, M., George, E. L., Kim, A., Tamimi, R., Opitz, S. L., Turner, C. E., Imamoto, A., and Thomas, S. M. (2002). The adaptor protein paxillin is essential for normal development in the mouse and is a critical transducer of fibronectin signaling. Mol. Cell. Biol. 22, 901-915.

Han, J., Liu, S., Rose, D. M., Schlaepfer, D. D., McDonald, H., and Ginsberg, M. H. (2001). Phosphorylation of the integrin alpha 4 cytoplasmic domain regulates paxillin binding. J. Biol. Chem. 276, 40903-40909.

Hohenester E, Hussain S, Howitt J A. Interaction of the guidance molecule Slit with cellular receptors. Biochem Soc Trans 2006; 34(Pt 3):418-21.

Hohenester, E., Hussain, S., and Howitt, J. A. (2006). Interaction of the guidance molecule Slit with cellular receptors. Biochem. Soc. Trans. 34, 418-421.

Hong K, Hinck L, Nishiyama M, Poo M M, Tessier-Lavigne M, Stein E. A ligand-gated association between cytoplasmic domains of UNC5 and DCC family receptors converts netrin-induced growth cone attraction to repulsion. Cell 1999; 97(7):927-41.

Howitt J A, Clout N J, Hohenester E. Binding site for Robo receptors revealed by dissection of the leucine-rich repeat region of Slit. Embo J 2004; 23(22):4406-12.

Hu, H., Li, M., Labrador, J. P., McEwen, J., Lai, E. C., Goodman, C. S., and Bashaw, G. J. (2005). Cross GTPase-activating protein (CrossGAP)/Vilse links the Roundabout receptor to Rac to regulate midline repulsion. Proc. Natl. Acad. Sci. U.S.A. 102, 4613-4618.

Huminiecki, L., and Bicknell, R. (2000). In silico cloning of novel endothelialspecific genes. Genome Res. 10, 1796-1806.

Huminiecki L, Gorn M, Suchting S, Poulsom R, Bicknell R. Magic roundabout is a new member of the roundabout receptor family that is endothelial specific and expressed at sites of active angiogenesis. Genomics 2002; 79(4):547-52.

Huminiecki, L., Gorn, M., Suchting, S., Poulsom, R., and Bicknell, R. (2002). Magic roundabout is a new member of the roundabout receptor family that is endothelial specific and expressed at sites of active angiogenesis. Genomics 79, 547-552.

Jain R K. Molecular regulation of vessel maturation. Nat Med 2003; 9(6):685-93.

Jin, S. W., Beis, D., Mitchell, T., Chen, J. N., and Stainier, D. Y. (2005). Cellular and molecular analyses of vascular tube and lumen formation in zebrafish. Development 132, 5199-5209.

Jones C A, Li D Y. Common cues regulate neural and vascular patterning. Curr Opin Genet Dev. 2007 August; 17(4):332-6.

Kanellis, J., Garcia, G. E., Li, P., Parra, G., Wilson, C. B., Rao, Y., Han, S., Smith, C. W., Johnson, R. J., Wu, J. Y., and Feng, L. (2004). Modulation of inflammation by slit protein in vivo in experimental crescentic glomerulonephritis. Am. J. Pathol. 165, 341-352.

Katoh Y, Katoh M. Comparative genomics on SLIT1, SLIT2, and SLIT3 orthologs. Oncol Rep 2005; 14(5):1351-5.

Kaur, S., Castellone, M. D., Bedell, V. M., Konar, M., Gutkind, J. S., and Ramchandran, R. (2006). Robo4 signaling in endothelial cells implies attraction guidance mechanisms. J. Biol. Chem. 281, 11347-11356.

Kidd, T., Bland, K. S., and Goodman, C. S. (1999). Slit is the midline repellent for the robo receptor in *Drosophila*. Cell 96, 785-794.

Kidd, T., Brose, K., Mitchell, K. J., Fetter, R. D., Tessier-Lavigne, M., Goodman, C. S., and Tear, G. (1998). Roundabout controls axon crossing of the CNS midline and defines a novel subfamily of evolutionarily conserved guidance receptors. Cell 92, 205-215.

Kidd, T., et al. Roundabout controls axon crossing of the CNS midline and defines a novel subfamily of evolutionarily conserved guidance receptors. Cell 92, 205-215 (1998).

Kimmel, C. B., Ballard, W. W., Kimmel, S. R., Ullmann, B., and Schilling, T. F. (1995). Stages of embryonic development of the zebrafish. Dev. Dyn. 203, 253-310.

Lantry L E. Ranibizumab, a mAb against VEGF-A for the potential treatment of age-related macular degeneration and other ocular complications. Curr Opin Mol. Ther. 2007 9(6): 592-602.

Lauffenburger, D. A., and Horwitz, A. F. (1996). Cell migration: a physically integrated molecular process. Cell 84, 359-369.

Lawson, N. D., and Weinstein, B. M. (2002). In vivo imaging of embryonic vascular development using transgenic zebrafish. Dev. Biol. 248, 307-318.

Li, H. S., Chen, J. H., Wu, W., Fagaly, T., Zhou, L., Yuan, W., Dupuis, S., Jiang, Z. H., Nash, W., Gick, C., Ornitz, D. M., Wu, J. Y., and Rao, Y. (1999). Vertebrate slit, a secreted ligand for the transmembrane protein roundabout, is a repellent for olfactory bulb axons. Cell 19, 807-818.

Li Q, Olsen B R. Increased angiogenic response in aortic explants of collagen XVIII/endostatin-null mice. Am J Pathol 2004; 165(2):415-24.

Lim Y C, Garcia-Cardena G, Allport J R, et al. Heterogeneity of endothelial cells from different organ sites in T-cell subset recruitment. Am J Pathol 2003; 162(5):1591-601.

Lima e Silva R, Saishin Y, Saishin Y, et al. Suppression and regression of choroidal neovascularization by polyamine analogues. Investigative ophthalmology & visual science 2005; 46(9):3323-30.

Little M, Rumballe B, Georgas K, Yamada T, Teasdale R D. Conserved modularity and potential for alternate splicing in mouse and human Slit genes. Int J Dev Biol 2002; 46(4):385-91.

Liu, S., and Ginsberg, M. H. (2000). Paxillin binding to a conserved sequence motif in the alpha 4 integrin cytoplasmic domain. J. Biol. Chem. 275, 22736-22742.

Liu, S., Kiosses, W. B., Rose, D. M., Slepak, M., Salgia, R., Griffin, J. D., Turner, C. E., Schwartz, M. A., and Ginsberg, M. H. (2002). A fragment of paxillin binds the alpha 4 integrin cytoplasmic domain (tail) and selectively inhibits alpha 4-mediated cell migration. J. Biol. Chem. 277, 20887-20894.

Liu, S., Thomas, S. M., Woodside, D. G., Rose, D. M., Kiosses, W. B., Pfaff, M., and Ginsberg, M. H. (1999). Binding of paxillin to alpha4 integrins modifies integrin-dependent biological responses. Nature 402, 676-681.

Long, H., et al. Conserved roles for Slit and Robo proteins in midline commissural axon guidance. *Neuron* 42, 213-223 (2004).

Lundstrom, A., Gallio, M., Englund, C., Steneberg, P., Hemphala, J., Aspenstrom, P., Keleman, K., Falileeva, L., Dickson, B. J., and Samakovlis, C. (2004). Vilse, a conserved Rac/Cdc42 GAP mediating Robo repulsion in tracheal cells and axons. Genes Dev. 18, 2161-2171.

Manilla, V., Cases, O., Nguyen-Ba-Charvet, K. T., Tessier-Lavigne, M., Sotelo, C., and Chedotal, A. (2002). Spatiotemporal expression patterns of slit and robo genes in the rat brain. J. Comp. Neurol. 442, 130-155.

Matthay M A, Zimmerman G A. (2005). Acute lung injury and the acute respiratory distress syndrome: four decades of inquiry into pathogenesis and rational management. Am J Respir Cell Mol. Biol.; 33(4):319-27.

Nakamura, K., Yano, H., Uchida, H., Hashimoto, S., Schaefer, E., and Sabe, H. (2000). Tyrosine phosphorylation of paxillin alpha is involved in temporospatial regulation of paxillin-containing focal adhesion formation and F-actin organization in motile cells. J. Biol. Chem. 275, 27155-27164.

Navankasattusas, S., K. J. Whitehead, A. Suli, L. K. Sorensen, A. H. Lim, J. Zhao, K. R. Thomas, C. B. Chien, and D. Y. Li. The netrin receptor, Unc5b, promotes angiogenesis in specific vascular beds. *Development* (in press).

Nishiya, N., Kiosses, W. B., Han, J., and Ginsberg, M. H. (2005). An alpha4 integrin-paxillin-Arf-GAP complex restricts Rac activation to the leading edge of migrating cells. Nat. Cell Biol. 7, 343-352.

Nobes, C. D., and Hall, A. (1995). Rho, rac, and cdc42 GTPases regulate the assembly of multimolecular focal complexes associated with actin stress fibers, lamellipodia, and filopodia. Cell 81, 53-62.

Ojima T, Takagi H, Suzuma K, Oh H, Suzuma I, Ohashi H, Watanabe D, Suganami E, Murakami T, Kurimoto M, Honda Y, Yoshimura N. EphrinA1 inhibits vascular endothelial growth factor-induced intracellular signaling and suppresses retinal neovascularization and blood-retinal barrier breakdown. Am J Pathol. 2006 January; 168(1):331-9.

Ozaki H, Seo M S, Ozaki K, et al. Blockade of vascular endothelial cell growth factor receptor signaling is sufficient to completely prevent retinal neovascularization. Am J Pathol 2000; 156(2):697-707.

Park K W, Crouse D, Lee M, et al. The axonal attractant Netrin-1 is an angiogenic factor. Proc Natl Acad Sci USA 2004; 101(46):16210-5.

Park K W, Morrison C M, Sorensen L K, et al. Robo4 is a vascular-specific receptor that inhibits endothelial migration. Dev Biol 2003; 261(1):251-67.

Park, K. W., Morrison, C. M., Sorensen, L. K., Jones, C. A., Rao, Y., Chien, C. B., Wu, J. Y., Urness, L. D., and Li, D. Y. (2003). Robo4 is a vascular-specific receptor that inhibits endothelial migration. Dev. Biol. 261, 251-267.

Raper J A. Semaphorins and their receptors in vertebrates and invertebrates. Curr Opin Neurobiol 2000; 10(1):88-94.

Reutershan J, Morris M A, Burcin T L, Smith D F, Chang D, Saprito M S, Ley K. Critical role of endothelial CXCR2 in LPS-induced neutrophil migration into the lung. J Clin Invest. 2006 116(3):695-702.

Ridley, A. J., Schwartz, M. A., Burridge, K., Firtel, R. A., Ginsberg, M. H., Borisy, G., Parsons, J. T., and Horwitz, A. R. (2003). Cell migration: integrating signals from front to back. Science. 302, 1704-1709.

Rosenfeld P J, Brown D M, Heier J S, et al. Ranibizumab for neovascular age-related macular degeneration. N Engl J Med 2006; 355(14):1419-31.

Ruhrberg C, Gerhardt H, Golding M, et al. Spatially restricted patterning cues provided by heparin-binding VEGF-A control blood vessel branching morphogenesis. Genes & development 2002; 16(20):2684-98.

Salgia, R., Li, J. L., Ewaniuk, D. S., Wang, Y. B., Sattler, M., Chen, W. C., Richards, W., Pisick, E., Shapiro, G. I., Rollins, B. J., Chen, L. B., Griffin, J. D., and Sugarbaker, D. J. (1999). Expression of the focal adhesion protein paxillin in lung cancer and its relation to cell motility. Oncogene. 18, 67-77.

Seeger, M., Tear, G., Ferres-Marco, D., and Goodman, C. S. (1993). Mutations affecting growth cone guidance in *Drosophila*: genes necessary for guidance toward or away from the midline. Neuron 10, 409-426.

Senger, D. R., Claffey, K. P., Benes, J. E., Perruzzi, C. A., Sergiou, A. P., and Detmar, M. (1997). Angiogenesis promoted by vascular endothelial growth factor: regulation through alphalbetal and alpha2beta1 integrins. Proc. Natl. Acad. Sci. U.S.A. 94, 13612-13617.

Seth, P., Lin, Y., Hanai, J., Shivalingappa, V., Duyao, M. P., and Sukhatme, V. P. Magic roundabout, a tumor endothelial marker: expression and signaling. Biochem. Biophys. Res. Commun. 332, 533-541.

Seth P, Lin Y, Hanai J, Shivalingappa V, Duyao M P, Sukhatme V P. Magic roundabout, a tumor endothelial marker: expression and signaling. Biochem Biophys Res Commun 2005; 332(2):533-41.

Shields R L, Namenuk A K, Hong K, et al. High resolution mapping of the binding site on human IgG1 for Fc gamma RI, Fc gamma RH, Fc gamma RIII and FcRn and design of IgG1 variants with improved binding to the Fc gamma R. J Biol Chem 2001; 276(9):6591-604.

Smith L E, Wesolowski E, McLellan A, et al. Oxygen-induced retinopathy in the mouse. Investigative ophthalmology & visual science 1994; 35(1):101-11.

Soga, N., Connolly, J. O., Chellaiah, M., Kawamura, J., and Hruska, K. A. (2001). Rac regulates vascular endothelial growth factor stimulated motility. Cell Commun. Adhes. 8, 1-13.

Soga, N., Namba, N., McAllister, S., Cornelius, L., Teitelbaum, S. L., Dowdy, S. F., Kawamura, J., and Hruska, K. A. (2001). Rho family GTPases regulate VEGFstimulated endothelial cell motility. Exp. Cell Res. 269, 73-87.

Soldi, R., Mitola, S., Strasly, M., Defilippi, P., Tarone, G., and Bussolino, F. (1999). Role of alphavbeta3 integrin in the activation of vascular endothelial growth factor receptor-2. EMBO J. 18, 882-892.

Stein E, Tessier-Lavigne M. Hierarchical organization of guidance receptors: silencing of netrin attraction by slit through a Robo/DCC receptor complex. Science 2001; 291 (5510):1928-38.

Suchting, S., Heal, P., Tahtis, K., Stewart, L. M., and Bicknell, R. (2005). Soluble Robo4 receptor inhibits in vivo angiogenesis and endothelial cell migration. FASEB J. 19, 121-138.

Turner, C. E. (2000). Paxillin interactions. J. Cell Sci. 113, 139-140. Wang, K. H., Brose, K., Arnott, D., Kidd, T., Goodman, C. S., Henzel, W., and Tessier-Lavigne, M. (1999). Biochemical purification of a mammalian slit protein as a positive regulator of sensory axon elongation and branching. Cell 96, 771-784.

Uemura A, Kusuhara S, Katsuta H, Nishikawa S. Angiogenesis in the mouse retina: a model system for experimental manipulation. Experimental cell research 2006; 312(5):676-83.

Urness L D, Li D Y. Wiring the vascular circuitry: from growth factors to guidance cues. Curr Top Dev Biol 2004; 62:87-126.

Wang, B., Xiao, Y., Ding, B. B., Zhang, N., Yuan, X., Gui, L., Qian, K. X., Duan, S., Chen, Z., Rao, Y., and Geng, J. G. (2003). Induction of tumor angiogenesis by Slit-Robo signaling and inhibition of cancer growth by blocking Robo activity. Cancer Cell 4, 19-29.

Watanabe D, Suzuma K, Matsui S, Kurimoto M, Kiryu J, Kita M, Suzuma I, Ohashi H, Ojima T, Murakami T, Kobayashi T, Masuda S, Nagao M, Yoshimura N, Takagi H. Erythropoietin as a retinal angiogenic factor in proliferative diabetic retinopathy. N Engl J. Med. 2005 353(8):782-92.

Weinstein, B. M. (2002). Plumbing the mysteries of vascular development using the zebrafish. Semin. Cell Dev. Biol. 13, 515-522.

Werdich X Q, McCollum G W, Rajaratnam V S, Penn J S. Variable oxygen and retinal VEGF levels: correlation with incidence and severity of pathology in a rat model of oxygen-induced retinopathy. Exp Eye Res 2004; 79(5):623-30.

West, K. A., Zhang, H., Brown, M. C., Nikolopoulos, S. N., Riedy, M. C., Horwitz, A. F., and Turner, C. E. (2001). The LD4 motif of paxillin regulates cell spreading and motility through an interaction with paxillin kinase linker (PKL). J. Cell Biol. 154, 161-176.

Westerfield, M. (2000). The zebrafish book. A guide for the laboratory use of zebrafish (Danio rerio). 4th ed. (Univ. of Oregon Press, Eugene).

Wilkinson D G, Bhatt S, Herrmann B G. Expression pattern of the mouse T gene and its role in mesoderm formation. Nature 1990; 343(6259):657-9.

Wilson B D, Ii M, Park K W, et al. Netrins promote developmental and therapeutic angiogenesis. Science 2006; 313 (5787):640-4.

Wojciak-Stothard, B., Potempa, S., Eichholtz, T., and Ridley, A. J. (2001). Rho and Rac but not Cdc42 regulate endothelial cell permeability. J. Cell Sci. 114, 1343-1355.

Wong, K., Ren, X. R., Huang, Y. Z., Xie, Y., Liu, G., Saito, H., Tang, H., Wen, L., Brady-Kalnay, S. M., Mei, L., Wu, J. Y., Xiong, W. C., and Rao, Y. (2001). Signal transduction in neuronal migration: roles of GTPase activating proteins and the small GTPase Cdc42 in the Slit-Robo pathway. Cell 107, 209-221.

Wu, J. Y., Feng, L., Park, H. T., Havlioglu, N., Wen, L., Tang, H., Bacon, K. B., Jiang, Z., Zhang, X., and Rao, Y. (2001). The neuronal repellent Slit inhibits leukocyte chemotaxis induced by chemotactic factors. Nature 410, 948-952.

Wu, W., Wong, K., Chen, J., Jiang, Z., Dupuis, S., Wu, J. Y., and Rao, Y. (1999). Directional guidance of neuronal migration in the olfactory system by the protein Slit. Nature 400, 331-336.

Xu Q, Qaum T, Adamis A P. Sensitive blood-retinal barrier breakdown Quantitation using evans blue. Invest Ophthalmol V is Sci. 2001; 42(3):789-94.

Yano, H., Mazaki, Y., Kurokawa, K., Hanks, S. K., Matsuda, M., and Sabe, H. (2004). Roles played by a subset of integrin signaling molecules in cadherinbased cell-cell adhesion. J. Cell Biol. 166, 283-295.

Yano, H., Uchida, H., Iwasaki, T., Mukai, M., Akedo, H., Nakamura, K., Hashimoto, S., and Sabe, H. (2000). Paxillin alpha and Crk-associated substrate exert opposing effects on cell migration and contact inhibition of growth through tyrosine phosphorylation. Proc. Natl. Acad. Sci. U.S.A. 97, 9076-9081.

Yu, T. W., Hao, J. C., Lim, W., Tessier-Lavigne, M., and Bargmann, C. I. (2002). Shared receptors in axon guidance: SAX-3/Robo signals via UNC-34/Enabled and a Netrin-independent UNC-40/DCC function. Nat. Neurosci. 5, 1147-1154.

Yuan, W., Zhou, L., Chen, J. H., Wu, J. Y., Rao, Y., and Ornitz, D. M. (1999). The mouse SLIT family: secreted ligands for ROBO expressed in patterns that suggest a role in morphogenesis and axon guidance. Dev. Biol. 212, 290-306.

Yuminamochi, T., Yatomi, Y., Osada, M., Ohmori, T., Ishii, Y., Nakazawa, K., Hosogaya, S., and Ozaki, Y. (2003). Expression of the LIM proteins paxillin and Hic-5 in human tissues. J. Histochem. Cytochem. 51, 513-521.

Zallen, J. A., Yi, B. A., and Bargmann, C. I. (1998). The conserved immunoglobulin superfamily member SAX-3/Robo directs multiple aspects of axon guidance in C. elegans. Cell 92, 217-227.

Zhu, Y., Li, H., Zhou, L., Wu, J. Y., and Rao, Y. (1999). Cellular and molecular guidance of GABAergic neuronal migration from an extracortical origin to the neocortex. Neuron 23, 473-485.

What is claimed is:

1. A method of inhibiting vascular permeability in tissue, comprising:
    administering to the tissue a ligand of roundabout-4 (Robo4) receptor;
    wherein the ligand of Robo4 is a Slit peptide comprising at least one of the amino acid sequence of SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, and SEQ ID NO: 47, and vascular permeability inhibiting fragments thereof.

2. The method of claim 1, wherein inhibiting vascular permeability is associated with a disease state selected from at least one of cytokine storm, avian influenza, graft versus host disease (GVHD), adult respiratory distress syndrome (ARDS), systemic inflammatory response syndrome (SIRS), ischemia injury, reperfusion injury, stroke, myocardial infarction, and retinopathies.

* * * * *